(12) United States Patent
    Satterfield

(10) Patent No.: US 10,227,286 B2
(45) Date of Patent: Mar. 12, 2019

(54) 3-OXO-3-(ARYLAMINO)PROPANOATES, A PROCESS FOR THEIR PREPARATION, AND THEIR USE IN PREPARING PYRROLIDINONES

(71) Applicant: E I DU PONT DE NEMOURS AND COMPANY, Wilmington, DE (US)

(72) Inventor: Andrew Duncan Satterfield, Hockessin, DE (US)

(73) Assignee: FMC Corporation, Philadelphia, PA (US)

( * ) Notice: Subject to any disclaimer, the term of this patent is extended or adjusted under 35 U.S.C. 154(b) by 0 days.

(21) Appl. No.: 15/533,448

(22) PCT Filed: Dec. 1, 2015

(86) PCT No.: PCT/US2015/063101
§ 371 (c)(1),
(2) Date: Jun. 6, 2017

(87) PCT Pub. No.: WO2016/094117
PCT Pub. Date: Jun. 16, 2016

(65) Prior Publication Data
US 2018/0057442 A1    Mar. 1, 2018

Related U.S. Application Data

(60) Provisional application No. 62/088,971, filed on Dec. 8, 2014.

(51) Int. Cl.
*C07C 233/07* (2006.01)
*C07C 205/40* (2006.01)
(Continued)

(52) U.S. Cl.
CPC .............. *C07C 69/02* (2013.01); *C07B 31/00* (2013.01); *C07C 233/07* (2013.01); *C07D 207/27* (2013.01); *C07D 207/277* (2013.01)

(58) Field of Classification Search
CPC ............................ C07C 233/07; C07C 205/40
(Continued)

(56) References Cited

U.S. PATENT DOCUMENTS 3,741,989 A    6/1973  Zaugg
4,594,094 A    6/1986  Kollmeyer
(Continued)

FOREIGN PATENT DOCUMENTS

CN    102531918 B    10/2013
DE    1 262 277 B    3/1968
(Continued)

OTHER PUBLICATIONS

Rajanarendar, E., K. Murthy, F. Shaik and M. Reddy, "A fast, highly efficient and green protocol for Michael addition of active methylene compounds to styrylisoxazoles using task-specific basic ionic liquid [bmlm]OH as catalyst and green solvent", Indian. Journ. Chem. (2011), 50B, pp. 587-592. (Year: 2011).*
(Continued)

*Primary Examiner* — Matthew P Coughlin
*Assistant Examiner* — Sagar Patel
(74) *Attorney, Agent, or Firm* — Reed A Coats

(57) ABSTRACT

Disclosed are compounds of Formula I, including all stereoisomers and salts thereof,

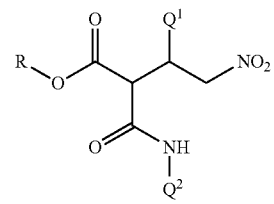

wherein $Q^1$, $Q^2$ and R are as defined in the disclosure.

Also disclosed is a method for preparing a compound of Formula I, comprising contacting a compound of Formula II

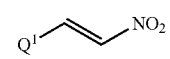

with a compound of Formula III

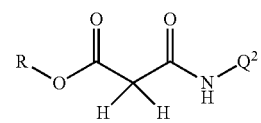

optionally in the presence of a catalyst or a base to form a compound of Formula I. Further disclosed is a method for preparing a compound of Formula IV,

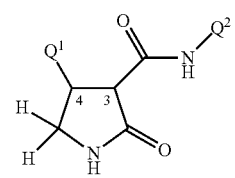

comprising reductively cyclizing a compound of Formula I in the presence of a reducing agent.

21 Claims, No Drawings

(51) Int. Cl.
*C07C 69/02* (2006.01)
*C07D 207/27* (2006.01)
*C07B 31/00* (2006.01)
*C07D 207/277* (2006.01)

(58) Field of Classification Search
USPC .................................. 564/166, 168, 161
See application file for complete search history.

(56) References Cited

U.S. PATENT DOCUMENTS

| | | | |
|---|---|---|---|
| 4,874,422 | A | 10/1989 | Woolard |
| 7,205,318 | B2 | 4/2007 | Qiao et al. |
| 8,293,926 | B2 | 10/2012 | Yasuoka et al. |
| 8,461,202 | B2 | 6/2013 | Sancho Sanz et al. |
| 8,575,154 | B2 | 11/2013 | Kori et al. |
| 8,946,216 | B2 | 2/2015 | Deng et al. |
| 9,944,602 | B2 | 4/2018 | Satterfield et al. |
| 2004/0242671 | A1 | 12/2004 | Grimee et al. |
| 2006/0019831 | A1 | 1/2006 | Reinhard et al. |
| 2007/0123508 | A1 | 5/2007 | Olsson et al. |
| 2011/0218199 | A1 | 9/2011 | Georges et al. |
| 2016/0137639 | A1 | 5/2016 | Kotoku et al. |
| 2016/0289228 | A1 | 10/2016 | Defays et al. |
| 2016/0297756 | A1 | 10/2016 | Satterfield et al. |
| 2017/0158638 | A1 | 6/2017 | Satterfield et al. |
| 2018/0049437 | A1 | 2/2018 | Satterfield et al. |
| 2018/0077931 | A1 | 3/2018 | Stevenson et al. |
| 2018/0099935 | A1 | 4/2018 | Satterfield et al. |
| 2018/0141904 | A1 | 5/2018 | Satterfield et al. |
| 2018/0213788 | A1 | 8/2018 | Satterfield et al. |
| 2018/0215760 | A1 | 8/2018 | Campbell et al. |

FOREIGN PATENT DOCUMENTS

| | | |
|---|---|---|
| EP | 2336104 A1 | 6/2011 |
| IN | 1462DEL08 | 6/2008 |
| JP | 53-056288 A | 5/1978 |
| JP | 54-088114 A | 7/1979 |
| JP | 08-269145 A | 10/1996 |
| KR | 20130142477 A | 12/2013 |
| RU | 2555370 C1 | 7/2015 |
| WO | 2000/09481 A1 | 2/2000 |
| WO | 2004/046081 A1 | 6/2004 |
| WO | 2006/081562 A2 | 8/2006 |
| WO | 2009/062371 A1 | 5/2009 |
| WO | 2015/084796 A1 | 6/2015 |
| WO | 2016/003997 A1 | 1/2016 |
| WO | 2016/164201 A1 | 10/2016 |
| WO | 2016/176082 A1 | 11/2016 |
| WO | 2016/182780 A | 11/2016 |
| WO | 2016/196019 A1 | 12/2016 |
| WO | 2016/196593 A1 | 12/2016 |
| WO | 2017/023515 A1 | 2/2017 |
| WO | 2018/118384 A | 6/2018 |
| WO | 2018/175226 A1 | 9/2018 |
| WO | 2018/175231 A1 | 9/2018 |

OTHER PUBLICATIONS

XP002734980.
XP002759805.
XP002759806.
XP002734980; Jan. 20, 2002.
WO0009481; Feb. 24, 2000 (XP002734981).
XP002759805; Jan. 20, 2002.
XP002759806; Mar. 23, 2009.
Murata et al.; "Oxidation of N-Acyl-Pyrrolidines and-Piperidines with Iron(II)-Hydrogen Peroxide and an Iron Complex-Molecular Oxygen"; *J. Chem. Soc. Perkin Trans.*; 1987; 1259-1262. (XP055297105).
Cauliez et al.; "Studies on Pyrrolidinones. On the Carbamoylation of Some Pyroglutamic Derivatives"; *J. Het. Chem.*; 33; 1996; 1233-1237. (XP055297107).
Hwang et al.; "Diastereoselective Synthesis of Oxazolidinone Derivatives and Their Antifungal Activities"; *Korean J. of Med. Chem.*; vol. 4, No. 1; 1994; 52-56. (XP009191451).
Campaigne et al.; Synthesis of Some Ureidodihydrofurans and Related Pyrimidones as Potential Antimalarials; *J. Med. Chem.*; 1969; 339-342. (XP002278920).
IPCOM000241978D; Jun. 11, 2015.
PubChemCID29937915; May 28, 2009.

* cited by examiner

3-OXO-3-(ARYLAMINO)PROPANOATES, A PROCESS FOR THEIR PREPARATION, AND THEIR USE IN PREPARING PYRROLIDINONES

BACKGROUND OF THE INVENTION

This invention relates to certain 3-oxo-3-(arylamino)propanoates, their salts and compositions, a process to prepare them and their use in preparing certain pyrrolidinones useful as herbicides.

SUMMARY OF THE INVENTION

This invention is directed to a compound of Formula I and salts thereof

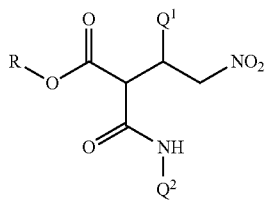

wherein
- $Q^1$ is a phenyl ring or a naphthalenyl ring system, each ring or ring system optionally substituted with up to 5 substituents independently selected from $R^1$; or a 5- to 6-membered fully unsaturated heterocyclic ring or an 8- to 10-membered heteroaromatic bicyclic ring system, each ring or ring system containing ring members selected from carbon atoms and 1 to 4 heteroatoms independently selected from up to 2 O, up to 2 S and up to 4 N atoms, wherein up to 3 carbon ring members are independently selected from $C(=O)$ and $C(=S)$, and the sulfur atom ring members are independently selected from $S(=O)_u(=NR^2)_v$, each ring or ring system optionally substituted with up to 5 substituents independently selected from $R^1$ on carbon atom ring members and selected from $R^3$ on nitrogen atom ring members;
- $Q^2$ is a phenyl ring or a naphthalenyl ring system, each ring or ring system optionally substituted with up to 5 substituents independently selected from $R^4$; or a 5- to 6-membered fully unsaturated heterocyclic ring or an 8- to 10-membered heteroaromatic bicyclic ring system, each ring or ring system containing ring members selected from carbon atoms and 1 to 4 heteroatoms independently selected from up to 2 O, up to 2 S and up to 4 N atoms, wherein up to 3 carbon ring members are independently selected from $C(=O)$ and $C(=S)$, and the sulfur atom ring members are independently selected from $S(=O)_u(=NR^2)_v$, each ring or ring system optionally substituted with up to 5 substituents independently selected from $R^4$ on carbon atom ring members and selected from $R^5$ on nitrogen atom ring members;
- R is $C_1$-$C_8$ alkyl or phenyl;
- each $R^1$ and $R^4$ is independently halogen, cyano, nitro, $C_1$-$C_8$ alkyl, $C_1$-$C_8$ haloalkyl, $C_1$-$C_8$ nitroalkyl, $C_2$-$C_8$ alkenyl, $C_2$-$C_8$ haloalkenyl, $C_2$-$C_8$ haloalkoxyalkoxy, $C_2$-$C_8$ nitroalkenyl, $C_2$-$C_8$ alkynyl, $C_2$-$C_8$ haloalkynyl, $C_4$-$C_{10}$ cycloalkylalkyl, $C_4$-$C_{10}$ halocycloalkylalkyl, $C_5$-$C_{12}$ alkylcycloalkylalkyl, $C_5$-$C_{12}$ cycloalkylalkenyl, $C_5$-$C_{12}$ cycloalkylalkynyl, $C_3$-$C_8$ cycloalkyl, $C_3$-$C_8$ halocycloalkyl, $C_4$-$C_{10}$ alkylcycloalkyl, $C_6$-$C_{12}$ cycloalkylcycloalkyl, $C_3$-$C_8$ cycloalkenyl, $C_3$-$C_8$ halocycloalkenyl, $C_2$-$C_8$ alkoxyalkyl, $C_2$-$C_8$ haloalkoxyalkyl, $C_4$-$C_{10}$ cycloalkoxyalkyl, $C_3$-$C_{10}$ alkoxyalkoxyalkyl, $C_2$-$C_8$ alkylthioalkyl, $C_2$-$C_8$ alkylsulfinylalkyl, $C_2$-$C_8$ alkylsulfonylalkyl, $C_2$-$C_8$ alkylaminoalkyl, $C_2$-$C_8$ haloalkylaminoalkyl, $C_4$-$C_{10}$ cycloalkylaminoalkyl, $C_3$-$C_{10}$ dialkylaminoalkyl, —CHO, $C_2$-$C_8$ alkylcarbonyl, $C_2$-$C_8$ haloalkylcarbonyl, $C_4$-$C_{10}$ cycloalkylcarbonyl, —C(=O)OH, $C_2$-$C_8$ alkoxycarbonyl, $C_2$-$C_8$ haloalkoxycarbonyl, $C_4$-$C_{10}$ cycloalkoxycarbonyl, $C_5$-$C_{12}$ cycloalkylalkoxycarbonyl, —C(=O)NH_2, $C_2$-$C_8$ alkylaminocarbonyl, $C_4$-$C_{10}$ cycloalkylaminocarbonyl, $C_3$-$C_{10}$ dialkylaminocarbonyl, $C_1$-$C_8$ alkoxy, $C_1$-$C_8$ haloalkoxy, $C_2$-$C_8$ alkoxyalkoxy, $C_2$-$C_8$ alkenyloxy, $C_2$-$C_8$ haloalkenyloxy, $C_3$-$C_8$ alkynyloxy, $C_3$-$C_8$ haloalkynyloxy, $C_3$-$C_8$ cycloalkoxy, $C_3$-$C_8$ halocycloalkoxy, $C_4$-$C_{10}$ cycloalkylalkoxy, $C_3$-$C_{10}$ alkylcarbonylalkoxy, $C_2$-$C_8$ alkylcarbonyloxy, $C_2$-$C_8$ haloalkylcarbonyloxy, $C_4$-$C_{10}$ cycloalkylcarbonyloxy, $C_1$-$C_8$ alkylsulfonyloxy, $C_1$-$C_8$ haloalkylsulfonyloxy, $C_1$-$C_8$ alkylthio, $C_1$-$C_8$ haloalkylthio, $C_3$-$C_8$ cycloalkylthio, $C_1$-$C_8$ alkylsulfinyl, $C_1$-$C_8$ haloalkylsulfinyl, $C_1$-$C_8$ alkylsulfonyl, $C_1$-$C_8$ haloalkylsulfonyl, $C_3$-$C_8$ cycloalkylsulfonyl, formylamino, $C_2$-$C_8$ alkylcarbonylamino, $C_2$-$C_8$ haloalkylcarbonylamino, $C_2$-$C_8$ alkoxycarbonylamino, $C_1$-$C_6$ alkylsulfonylamino, $C_1$-$C_6$ haloalkylsulfonylamino, —SF_5, —SCN, $C_3$-$C_{12}$ trialkylsilyl, $C_4$-$C_{12}$ trialkylsilylalkyl or $C_4$-$C_{12}$ trialkylsilylalkoxy;
- each $R^2$ is independently H, cyano, $C_2$-$C_3$ alkylcarbonyl or $C_2$-$C_3$ haloalkylcarbonyl;
- each $R^3$ and $R^5$ is independently cyano, $C_1$-$C_3$ alkyl, $C_2$-$C_3$ alkenyl, $C_2$-$C_3$ alkynyl, $C_3$-$C_6$ cycloalkyl, $C_2$-$C_3$ alkoxyalkyl, $C_1$-$C_3$ alkoxy, $C_2$-$C_3$ alkylcarbonyl, $C_2$-$C_3$ alkoxycarbonyl, $C_2$-$C_3$ alkylaminoalkyl, $C_3$-$C_4$ dialkylaminoalkyl or $C_2$-$C_3$ haloalkyl; and
- each u and v are independently 0, 1 or 2 in each instance of $S(=O)_u(=NR^2)_v$, provided that the sum of u and v is 0, 1 or 2.

This invention also relates to a method for preparing a compound of Formula I, comprising contacting a compound of Formula II

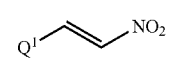

with a compound of Formula III

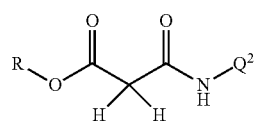

optionally in the presence of a catalyst or a base to form a compound of Formula I.

This invention further relates to a method for preparing a compound of Formula IV

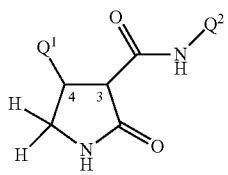

comprising reductively cyclizing a compound of Formula I in the presence of a reducing agent.

DETAILS OF THE INVENTION

As used herein, the terms "comprises," "comprising," "includes," "including," "has," "having," "contains", "containing," "characterized by" or any other variation thereof, are intended to cover a non-exclusive inclusion, subject to any limitation explicitly indicated. For example, a composition, mixture, process, method, article, or apparatus that comprises a list of elements is not necessarily limited to only those elements but may include other elements not expressly listed or inherent to such composition, mixture, process, method, article, or apparatus.

The transitional phrase "consisting of" excludes any element, step, or ingredient not specified. If in the claim, such would close the claim to the inclusion of materials other than those recited except for impurities ordinarily associated therewith. When the phrase "consisting of" appears in a clause of the body of a claim, rather than immediately following the preamble, it limits only the element set forth in that clause; other elements are not excluded from the claim as a whole.

The transitional phrase "consisting essentially of" is used to define a composition, method or apparatus that includes materials, steps, features, components, or elements, in addition to those literally disclosed, provided that these additional materials, steps, features, components, or elements do not materially affect the basic and novel characteristic(s) of the claimed invention. The term "consisting essentially of" occupies a middle ground between "comprising" and "consisting of".

Where applicants have defined an invention or a portion thereof with an open-ended term such as "comprising," it should be readily understood that (unless otherwise stated) the description should be interpreted to also describe such an invention using the terms "consisting essentially of" or "consisting of."

Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

In the above recitations, the term "alkyl", used either alone or in compound words such as "alkylthio" or "haloalkyl" includes straight-chain or branched alkyl, such as, methyl, ethyl, n-propyl, i-propyl, or the different butyl, pentyl or hexyl isomers. "Alkenyl" includes straight-chain or branched alkenes such as ethenyl, 1-propenyl, 2-propenyl, and the different butenyl, pentenyl and hexenyl isomers. "Alkenyl" also includes polyenes such as 1,2-propadienyl and 2,4-hexadienyl. "Alkynyl" includes straight-chain or branched alkynes such as ethynyl, 1-propynyl, 2-propynyl and the different butynyl, pentynyl and hexynyl isomers. "Alkynyl" can also include moieties comprised of multiple triple bonds such as 2,5-hexadiynyl.

"Alkoxy" includes, for example, methoxy, ethoxy, n-propyloxy, isopropyloxy and the different butoxy, pentoxy and hexyloxy isomers. "Alkoxyalkyl" denotes alkoxy substitution on alkyl. Examples of "alkoxyalkyl" include $CH_3OCH_2$, $CH_3OCH_2CH_2$, $CH_3CH_2OCH_2$, $CH_3CH_2CH_2CH_2OCH_2$ and $CH_3CH_2OCH_2CH_2$. "Alkoxyalkoxy" denotes alkoxy substitution on alkoxy. "Alkenyloxy" includes straight-chain or branched alkenyloxy moieties. Examples of "alkenyloxy" include $H_2C=CHCH_2O$, $(CH_3)_2C=CHCH_2O$, $(CH_3)CH=CHCH_2O$, $(CH_3)CH=C(CH_3)CH_2O$ and $CH_2=CHCH_2CH_2O$. "Alkynyloxy" includes straight-chain or branched alkynyloxy moieties. Examples of "alkynyloxy" include $HC{\equiv}CCH_2O$, $CH_3C{\equiv}CCH_2O$ and $CH_3C{\equiv}CCH_2CH_2O$. "Alkylthio" includes branched or straight-chain alkylthio moieties such as methylthio, ethylthio, and the different propylthio, butylthio, pentylthio and hexylthio isomers. "Alkylsulfinyl" includes both enantiomers of an alkylsulfinyl group. Examples of "alkylsulfinyl" include $CH_3S(O)$—, $CH_3CH_2S(O)$—, $CH_3CH_2CH_2S(O)$—, $(CH_3)_2CHS(O)$— and the different butylsulfinyl, pentylsulfinyl and hexylsulfinyl isomers. Examples of "alkyl sulfonyl" include $CH_3S(O)_2$—, $CH_3CH_2S(O)_2$—, $CH_3CH_2CH_2S(O)_2$—, $(CH_3)_2CHS(O)_2$—, and the different butylsulfonyl, pentylsulfonyl and hexylsulfonyl isomers. "Alkylthioalkyl" denotes alkylthio substitution on alkyl. Examples of "alkylthioalkyl" include $CH_3SCH_2$, $CH_3SCH_2CH_2$, $CH_3CH_2SCH_2$, $CH_3CH_2CH_2CH_2SCH_2$ and $CH_3CH_2SCH_2CH_2$. "Alkylamino", "Alkylaminoalkyl", and the like, are defined analogously to the above examples.

"Cycloalkyl" includes, for example, cyclopropyl, cyclobutyl, cyclopentyl and cyclohexyl. The term "alkylcycloalkyl" denotes alkyl substitution on a cycloalkyl moiety and includes, for example, ethylcyclopropyl, i-propylcyclobutyl, 3-methylcyclopentyl and 4-methylcyclohexyl. The term "cycloalkylalkyl" denotes cycloalkyl substitution on an alkyl moiety. Examples of "cycloalkylalkyl" include cyclopropylmethyl, cyclopentylethyl, and other cycloalkyl moieties bonded to straight-chain or branched alkyl groups. The term "cycloalkoxy" denotes cycloalkyl linked through an oxygen atom such as cyclopentyloxy and cyclohexyloxy. "Cycloalkylalkoxy" denotes cycloalkylalkyl linked through an oxygen atom attached to the alkyl chain. Examples of "cycloalkylalkoxy" include cyclopropylmethoxy, cyclopentylethoxy, and other cycloalkyl moieties bonded to straight-chain or branched alkoxy groups.

The term "halogen", either alone or in compound words such as "haloalkyl", or when used in descriptions such as "alkyl substituted with halogen" includes fluorine, chlorine, bromine or iodine. Further, when used in compound words such as "haloalkyl", or when used in descriptions such as "alkyl substituted with halogen" said alkyl may be partially or fully substituted with halogen atoms which may be the same or different. Examples of "haloalkyl" or "alkyl substituted with halogen" include $F_3C$, $ClCH_2$, $CF_3CH_2$ and $CF_3CCl_2$. The terms "halocycloalkyl", "haloalkoxy", "haloalkylthio", "haloalkenyl", "haloalkynyl", and the like, are defined analogously to the term "haloalkyl". Examples of "haloalkoxy" include $CF_3O$—, $CCl_3CH_2O$—, HCF$_2$CH$_2$CH$_2$O— and CF$_3$CH$_2$O—. Examples of "haloalkylthio" include CCl$_3$S—, CF$_3$S—, CCl$_3$CH$_2$S— and ClCH$_2$CH$_2$CH$_2$S—. Examples of "haloalkylsulfinyl" include CF$_3$S(O)—, CCl$_3$S(O)—, CF$_3$CH$_2$S(O)— and CF$_3$CF$_2$S(O)—. Examples of "haloalkylsulfonyl" include CF$_3$S(O)$_2$—, CCl$_3$S(O)$_2$—, CF$_3$CH$_2$S(O)$_2$— and CF$_3$CF$_2$S(O)$_2$—. Examples of "haloalkenyl" include (Cl)$_2$C=CHCH$_2$— and CF$_3$CH$_2$CH=CH—CH$_2$—. Examples of "haloalkynyl" include HC≡CCHCl—, CF$_3$C≡C—, CCl$_3$C≡C— and FCH$_2$C≡CCH$_2$—. Examples of "haloalkoxyalkoxy" include CF$_3$OCH$_2$O—, ClCH$_2$CH$_2$OCH$_2$CH$_2$O—, Cl$_3$CCH$_2$OCH$_2$O— as well as branched alkyl derivatives.

"Alkylcarbonyl" denotes a straight-chain or branched alkyl moieties bonded to a C(=O) moiety. Examples of "alkylcarbonyl" include CH$_3$C(=O)—, CH$_3$CH$_2$CH$_2$C(=O)— and (CH$_3$)$_2$CHC(=O)—. Examples of "alkoxycarbonyl" include CH$_3$OC(=O)—, CH$_3$CH$_2$OC(=O)—, CH$_3$CH$_2$CH$_2$OC(=O)—, (CH$_3$)$_2$CHOC(=O)— and the different butoxy- or pentoxycarbonyl isomers.

The total number of carbon atoms in a substituent group is indicated by the "C$_i$-C$_j$" prefix where i and j are numbers from 1 to 12. For example, C$_1$-C$_4$ alkylsulfonyl designates methylsulfonyl through butylsulfonyl; C$_2$ alkoxyalkyl designates CH$_3$OCH$_2$—; C$_3$ alkoxyalkyl designates, for example, CH$_3$CH(OCH$_3$)—, CH$_3$OCH$_2$CH$_2$— or CH$_3$CH$_2$OCH$_2$—; and C$_4$ alkoxyalkyl designates the various isomers of an alkyl group substituted with an alkoxy group containing a total of four carbon atoms, examples including CH$_3$CH$_2$CH$_2$OCH$_2$— and CH$_3$CH$_2$OCH$_2$CH$_2$—.

When a compound is substituted with a substituent bearing a subscript that indicates the number of said substituents can exceed 1, said substituents (when they exceed 1) are independently selected from the group of defined substituents, e.g., ([R$^1$]$_n$], n is 0, 1, 2, 3, 4 or 5). When a group contains a substituent which can be hydrogen, for example Q$^1$, then when this substituent is taken as hydrogen, it is recognized that this is equivalent to said group being unsubstituted. When a variable group is shown to be optionally attached to a position, for example R$^1$, then hydrogen may be at the position even if not recited in the variable group definition. When one or more positions on a group are said to be "not substituted" or "unsubstituted", then hydrogen atoms are attached to take up any free valency.

The expression "fully saturated" in relation to a ring of atoms means that the bonds between the atoms of the ring are all single. The expression "fully unsaturated" in relation to a ring means that the bonds between the atoms in the ring are single or double bonds according to valence bond theory and furthermore the bonds between the atoms in the ring include as many double bonds as possible without double bonds being cumulative (i.e. no C=C=C, N=C=C, etc.). The term "partially unsaturated" in relation to a ring denotes a ring comprising at least one ring member bonded to an adjacent ring member though a double bond and which conceptually potentially accommodates a number of non-cumulated double bonds through adjacent ring members (i.e. in its fully unsaturated counterpart form) greater than the number of double bonds present (i.e. in its partially unsaturated form). When a fully unsaturated ring satisfies Hückel's rule then it can also be described as aromatic.

Unless otherwise indicated, a "ring" or "ring system" as a component of Formula I (e.g., substituent Q$^1$) is carbocyclic or heterocyclic. The term "ring system" denotes two or more fused rings. The term "bicyclic ring system" denotes a ring system consisting of two fused rings, in which either ring can be saturated, partially unsaturated, or fully unsaturated unless otherwise indicated. The term "heteroaromatic bicyclic ring system" denotes a bicyclic ring system in which at least one ring atom is not carbon. The term "ring member" refers to an atom or other moiety (e.g., C(=O), C(=S), S(O) or S(O)$_2$) forming the backbone of a ring or ring system.

The terms "carbocyclic ring" denotes a ring or ring system wherein the atoms forming the ring backbone are selected only from carbon. Unless otherwise indicated, a carbocyclic ring can be a saturated, partially unsaturated, or fully unsaturated ring. When a fully unsaturated carbocyclic ring satisfies Hückel's rule, then said ring is also called an "aromatic ring".

The term "heterocyclic ring" denotes a ring or ring system in which at least one atom forming the ring backbone is not carbon, e.g., nitrogen, oxygen or sulfur. Typically a heterocyclic ring contains no more than 4 nitrogens, no more than 2 oxygens and no more than 2 sulfurs. Unless otherwise indicated, a heterocyclic ring can be a saturated, partially unsaturated, or fully unsaturated ring. When a fully unsaturated heterocyclic ring satisfies Hückel's rule, then said ring is also called a "heteroaromatic ring" or "aromatic heterocyclic ring". Unless otherwise indicated, heterocyclic rings and ring systems can be attached through any available carbon or nitrogen by replacement of a hydrogen on said carbon or nitrogen.

"Aromatic" indicates that each of the ring atoms is essentially in the same plane and has a p-orbital perpendicular to the ring plane, and that (4n+2) π electrons, where n is a positive integer, are associated with the ring to comply with Hückel's rule.

The term "optionally substituted" in connection with the heterocyclic rings refers to groups which are unsubstituted or have at least one non-hydrogen substituent that does not extinguish the biological activity possessed by the unsubstituted analog. As used herein, the following definitions shall apply unless otherwise indicated. The term "optionally substituted" is used interchangeably with the phrase "substituted or unsubstituted" or with the term "(un)substituted." Unless otherwise indicated, an optionally substituted group may have a substituent at each substitutable position of the group, and each substitution is independent of the other.

When Q$^1$ and Q$^2$ is a 5- or 6-membered nitrogen-containing heterocyclic ring, it may be attached to the remainder of Formula I though any available carbon or nitrogen ring atom, unless otherwise described. As noted above, Q$^1$ or Q$^2$ can be (among others) phenyl optionally substituted with one or more substituents selected from a group of substituents as defined in the Summary of the Invention. An example of phenyl optionally substituted with one to five substituents is the ring illustrated as U-1 in Exhibit 1, wherein, for example, R$^v$ is R$^1$ as defined in the Summary of the Invention for Q$^1$, or R$^v$ is R$^4$ as defined in the Summary of the Invention for Q$^2$, and r is an integer (from 0 to 5).

As noted above, Q$^1$ and Q$^2$ can be (among others) 5- or 6-membered fully unsaturated heterocyclic ring, optionally substituted with one or more substituents selected from a group of substituents as defined in the Summary of the Invention. Examples of a 5- or 6-membered fully unsaturated heterocyclic ring optionally substituted with from one or more substituents include the rings U-2 through U-61 illustrated in Exhibit 1 wherein R$^v$ is any substituent as defined in the Summary of the Invention for Q$^1$ (i.e. R$^1$ or R$^3$) or Q$^2$ (i.e. R$^4$ or R$^5$) and r is an integer from 0 to 4, limited by the number of available positions on each U group. As U-29, U-30, U-36, U-37, U-38, U-39, U-40, U-41, U-42 and U-43 have only one available position, for these U groups r is limited to the integers 0 or 1, and r being 0 means that the U group is unsubstituted and a hydrogen is present at the position indicated by $(R^v)_r$.
Exhibit 1
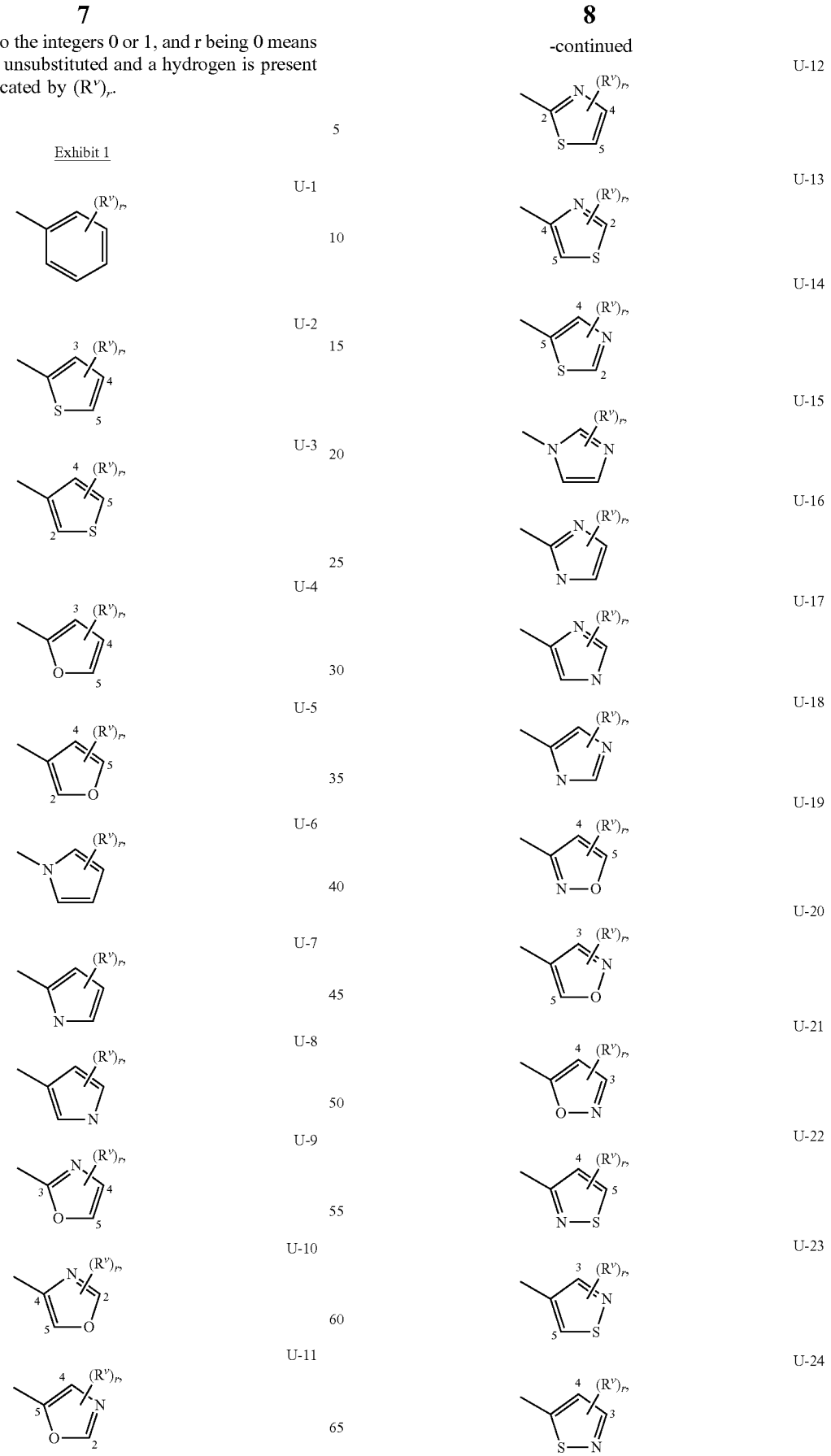

-continued
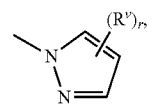 U-25
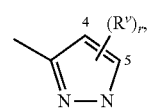 U-26
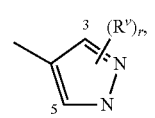 U-27
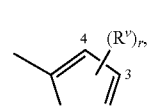 U-28
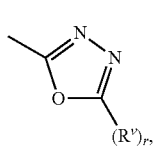 U-29
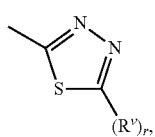 U-30
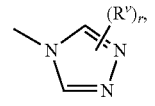 U-31
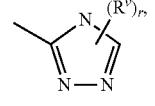 U-32
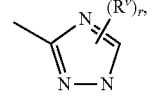 U-33
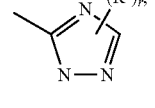 U-34
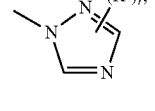 U-35
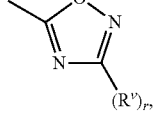 U-36
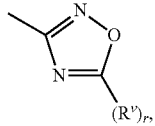 U-37
-continued
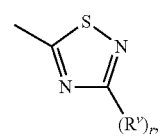 U-38
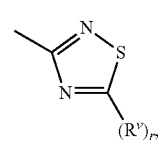 U-39
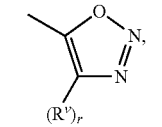 U-40
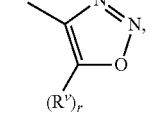 U-41
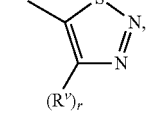 U-42
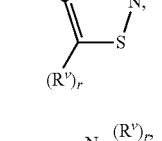 U-43
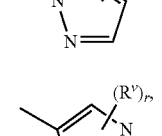 U-44
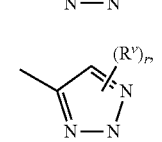 U-45
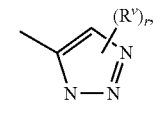 U-46
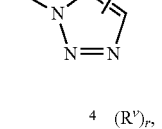 U-47
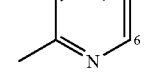 U-48
U-49

-continued

U-50 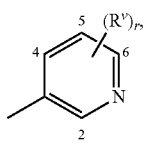

U-51 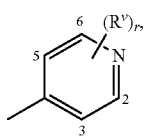

U-52 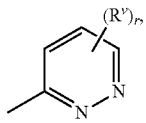

U-53 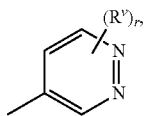

U-54 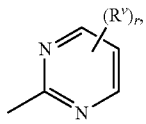

U-55 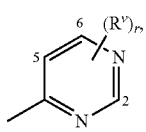

U-56 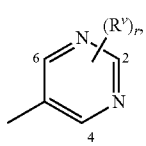

U-57 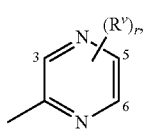

U-58 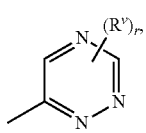

U-59 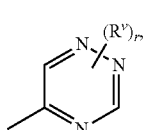

U-60 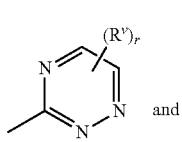 and

-continued

U-61 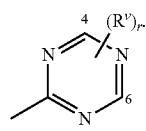

As noted above, $Q^1$ and $Q^2$ can be (among others) an 8- to 10-membered heteroaromatic bicyclic ring system optionally substituted with one or more substituents selected from a group of substituents as defined in the Summary of the Invention for $Q^1$ and $Q^2$. Examples of an 8- to 10-membered heteroaromatic bicyclic ring system optionally substituted with one or more substituents include the rings U-62 through U-100 illustrated in Exhibit 2 wherein $R^v$ is any substituent as defined in the Summary of the Invention for $Q^1$ or $Q^2$, and r is typically an integer from 0 to 4.

Exhibit 2

U-62 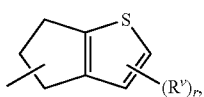

U-63 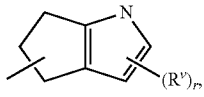

U-64 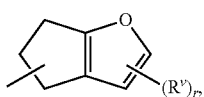

U-65 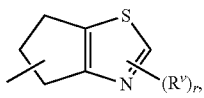

U-66 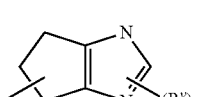

U-67 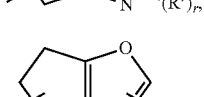

U-68

U-69 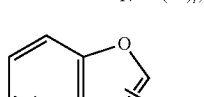

U-70

U-71

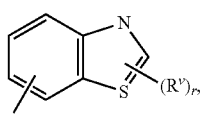 U-72
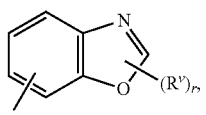 U-73
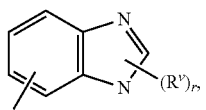 U-74
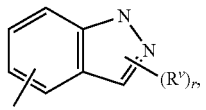 U-75
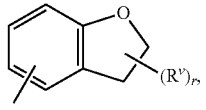 U-76
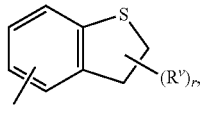 U-77
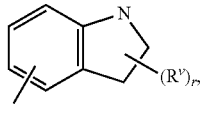 U-78
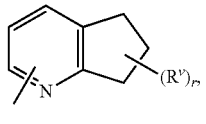 U-79
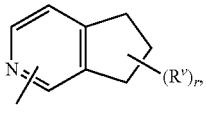 U-80
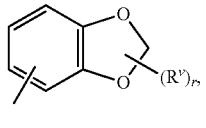 U-81
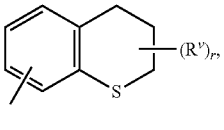 U-82
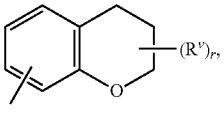 U-83
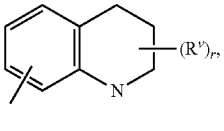 U-84
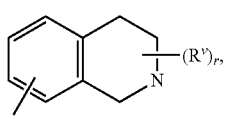 U-85
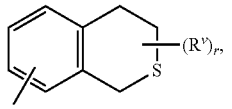 U-86
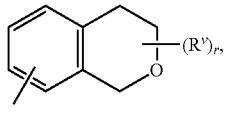 U-87
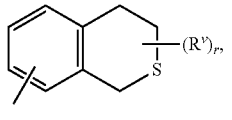 U-88
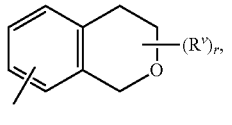 U-89
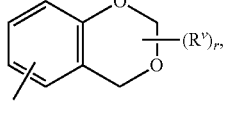 U-90
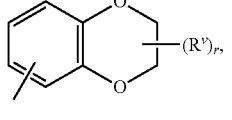 U-91
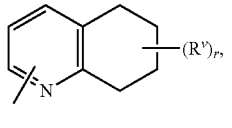 U-92
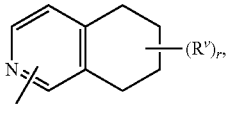 U-93
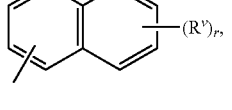 U-94
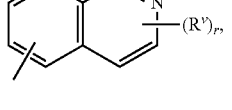 U-95
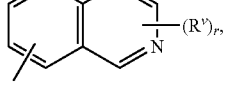 U-96
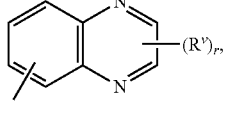 U-97

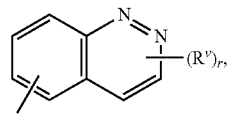
U-98

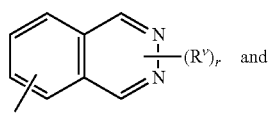
U-99 and

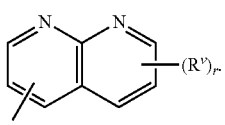
U-100

Although $R^v$ groups are shown in the structures U-1 through U-100, it is noted that they do not need to be present since they are optional substituents. Note that when $R^v$ is H when attached to an atom, this is the same as if said atom is unsubstituted. The nitrogen atoms that require substitution to fill their valence are substituted with H or $R^v$. Note that when the attachment point between $(R^v)_r$ and the U group is illustrated as floating, $(R^v)_r$ can be attached to any available carbon atom or nitrogen atom of the U group. Note that when the attachment point on the U group is illustrated as floating, the U group can be attached to the remainder of Formula I through any available carbon or nitrogen of the U group by replacement of a hydrogen atom. Note that some U groups can only be substituted with less than 4 $R^v$ groups (e.g., U-2 through U-5, U-7 through U-48, and U-52 through U-61).

A wide variety of synthetic methods are known in the art to enable preparation of aromatic and nonaromatic heterocyclic rings and ring systems; for extensive reviews see the eight volume set of *Comprehensive Heterocyclic Chemistry*, A. R. Katritzky and C. W. Rees editors-in-chief, Pergamon Press, Oxford, 1984 and the twelve volume set of *Comprehensive Heterocyclic Chemistry II*, A. R. Katritzky, C. W. Rees and E. F. V. Scriven editors-in-chief, Pergamon Press, Oxford, 1996.

Compounds of this invention can exist as one or more stereoisomers. The various stereoisomers include enantiomers, diastereomers, atropisomers and geometric isomers. Stereoisomers are isomers of identical constitution but differing in the arrangement of their atoms in space and include enantiomers, diastereomers, cis-trans isomers (also known as geometric isomers) and atropisomers. Atropisomers result from restricted rotation about single bonds where the rotational barrier is high enough to permit isolation of the isomeric species. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. The compounds of the invention may be present as a mixture of stereoisomers, individual stereoisomers or as an optically active form.

For example the $C(O)N(Q^2)(R^6)$ moiety (bonded to the carbon at the 3-position of the pyrrolidinone ring) and $Q^1$ (bonded to the carbon at the 4-position of the pyrrolidinone ring) are generally found in the trans configuration. These two carbon atoms (i.e. at the 3- and 4-positions each posses the pyrroldinone ring of Formula IV) both possess a chiral center. The two most prevelant pairs of enantiomers are depicted as Formula IV' and Formula IV" where the chiral centers are identified (i.e. as 3R, 4S or as 3S, 4R). While this invention pertains to all stereoisomers, the preferred enantiomeric pair for biological operability is identified as Formula IV' (i.e. the 3R, 4S configuration). For a comprehensive discussion of all aspects of stereoisomerism, see Ernest L. Eliel and Samuel H. Wilen, *Stereochemistry of Organic Compounds*, John Wiley & Sons, 1994.

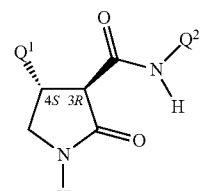
IV'

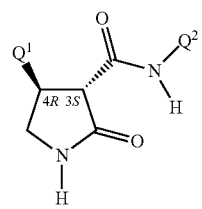
IV"

Molecular depictions drawn herein follow standard conventions for depicting stereochemistry. To indicate stereoconfiguration, bonds rising from the plane of the drawing and towards the viewer are denoted by solid wedges wherein the broad end of the wedge is attached to the atom rising from the plane of the drawing towards the viewer. Bonds going below the plane of the drawing and away from the viewer are denoted by dashed wedges wherein the narrow end of the wedge is attached to the atom further away from the viewer. Constant width lines indicate bonds with a direction opposite or neutral relative to bonds shown with solid or dashed wedges; constant width lines also depict bonds in molecules or parts of molecules in which no particular stereoconfiguration is intended to be specified. This invention comprises racemic mixtures, for example, equal amounts of the enantiomers of Formulae IV' and IV". In addition, this invention includes compounds that are enriched compared to the racemic mixture in an enantiomer of Formula IV. Also included are the essentially pure enantiomers of compounds of Formula I, for example, Formula IV' and Formula IV".

When enantiomerically enriched, one enantiomer is present in greater amounts than the other, and the extent of enrichment can be defined by an expression of enentiomeric ratio (ER) expressed as the relative area % of the two entantiomers determined by chiral high-performance liquid chromatography.

Preferably the compositions of this invention have at least a 50% ER; more preferably at least a 75% ER; still more preferably at least a 90% ER; and the most preferably at least a 94% ER of the more active isomer. Of particular note are enantiomerically pure embodiments of the more active isomer.

Compounds of Formula IV can comprise additional chiral centers. For example, substituents and other molecular constituents such as $R^1$, $R^3$, $R^4$ and $R^5$ may themselves contain chiral centers. This invention comprises racemic mixtures as well as enriched and essentially pure stereoconfigurations at these additional chiral centers.

Compounds of this invention can exist as one or more conformational isomers due to restricted rotation about the amide bond (e.g., C(O)—N) in Formula I and IV. This invention comprises mixtures of conformational isomers. In addition, this invention includes compounds that are enriched in one conformer relative to others.

Compounds of Formula I typically exist in more than one form, and Formula I thus include all crystalline and non-crystalline forms of the compounds they represent. Non-crystalline forms include embodiments which are solids such as waxes and gums as well as embodiments which are liquids such as solutions and melts. Crystalline forms include embodiments which represent essentially a single crystal type and embodiments which represent a mixture of polymorphs (i.e. different crystalline types). The term "polymorph" refers to a particular crystalline form of a chemical compound that can crystallize in different crystalline forms, these forms having different arrangements and/or conformations of the molecules in the crystal lattice. Although polymorphs can have the same chemical composition, they can also differ in composition due the presence or absence of co-crystallized water or other molecules, which can be weakly or strongly bound in the lattice. Polymorphs can differ in such chemical, physical and biological properties as crystal shape, density, hardness, color, chemical stability, melting point, hygroscopicity, suspensibility, dissolution rate and biological availability. One skilled in the art will appreciate that a polymorph of a compound of Formula I can exhibit beneficial effects (e.g., suitability for preparation of useful formulations, improved biological performance) relative to another polymorph or a mixture of polymorphs of the same compound of Formula I. Preparation and isolation of a particular polymorph of a compound of Formula I can be achieved by methods known to those skilled in the art including, for example, crystallization using selected solvents and temperatures. For a comprehensive discussion of polymorphism see R. Hilfiker, Ed., *Polymorphism in the Pharmaceutical Industry*, Wiley-VCH, Weinheim, 2006.

One skilled in the art will appreciate that not all nitrogen-containing heterocycles can form N-oxides since the nitrogen requires an available lone pair for oxidation to the oxide; one skilled in the art will recognize those nitrogen-containing heterocycles which can form N-oxides. One skilled in the art will also recognize that tertiary amines can form N-oxides. Synthetic methods for the preparation of N-oxides of heterocycles and tertiary amines are very well known by one skilled in the art including the oxidation of heterocycles and tertiary amines with peroxy acids such as peracetic and m-chloroperbenzoic acid (MCPBA), hydrogen peroxide, alkyl hydroperoxides such as t-butyl hydroperoxide, sodium perborate, and dioxiranes such as dimethyldioxirane. These methods for the preparation of N-oxides have been extensively described and reviewed in the literature, see for example: T. L. Gilchrist in *Comprehensive Organic Synthesis*, vol. 7, pp 748-750, S. V. Ley, Ed., Pergamon Press; M. Tisler and B. Stanovnik in *Comprehensive Heterocyclic Chemistry*, vol. 3, pp 18-20, A. J. Boulton and A. McKillop, Eds., Pergamon Press; M. R. Grimmett and B. R. T. Keene in *Advances in Heterocyclic Chemistry*, vol. 43, pp 149-161, A. R. Katritzky, Ed., Academic Press; M. Tisler and B. Stanovnik in *Advances in Heterocyclic Chemistry*, vol. 9, pp 285-291, A. R. Katritzky and A. J. Boulton, Eds., Academic Press; and G. W. H. Cheeseman and E. S. G. Werstiuk in *Advances in Heterocyclic Chemistry*, vol. 22, pp 390-392, A. R. Katritzky and A. J. Boulton, Eds., Academic Press.

One skilled in the art recognizes that because in the environment and under physiological conditions salts of chemical compounds are in equilibrium with their corresponding nonsalt forms, salts share the biological utility of the nonsalt forms. Thus a wide variety of salts of a compound of Formula I are useful for control of undesired vegetation (i.e. are agriculturally suitable). The salts of a compound of Formula I include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids. When a compound of Formula I contains an acidic moiety such as a carboxylic acid or phenol, salts also include those formed with organic or inorganic bases such as pyridine, triethylamine or ammonia, or amides, hydrides, hydroxides or carbonates of sodium, potassium, lithium, calcium, magnesium or barium. Accordingly, the present invention comprises compounds selected from Formula I, N-oxides and agriculturally suitable salts thereof.

Embodiments of the present invention as described in the Summary of the Invention include (where Formula I as used in the following Embodiments includes N-oxides and salts thereof):

Embodiment A1. A compound of Formula I as described in the Summary of Invention.

Embodiment A2. A compound of Embodiment A1 wherein $Q^1$ is a phenyl ring optionally substituted with up to 5 substituents independently selected from $R^1$.

Embodiment A3. A compound of Embodiment A2 wherein $Q^1$ is a phenyl ring substituted with 1 to 4 substituents independently selected from $R^1$.

Embodiment A4. A compound of Embodiment A3 wherein $Q^1$ is a phenyl ring substituted with 1 to 3 substituents independently selected from $R^1$.

Embodiment A5. A compound of any one of Embodiments A1 through A4 wherein $Q^1$ is a phenyl ring having a substituent selected from $R^1$ at the meta (3-) position and optionally up to 2 additional $R^1$ substituents.

Embodiment A6. A compound of any one of Embodiments A1 through A4 wherein $Q^1$ is a phenyl ring having a substituent selected from $R^1$ at the para (4-) position and optionally up to 2 additional $R^1$ substituents.

Embodiment A7. A compound of Embodiment A1 wherein $Q^1$ is a 5- to 6-membered fully unsaturated heterocyclic ring optionally substituted with up to 5 substituents independently selected from $R^1$ on carbon atom ring members and selected from $R^3$ on nitrogen atom ring members.

Embodiment A8. A compound of Embodiment A7 wherein $Q^1$ is a pyridyl ring optionally substituted with up to 2 $R^1$.

Embodiment A9. A compound of Embodiment A8 wherein $Q^1$ is a 3-pyridyl ring substituted with $R^1$ at the position para to the bond connecting $Q^1$ to the remainder of the compound of Formula I.

Embodiment A10. A compound of Embodiment A7 wherein $Q^1$ is a thiophenyl or furanyl ring optionally substituted with up to 2 $R^1$.

Embodiment A11. A compound of Embodiment A1 wherein $Q^1$ is an 8- to 10-membered heteroaromatic bicyclic ring system optionally substituted with $R^1$ and $R^3$, the remainder of Formula I is bonded to a fully unsaturated ring of said bicyclic ring system.

Embodiment A12. A compound of Embodiment A1 wherein $Q^2$ is a phenyl ring optionally substituted with up to 5 substituents independently selected from $R^4$.

Embodiment A13. A compound of Embodiment A12 wherein $Q^2$ is a phenyl ring substituted with 1 to 4 substituents independently selected from $R^4$.

Embodiment A14. A compound of Embodiment A13 wherein $Q^2$ is a phenyl ring substituted with 1 to 3 substituents independently selected from $R^4$.

Embodiment A15. A compound of any one of Embodiments A12 through A14 wherein $Q^2$ is a phenyl ring having a substituent selected from $R^4$ at the ortho (2-) position and optionally up to 2 additional $R^4$ substituents.

Embodiment A16. A compound of Embodiment A1 wherein $Q^2$ is a pyridyl ring optionally substituted with up to 2 $R^4$.

Embodiment A17. A compound of Embodiment A16 wherein $Q^2$ is a 2-pyridyl or 3-pyridyl ring optionally substituted with up to 2 $R^4$.

Embodiment A18. A compound of Embodiment A1 wherein $Q^2$ is a 5-membered fully unsaturated heterocyclic ring optionally substituted with up to 2 $R^4$.

Embodiment A19. A compound of Embodiment A18 wherein $Q^2$ is a oxazolyl ring optionally substituted with up to 2 $R^4$.

Embodiment A20. A compound of any of Embodiments A1 through A19 wherein R is $C_1$-$C_4$ alkyl.

Embodiment A21. A compound of Embodiment A20 wherein R is methyl or ethyl.

Embodiment A22. A compound of Embodiment A21 wherein R is methyl.

Embodiment A23. A compound of Embodiment A21 wherein R is ethyl.

Embodiment A24. A compound of any of Embodiments A1 through A23 wherein $R^1$ is independently halogen, cyano, nitro, $C_1$-$C_8$ alkyl, $C_1$-$C_8$ haloalkyl, $C_1$-$C_8$ nitroalkyl, $C_2$-$C_8$ alkenyl, $C_2$-$C_8$ haloalkenyl, $C_2$-$C_8$ haloalkoxyalkoxy, $C_2$-$C_8$ nitroalkenyl, $C_2$-$C_8$ alkynyl or $C_2$-$C_8$ haloalkynyl.

Embodiment A25. A compound of Embodiment A24 wherein $R^1$ is independently halogen, cyano, nitro, $C_1$-$C_8$ alkyl, $C_1$-$C_8$ haloalkyl or $C_2$-$C_8$ haloalkoxyalkoxy.

Embodiment A26. A compound of Embodiment A25 wherein $R^1$ is independently halogen, $C_1$-$C_3$ alkyl or $C_1$-$C_3$ haloalkyl.

Embodiment A27. A compound of Embodiment A26 wherein $R^1$ is independently halogen or $C_1$-$C_3$ haloalkyl.

Embodiment A28. A compound of Embodiment A27 wherein $R^1$ is independently F or $CF_3$.

Embodiment A29. A compound of Embodiment A28 wherein $R^1$ is $CF_3$.

Embodiment A30. A compound of Embodiment A28 wherein $R^1$ is F.

Embodiment A31. A compound of any of Embodiments A1 through A30 wherein $R^3$ is independently $C_1$-$C_3$ alkyl, $C_2$-$C_3$ alkenyl, $C_2$-$C_3$ alkynyl, $C_3$-$C_6$ cycloalkyl or $C_1$-$C_3$ alkoxy.

Embodiment A32. A compound of Embodiment A31 wherein $R^3$ is independently $C_1$-$C_3$ alkyl.

Embodiment A33. A compound of any of Embodiments A1 through A32 wherein $R^4$ is independently halogen, cyano, nitro, $C_1$-$C_8$ alkyl, $C_1$-$C_8$ haloalkyl, $C_1$-$C_8$ nitroalkyl, $C_2$-$C_8$ alkenyl, $C_2$-$C_8$ haloalkenyl, $C_2$-$C_8$ haloalkoxyalkoxy, $C_2$-$C_8$ nitroalkenyl, $C_2$-$C_8$ alkynyl or $C_2$-$C_8$ haloalkynyl.

Embodiment A34. A compound of Embodiment A33 wherein $R^4$ is independently halogen, $C_1$-$C_3$ alkyl or $C_1$-$C_3$ haloalkyl.

Embodiment A35. A compound of Embodiment A34 wherein $R^4$ is independently halogen or $C_1$-$C_3$ haloalkyl.

Embodiment A36. A compound of Embodiment A35 wherein $R^4$ is independently F or $CF_3$.

Embodiment A37. A compound of Embodiment A36 wherein $R^4$ is F.

Embodiment A38. A compound of Embodiment A36 wherein $R^4$ is $CF_3$.

Embodiment A39. A compound of any one of Embodiments A1 through A38 wherein the stereochemistry of the carbon center connecting $Q^1$ to the remainder of Formula I is S.

Embodiment A40. A compound of any one of Embodiments A1 through A38 wherein the stereochemistry of the carbon center connecting $Q^1$ to the remainder of Formula I is R.

Embodiment B1. A method for preparing a compound of Formula I as described in the Summary of Invention.

Embodiment B2. A method of Embodiment B1 wherein $Q^1$ is a phenyl ring optionally substituted with up to 5 substituents independently selected from $R^1$.

Embodiment B3. A method of Embodiment B2 wherein $Q^1$ is a phenyl ring substituted with 1 to 4 substituents independently selected from $R^1$.

Embodiment B4. A method of Embodiment B3 wherein $Q^1$ is a phenyl ring substituted with 1 to 3 substituents independently selected from $R^1$.

Embodiment B5. A method of any one of Embodiments B1 through B4 wherein $Q^1$ is a phenyl ring having a substituent selected from $R^1$ at the meta (3-) position and optionally up to 2 additional $R^1$ substituents.

Embodiment B6. A method of any one of Embodiments B1 through B5 wherein $Q^1$ is a phenyl ring having a substituent selected from $R^1$ at the para (4-) position and optionally up to 2 additional $R^1$ substituents.

Embodiment B7. A method of Embodiment B1 wherein $Q^1$ is a 5- to 6-membered fully unsaturated heterocyclic ring optionally substituted with up to 5 substituents independently selected from $R^1$ on carbon atom ring members and selected from $R^3$ on nitrogen atom ring members.

Embodiment B8. A method of Embodiment B7 wherein $Q^1$ is a pyridyl ring optionally substituted with up to 2 $R^1$.

Embodiment B9. A method of Embodiment B8 wherein $Q^1$ is a 3-pyridyl ring substituted with $R^1$ at the position para to the bond connecting $Q^1$ to the remainder of the method of Formula I.

Embodiment B10. A method of Embodiment B7 wherein $Q^1$ is a thiophenyl or furanyl ring optionally substituted with up to 2 $R^1$.

Embodiment B11. A method of Embodiment B1 wherein $Q^1$ is an 8- to 10-membered heteroaromatic bicyclic ring system optionally substituted with $R^1$ and $R^3$, the remainder of Formula I is bonded to a fully unsaturated ring of said bicyclic ring system.

Embodiment B12. A method of Embodiment B1 wherein $Q^2$ is a phenyl ring optionally substituted with up to 5 substituents independently selected from $R^4$.

Embodiment B13. A method of Embodiment B12 wherein $Q^2$ is a phenyl ring substituted with 1 to 4 substituents independently selected from $R^4$.

Embodiment B14. A method of Embodiment B13 wherein $Q^2$ is a phenyl ring substituted with 1 to 3 substituents independently selected from $R^4$.

Embodiment B15. A method of any one of Embodiments B12 through B14 wherein $Q^2$ is a phenyl ring having a substituent selected from $R^4$ at the ortho (2-) position and optionally up to 2 additional $R^4$ substituents.

Embodiment B16. A method of Embodiment B1 wherein $Q^2$ is a pyridyl ring optionally substituted with up to 2 $R^4$.

Embodiment B17. A method of Embodiment B16 wherein $Q^2$ is a 2-pyridyl or 3-pyridyl ring optionally substituted with up to 2 $R^4$.

Embodiment B18. A method of Embodiment B1 wherein $Q^2$ is a 5-membered fully unsaturated heterocyclic ring optionally substituted with up to 2 $R^4$.

Embodiment B19. A method of Embodiment B18 wherein $Q^2$ is a oxazolyl ring optionally substituted with up to 2 $R^4$.

Embodiment B20. A method of any of Embodiments B1 through B19 wherein R is $C_1$-$C_4$ alkyl.

Embodiment B21. A method of Embodiment B20 wherein R is methyl or ethyl.

Embodiment B22. A method of Embodiment B21 wherein R is methyl.

Embodiment B23. A method of Embodiment B21 wherein R is ethyl.

Embodiment B24. A method of any of Embodiments B1 through B23 wherein $R^1$ is independently halogen, cyano, nitro, $C_1$-$C_8$ alkyl, $C_1$-$C_8$ haloalkyl, $C_1$-$C_8$ nitroalkyl, $C_2$-$C_8$ alkenyl, $C_2$-$C_8$ haloalkenyl, $C_2$-$C_8$ haloalkoxyalkoxy, $C_2$-$C_8$ nitroalkenyl, $C_2$-$C_8$ alkynyl or $C_2$-$C_8$ haloalkynyl.

Embodiment B25. A method of Embodiment B24 wherein $R^1$ is independently halogen, cyano, nitro, $C_1$-$C_8$ alkyl, $C_1$-$C_8$ haloalkyl or $C_2$-$C_8$ haloalkoxyalkoxy.

Embodiment B26. A method of Embodiment B25 wherein $R^1$ is independently halogen, $C_1$-$C_3$ alkyl or $C_1$-$C_3$ haloalkyl.

Embodiment B27. A method of Embodiment B26 wherein $R^1$ is independently halogen or $C_1$-$C_3$ haloalkyl.

Embodiment B28. A method of Embodiment B27 wherein $R^1$ is independently F or $CF_3$.

Embodiment B29. A method of any of Embodiments B7 through B28 wherein $R^3$ is independently $C_1$-$C_3$ alkyl, $C_2$-$C_3$ alkenyl, $C_2$-$C_3$ alkynyl, $C_3$-$C_6$ cycloalkyl or $C_1$-$C_3$ alkoxy.

Embodiment B30. A method of Embodiment B29 wherein $R^3$ is independently $C_1$-$C_3$ alkyl.

Embodiment B31. A method of any of Embodiments B1 through B30 wherein $R^4$ is independently halogen, cyano, nitro, $C_1$-$C_8$ alkyl, $C_1$-$C_8$ haloalkyl, $C_1$-$C_8$ nitroalkyl, $C_2$-$C_8$ alkenyl, $C_2$-$C_8$ haloalkenyl, $C_2$-$C_8$ haloalkoxyalkoxy, $C_2$-$C_8$ nitroalkenyl, $C_2$-$C_8$ alkynyl or $C_2$-$C_8$ haloalkynyl.

Embodiment B32. A method of Embodiment B31 wherein $R^4$ is independently halogen, $C_1$-$C_3$ alkyl or $C_1$-$C_3$ haloalkyl.

Embodiment B33. A method of Embodiment B32 wherein $R^4$ is independently halogen or $C_1$-$C_3$ haloalkyl.

Embodiment B34. A method of Embodiment B33 wherein $R^4$ is independently F or $CF_3$.

Embodiment B35. A method of any one of Embodiments B1 through B34 wherein the stereochemistry of the carbon center connecting $Q^1$ to the remainder of Formula I is S.

Embodiment B36. A method of any one of Embodiments B1 through B34 wherein the stereochemistry of the carbon center connecting $Q^1$ to the remainder of Formula I is R.

Embodiment B37. A method of any one of Embodiments B1 through B36 wherein a catalyst is present.

Embodiment B38. A method of Embodiment B37 wherein the catalyst is an organometallic complex.

Embodiment B39. A method of Embodiment B38 wherein the catalyst is a nickel complex.

Embodiment B40. A method of Embodiment B39 wherein the nickel complex is chiral.

Embodiment B41. A method of Embodiment B40 wherein the nickel complex is Ni(II) with vicinal diamine ligands.

Embodiment B42. A method of Embodiment B41 wherein the ligands are N substituted cyclohexane-1,2 diamines or 1,1'-Bi(tetrahydroisoquinoline)-diamines.

Embodiment B43. A method of Embodiment B42 wherein the nickel complex is Ni(II) Bis[(R,R)—N,N'-dibenzylcyclohexane-1,2-diamine]bromide or Ni(II) Bis[(S,S)—N,N'-dibenzylcyclohexane-1,2-diamine]bromide.

Embodiment B44. A method of any one of Embodiments B1 through B43 wherein a base is present.

Embodiment B45. A method of Embodiments B44 wherein the base is an organic base.

Embodiment B46. A method of Embodiments B45 wherein the base is triethylamine, morpholine or piperidine.

Embodiment C1. A method for preparing a compound of Formula IV as described in the Summary of Invention.

Embodiment C2. A method of Embodiment C1 wherein $Q^1$ is a phenyl ring optionally substituted with up to 5 substituents independently selected from $R^1$.

Embodiment C3. A method of Embodiment C2 wherein $Q^1$ is a phenyl ring substituted with 1 to 4 substituents independently selected from $R^1$.

Embodiment C4. A method of Embodiment C3 wherein $Q^1$ is a phenyl ring substituted with 1 to 3 substituents independently selected from $R^1$.

Embodiment C5. A method of any one of Embodiments C1 through C4 wherein $Q^1$ is a phenyl ring having a substituent selected from $R^1$ at the meta (3-) position and optionally up to 2 additional $R^1$ substituents.

Embodiment C6. A method of any one of Embodiments C1 through C4 wherein $Q^1$ is a phenyl ring having a substituent selected from $R^1$ at the para (4-) position and optionally up to 2 additional $R^1$ substituents.

Embodiment C7. A method of Embodiment C1 wherein $Q^1$ is a 5- to 6-membered fully unsaturated heterocyclic ring optionally substituted with up to 5 substituents independently selected from $R^1$ on carbon atom ring members and selected from $R^3$ on nitrogen atom ring members.

Embodiment C8. A method of Embodiment C7 wherein $Q^1$ is a pyridyl ring optionally substituted with up to 2 $R^1$.

Embodiment C9. A method of Embodiment C8 wherein $Q^1$ is a 3-pyridyl ring substituted with $R^1$ at the position para to the bond connecting $Q^1$ to the remainder of Formula IV.

Embodiment C10. A method of Embodiment C7 wherein $Q^1$ is a thiophene or furan ring optionally substituted with up to 2 $R^1$.

Embodiment C11. A method of Embodiment C1 wherein $Q^1$ is an 8- to 10-membered heteroaromatic bicyclic ring system optionally substituted with $R^1$ and $R^3$, the remainder of Formula I is bonded to a fully unsaturated ring of said bicyclic ring system.

Embodiment C12. A method of Embodiment C1 wherein $Q^2$ is a phenyl ring optionally substituted with up to 5 substituents independently selected from $R^4$.

Embodiment C13. A method of Embodiment C12 wherein $Q^2$ is a phenyl ring substituted with 1 to 4 substituents independently selected from $R^4$.

Embodiment C14. A method of Embodiment C13 wherein $Q^2$ is a phenyl ring substituted with 1 to 3 substituents independently selected from $R^4$.

Embodiment C15. A method of any one of Embodiments C12 through C14 wherein $Q^2$ is a phenyl ring having a substituent selected from $R^4$ at the ortho (2-) position and optionally up to 2 additional $R^4$ substituents.

Embodiment C16. A method of Embodiment C1 wherein $Q^2$ is a pyridyl ring optionally substituted with up to 2 $R^4$.

Embodiment C17. A method of Embodiment C16 wherein $Q^2$ is a 2-pyridyl or 3-pyridyl ring optionally substituted with up to 2 $R^4$.

Embodiment C18. A method of Embodiment C1 wherein $Q^2$ is a 5-membered fully unsaturated heterocyclic ring optionally substituted with up to 2 $R^4$.

Embodiment C19. A method of Embodiment C18 wherein $Q^2$ is an oxazole ring optionally substituted with up to 2 $R^4$.

Embodiment C20. A method of any of Embodiments C1 through C19 wherein $R^1$ is independently halogen, cyano, nitro, $C_1$-$C_8$ alkyl, $C_1$-$C_8$ haloalkyl, $C_1$-$C_8$ nitroalkyl, $C_2$-$C_8$ alkenyl, $C_2$-$C_8$ haloalkenyl, $C_2$-$C_8$ haloalkoxyalkoxy, $C_2$-$C_8$ nitroalkenyl, $C_2$-$C_8$ alkynyl or $C_2$-$C_8$ haloalkynyl.

Embodiment C21. A method of Embodiment C20 wherein $R^1$ is independently halogen, cyano, nitro, $C_1$-$C_8$ alkyl, $C_1$-$C_8$ haloalkyl or $C_2$-$C_8$ haloalkoxyalkoxy.

Embodiment C22. A method of Embodiment C21 wherein $R^1$ is independently halogen, $C_1$-$C_3$ alkyl or $C_1$-$C_3$ haloalkyl.

Embodiment C23. A method of Embodiment C22 wherein $R^1$ is independently halogen or $C_1$-$C_3$ haloalkyl.

Embodiment C24. A method of Embodiment C23 wherein $R^1$ is independently F or $CF_3$.

Embodiment C25. A method of any of Embodiments C7 through C24 wherein $R^3$ is independently $C_1$-$C_3$ alkyl, $C_2$-$C_3$ alkenyl, $C_2$-$C_3$ alkynyl, $C_3$-$C_6$ cycloalkyl or $C_1$-$C_3$ alkoxy.

Embodiment C26. A method of Embodiment C25 wherein $R^3$ is independently $C_1$-$C_3$ alkyl.

Embodiment C27. A method of any of Embodiments C1 through C26 wherein $R^4$ is independently halogen, cyano, nitro, $C_1$-$C_8$ alkyl, $C_1$-$C_8$ haloalkyl, $C_1$-$C_8$ nitroalkyl, $C_2$-$C_8$ alkenyl, $C_2$-$C_8$ haloalkenyl, $C_2$-$C_8$ haloalkoxyalkoxy, $C_2$-$C_8$ nitroalkenyl, $C_2$-$C_8$ alkynyl or $C_2$-$C_8$ haloalkynyl.

Embodiment C28. A method of Embodiment C27 wherein $R^4$ is independently halogen, $C_1$-$C_3$ alkyl or $C_1$-$C_3$ haloalkyl.

Embodiment C29. A method of Embodiment C28 wherein $R^4$ is independently halogen or $C_1$-$C_3$ haloalkyl.

Embodiment C30. A method of Embodiment C29 wherein $R^4$ is independently F or $CF_3$.

Embodiment C31. A method of any one of Embodiments C1 through C30 wherein the stereochemistry of a compound of Formula IV is (3R,4S).

Embodiment C31a. A method of any one of Embodiments C1 through C30 wherein the stereochemistry of a compound of Formula IV is (3S,4R).

Embodiment C32. A method of any one of Embodiments C1 through C31 wherein the reducing agent is hydrogen in the presence of a catalyst.

Embodiment C33. A method of Embodiment C32 wherein the catalyst is Pd/C.

Embodiment C34. A method of any one of Embodiments C1 through C31 wherein the reducing agent is metal in acid.

Embodiment C35. A method of Embodiment C34 wherein the metal is zinc and the acid is acetic acid.

Embodiments of this invention, including any one of Embodiments A1 through A34, B1 through B41 and C1 through C35 above as well as any other embodiments described herein, can be combined in any manner, and the descriptions of variables in the embodiments pertain not only to the compounds of Formula I and IV but also to the starting compounds and intermediate compounds useful for preparing the compounds of Formula I and IV.

Combinations of Embodiments A1 through A34, B1 through B41 and C1 through C35 are illustrated by:

Embodiment AA1. A compound of Formula I wherein
$Q^1$ is a phenyl ring substituted with 1 to 3 substituents independently selected from $R^1$;
$Q^2$ is a phenyl ring substituted with 1 to 3 substituents independently selected from $R^4$;
R is $C_1$-$C_4$ alkyl;
$R^1$ is independently halogen, cyano, nitro, $C_1$-$C_8$ alkyl, $C_1$-$C_8$ haloalkyl or $C_2$-$C_8$ haloalkoxyalkoxy; and
$R^4$ is independently halogen, $C_1$-$C_3$ alkyl or $C_1$-$C_3$ haloalkyl.

Embodiment AA2. A compound of Embodiment AA1 wherein
$Q^1$ is a phenyl ring having a substituent selected from $R^1$ at the meta (3-) position and optionally up to 2 additional $R^1$ substituents;
$Q^2$ is a phenyl ring having a substituent selected from $R^4$ at the ortho (2-) position and optionally up to 2 additional $R^4$ substituents;
R is methyl or ethyl;
$R^1$ is independently halogen, $C_1$-$C_3$ alkyl or $C_1$-$C_3$ haloalkyl; and
$R^4$ is independently halogen or $C_1$-$C_3$ haloalkyl.

Embodiment AA3. A compound of Embodiment AA1 wherein
$Q^1$ is a phenyl ring having a substituent selected from $R^1$ at the para (4-) position and optionally up to 2 additional $R^1$ substituents;
$Q^2$ is a phenyl ring having a substituent selected from $R^4$ at the ortho (2-) position and optionally up to 2 additional $R^4$ substituents;
R is methyl or ethyl;
$R^1$ is independently halogen, $C_1$-$C_3$ alkyl or $C_1$-$C_3$ haloalkyl; and
$R^4$ is independently halogen or $C_1$-$C_3$ haloalkyl.

Embodiment AA4. A compound of Formula I wherein
$Q^1$ is a 5- to 6-membered fully unsaturated heterocyclic ring optionally substituted with up to 5 substituents independently selected from $R^1$ on carbon atom ring members and selected from $R^3$ on nitrogen atom ring members;
$Q^2$ is a phenyl ring substituted with 1 to 3 substituents independently selected from $R^4$;
R is $C_1$-$C_4$ alkyl;
$R^1$ is independently halogen, cyano, nitro, $C_1$-$C_8$ alkyl, $C_1$-$C_8$ haloalkyl or $C_2$-$C_8$ haloalkoxyalkoxy;
$R^3$ is independently $C_1$-$C_3$ alkyl, $C_2$-$C_3$ alkenyl, $C_2$-$C_3$ alkynyl, $C_3$-$C_6$ cycloalkyl or $C_1$-$C_3$ alkoxy; and
$R^4$ is independently halogen, $C_1$-$C_3$ alkyl or $C_1$-$C_3$ haloalkyl.

Embodiment AA5. A compound of Embodiment AA4 wherein
$Q^1$ is a pyridyl ring optionally substituted with up to 2 $R^1$;
$Q^2$ is a phenyl ring substituted with 1 to 2 substituents independently selected from $R^4$;
R is methyl or ethyl;
$R^1$ is independently halogen or $C_1$-$C_3$ haloalkyl; and
$R^4$ is independently halogen or $C_1$-$C_3$ haloalkyl.

Embodiment AA6. A compound of AA4 wherein
$Q^1$ is a 3-pyridyl ring substituted with $R^1$ at the position para to the bond connecting $Q^1$ to the remainder of the compound of Formula I; or $Q^1$ is a thiophene or furan ring optionally substituted with up to 2 $R^1$;
$Q^2$ is a phenyl ring substituted with 1 to 2 substituents independently selected from $R^4$;
R is methyl or ethyl;
$R^1$ is independently halogen or $C_1$-$C_3$ haloalkyl; and
$R^4$ is independently halogen or $C_1$-$C_3$ haloalkyl.

Embodiment AA7. A compound of Formula I wherein
$Q^2$ is a 2-pyridyl or 3-pyridyl ring optionally substituted with up to 2 $R^4$;
R is methyl or ethyl;
$R^1$ is independently halogen or $C_1$-$C_3$ haloalkyl; and
$R^4$ is independently halogen or $C_1$-$C_3$ haloalkyl.

Embodiment AA8. A compound of Formula I wherein
$Q^2$ is a oxazolyl ring optionally substituted with up to 2 $R^4$;
R is methyl or ethyl;
$R^1$ is independently halogen or $C_1$-$C_3$ haloalkyl; and
$R^4$ is independently halogen or $C_1$-$C_3$ haloalkyl.

Embodiment AA9. A compound of any one of Embodiments AA1 through AA8 wherein the stereochemistry of the carbon center connecting $Q^1$ to the remainder of Formula I is S or R.

Embodiment BB1. A method for preparing a compound of Formula I as described in the Summary of the Invention wherein
$Q^1$ is a phenyl ring substituted with 1 to 3 substituents independently selected from $R^1$;
$Q^2$ is a phenyl ring substituted with 1 to 3 substituents independently selected from $R^4$;
R is $C_1$-$C_4$ alkyl;
$R^1$ is independently halogen, cyano, nitro, $C_1$-$C_8$ alkyl, $C_1$-$C_8$ haloalkyl or $C_2$-$C_8$ haloalkoxyalkoxy; and
$R^4$ is independently halogen, $C_1$-$C_3$ alkyl or $C_1$-$C_3$ haloalkyl.

Embodiment BB2. A method of Embodiment BB1 wherein
$Q^1$ is a phenyl ring having a substituent selected from $R^1$ at the meta (3-) position and optionally up to 2 additional $R^1$ substituents;
$Q^2$ is a phenyl ring having a substituent selected from $R^4$ at the ortho (2-) position and optionally up to 2 additional $R^4$ substituents;
R is methyl or ethyl;
$R^1$ is independently halogen, $C_1$-$C_3$ alkyl or $C_1$-$C_3$ haloalkyl;
$R^4$ is independently halogen or $C_1$-$C_3$ haloalkyl;

Embodiment BB3. A method of any one of Embodiments BB1 and BB2 wherein
the catalyst is a nickel complex; and
the base is an organic base.

Embodiment BB4. A method of Embodiment BB3 wherein
the nickel complex is Ni(II) with chiral vicinal diamine ligands.

Embodiment BB5. A method of Embodiment BB4 wherein
the ligands are N substituted cyclohexane-1,2 diamines or 1,1′-Bi(tetrahydroisoquinoline)-diamines; and
the base is triethylamine, morpholine or piperidine.

Embodiment BB6. A method of any one of Embodiments BB1 through BB5 wherein the stereochemistry of the carbon center connecting $Q^1$ to the remainder of Formula I is S or R.

Embodiment CC1. A method for preparing a compound of Formula IV as described in the Summary of Invention wherein
$Q^1$ is a phenyl ring substituted with 1 to 3 substituents independently selected from $R^1$;
$Q^2$ is a phenyl ring substituted with 1 to 3 substituents independently selected from $R^4$;
R is $C_1$-$C_4$ alkyl;
$R^1$ is independently halogen, cyano, nitro, $C_1$-$C_8$ alkyl, $C_1$-$C_8$ haloalkyl or $C_2$-$C_8$ haloalkoxyalkoxy; and
$R^4$ is independently halogen, $C_1$-$C_3$ alkyl or $C_1$-$C_3$ haloalkyl.

Embodiment CC2. A method of Embodiment CC1 wherein
$Q^1$ is a phenyl ring having a substituent selected from $R^1$ at the meta (3-) position and optionally up to 2 additional $R^1$ substituents;
$Q^2$ is a phenyl ring having a substituent selected from $R^4$ at the ortho (2-) position and optionally up to 2 additional $R^4$ substituents;
$R^1$ is independently halogen, $C_1$-$C_3$ alkyl or $C_1$-$C_3$ haloalkyl;
$R^4$ is independently halogen or $C_1$-$C_3$ haloalkyl; and Embodiment CC3. A method for preparing a compound of Formula IV as described in the Summary of Invention wherein
$Q^1$ is a pyridyl ring optionally substituted with up to 2 $R^1$;
$Q^2$ is a phenyl ring substituted 1 to 3 substituents independently selected from $R^4$;
$R^1$ is independently halogen or $C_1$-$C_3$ haloalkyl; and
$R^4$ is independently halogen or $C_1$-$C_3$ haloalkyl.

Embodiment CC4. A method of any one of Embodiments CC1 through CC3 wherein the stereochemistry of a compound of Formula IV is (3R,4S) or (3S,4R).

Embodiment CC5. A method of any one of Embodiments CC1 through CC4 wherein the reducing agent is hydrogen in the presence of a catalyst or metal in acid.

Specific embodiments include compounds of Formula I selected from the group consisting of:
Ethyl (βS)-α-[[(2-fluorophenyl)amino]carbonyl]-β-(nitromethyl)-3-(trifluoromethyl)benzenepropanoate;
Ethyl α-[[(2-fluorophenyl)amino]carbonyl]-β-(nitromethyl)-3-(trifluoromethyl)benzenepropanoate;
(3R,4S)—N-(2-fluorophenyl)-2-oxo-4-[3-(trifluoromethyl)phenyl]-3-pyrrolidinecarboxamide; and
rel-(3R,4S)—N-(2-fluorophenyl)-2-oxo-4-[3-(trifluoromethyl)phenyl]-3-pyrrolidinecarboxamide.

The pyrrolidinones of Formula IV are useful as herbicides as disclosed in PCT/US14/68073.

The compounds of Formula I and IV can be prepared by general methods known in the art of synthetic organic chemistry. One or more of the following methods and variations as described in Schemes 1-5 can be used to prepare the compounds of Formula I and IV. The definitions of $Q^1$, $Q^2$, R in the compounds of Formulae I, II, III, IV, a, b, c, d, e and f below are as defined above in the Summary of the Invention unless otherwise noted. All substituents for Formulae a, b, c, d, e and f are as defined above for Formulae I, II, III and IV unless otherwise noted.

As shown in Scheme 1, a compound of Formula IV can be obtained by the reduction of a compound of Formula I and subsequent in situ cyclization of the resulting intermediate amine. A wide variety of methods for reduction of the aliphatic nitro group in compounds of Formula I are known in the literature. Methods well known to those skilled in the art include catalytic hydrogenation in the presence of palladium on carbon, reduction using Raney nickel, iron or zinc metal in acidic medium (see, for example, *Berichte der Deutschen Chemischen Gesellschaft* 1904, 37, 3520-3525) and reduction using lithium aluminum hydride. Reduction can also be achieved with samarium(II) iodide in the presence of a proton source such as methanol (see for example, *Tetrahedron Letters* 1991, 32 (14), 1699-1702). Alternatively sodium borohydride in the presence of a nickel catalyst such as nickel(II) acetate or nickel(II) chloride can be used (see for example, *Tetrahedron Letters* 1985, 26 (52), 6413-6416). The method of utilizing sodium borohydride in the presence of nickel(II) chloride is illustrated by Step C of Synthesis Example 1.

Scheme 1

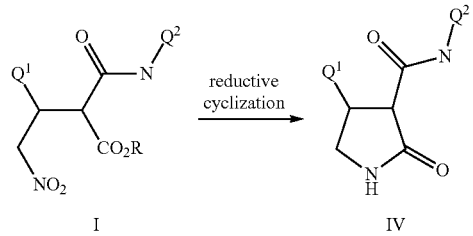

As shown in Scheme 2, a compound of Formula I can be prepared by reacting compounds of Formula a with nitromethane in the presence of a base. Suitable bases for the reaction include alkali metal lower alkoxides such as sodium methoxide in methanol or sodium ethoxide in ethanol.

Scheme 2

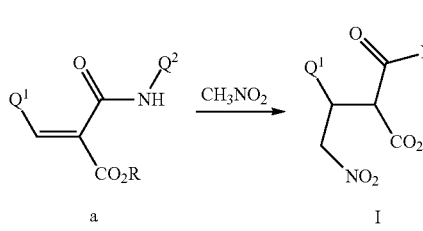

Alternatively, as shown in Scheme 3, a compound of Formula I can be prepared by reacting nitroalkenes of Formula II with malonates of Formula III in the presence of a catalyst, a base or both a catalyst and a base. Suitable catalysts for this reaction include, but are not limited to, a Ni(II) complex with vicinal diamine ligrands such as Ni(II) Bis[(R,R)—N,N'-dibenzylcyclohexane-1,2-diamine]bromide or Ni(II)Br$_2$ complexed with chiral 1,1'-Bi(tetrahydroisoquinoline)-diamines. Suitable bases for this reaction include, but are not limited to, alkali metal lower alkoxides such as sodium methoxide in methanol or sodium ethoxide in ethanol, organic bases such as piperidine, morpholine, triethyl amine, N-methyl morpholine or N, N-diisopropylehtyl amine, or bases such as lithium bis(trimethylsilyl) amide, sodium bis(trimethylsilyl)amide and lithium diisopropylamide in solvents such as tetrahydrofuran, toluene or dichloromethane. Typically, the reaction is carried out at a temperature from about −78° C. to about 23° C. optionally in the presence of 0 to 2 equivalents of catalyst or/and base. See *Synthesis* 2005, 2239-2245 for conditions for effecting this transformation and see *J. Am. Chem. Soc.* 2005, 9958-9959 or *Eur. J. Org. Chem.* 2011, 5441-5446 for conditions to accomplish this transformation stereoselectively. Condiitions for effecting this transformation in refluxing water in the absence of catalyst have been reported in *Synthetic Communications* 2013, 43, 744-748. Nitroalkenes of Formula II can readily be prepared from aldehydes and nitromethane by methods known to those skilled in the art.

Scheme 3

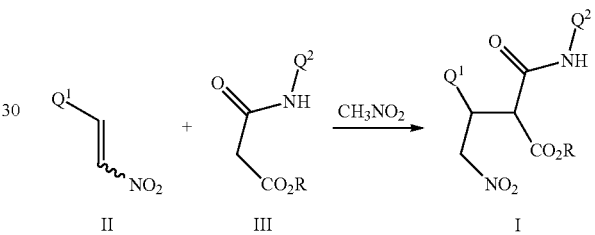

As shown in Scheme 4, compounds of Formula a can be prepared by reaction of malonates of Formula d with aldehydes of Formula e by methods known to those skilled in the art, e.g., by Knoevenagel condensation of aldehydes and malonates (see for example, Jones, G., *Organic Reactions*; Volume 15, John Wiley & Sons, 1967). As also shown in Scheme 4, malonates of Formula d can readily be prepared from lower alkyl malonyl chlorides of Formula b such as methyl malonyl chloride and amines of Formula c by methods known to those skilled in the art.

Scheme 4

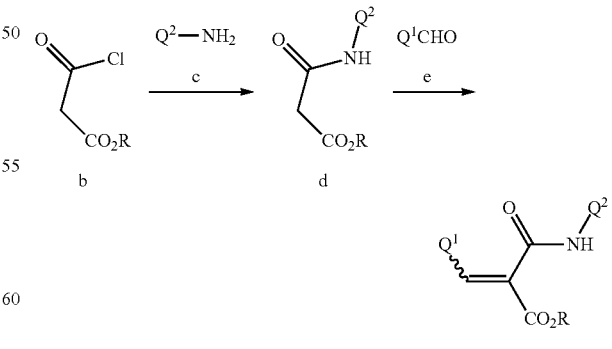

As shown in Scheme 5, compounds of Formula II can be prepared by reaction of nitromethane with an aldehyde of Formula e in the presence of a base. Dehydration of the intermediate f may be accomplished by azeotropic distillation of water from the reaction mixture or reacting with methanesulfonyl chloride in the presence of a base such as triethylamine. Suitable bases for this reaction include, but are not limited to, alkali metal lower alkoxides such as sodium hydroxide, sodium methoxide in methanol or sodium ethoxide in ethanol, ammonium acetate; or organic bases such as piperidine, morpholine or triethyl amine in solvents such as methanol, toluene, acetic acid or 1-chlorobutane. Typically, the reaction is carried out at a temperature from about −78° C. to 130° C. in the presence of 0 to 2 equivalents of catalyst or base. For representative conditions to prepare nitrostyrenes, see WO 2012/158413, US2011/207944 and WO2004/18455.

Scheme 5

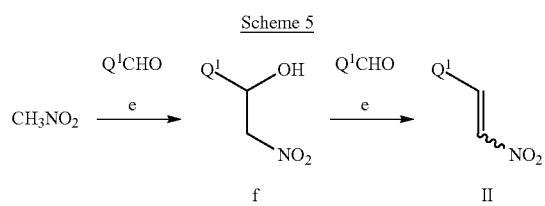

It is recognized by one skilled in the art that various functional groups can be converted into others to provide different compounds of Formula I. For a valuable resource that illustrates the interconversion of functional groups in a simple and straightforward fashion, see Larock, R. C., *Comprehensive Organic Transformations: A Guide to Functional Group Preparations,* 2nd Ed., Wiley-VCH, New York, 1999. For example, intermediates for the preparation of compounds of Formula I may contain aromatic nitro groups, which can be reduced to amino groups, and then be converted via reactions well known in the art such as the Sandmeyer reaction, to various halides, providing compounds of Formula I. The above reactions can also in many cases be performed in alternate order It is recognized that some reagents and reaction conditions described above for preparing compounds of Formula I may not be compatible with certain functionalities present in the intermediates. In these instances, the incorporation of protection/deprotection sequences or functional group interconversions into the synthesis will aid in obtaining the desired products. The use and choice of the protecting groups will be apparent to one skilled in chemical synthesis (see, for example, Greene, T. W.; Wuts, P. G. M. *Protective Groups in Organic Synthesis,* 2nd ed.; Wiley: New York, 1991). One skilled in the art will recognize that, in some cases, after the introduction of a given reagent as it is depicted in any individual scheme, it may be necessary to perform additional routine synthetic steps not described in detail to complete the synthesis of compounds of Formula I. One skilled in the art will also recognize that it may be necessary to perform a combination of the steps illustrated in the above schemes in an order other than that implied by the particular presented to prepare the compounds of Formula I.

One skilled in the art will also recognize that compounds of Formula I and the intermediates described herein can be subjected to various electrophilic, nucleophilic, radical, organometallic, oxidation, and reduction reactions to add substituents or modify existing substituents.

Without further elaboration, it is believed that one skilled in the art using the preceding description can utilize the present invention to its fullest extent. The following Examples are, therefore, to be construed as merely illustrative, and not limiting of the disclosure in any way whatsoever. Steps in the following Examples illustrate a procedure for each step in an overall synthetic transformation, and the starting material for each step may not have necessarily been prepared by a particular preparative run whose procedure is described in other Examples or Steps. Percentages are by weight except for chromatographic solvent mixtures or where otherwise indicated. Parts and percentages for chromatographic solvent mixtures are by volume unless otherwise indicated. $^1$H NMR spectra are reported in ppm downfield from tetramethylsilane in $CDCl_3$ solution unless indicated otherwise; "s" means singlet, "d" means doublet, "t" means triplet, "q" means quartet, "m" means multiplet and "br s" means broad singlet. $^{19}$F NMR spectra are reported in ppm downfield from $CFCl_3$ in $CDCl_3$ unluess indicated otherwise. The enentiomeric ratio (ER) was determined by chiral high performance liquid chromatography analysis using a Chiralpak AD-RH column and eluting with a 50:50 isopropanol/water mixture at 40° C. at 0.3 mL/min.

Synthesis Example 1

Preparation of rel-(3R,4S)—N-(2-Fluorophenyl)-2-oxo-4-[3-(trifluoromethyl)phenyl]-3-pyrrolidinecarboxamide Step A: Preparation of 1-[(E)-2-nitroethenyl]-3-(trifluoromethyl)benzene To a stirred solution of 3-(trifluoromethyl)benzaldehyde (12.2 g, 70.1 mmol) in methanol (50 mL) was added nitromethane (4.34 g, 71.1 mmol). The mixture was cooled to 2° C. and sodium hydroxide (5.65 g, 70.6 mmol) was added as a 50% solution in 24.3 mL of water dropwise over 15 min. An exotherm was noted and additional ice was added to maintain the internal temperature below 10° C. while stirring for an additional 1 h. The reaction mixture was poured into 75 mL of 1 N hydrochloric acid, rinsing the flask with 10 mL of methanol/water. The quenched reaction mixture was transferred to a separatory funnel and extracted with 150 mL of toluene. The aqueous layer was separated and the organic layer was concentrated under vacuum to yield 15.84 g of a yellow oil.

The yellow oil (15.84 g, 67.3 mmol) thus obtained was taken up in 160 mL of dichloromethane. The solution was cooled to 3° C. and methanesulfonyl chloride (8.03 g, 71.1 mmol) was added via pipette as a solution in 50 mL of dichloromethane. A solution of triethylamine (14.2 g, 140 mmol) in 50 ml of dichloromethane was then added dropwise over 50 min. The mixture was stirred for 2 h and then poured into 150 mL of 1 N hydrochloric acid and transferred to a separatory funnel. The layers were separated and the organic layer was washed with 150 mL water and then filtered. The organic layer was concentrated under reduced pressure and the crude solid was triturated with hexanes to yield 12.09 g (79.4% yield over two steps) of product as a yellow solid.

$^1$H NMR (500 MHz) δ 7.96-8.08 (m, 1H), 7.69-7.84 (m, 3H), 7.54-7.66 (m, 2H).

Step B: Preparation of ethyl 3-[(2-fluorophenyl)amino]-3-oxopropanote

To a stirred solution of 2-fluoroaniline (10 g, 90.0 mmol) and triethylamine (9.1 g, 90.0 mmol) in dichloromethane (50 mL) at 0° C. was added dropwise over 10 minutes a solution of ethyl malonyl chloride (15.5 g, 90.0 mmol) in dichloromethane (30 mL). The resulting mixture was stirred at room temperature for 24 h. The reaction mixture was then poured into water (100 mL), and the organic layer was separated, washed with water (50 mL) and brine (50 mL), dried ($MgSO_4$) and concentrated under reduced pressure to provide the title compound as an amber oil (19.0 g).

¹H NMR δ 9.46 (br s, 1H), 8.28 (m, 1H), 7.10 (m, 2H), 4.26 (m, 2H), 3.51 (s, 2H), 1.32 (t, 3H).

Step C: Preparation of Ethyl α-[[(2-fluorophenyl)amino]carbonyl]-β-(nitromethyl)-3-(trifluoromethyl)benzenepropanoate A stirred solution of 1-[(E)-2-nitrovinyl]-3-(trifluoromethyl)benzene (i.e. the product of Step A, 12 g, 55 mmol) and ethyl 3-[(2-fluorophenyl)amino]-3-oxopropanote (i.e. the product of Step B, 12.4 g, 55 mmol) in anhydrous tetrahydrofuran (55 mL) was cooled to −5° C. under an atmosphere of nitrogen. To this mixture was added triethylamine (7.7 mL, 55 mmol) as a solution in anhydrous tetrahydrofuran (15 mL) over the course of 10 min. The reaction was stirred and allowed to warm to ambient temperature over the course of 1.5 h. The solution was concentrated under reduced pressure. The resulting crude solid was triturated with Et$_2$O, filtered and washed with a small amount of Et$_2$O and then hexanes. After drying with suction under nitrogen, 16.25 g of a white solid was isolated. Concentration of the filtrate and trituration with 1-chlorobutane at 50° C. yielded 3.45 g of additional product (NMR data is a 1:1 mixture of two diastereomers).

¹H NMR (500 MHz, DMSO-d$_6$) δ 10.16 (s, 1H), 10.03 (s, 1H), 7.44-7.88 (m, 8H), 6.85-7.33 (m, 8H), 4.95-5.16 (m, 4H), 4.10-4.38 (m, 6H), 3.84-4.01 (m, 2H), 1.17-1.24 (m, 3H), 0.90-1.00 (m, 3H); ¹⁹F NMR (471 MHz, DMSO-d$_6$) δ−124.41--124.17 (m, 2F), −61.56--60.99 (m, 6F).

Step D: Preparation of rel-(3R,4S)—N-(2-Fluorophenyl)-2-oxo-4-[3-(trifluoromethyl)phenyl]-3-pyrrolidinecarboxamide To a solution of Ethyl α-[[(2-fluorophenyl)amino]carbonyl]-β-(nitromethyl)-3-(trifluoromethyl)benzenepropanoate (i.e. the product of Step C, 15.1 g, 34 mmol) in anhydrous N,N-dimethyformamide (30 mL) and methanol (160 mL) was added NiCl$_2$.6H$_2$O dust (8.1 g, 34 mmol) in one portion. After the solution became clear the mixture was cooled to −7° C. NaBH$_4$ (3.8 g, 100 mmol) was added in 0.5 g portions maintaining the internal temperature below 0° C. The reaction mixture was warmed to ambient temperature with stirring overnight. The solution was concentrated under reduced pressure and the crude material was suspended in dichloromethane (300 ml) and adsorbed onto of mixture of silica gel (60 g) and celite (25 g). Following concentration in vacuo, the sample was filtered through a plug of silica gel (160 g), eluting with ethyl acetate until no more product came through the plug. Concentration under reduced pressure gave 9.55 g of the desired product as an oily, off white solid. ¹H NMR (500 MHz) δ 9.70 (br s, 1H), 8.15-8.25 (m, 1H), 7.42-7.68 (m, 4H), 6.97-7.12 (m, 3H), 6.49 (br s, 1H), 4.23-4.34 (m, 1H), 3.81-3.89 (m, 1H), 3.56-3.67 (m, 1H), 3.41-3.53 (m, 1H);
¹⁹F NMR (471 MHz) δ ppm −129.69--129.51 (m, 1F), −62.56 (s, 3F).

Synthesis Example 2

Preparation of (3R,4S)—N-(2-fluorophenyl)-2-oxo-4-[3-(trifluoromethyl)phenyl]-3-pyrrolidinecarboxamide Step A: Preparation of Ethyl (βS)-α-[[(2-fluorophenyl)amino]carbonyl]-β-(nitromethyl)-3-(trifluoromethyl)benzenepropanoate To a mechanically stirred solution of 1-[(E)-2-nitroethenyl]-3-(trifluoromethyl)benzene (i.e. the product of Step A in Synthesis Example 1, 70 g, 0.32 mol) and ethyl 3-[(2-fluorophenyl)amino]-3-oxopropanote (i.e. the product of Step B in Synthesis Example 1, 72.6 g, 0.3225 mol) in toluene (350 mL) was added Ni(II)-Bis[(R,R)—N,N'-dibenzylcyclohexane-1,2-diamine]bromide (3.9 g, 0.0048 mol). The resulting mixture was stirred for 48 h at ambient temperature. The solution was then diluted with dichloromethane (500 mL) and adsorbed onto silica gel and purified by chromatography (70/30 petroleum ether/ethyl acetate). After standing at ambient temperature, 130 g of a white solid was obtained. Analysis by chiral HPLC (Chiral Pak IA (250×4.6) mm 5µ, 0.1% diethylamine in hexane:ethanol (90:10) at 1.0 mL/min) showed an ER of 89:10.

¹H NMR (500 MHz) δ 8.66 (br s, 2H), 8.16-8.25 (m, 1H), 7.99-8.09 (m, 1H), 7.52-7.62 (m, 3H), 7.39-7.51 (m, 5H), 7.01-7.20 (m, 6H), 5.04-5.09 (m, 2H), 4.87-5.01 (m, 2H), 4.39-4.46 (m, 1H), 4.30 (q, J=7.15 Hz, 3H), 4.02 (q, J=7.20 Hz, 2H), 3.82-3.91 (m, 2H), 1.28-1.37 (m, 3H), 0.93-1.05 (m, 3H);
¹⁹F NMR (471 MHz) δ−130.24--130.09 (m, 1F), −129.92--129.76 (m, 1F), −62.84 (s, 3F), −62.80 (s, 3F); NMR data is a 1:1 mixture of two diastereomers.

MP: 130.6-134.6° C.: ESI [M+1] 443.6.

Step B: Preparation of (3R,4S)—N-(2-fluorophenyl)-2-oxo-4-[3-(trifluoromethyl)phenyl]-3-pyrrolidinecarboxamide To a solution of Ethyl (βS)-α-[[(2-fluorophenyl)amino]carbonyl]-β-(nitromethyl)-3-(trifluoromethyl)benzenepropanoate (i.e. the product of Step C, 100 g, 0.226 mol) in ethanol (1000 mL) was added zinc dust (144.7 g, 2.26 mol) in one portion. The reaction mixture was heated to 80° C. Acetic acid (108 g, 1.81 mol) was added dropwise over a period of 45 min. After the addition of acetic acid, the solution was heated to 90° C. and stirred for 3 h. The solution was cooled to ambient temperature and diluted with ethyl acetate (1 L) and filtered through a bed of Celite® diatomaceous earth filter aid. The filtrate was concentrated under reduced pressure and the residue was taken up in ethyl acetate (2 L). The organic layer was washed with 0.5 N HCl, water and brine and then dried over Na$_2$SO$_4$, filtered and concentrated in vacuo. The thick liquid obtained was triturated with 500 mL of 10% methyl tert-butyl ether/petroleum ether to give a white solid. Filtration and drying provided the title compound as an white solid (56 g, 67% yield). Analysis by chiral HPLC (Chiral Pak IA (250×4.6) mm 5µ, 0.1% DEA in hexane:ethanol (90:10) at 1.0 mL/min) showed an ER of 86:14.

¹H NMR (500 MHz, Acetone-d6) δ 10.05 (br s, 1H), 8.24-8.33 (m, 1H), 7.78-7.90 (m, 2H), 7.57-7.65 (m, 2H), 7.52 (br s, 1H), 7.00-7.22 (m, 3H), 4.20-4.29 (m, 1H), 3.96-4.02 (m, 1H), 3.83-3.92 (m, 1H), 3.41-3.53 (m, 1H);
¹⁹F NMR (471 MHz, Acetone-d6) δ ppm −131.19--131.01 (m, 1F), −62.93 (s, 3F); MP 141.8-144.7° C.; ESI [M+1] 367.0.

By the procedures described herein together with methods known in the art, the following compounds of Tables 1 to 688 can be prepared. The following abbreviations are used in the Tables which follow: t means tertiary, n means normal, i means iso, c means cyclo, Me means methyl, Et means ethyl, Pr means propyl, Bu means butyl, i-Pr means isopropyl, Bu means butyl, c-Pr cyclopropyl, c-Bu means cyclobutyl, Ph means phenyl, OMe means methoxy, OEt means ethoxy, SMe means methylthio, SEt means ethylthio, NHMe methylamino, —CN means cyano, —NO$_2$ means nitro, TMS means trimethylsilyl, S(O)Me means methylsulfinyl, and S(O)$_2$Me means methylsulfonyl.

TABLE 1

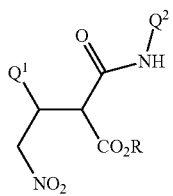

R is Me; Q² is Ph(2-F) and Q¹ is

| Q¹ | Q¹ | Q¹ |
|---|---|---|
| Ph(2-Cl) | Ph(2-OCO₂Me) | Ph(2-CH₂CH=CCl₂) |
| Ph(2-F) | Ph(2-TMS) | Ph(2-CH₂CH=CBr₂) |
| Ph(2-Br) | Ph(2-Ph) | Ph(2-OCH₂CH=CH₂) |
| Ph(2-I) | Ph[2-(1H-pyrazol-1-yl] | Ph(2-OCH₂CH=CF₂) |
| Ph(2-Me) | Ph[2-(2H-1,2,3-triazol-2-yl)] | Ph(2-OCH₂CH=CCl₂) |
| Ph(2-Et) | Ph[2-(1H-imidazol-1-yl)] | Ph(2-OCH₂CH=CBr₂) |
| Ph(2-n-Pr) | Ph[2-(3-pyridinyl)] | Ph(2-SCF₂H) |
| Ph(2-t-Bu) | Ph[2-(4-pyridinyl)] | Ph(2-SCF₂CF₂H) |
| Ph(2-i-Pr) | Ph[2-(2-pyridinyl)] | Ph(3-Cl) |
| Ph(2-c-Pr) | Ph(2-CF₂CF₃) | Ph(3-F) |
| Ph(2-cyclohexyl) | Ph(2-CF₂CF₂H) | Ph(3-Br) |
| Ph(2-CH=CH₂) | Ph(2-OCF₂CF₂H) | Ph(3-I) |
| Ph(2-CF₃) | Ph(2-OCF₂CF₃) | Ph(3-Me) |
| Ph(2-CH₂CF₃) | Ph(2-OCH₂CF₃) | Ph(3-Et) |
| Ph(2-CF₂H) | Ph(2-OCH₂C≡CH) | Ph(3-n-Pr) |
| Ph(2-CH₂F) | Ph(2-OCH₂C≡CCF₃) | Ph(3-t-Bu) |
| Ph(2-OCF₃) | Ph(2-OCH₂C≡CCF₂H) | Ph(3-i-Pr) |
| Ph(2-OCH₂F) | Ph(2-OCH₂C≡CCH₃) | Ph(3-c-Pr) |
| Ph(2-OCF₂H) | Ph(2-OCH₂C≡C-C-Pr) | Ph(3-cyclohexyl) |
| Ph(2-SCF₃) | Ph(2-C≡CCF₂H) | Ph(3-CH=CH₂) |
| Ph(2-SMe) | Ph(2-C≡CCH₃) | Ph(3-CF₃) |
| Ph(2-SOMe) | Ph(2-C≡CCF₃) | Ph(3-CH₂CF₃) |
| Ph(2-SO₂Me) | Ph(2-OPh) | Ph(3-CF₂H) |
| Ph(2-OSO₂Me) | Ph(2-C≡CCF₃) | Ph(3-CH₂F) |
| Ph(2-C≡CH) | Ph(2-C≡CCF₂H) | Ph(3-OCF₃) |
| Ph(2-OMe) | Ph(2-C≡CCH₃) | Ph(3-OCH₂F) |
| Ph(2-OEt) | Ph(2-C≡C-C-Pr) | Ph(3-OCF₂H) |
| Ph(2-NHCO₂-t-Bu) | Ph(2-CH=CF₂) | Ph(3-SCF₃) |
| Ph(2-NHCOMe) | Ph(2-CH=CCl₂) | Ph(3-SMe) |
| Ph(2-NHCOCF₃) | Ph(2-CH=CBr₂) | Ph(3-SOMe) |
| Ph(2-CN) | Ph(2-OCH=CH₂) | Ph(3-SO₂Me) |
| Ph(2-NO₂) | Ph(2-OCH=CF₂) | Ph(3-OSO₂Me) |
| Ph(2-Ph) | Ph(2-OCH=CCl₂) | Ph(3-CCH) |
| Ph(2-COMe) | Ph(2-OCH=CBr₂) | Ph(3-OMe) |
| Ph(2-OCOMe) | Ph(2-CH₂CH=CH₂) | Ph(3-OEt) |
| Ph(2-CO₂Me) | Ph(2-CH₂CH=CF₂) | Ph(3-NHCO₂-t-Bu) |
| Ph(3-NHCOMe) | Ph(3-CH=CF₂) | Ph(2-Cl,3-OCF₂H) |
| Ph(3-NHCOCF₃) | Ph(3-CH=CCl₂) | Ph(2-Cl, 3-SCF₃) |
| Ph(3-CN) | Ph(3-CH=CBr₂) | Ph(2-Cl,3-SMe) |
| Ph(3-NO₂) | Ph(3-OCH=CH₂) | Ph(2-Cl,3-SOMe) |
| Ph(3-Ph) | Ph(3-OCH=CF₂) | Ph(2-Cl,3-SO₂Me) |
| Ph(3-COMe) | Ph(3-OCH=CCl₂) | Ph(2-Cl,3-OSO₂Me) |
| Ph(3-OCOMe) | Ph(3-OCH=CBr₂) | Ph(2-Cl,3-CCH) |
| Ph(3-CO₂Me) | Ph(3-CH₂CH=CH₂) | Ph(2-Cl,3-OMe) |
| Ph(3-OCO₂Me) | Ph(3-CH₂CH=CF₂) | Ph(2-Cl,3-OEt) |
| Ph(3-TMS) | Ph(3-CH₂CH=CCl₂) | Ph(2-Cl,3-NHCO₂-t-Bu) |
| Ph(3-Ph) | Ph(3-CH₂CH=CBr₂) | Ph(2-Cl,3-NHCOMe) |
| Ph[3-(1H-pyrazol-1-yl] | Ph(3-OCH₂CH=CH₂) | Ph(2-Cl,3-NHCOCF₃) |
| Ph[3-(2H-1,2,3-triazol-2-yl] | Ph(3-OCH₂CH=CF₂) | Ph(2-Cl,3-CN) |
| Ph[3-(1H-imidazol-1-yl] | Ph(3-OCH₂CH=CCl₂) | Ph(2-Cl,3-NO₂) |
| Ph[3-(3-pyridinyl)] | Ph(3-OCH₂CH=CBr₂) | Ph(2-Cl,3-Ph) |
| Ph[3-(4-pyridinyl)] | Ph(3-SCF₂H) | Ph(2-Cl,3-COMe) |
| Ph[3-(2-pyridinyl)] | Ph(3-SCF₂CF₂H) | Ph(2-Cl,3-OCOMe) |
| Ph(3-CF₂CF₃) | Ph(2-Cl,3-Cl) | Ph(2-Cl,3-CO₂Me) |
| Ph(3-CF₂CF₂H) | Ph(2-Cl,3-F) | Ph(2-Cl,3-OCO₂Me) |
| Ph(3-OCF₂CF₂H) | Ph(2-Cl,3-Br) | Ph(2-Cl,3-TMS) |
| Ph(3-OCF₂CF₃) | Ph(2-Cl,3-I) | Ph(2-Cl,3-Ph) |
| Ph(3-OCH₂CF₃) | Ph(2-Cl,3-Me) | |
| Ph(3-OCH₂C≡CH) | Ph(2-Cl,3-Et) | |
| Ph(3-OCH₂C≡CCF₃) | Ph(2-Cl,3-n-Pr) | Ph[3-(2-Cl,1H-imidazol-1-yl] |
| Ph(3-OCH₂C≡CCF₂H) | Ph(2-Cl,3-t-Bu) | Ph[3-(2-Cl,3-pyridinyl)] |
| Ph(3-OCH₂C≡CCH₃) | Ph(2-Cl,3-i-Pr) | Ph[3-(2-Cl,4-pyridinyl)] |
| Ph(3-OCH₂C≡C-c-Pr) | Ph(2-Cl,3-c-Pr) | Ph[3-(2-Cl,2-pyridinyl)] |
| Ph(3-C≡CCF₂H) | Ph(2-Cl,3-cyclohexyl) | Ph(2-Cl,3-CF₂CF₃) |
| Ph(3-C≡CCH₃) | Ph(2-Cl,3-CH=CH₂) | Ph(2-Cl,3-CF₂CF₂H) |
| Ph(3-C≡C-c-Pr) | Ph(2-Cl,3-CF₃) | Ph(2-Cl,3-OCF₂CF₂H) |
| Ph(3-OPh) | Ph(2-Cl,3-CH₂CF₃) | Ph(2-Cl,3-OCF₂CF₃) |

TABLE 1-continued

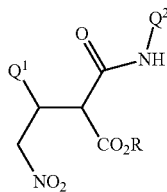

R is Me; $Q^2$ is Ph(2-F) and $Q^1$ is

| | | |
|---|---|---|
| Ph(3-C≡CCF₃) | Ph(2-Cl,3-CF₂H) | Ph(2-Cl,3-OCH₂CF₃) |
| Ph(3-C≡CCF₂H) | Ph(2-Cl,3-CH₂F) | Ph(2-Cl,3-OCH₂C≡CH) |
| Ph(3-C≡CCH₃) | Ph(2-Cl,3-OCF₃) | Ph(2-Cl,3-OCH₂C≡CCF₃) |
| Ph(3-C≡C-c-Pr) | Ph(2-Cl, 3-OCH₂F) | Ph(2-Cl,3-OCH₂C≡CCF₂H) |
| Ph(2-Cl,3-OCH₂C≡CCH₃) | Ph(2-F,3-i-Pr) | Ph[3-(2-F,4-pyridinyl)] |
| Ph(2-Cl,3-OCH₂C≡C-c-Pr) | Ph(2-F,3-c-Pr) | Ph[3-(2-F,2-pyridinyl)] |
| Ph(2-Cl,3-C≡CCF₂H) | Ph(2-F,3-cyclohexyl) | Ph(2-F,3-CF₂CF₃) |
| Ph(2-Cl,3-C≡CCH₃) | Ph(2-F,3-CH=CH₂) | Ph(2-F,3-OCF₂CF₂H) |
| Ph(2-Cl,3-C≡C-c-Pr) | Ph(2-F,3-CF₃) | Ph(2-F,3-OCF₂CF₂H) |
| Ph(2-Cl,3-OPh) | Ph(2-F,3-CH₂CF₃) | Ph(2-F,3-OCF₂CF₃) |
| Ph(2-Cl,3-C≡CCF₃) | Ph(2-F,3-CF₂H) | Ph(2-F,3-OCH₂CF₃) |
| Ph(2-Cl,3-C≡CCF₂H) | Ph(2-F,3-CH₂F) | Ph(2-F,3-OCH₂C≡CH) |
| Ph(2-Cl,3-C≡CCH₃) | Ph(2-F,3-OCF₃) | Ph(2-F,3-OCH₂C≡CCF₃) |
| Ph(2-Cl,3-C≡C-c-Pr) | Ph(2-F,3-OCH₂F) | Ph(2-F,3-OCH₂C≡CCF₂H) |
| Ph(2-Cl,3-CH=CF₂) | Ph(2-F,3-OCF₂H) | Ph(2-F,3-OCH₂C≡CCH₃) |
| Ph(2-Cl,3-CH=CCl₂) | Ph(2-F,3-SCF₃) | Ph(2-F,3-OCH₂C≡C-c-Pr) |
| Ph(2-Cl,3-CH=CBr₂) | Ph(2-F,3-SMe) | Ph(2-F,3-C≡CCF₂H) |
| Ph(2-Cl,3-OCH=CH₂) | Ph(2-F,3-SOMe) | Ph(2-F,3-C≡CCH₃) |
| Ph(2-Cl,3-OCH=CF₂) | Ph(2-F,3-SO₂Me) | Ph(2-F,3-C≡C-c-Pr) |
| Ph(2-Cl,3-CH₂CH=CCl₂) | Ph(2-F,3-OSO₂Me) | Ph(2-F,3-OPh) |
| Ph(2-Cl,3-CH₂CH=CBr₂) | Ph(2-F,3-C≡CH) | Ph(2-F,3-C≡CCF₃) |
| Ph(2-Cl,3-OCH₂CH=CH₂) | Ph(2-F,3-OMe) | Ph(2-F,3-C≡CCF₂H) |
| Ph(2-Cl,3-OCH₂CH=CF₂) | Ph(2-F,3-OEt) | Ph(2-F,3-C≡CCH₃) |
| Ph(2-Cl,3-OCH₂CH=CCl₂) | Ph(2-F,3-NHCO₂-t-Bu) | Ph(2-F,3-C≡C-c-Pr) |
| Ph(2-Cl,3-CH₂CH=CBr₂) | Ph(2-F,3-NHCOMe) | Ph(2-F,3-CH=CF₂) |
| Ph(2-Cl,3-OCH₂CH=CH₂) | Ph(2-F,3-NHCOCF₃) | Ph(2-F,3-CH=CCl₂) |
| Ph(2-Cl,3-OCH₂CH=CF₂) | Ph(2-F,3-CN) | Ph(2-F,3-CH=CBr₂) |
| Ph(2-Cl,3-OCH₂CH=CCl₂) | Ph(2-F,3-NO₂) | Ph(2-F,3-CH₂CH=CH₂) |
| Ph(2-Cl,3-OCH₂CH=CBr₂) | Ph(2-F,3-Ph) | Ph(2-F,3-OCH=CF₂) |
| Ph(2-Cl,3-SCF₂H) | Ph(2-F,3-COMe) | Ph(2-F,3-CH₂CH=CCl₂) |
| Ph(2-Cl,3-SCF₂CF₂H) | Ph(2-F,3-OCOMe) | Ph(2-F,3-CH₂CH=CBr₂) |
| Ph(2-F,3-Cl) | Ph(2-F,3-CO₂Me) | Ph(2-F,3-CH₂CH=CH₂) |
| Ph(2-F,3-F) | Ph(2-F,3-OCO₂Me) | Ph(2-F,3-CH₂CH=CF₂) |
| Ph(2-F,3-Br) | Ph(2-F,3-TMS) | Ph(2-F,3-CH₂CH=CCl₂) |
| Ph(2-F,3-I) | Ph(2-F,3-Ph) | Ph(2-F,3-CH₂CH=CBr₂) |
| Ph(2-F,3-Me) | | Ph(2-F,3-OCH₂CH=CH₂) |
| Ph(2-F,3-Et) | | Ph(2-F,3-OCHHd 2CH=CF₂) |
| Ph(2-F,3-n-Pr) | Ph[3-(2-F,1H-imidazol-1-yl)] | Ph(2-F,3-OCH₂CH=CCl₂) |
| Ph(2-F,3-t-Bu) | Ph[3-(2-F,3-pyridinyl)] | Ph(2-F,3-OCH₂CH=CBr₂) |
| Ph(2-F,3-SCF₂H) | 2-Thienyl(5-c-Pr) | Ph(4-c-Pr) |
| Ph(2-F,3-SCF₂CF₂H) | 2-Thienyl(5-CF₂H) | Ph(4-cyclohexyl) |
| 4-Pyridinyl(2-CF₃) | 2-Thienyl(5-OCF₂H) | Ph(4-CH=CH₂) |
| 4-Pyridinyl(2-Cl) | 2-Thienyl(5-OCF₂CF₂H) | Ph(4-CF₃) |
| 4-Pyridinyl(2-F) | 2-Thienyl(5-OCF₂CF₃) | Ph(4-CH₂CF₃) |
| 4-Pyridinyl(5-OCF₂H) | 2-Furanyl(4-F) | Ph(4-CHF₂) |
| 4-Pyridinyl(5-CF₂H) | 2-Furanyl(4-Cl) | Ph(4-CH₂F) |
| 4-Pyridinyl(5-OCF₂CF₂H) | 2-Furanyl(4-CF₃) | Ph(4-OCF₃) |
| 4-Pyridinyl(2-OCF₃) | 2-Furanyl(5-F) | Ph(4-OCH) |
| 4-Pyridinyl(2-Me) | 2-Furanyl(5-Cl) | Ph(4-OCHF₂) |
| 4-Pyridinyl(2-Br) | 2-Furanyl(5-CF₃) | Ph(4-SCF₃) |
| 4-Pyridinyl | 2-Furanyl(4-Me) | Ph(4-SMe) |
| 1H-Pyrazol-4-yl(1-Me) | 2-Furanyl(4-Et) | Ph(4-SOMe) |
| 1H-Pyrazol-4-yl(1-CH₂CF₃) | 2-Furanyl(4-i-Pr) | Ph(4-SO₂Me) |
| 1H-Imidazol-2-yl(1-Me) | 2-Furanyl(4-c-Pr) | Ph(4-OSO₂Me) |
| 1H-Imidazol-2-yl(1-CH₂CF₃) | 2-Furanyl(4-CF₂H) | Ph(4-C≡CH) |
| 1H-Imidazol-2-yl(1-Me,5-Cl) | 2-Furanyl(4-OCF₂H) | Ph(4-OMe) |
| 1H-Imidazol-2-yl(1-Me,5-F) | 2-Furanyl(4-OCF₂CF₂H) | Ph(4-OEt) |
| 2-Thienyl | 2-Furanyl(5-Me) | Ph(4-NHCO₂-t-Bu) |
| 2-Thienyl(4-F) | 2-Furanyl(5-Et) | Ph(4-NHCOMe) |
| 2-Thienyl(4-Cl) | 2-Furanyl(5-i-Pr) | Ph(4-NHCOCF₃) |
| 2-Thienyl(4-CF₃) | 2-Furanyl(5-c-Pr) | Ph(4-CN) |
| 2-Thienyl(5-F) | 2-Furanyl(5-CF₂H) | Ph(4-NO₂) |
| 2-Thienyl(5-Cl) | 2-Furanyl(5-OCF₂H) | Ph(4-Ph) |
| 2-Thienyl(5-CF₃) | 2-Furanyl(5-OCF₂CF₂H) | Ph(4-COMe) |
| 2-Thienyl(4-Me) | 2-Furanyl(5-OCF₂CF₃) | Ph(4-OCOMe) |
| 2-Thienyl(4-Et) | Ph(4-Cl) | Ph(4-CO₂Me) |
| 2-Thienyl(4-i-Pr) | Ph(4-F) | Ph(4-OCO₂Me) |
| 2-Thienyl(4-c-Pr) | Ph(4-Br) | Ph(4-TMS) |
| 2-Thienyl(4-CF₂H) | Ph(4-I) | Ph(4-Ph) |

TABLE 1-continued

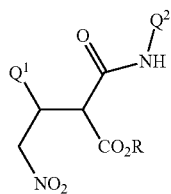

R is Me; Q² is Ph(2-F) and Q¹ is

| | | |
|---|---|---|
| 2-Thienyl(4-OCF₂H) | Ph(4-Me) | Ph(4-CF₂CF3) |
| 2-Thienyl(4-OCF₂CF₂H) | Ph(4-Et) | Ph(4-CF₂CF₂H) |
| 2-Thienyl(5-Me) | Ph(4-n-Pr) | Ph(4-OCF₂CF₂H) |
| 2-Thienyl(5-Et) | Ph(4-t-Bu) | Ph(4-OCF₂CF₃) |
| 2-Thienyl(5-i-Pr) | Ph(4-i-Pr) | Ph(4-OCH₂CF₃) |
| Ph(4-OCH₂C≡CH) | Ph(4-Cl,4-Et) | Ph(2-Cl,4-CF₂CF₂H) |
| Ph(4-OCH₂C≡CCF₃) | Ph(2-Cl,4-n-Pr) | Ph(2-Cl,4-OCF₂CF₂H) |
| Ph(4-OCH₂C≡CCF₂H) | Ph(2-Cl,4-t-Bu) | Ph(2-Cl,4-OCF₂CF₃) |
| Ph(4-OCH₂C≡CCH₃) | Ph(2-Cl,4-i-Pr) | Ph(2-Cl,4-OCH₂CF₃) |
| Ph(4-OCH₂C≡C-c-Pr) | Ph(2-Cl,4-c-Pr) | Ph(2-Cl,4-OCH₂C≡CH) |
| Ph(4-C≡CCF₂H) | Ph(2-Cl,4-cyclohexyl) | Ph(2-Cl,4-OCH₂C≡CCF₃) |
| Ph(4-C≡CCH₃) | Ph(2-Cl,4-CH═CH₂) | Ph(2-Cl,4-OCH₂C≡CCF₂H) |
| Ph(4-C≡C-c-Pr) | Ph(2-Cl,4-CF₃) | Ph(2-Cl,4-OCH₂C≡CCH₃) |
| Ph(4-OPh) | Ph(2-Cl,4-CH₂CF₃) | Ph(2-Cl,4-OCH₂C≡C-c-Pr) |
| Ph(4-C≡CCF₃) | Ph(2-Cl,4-CHF₂) | Ph(2-Cl,4-C≡CCF₂H) |
| Ph(4-C≡CCF₂H) | Ph(2-Cl,4-CH₂F) | Ph(2-Cl,4-C≡CCH₃) |
| Ph(4-C≡CCH₃) | Ph(2-Cl,4-OCF₃) | Ph(2-Cl,4-C≡C-c-Pr) |
| Ph(4-C≡C-c-Pr) | Ph(2-Cl,4-OCH₂F) | Ph(2-Cl,4-OPh) |
| Ph(4-CH═CF₂) | Ph(2-Cl,4-OCHF₂) | Ph(2-Cl,4-C≡CCF₃) |
| Ph(4-CH═CCl₂) | Ph(2-Cl,4-SCF₃) | Ph(2-Cl,4-C≡CCF₂H) |
| Ph(4-OCH═CBr₂) | Ph(2-Cl,4-SMe) | Ph(2-Cl,4-C≡CCH₃) |
| Ph(4-OCH═CH₂) | Ph(2-Cl,4-SOMe) | Ph(2-Cl,4-C≡C-c-Pr) |
| Ph(4-OCH═CF₂) | Ph(2-Cl,4-SO₂Me) | Ph(2-Cl,4-CH═CF₂) |
| Ph(4-OCH═CCl₂) | Ph(2-Cl,4-OSO₂Me) | Ph(2-Cl,4-CH═CCl₂) |
| Ph(4-OCH═CBr₂) | Ph(2-Cl,4-C≡CH) | Ph(2-Cl,4-CH═CBr₂) |
| Ph(4-CH₂CH═CH₂) | Ph(2-Cl,4-OMe) | Ph(2-Cl,4-OCH═CH₂) |
| Ph(4-CH₂CH═CF₂) | Ph(2-Cl,4-OEt) | Ph(2-Cl,4-OCH═CF₂) |
| Ph(4-CH₂CH═CCl₂) | Ph(2-Cl,4-NHCO₂-t-Bu) | Ph(2-Cl,4-OCH═CCl₂) |
| Ph(4-CH₂CH═CBr₂) | Ph(2-Cl,4-NHCOMe) | Ph(2-Cl,4-OCH═CBr₂) |
| Ph(4-OCH₂CH═CH₂) | Ph(2-Cl,4-NHCOCF₃) | Ph(2-Cl,4-CH₂CH═CH₂) |
| Ph(4-OCH₂CH═CF₂) | Ph(2-Cl,4-CN) | Ph(2-Cl,4-CH₂CH═CF₂) |
| Ph(4-OCH₂CH═CCl₂) | Ph(2-Cl,4-NO₂) | Ph(2-Cl,4-CH₂CH═CCl₂) |
| Ph(4-OCH₂CH═CBr₂) | Ph(2-Cl,4-Ph) | Ph(2-Cl,4-CH₂CH═CBr₂) |
| Ph(4-SCF₂H) | Ph(2-Cl,4-COMe) | Ph(2-Cl,4-OCH₂CH═CH₂) |
| Ph(4-SCF₂CF₂H) | Ph(2-Cl,4-OCOMe) | Ph(2-Cl,4-OCH₂CH═CF₂) |
| Ph(2,4-di-Cl) | Ph(2-Cl,4-CO₂Me) | Ph(2-Cl,4-OCH₂CH═CCl₂) |
| Ph(2-Cl,4-F) | Ph(2-Cl,4-OCO₂Me) | Ph(2-Cl,4-OCH₂CH═CBr₂) |
| Ph(2-Cl,4-Br) | Ph(2-Cl,4-TMS) | Ph(2-Cl,4-SCF₂H) |
| Ph(2-Cl,4-I) | Ph(2-Cl,4-Ph) | Ph(2-Cl,4-SCF₂CF₂H) |
| Ph(2-Cl,4-Me) | Ph(2-Cl,4-CF₂CF₃) | Ph(2-F,4-Cl) |
| Ph(2,4-di-F) | Ph(2-F,4-OCO₂Me) | Ph(2-F,4-OCH₂CH═CBr₂) |
| Ph(2-F,4-Br) | Ph(2-F,4-TMS) | Ph(2-F,4-SCF₂H) |
| Ph(2-F,4-I) | Ph(2-F,4-Ph) | Ph(2-F,4-SCF₂CF₂H) |
| Ph(2-F,4-Me) | Ph(2-F,4-CF₂CF₃) | Ph(1H-pyrazol-1-yl) |
| Ph(2-F,4-Et) | Ph(2-F,4-CF₂CF₂H) | Ph(2H-1,2,3-triazol-2-yl) |
| Ph(2-F,4-n-Pr) | Ph(2-F,4-OCF₂CF₂H) | Ph(1H-imidazol-1-yl) |
| Ph(2-F,4-t-Bu) | Ph(2-F,4-OCF₂CF₃) | Ph[4-(3-pyridinyl)] |
| Ph(2-F,4-i-Pr) | Ph(2-F,4-OCH₂CF₃) | Ph[4-(4-pyridinyl)] |
| Ph(2-F,4-c-Pr) | Ph(2-F,4-OCH₂C≡CH) | Ph[4-(2-pyridinyl)] |
| Ph(2-F,4-cyclohexyl) | Ph(2-F,4-OCH₂C≡CCF₃) | 3-pyridinyl(5-CF₃) |
| Ph(2-F,4-CH═CH₂) | Ph(2-F,4-OCH₂C≡CCF₂H) | 3-Pyridinyl(5-Cl) |
| Ph(2-F,4-CF₃) | Ph(2-F,4-OCH₂C≡CCH₃) | 3-Pyridinyl(5-F) |
| Ph(2-F,4-CH₂CF₃) | Ph(2-F,4-OCH₂C≡C-c-Pr) | 3-Pyridinyl(5-OCF₂H) |
| Ph(2-F,4-CHF₂) | Ph(2-F,4-C≡CCF₂H) | 3-Pyridinyl(5-CF₂H) |
| Ph(2-F,4-CH₂F) | Ph(2-F,4-C≡CCH₃) | 3-Pyridinyl(5-F) |
| Ph(2-F,4-OCF₃) | Ph(2-F,4-C≡C-c-Pr) | 3-Pyridinyl(5-OCF₃) |
| Ph(2-F,4-OCH₂F) | Ph(2-F,4-OPh) | 3-Pyridinyl(5-Me) |
| Ph(2-F,4-OCH₂) | Ph(2-F,4-C≡CCF₃) | 3-Pyridinyl(5-Br) |
| Ph(2-F,4-SCF₃) | Ph(2-F,4-C≡CCF₂H) | 3-Pyridinyl |
| Ph(2-F,4-SMe) | Ph(2-F,4-C≡CCH₃) | 1H-Pyrazol-3-yl(1-Me) |
| Ph(2-F,4-SOMe) | Ph(2-F,4-C≡C—c-Pr) | 1H-Pyrazol-3-yl(1-CH₂CF₃) |
| Ph(2-F,4-SO₂Me) | Ph(2-F,4-CH═CF₂) | 1H-Pyrazol-3-yl(1-Me,4-F) |
| Ph(2-F,4-OSO₂Me) | Ph(2-F,4-CH═CCl₂) | 1H-Pyrazol-3-yl(1-Me,4-Cl) |
| Ph(2-F,4-C≡CH) | Ph(2-F,4-CH═CBr₂) | 1H-Imidazol-5-yl(1-Me) |
| Ph(2-F,4-OMe) | Ph(2-F,4-OCH═CH₂) | 1H-Imidazol-5-yl(1-CH₂CF₃) |
| Ph(2-F,4-OEt) | Ph(2-F,4-OCH═CF₂) | 1H-Imidazol-4-yl(1-Me) |
| Ph(2-F,4-NHCO₂-t-Bu) | Ph(2-F,4-OCH═CCl₂) | 1H-Imidazol-4-yl(1-CH₂CF₃) |
| Ph(2-F,4-NHCOMe) | Ph(2-F,4-OCH═CBr₂) | 3-Thienyl |
| Ph(2-F,4-NHCOCF₃) | Ph(2-F,4-CH₂CH═CH₂) | 3-Thienyl(5-F) |

TABLE 1-continued

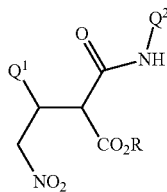

R is Me; $Q^2$ is Ph(2-F) and $Q^1$ is

| | | |
|---|---|---|
| Ph(2-F,4-CN) | Ph(2-F,4-CH$_2$CH=CF$_2$) | 3-Thienyl(5-Cl) |
| Ph(2-F,4-NO$_2$) | Ph(2-F,4-CH$_2$CH=CCl$_2$) | 3-Thienyl(5-CF$_3$) |
| Ph(2-F,4-Ph) | Ph(2-F,4-CH$_2$CH=CBr$_2$) | 3-Thienyl(4-Me) |
| Ph(2-F,4-COMe) | Ph(2-F,4-OCH$_2$CH=CH$_2$) | 3-Thienyl(4-Et) |
| Ph(2-F,4-OCOMe) | Ph(2-F,4-OCH$_2$CH=CF$_2$) | 3-Thienyl(4-i-Pr) |
| Ph(2-F,4-CO$_2$Me) | Ph(2-F,4-OCH$_2$CH=CCl$_2$) | 3-Thienyl(4-c-Pr) |
| 3-Thienyl(4-CF$_2$H) | Ph(3-Cl,4-TMS) | Ph(3-Br,4-CF$_2$CF$_3$) |
| 3-Thienyl(4-OCF$_2$H) | Ph(3-Cl,4-CN) | Ph(3-Br,4-CF$_2$CF$_2$H) |
| 3-Thienyl(4-OCF$_2$CF$_2$H) | Ph(3-F,4-Cl) | Ph(3-Br,4-CF$_2$H) |
| 3-Thienyl(4-OCF$_2$CF$_3$) | Ph(3,4-di-F) | Ph(3-Br,4-OMe) |
| 3-Furanyl(5-F) | Ph(3-F,4-Br) | Ph(3-Br,4-OCF$_3$) |
| 3-Furanyl(5-Cl) | Ph(3-F,4-I) | Ph(3-Br,4-OCHF$_2$) |
| 3-Furanyl(5-CF$_3$) | Ph(3-F,4-Me) | Ph(3-Br,4-OCF$_2$CF$_2$H) |
| 3-Furanyl(4-Me) | Ph(3-F,4-Et) | Ph(3-Br,4-OCF$_2$CF$_3$) |
| 3-Furanyl(4-Et) | Ph(3-F,4-n-Pr) | Ph(3-Br,4-SO$_2$Me) |
| 3-Furanyl(4-i-Pr) | Ph(3-F,4-t-Bu) | Ph(3-Br,4-TMS) |
| 3-Furanyl(4-c-Pr) | Ph(3-F,4-i-Pr) | Ph(3-Br,4-CN) |
| 3-Furanyl(4-CF$_2$H) | Ph(3-F,4-c-Pr) | Ph(3-I,4-Cl) |
| 3-Furanyl(4-OCF$_2$H) | Ph(3-F,4-CF$_3$) | Ph(3-I,4-F) |
| 3-Furanyl(4-OCF$_2$CF$_2$H) | Ph(3-F,4-CF$_2$CF$_3$) | Ph(3-I,4-Br) |
| 3-Furanyl(4-OCF$_2$CF$_3$) | Ph(3-F,4-CF$_2$CF$_2$H) | Ph(3,4-di-I) |
| Ph(3,4-di-Cl) | Ph(3-F,4-CF$_2$H) | Ph(3-I,4-Me) |
| Ph(3-Cl,4-F) | Ph(3-F,4-CF$_2$H) | Ph(3-I,4-Et) |
| Ph(3-Cl,4-Br) | Ph(3-F,4-OMe) | Ph(3-I,4-n-Pr) |
| Ph(3-Cl,4-I) | Ph(3-F,4-OCF$_3$) | Ph(3-I,4-t-Bu) |
| Ph(3-Cl,4-Me) | Ph(3-F,4-OCH$_2$) | Ph(3-I,4-i-Pr) |
| Ph(3-Cl,4-Et) | Ph(3-F,4-OCF$_2$CF$_2$H) | Ph(3-I,4-c-Pr) |
| Ph(3-Cl,4-n-Pr) | Ph(3-F,4-OCF$_2$CF$_3$) | Ph(3-I,4-CF$_3$) |
| Ph(3-Cl,4-t-Bu) | Ph(3-F,4-SO$_2$Me) | Ph(3-I,4-CF$_2$CF$_3$) |
| Ph(3-Cl,4-i-Pr) | Ph(3-F,4-TMS) | Ph(3-I,4-CF$_2$CF$_2$H) |
| Ph(3-Cl,4-c-Pr) | Ph(3-F,4-CN) | Ph(3-I,4-CF$_2$H) |
| Ph(3-Cl,4-CF$_3$) | Ph(3-Br,4-Cl) | Ph(3-I,4-OMe) |
| Ph(3-Cl,4-CF$_3$) | Ph(3-Br,4-F) | Ph(3-I,4-OCF$_3$) |
| Ph(3-Cl,4-CF$_2$CF$_2$H) | Ph(3,4-di-Br) | Ph(3-I,4-OCHF$_2$) |
| Ph(3-Cl,4-CF$_2$H) | Ph(3-Br,4-I) | Ph(3-I,4-OCF$_2$CF$_2$H) |
| Ph(3-Cl,4-OMe) | Ph(3-Br,4-Me) | Ph(3-I,4-OCF$_2$CF$_3$) |
| Ph(3-Cl,4-OCF$_3$) | Ph(3-Br,4-Et) | Ph(3-I,4-SO$_2$Me) |
| Ph(3-Cl,4-OCHF$_2$) | Ph(3-Br,4-n-Pr) | Ph(3-I,4-TMS) |
| Ph(3-Cl,4-OCF$_2$CF$_2$H) | Ph(3-Br,4-t-Bu) | Ph(3-I,4-CN) |
| Ph(3-Cl,4-OCF$_2$CF$_3$) | Ph(3-Br,4-i-Pr) | Ph(3-Me,4-Cl) |
| Ph(3-Cl,4-SO$_2$Me) | Ph(3-Br,4-c-Pr) | Ph(3-Me,4-F) |
| Ph(3-Me,4-Br) | Ph(3-Br,4-CF$_3$) | Ph(3-t-Bu,4-n-Pr) |
| Ph(3-Me,4-I) | Ph(3-Et,4-OCF$_3$) | Ph(3,4-di-t-Bu) |
| Ph(3,4-di-Me) | Ph(3-Et,4-OCHF$_2$) | Ph(3-t-Bu,4-i-Pr) |
| Ph(3-Me,4-Et) | Ph(3-Et,4-OCF$_2$CF$_2$H) | Ph(3-t-Bu,4-c-Pr) |
| Ph(3-Me,4-n-Pr) | Ph(3-Et,4-OCF$_2$CF$_3$) | Ph(3-t-Bu,4-CF$_3$) |
| Ph(3-Me,4-t-Bu) | Ph(3-Et,4-SO$_2$Me) | Ph(3-t-Bu,4-CF$_2$CF$_3$) |
| Ph(3-Me,4-i-Pr) | Ph(3-Et,4-TMS) | Ph(3-t-Bu,4-CF$_2$CF$_2$H) |
| Ph(3-Me,4-c-Pr) | Ph(3-Et,4-CN) | Ph(3-t-Bu,4-CF$_2$H) |
| Ph(3-Me,4-CF$_3$) | Ph(3-n-Pr,4-Cl) | Ph(3-t-Bu,4-OMe) |
| Ph(3-Me,4-CF$_2$CF$_3$) | Ph(3-n-Pr,4-F) | Ph(3-t-Bu,4-OCF$_3$) |
| Ph(3-Me,4-CF$_2$CF$_2$H) | Ph(3-n-Pr,4-Br) | Ph(3-t-Bu,4-OCHF$_2$) |
| Ph(3-Me,4-CF$_2$H) | Ph(3-n-Pr,4-I) | Ph(3-t-Bu,4-OCF$_2$CF$_2$H) |
| Ph(3-Me,4-OMe) | Ph(3-n-Pr,4-Me) | Ph(3-t-Bu,4-OCF$_2$CF$_3$) |
| Ph(3-Me,4-OCF$_3$) | Ph(3-n-Pr,4-Et) | Ph(3-t-Bu,4-SO$_2$Me) |
| Ph(3-Me,4-OCHF$_2$) | Ph(3,4-di-n-Pr) | Ph(3-t-Bu,4-TMS) |
| Ph(3-Me,4-OCF$_2$CF$_2$H) | Ph(3-n-Pr,4-t-Bu) | Ph(3-t-Bu,4-CN) |
| Ph(3-Me,4-OCF$_2$CF$_3$) | Ph(3-n-Pr,4-i-Pr) | Ph(3-i-Pr,4-Cl) |
| Ph(3-Me,4-SO$_2$Me) | Ph(3-n-Pr,4-c-Pr) | Ph(3-i-Pr,4-F) |
| Ph(3-Me,4-TMS) | Ph(3-n-Pr,4-CF$_3$) | Ph(3-i-Pr,4-Br) |
| Ph(3-Me,4-CN) | Ph(3-n-Pr,4-CF$_2$CF$_3$) | Ph(3-i-Pr,4-I) |
| Ph(3-Et,4-Cl) | Ph(3-n-Pr,4-CF$_2$CF$_2$H) | Ph(3-i-Pr,4-Me) |
| Ph(3-Et,4-F) | Ph(3-n-Pr,4-CF$_2$H) | Ph(3-i-Pr,4-Ei) |
| Ph(3-Et,4-Br) | Ph(3-n-Pr,4-OMe) | Ph(3-i-Pr,4-n-Pr) |
| Ph(3-Et,4-I) | Ph(3-n-Pr,4-OCF$_3$) | Ph(3-i-Pr,4-t-Bu) |
| Ph(3-Et,4-Me) | Ph(3-n-Pr,4-OCHF$_2$) | Ph(3,4-di-i-Pr) |
| Ph(3,4-di-Et) | Ph(3-n-Pr,4-OCF$_2$CF$_2$H) | Ph(3-i-Pr,4-c-Pr) |
| Ph(3-Et,4-n-Pr) | Ph(3-n-Pr,4-OCF$_2$CF$_3$) | Ph(3-i-Pr,4-CF$_3$) |
| Ph(3-Et,4-t-Bu) | Ph(3-n-Pr,4-SO$_2$Me) | Ph(3-i-Pr,4-CF$_2$CF$_3$) |
| | Ph(3-n-Pr,4-TMS) | |

TABLE 1-continued

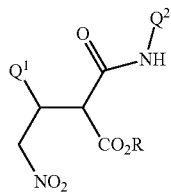

R is Me; $Q^2$ is Ph(2-F) and $Q^1$ is

| | | |
|---|---|---|
| Ph(3-Et,4-i-Pr) | Ph(3-n-Pr,4-CN) | Ph(3-i-Pr,4-$CF_2CF_2H$) |
| Ph(3-Et,4-c-Pr) | Ph(3-t-Bu,4-Cl) | Ph(3-i-Pr,4-$CF_2H$) |
| Ph(3-Et,4-$CF_3$) | Ph(3-t-Bu,4-F) | Ph(3-i-Pr,4-OMe) |
| Ph(3-Et,4-$CF_2CF_3$) | Ph(3-t-Bu,4-Br) | Ph(3-i-Pr,4-$OCF_3$) |
| Ph(3-Et,4-$CF_2CF_2H$) | Ph(3-t-Bu,4-I) | Ph(3-i-Pr,4-$OCHF_2$) |
| Ph(3-Et,4-$CF_2H$) | Ph(3-t-Bu,4-Me) | Ph(3-i-Pr,4-$OCF_2CF_2H$) |
| Ph(3-Et,4-OMe) | Ph(3-t-Bu,4-Et) | Ph(3-i-Pr,4-$OCF_2CF_3$) |
| Ph(3-i-Pr,4-$SO_2Me$) | Ph(3,4-di-$CF_3$) | Ph(3-$CF_2CF_2H$,4-F) |
| Ph(3-i-Pr,4-TMS) | Ph(3-$CF_3$,4-$CF_2CF_3$) | Ph(3-$CF_2CF_2H$,4-Br) |
| Ph(3-i-Pr,4-CN) | Ph(3-$CF_3$,4-$CF_2CF_2H$) | Ph(3-$CF_2CF_2H$,4-I) |
| Ph(3-c-Pr,4-Cl) | Ph(3-$CF_3$,4-$CF_2H$) | Ph(3-$CF_2CF_2H$,4-Me) |
| Ph(3-c-Pr,4-F) | Ph(3-$CF_3$,4-OMe) | Ph(3-$CF_2CF_2H$,4-Ei) |
| Ph(3-c-Pr,4-Br) | Ph(3-$CF_3$,4-$OCF_3$) | Ph(3-$CF_2CF_2H$,4-n-Pr) |
| Ph(3-c-Pr,4-I) | Ph(3-$CF_3$,4-$OCHF_2$) | Ph(3-$CF_2CF_2H$,4-t-Bu) |
| Ph(3-c-Pr,4-Me) | Ph(3-$CF_3$,4-$OCF_2CF_2H$) | Ph(3-$CF_2CF_2H$,4-i-Pr) |
| Ph(3-c-Pr,4-Ei) | Ph(3-$CF_3$,4-$OCF_2CF_3$) | Ph(3-$CF_2CF_2H$,4-c-Pr) |
| Ph(3-c-Pr,4-n-Pr) | Ph(3-$CF_3$,4-$SO_2Me$) | Ph(3-$CF_2CF_2HCF_3$,4-$CF_3$) |
| Ph(3-c-Pr,4-t-Bu) | Ph(3-$CF_3$,4-IMS) | Ph(3-$CF_2CF_2H$,4-$CF_2CF_3$) |
| Ph(3-c-Pr,4-i-Pr) | Ph(3-$CF_3$,4-CN) | Ph(3,4-di-$CF_2CF_2H$) |
| Ph(3,4-di-c-Pr) | Ph(3-$CF_2CF_3$,4-Cl) | Ph(3-$CF_2CF_2H$,4-$CF_2H$) |
| Ph(3-c-Pr,4-$CF_3$) | Ph(3-$CF_2CF_3$,4-F) | Ph(3-$CF_2CF_2H$,4-OMe) |
| Ph(3-c-Pr,4-$CF_2CF_3$) | Ph(3-$CF_2CF_3$,4-Br) | Ph(3-$CF_2CF_2H$,4-$OCF_3$) |
| Ph(3-c-Pr,4-$CF_2CF_2H$) | Ph(3-$CF_2CF_3$,4-I) | Ph(3-$CF_2CF_2H$,4-$OCHF_2$) |
| Ph(3-c-Pr,4-$CF_2H$) | Ph(3-$CF_2CF_3$,4-Me) | Ph(3-$CF_2CF_2H$,4-$OCF_2CF_2H$) |
| Ph(3-c-Pr,4-OMe) | Ph(3-$CF_2CF_3$,4-Ei) | Ph(3-$CF_2CF_2H$,4-$OCF_2CF_3$) |
| Ph(3-c-Pr,4-$OCF_3$) | Ph(3-$CF_2CF_3$,4-n-Pr) | Ph(3-$CF_2CF_2H$,4-$SO_2Me$) |
| Ph(3-c-Pr,4-$OCHF_2$) | Ph(3-$CF_2CF_3$,4-t-Bu) | Ph(3-$CF_2CF_2H$,4-TMS) |
| Ph(3-c-Pr,4-$OCF_2CF_2H$) | Ph(3-$CF_2CF_3$,4-i-Pr) | Ph(3-$CF_2CF_2H$,4-CN) |
| Ph(3-c-Pr,4-$OCF_2CF_3$) | Ph(3-$CF_2CF_3$,4-c-Pr) | Ph(3-$CF_2H$,4-Cl) |
| Ph(3-c-Pr,4-$SO_2Me$) | Ph(3-$CF_2CF_3CF_3$,4-$CF_3$) | Ph(3-$CF_2H$,4-F) |
| Ph(3-c-Pr,4-TMS) | Ph(3,4-di-$CF_2CF_3$) | Ph(3-$CF_2H$,4-Br) |
| Ph(3-c-Pr,4-CN) | Ph(3-$CF_2CF_3$,4-$CF_2CF_2H$) | Ph(3-$CF_2H$,4-I) |
| Ph(3-CF3,4-Cl) | Ph(3-$CF_2CF_3$,4-$CF_2H$) | Ph(3-$CF_2H$,4-Me) |
| Ph(3-CF3,4-F) | Ph(3-$CF_2CF_3$,4-OMe) | Ph(3-$CF_2H$,4-Ei) |
| Ph(3-CF3,4-Br) | Ph(3-$CF_2CF_3$,4-$OCF_3$) | Ph(3-$CF_2H$,4-n-Pr) |
| Ph(3-CF3,4-I) | Ph(3-$CF_2CF_3$,4-$OCHF_2$) | Ph(3-$CF_2H$,4-t-Bu) |
| Ph(3-CF3,4-Me) | Ph(3-$CF_2CF_3$,4-$OCF_2CF_2H$) | Ph(3-$CF_2H$,4-i-Pr) |
| Ph(3-CF3,4-Et) | Ph(3-$CF_2CF_3$,4-$OCF_2CF_3$) | Ph(3-$CF_2H$,4-c-Pr) |
| Ph(3-CF3,4-n-Pr) | Ph(3-$CF_2CF_3$,4-$SO_2Me$) | Ph(3-$CF_2H$,4-$CF_3$) |
| Ph(3-CF3,4-t-Bu) | Ph(3-$CF_2CF_3$,4-TMS) | Ph(3-$CF_2H$,4-$CF_2CF_3$) |
| Ph(3-CF3,4-i-Pr) | Ph(3-$CF_2CF_3$,4-CN) | Ph(3-$CF_2H$,4-$CF_2CF_2H$) |
| Ph(3-CF3,4-c-Pr) | Ph(3-$CF_2CF_2H$,4-Cl) | Ph(3,4-di-$CF_2H$) |
| Ph(3-$CF_2H$,4-OMe) | Ph(3-$OCF_3$,4-Ei) | Ph(3-$OCHF_2$,4-$OCF_2CF_3$) |
| Ph(3-$CF_2H$,4-$OCF_3$) | Ph(3-$OCF_3$,4-n-Pr) | Ph(3-$OCHF_2$,4-$SO_2Me$) |
| Ph(3-$CF_2H$,4-$OCHF_2$) | Ph(3-$OCF_3$,4-t-Bu) | Ph(3-$OCHF_2$,4-TMS) |
| Ph(3-$CF_2H$,4-$OCF_2CF_2H$) | Ph(3-$OCF_3$,4-i-Pr) | Ph(3-$OCHF_2$,4-CN) |
| Ph(3-$CF_2H$,4-$OCF_2CF_3$) | Ph(3-$OCF_3$,4-c-Pr) | Ph(3-$OCF_2CF_2H$,4-Cl) |
| Ph(3-$CF_2H$,4-$SO_2Me$) | Ph(3-$OCF_3$,4-$CF_3$) | Ph(3-$OCF_2CF_2H$,4-F) |
| Ph(3-$CF_2H$,4-TMS) | Ph(3-$OCF_3$,4-$CF_3$) | Ph(3-$OCF_2CF_2H$,4-Br) |
| Ph(3-$CF_2H$,4-CN) | Ph(3-$OCF_3$,4-$CF_2CF_2H$) | Ph(3-$OCF_2CF_2H$,4-I) |
| Ph(3-OMe,4-Cl) | Ph(3-$OCF_3$,4-$CF_2H$) | Ph(3-$OCF_2CF_2H$,4-Me) |
| Ph(3-OMe,4-F) | Ph(3-$OCF_3$,4-OMe) | Ph(3-$OCF_2CF_2H$,4-Ei) |
| Ph(3-OMe,4-Br) | Ph(3,4-di-$OCF_3$) | Ph(3-$OCF_2CF_2H$,4-n-Pr) |
| Ph(3-OMe,4-I) | Ph(3-$OCF_3$,4-$OCHF_2$) | Ph(3-$OCF_2CF_2H$,4-t-Bu) |
| Ph(3-OMe,4-Me) | Ph(3-$OCF_3$,4-$OCF_2CF_2H$) | Ph(3-$OCF_2CF_2H$,4-i-Pr) |
| Ph(3-OMe,4-Ei) | Ph(3-$OCF_3$,4-$OCF_2CF_3$) | Ph(3-$OCF_2CF_2H$,4-c-Pr) |
| Ph(3-OMe,4-n-Pr) | Ph(3-$OCF_3$,4-$SO_2Me$) | Ph(3-$OCF_2CF_2HCF_3$,4-$CF_3$) |
| Ph(3-OMe,4-t-Bu) | Ph(3-$OCF_3$,4-TMS) | Ph(3-$OCF_2CF_2H$,4-$CF_2CF_3$) |
| Ph(3-OMe,4-i-Pr) | Ph(3-$OCF_3$,4-CN) | Ph(3-$OCF_2CF_2H$,4-$CF_2CF_2H$) |
| Ph(3-OMe,4-c-Pr) | Ph(3-$OCHF_2$,4-Cl) | Ph(3-$OCF_2CF_2H$,4-$CF_2H$) |
| Ph(3-OMe$CF_3$,4-$CF_3$) | Ph(3-$OCHF_2$,4-F) | Ph(3-$OCF_2CF_2H$,4-OMe) |
| Ph(3-OMe,4-$CF_2CF_3$) | Ph(3-$OCHF_2$,4-Br) | Ph(3-$OCF_2CF_2H$,4-$OCF_3$) |
| Ph(3-OMe,4-$CF_2CF_2H$) | Ph(3-$OCHF_2$,4-I) | Ph(3-$OCF_2CF_2H$,4-$OCHF_2$) |
| Ph(3-OMe,4-$CF_2H$) | Ph(3-$OCHF_2$,4-Me) | Ph(3,4-di-$OCF_2CF_2H$) |
| Ph(3,4-di-OMe) | Ph(3-$OCHF_2$,4-Ei) | Ph(3-$OCF_2CF_2H$,4-$OCF_2CF_3$) |
| Ph(3-OMe,4-$OCF_3$) | Ph(3-$OCHF_2$,4-n-Pr) | Ph(3-$OCF_2CF_2H$,4-$SO_2Me$) |
| Ph(3-OMe,4-$OCHF_2$) | Ph(3-$OCHF_2$,4-t-Bu) | Ph(3-$OCF_2CF_2H$,4-TMS) |
| Ph(3-OMe,4-$OCF_2CF_2H$) | Ph(3-$OCHF_2$,4-i-Pr) | Ph(3-$OCF_2CF_2H$,4-CN) |
| Ph(3-OMe,4-$OCF_2CF_3$) | Ph(3-$OCHF_2$,4-c-Pr) | Ph(3-$OCF_2CF_3$,4-Cl) |

TABLE 1-continued

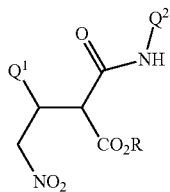

R is Me; $Q^2$ is Ph(2-F) and $Q^1$ is

| | | |
|---|---|---|
| Ph(3-OMe,4-SO$_2$Me) | Ph(3-OCHF$_2$CF$_3$,4-CF$_3$) | Ph(3-OCF$_2$CF$_3$,4-F) |
| Ph(3-OMe,4-TMS) | Ph(3-OCF$_2$CF$_3$,4-CF$_2$CF$_3$) | Ph(3-OCF$_2$CF$_3$,4-Br) |
| Ph(3-OMe,4-CN) | Ph(3-OCHF$_2$,4-CF$_2$CF$_2$H) | Ph(3-OCF$_2$CF$_3$,4-I) |
| Ph(3-OCF$_3$,4-Cl) | Ph(3-OCHF$_2$,4-CF$_2$H) | Ph(3-OCF$_2$CF$_3$,4-Me) |
| Ph(3-OCF$_3$,4-F) | Ph(3-OCHF$_2$,4-OMe) | Ph(3-OCF$_2$CF$_3$,4-Ei) |
| Ph(3-OCF$_3$,4-Br) | Ph(3-OCHF$_2$,4-OCF$_3$) | Ph(3-OCF$_2$CF$_3$,4-n-Pr) |
| Ph(3-OCF$_3$,4-I) | Ph(3,4-di-OCHF$_2$) | Ph(3-OCF$_2$CF$_3$,4-t-Bu) |
| Ph(3-OCF$_3$,4-Me) | Ph(3-OCHF$_2$,4-OCF$_2$CF$_2$H) | Ph(3-OCF$_2$CF$_3$,4-i-Pr) |
| Ph(3-OCF$_2$CF$_3$,4-c-Pr) | Ph(3-TMS,4-Cl) | Ph(3-CN,4-CF$_2$H) |
| Ph(3-OCF$_2$CF$_3$CF$_3$,4-CF$_3$) | Ph(3-TMS,4-F) | Ph(3-CN,4-OMe) |
| Ph(3-OCF$_2$CF$_3$,4-CF$_2$CF$_3$) | Ph(3-TMS,4-Br) | Ph(3-CN,4-OCF$_3$) |
| Ph(3-Ph-3-OCF$_2$CF$_3$,4-CF$_2$CF$_2$H) | Ph(3-TMS,4-I) | Ph(3-CN,4-OCHF$_2$) |
| Ph(3-OCF$_2$CF$_3$,4-CF$_2$H) | Ph(3-TMS,4-Me) | Ph(3-CN,4-OCHF$_2$CF$_2$H) |
| Ph(3-OCF$_2$CF$_3$,4-OMe) | Ph(3-TMS,4-Ei) | Ph(3-CN,4-OCF$_2$CF$_3$) |
| Ph(3-OCF$_2$CF$_3$,4-OCF$_3$) | Ph(3-TMS,4-n-Pr) | Ph(3-CN,4-SO$_2$Me) |
| Ph(3-OCF$_2$CF$_3$,4-OCHF$_2$) | Ph(3-TMS,4-t-Bu) | Ph(3-CN,4-TMS) |
| Ph(3-OCF$_2$CF$_3$,4-OCF$_2$CF$_2$H) | Ph(3-TMS,4-i-Pr) | Ph(3,4-di-CN) |
| Ph(3,4-di-OCF$_2$CF$_3$) | Ph(3-TMS,4-c-Pr) | Ph(3,5-di-Cl) |
| Ph(3-OCF$_2$CF$_3$,4-SO$_2$Me) | Ph(3-TMS,4-CF$_3$) | Ph(3-Cl,5-F) |
| Ph(3-OCF$_2$CF$_3$,4-TMS) | Ph(3-TMS,4-CF$_2$CF$_3$) | Ph(3-Cl,5-Br) |
| Ph(3-OCF$_2$CF$_3$,4-CN) | Ph(3-TMS,4-CF$_2$CF$_2$H) | Ph(3-Cl,5-I) |
| Ph(3-SO$_2$Me,4-Cl) | Ph(3-TMS,4-CF$_2$H) | Ph(3-Cl,5-Me) |
| Ph(3-SO$_2$Me,4-F) | Ph(3-TMS,4-OMe) | Ph(3-Cl,5-Et) |
| Ph(3-SO$_2$Me,4-Br) | Ph(3-TMS,4-OCF$_3$) | Ph(3-Cl,5-n-Pr) |
| Ph(3-SO$_2$Me,4-I) | Ph(3-TMS,4-OCHF$_2$) | Ph(3-Cl,5-t-Bu) |
| Ph(3-SO$_2$Me,4-Me) | Ph(3-TMS,4-OCF$_2$CF$_2$H) | Ph(3-Cl,5-i-Pr) |
| Ph(3-SO$_2$Me,4-Ei) | Ph(3-TMS,4-OCF$_2$CF$_3$) | Ph(3-Cl,5-c-Pr) |
| Ph(3-SO$_2$Me,4-n-Pr) | Ph(3-TMS,4-SO$_2$Me) | Ph(3-Cl,5-CF$_3$) |
| Ph(3-SO$_2$Me,4-t-Bu) | Ph(3,4-di-TMS) | Ph(3-Cl,5-CF$_2$CF$_3$) |
| Ph(3-SO$_2$Me,4-i-Pr) | Ph(3-TMS,4-CN) | Ph(3-Cl,5-CF$_2$CF$_2$H) |
| Ph(3-SO$_2$Me,4-c-Pr) | Ph(3-CN,4-Cl) | Ph(3-Cl,5-CF$_2$H) |
| Ph(3-SO$_2$MeCF$_3$,4-CF$_3$) | Ph(3-CN,4-F) | Ph(3-Cl,5-OMe) |
| Ph(3-SO$_2$Me,4-CF$_2$CF$_3$) | Ph(3-CN,4-Br) | Ph(3-Cl,5-OCF$_3$) |
| Ph(3-SO$_2$Me,4-CF$_2$CF$_2$H) | Ph(3-CN,4-I) | Ph(3-Cl,5-OCHF$_2$) |
| Ph(3-SO$_2$Me,4-CF$_2$H) | Ph(3-CN,4-Me) | Ph(3-Cl,5-OCF$_2$CF$_2$H) |
| Ph(3-SO$_2$Me,4-OMe) | Ph(3-CN,4-Ei) | Ph(3-Cl,5-OCF$_2$CF$_3$) |
| Ph(3-SO$_2$Me,4-OCF$_3$) | Ph(3-CN,4-n-Pr) | Ph(3-Cl,5-SO$_2$Me) |
| Ph(3-SO$_2$Me,4-OCHF$_2$) | Ph(3-CN,4-t-Bu) | Ph(3-Cl,5-TMS) |
| Ph(3-SO$_2$Me,4-OCF$_2$CF$_2$H) | Ph(3-CN,4-i-Pr) | Ph(3-Cl,5-CN) |
| Ph(3-SO$_2$Me,4-OCF$_2$CF$_3$) | Ph(3-CN,4-c-Pr) | Ph(3-F,5-Cl) |
| Ph(3,4-di-SO$_2$Me) | Ph(3-CN,4-CF$_3$) | Ph(3,5-di-F) |
| Ph(3-SO$_2$Me,4-TMS) | Ph(3-CN,4-CF$_2$CF$_3$) | Ph(3-F,5-Br) |
| Ph(3-SO$_2$Me,4-CN) | Ph(3-CN,4-CF$_2$CF$_3$) | Ph(3-F,5-I) |
| Ph(3-F,5-Me) | Ph(3-Br,5-OCF$_2$CF$_2$H) | Ph(3-Me,5-i-Pr) |
| Ph(3-F,5-Et) | Ph(3-Br,5-OCF$_2$CF$_3$) | Ph(3-Me,5-c-Pr) |
| Ph(3-F,5-n-Pr) | Ph(3-Br,5-SO$_2$Me) | Ph(3-Me,5-CF$_3$) |
| Ph(3-F,5-t-Bu) | Ph(3-Br,5-TMS) | Ph(3-Me,5-CF$_2$CF$_3$) |
| Ph(3-F,5-i-Pr) | Ph(3-Br,5-CN) | Ph(3-Me,5-CF$_2$CF$_2$H) |
| Ph(3-F,5-c-Pr) | Ph(3-I,5-Cl) | Ph(3-Me,5-CF$_2$H) |
| Ph(3-F,5-CF$_3$) | Ph(3-I,5-F) | Ph(3-Me,5-OMe) |
| Ph(3-F,5-CF$_2$CF$_3$) | Ph(3-I,5-Br) | Ph(3-Me,5-OCF$_3$) |
| Ph(3-F,5-CF$_2$CF$_2$H) | Ph(3,5-di-I) | Ph(3-Me,5-OCHF$_2$) |
| Ph(3-F,5-CF$_2$H) | Ph(3-I,5-Me) | Ph(3-Me,5-OCF$_2$CF$_2$H) |
| Ph(3-F,5-OMe) | Ph(3-I,5-Et) | Ph(3-Me,5-OCF$_2$CF$_3$) |
| Ph(3-F,5-OCF$_3$) | Ph(3-I,5-n-Pr) | Ph(3-Me,5-SO$_2$Me) |
| Ph(3-F,5-OCHF$_2$) | Ph(3-I,5-t-Bu) | Ph(3-Me,5-TMS) |
| Ph(3-F,5-OCF$_2$CF$_2$H) | Ph(3-I,5-i-Pr) | Ph(3-Me,5-CN) |
| Ph(3-F,5-OCF$_2$CF$_3$) | Ph(3-I,5-c-Pr) | Ph(3-Et,5-Cl) |
| Ph(3-F,5-SO$_2$Me) | Ph(3-I,5-CF$_3$) | Ph(3-Et,5-F) |
| Ph(3-F,5-TMS) | Ph(3-I,5-CF$_2$CF$_3$) | Ph(3-Et,5-Br) |
| Ph(3-F,5-CN) | Ph(3-I,5-CF$_2$CF$_2$H) | Ph(3-Et,5-I) |
| Ph(3-Br,5-Cl) | Ph(3-I,5-CF$_2$H) | Ph(3-Et,5-Me) |
| Ph(3-Br,5-F) | Ph(3-I,5-OMe) | Ph(3,5-di-Et) |
| Ph(3,5-di-Br) | Ph(3-I,5-OCF$_3$) | Ph(3-Et,5-n-Pr) |
| Ph(3-Br,5-I) | Ph(3-I,5-OCHF$_2$) | Ph(3-Et,5-t-Bu) |
| Ph(3-Br,5-Me) | Ph(3-I,5-OCF$_2$CF$_2$H) | Ph(3-Et,5-i-Pr) |
| Ph(3-Br,5-Et) | Ph(3-I,5OOCF$_2$CF$_3$) | Ph(3-Et,5-c-Pr) |
| Ph(3-Br,5-n-Pr) | Ph(3-I,5-SO$_2$Me) | Ph(3-Et,5-CF$_3$) |
| Ph(3-Br,5-t-Bu) | Ph(3-I,5-TMS) | Ph(3-Et,5-CF$_2$CF$_3$) |

TABLE 1-continued

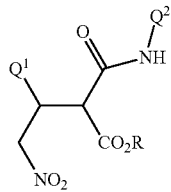

R is Me; Q² is Ph(2-F) and Q¹ is

| | | |
|---|---|---|
| Ph(3-Br,5-i-Pr) | Ph(3-I,5-CN) | Ph(3-Et,5-CF₂CF₂H) |
| Ph(3-Br,5-c-Pr) | Ph(3-Me,5-Cl) | Ph(3-Et,5-CF₂H) |
| Ph(3-Br,5-CF₃) | Ph(3-Me,5-F) | Ph(3-Et,5-OMe) |
| Ph(3-Br,5-CF₂CF₃) | Ph(3-Me,5-Br) | Ph(3-Et,5-OCF) |
| Ph(3-Br,5-CF₂CF₂H) | Ph(3-Me,5-I) | Ph(3-Et,5-OCHF₂) |
| Ph(3-Br,5-CF₂H) | Ph(3,5-di-Me) | Ph(3-Et,5-OCF₂CF₂H) |
| Ph(3-Br,5-OMe) | Ph(3-Me,5-Et) | Ph(3-Et,5-OCF₂CF₃) |
| Ph(3-Br,5-OCF₃) | Ph(3-Me,5-n-Pr) | Ph(3-Et,5-SO₂Me) |
| Ph(3-Br,5-OCHF₂) | Ph(3-Me,5-t-Bu) | Ph(3-Et,5-TMS) |
| Ph(3-Et,5-CN) | Ph(3-t-Bu,5-CF₂CF₂H) | Ph(3-c-Pr,5-I) |
| Ph(3-n-Pr,5-Cl) | Ph(3-t-Bu,5-CF₂H) | Ph(3-c-Pr,5-Me) |
| Ph(3-n-Pr,5-F) | Ph(3-t-Bu,5-OMe) | Ph(3-c-Pr,5-Ei) |
| Ph(3-n-Pr,5-Br) | Ph(3-t-Bu,5-OCF₃) | Ph(3-c-Pr,5-n-Pr) |
| Ph(3-n-Pr,5-I) | Ph(3-t-Bu,5-OCHF₂) | Ph(3-c-Pr,5-t-Bu) |
| Ph(3-n-Pr,5-Me) | Ph(3-t-Bu,5-OCF₂CF₃H) | Ph(3-c-Pr,5-i-Pr) |
| Ph(3-n-Pr,5-Et) | Ph(3-t-Bu,5-OCF₂CF₃) | Ph(3,5-di-c-Pr) |
| Ph(3,5-di-n-Pr) | Ph(3-t-Bu,5-SO₂Me) | Ph(3-c-Pr,5-CF₃) |
| Ph(3-n-Pr,5-t-Bu) | Ph(3-t-Bu,5-TMS) | Ph(3-c-Pr,5-CF₂CF₃) |
| Ph(3-n-Pr,5-i-Pr) | Ph(3-t-Bu,5-CN) | Ph(3-c-Pr,5-CF₂CF₂H) |
| Ph(3-n-Pr,5-c-Pr) | Ph(3-i-Pr,5-Cl) | Ph(3-c-Pr,5-CF₂H) |
| Ph(3-n-Pr,5-CF₃) | Ph(3-i-Pr,5-F) | Ph(3-c-Pr,5-OMe) |
| Ph(3-n-Pr,5-CF₂CF₃) | Ph(3-i-Pr,5-Br) | Ph(3-c-Pr,5-OCF₃) |
| Ph(3-n-Pr,5-CF₂CF₂H) | Ph(3-i-Pr,5-I) | Ph(3-c-Pr,5-OCHF₂) |
| Ph(3-n-Pr,5-CF₂H) | Ph(3-i-Pr,5-Me) | Ph(3-c-Pr,5-OCF₂CF₃H) |
| Ph(3-n-Pr,5-OMe) | Ph(3-i-Pr,5-Ei) | Ph(3-c-Pr,5-OCF₂CF₃) |
| Ph(3-n-Pr,5-OCF₃) | Ph(3-i-Pr,5-n-Pr) | Ph(3-c-Pr,5-SO₂Me) |
| Ph(3-n-Pr,5-OCHF₂) | Ph(3-i-Pr,5-t-Bu) | Ph(3-c-Pr,5-TMS) |
| Ph(3-n-Pr,5-OCF₂CF₂H) | Ph(3,5-di-i-Pr) | Ph(3-c-Pr,5-CN) |
| Ph(3-n-Pr,5-OCF₂CF₃) | Ph(3-i-Pr,5-c-Pr) | Ph(3-CF₃,5-Cl) |
| Ph(3-n-Pr,5-SO₂Me) | Ph(3-i-Pr,5-CF₃) | Ph(3-CF₃,5-F) |
| Ph(3-n-Pr,5-TMS) | Ph(3-i-Pr,5-CF₂CF₃) | Ph(3-CF₃,5-Br) |
| Ph(3-n-Pr,5-CN) | Ph(3-i-Pr,5-CF₂CF₂H) | Ph(3-CF₃,5-I) |
| Ph(3-t-Bu,5-Cl) | Ph(3-i-Pr,5-CF₂H) | Ph(3-CF₃,5-Me) |
| Ph(3-t-Bu,5-F) | Ph(3-i-Pr,5-OMe) | Ph(3-CF₃,5-Ei) |
| Ph(3-t-Bu,5-Br) | Ph(3-i-Pr,5-OCF₃) | Ph(3-CF₃,5-n-Pr) |
| Ph(3-t-Bu,5-I) | Ph(3-i-Pr,5-OCHF₂) | Ph(3-CF₃,5-t-Bu) |
| Ph(3-t-Bu,5-Me) | Ph(3-i-Pr,5-OCF₂CF₂H) | Ph(3-CF₃,5-i-Pr) |
| Ph(3-t-Bu,5-Et) | Ph(3-i-Pr,5-OCF₂CF₃) | Ph(3-CF₃,5-c-Pr) |
| Ph(3-t-Bu,5-n-Pr) | Ph(3-i-Pr,5-SO₂Me) | Ph(3,5-di-CF₃) |
| Ph(3,5-di-t-Bu) | Ph(3-i-Pr,5-TMS) | Ph(3-CF₃,5-CF₂CF₃) |
| Ph(3-t-Bu,5-i-Pr) | Ph(3-i-Pr,5-CN) | Ph(3-CF₃,5-CF₂CF₂H) |
| Ph(3-t-Bu,5-c-Pr) | Ph(3-c-Pr,5-Cl) | Ph(3-CF₃,5-CF₂H) |
| Ph(3-t-Bu,5-CF₃) | Ph(3-c-Pr,5-F) | Ph(3-CF₃,5-OMe) |
| Ph(3-t-Bu,5-CF₂CF₃) | Ph(3-c-Pr,5-Br) | Ph(3-CF₃,5-OCF₃) |
| Ph(3-CF₃,5-OCHF₂) | Ph(3-CF₂CF₂H,5-t-Bu) | Ph(3-CF₂H,5-TMS) |
| Ph(3-CF₃,5-OCF₂CF₂H) | Ph(3-CF₂CF₂H,5-i-Pr) | Ph(3-CF₂H,5-CN) |
| Ph(3-CF₃,5-OCF₂CF₃) | Ph(3-CF₂CF₂H,5-c-Pr) | Ph(3-OMe,5-Cl) |
| Ph(3-CF₃,5-SO₂Me) | Ph(3-CF₂CF₂HCF₃,5-CF₃) | Ph(3-OMe,5-F) |
| Ph(3-CF₃,5-IMS) | Ph(3-CF₂CF₂H,5-CF₂CF₃) | Ph(3-OMe,5-Br) |
| Ph(3-CF₃,5-CN) | Ph(3,5-di-CF₂CF₂H) | Ph(3-OMe,5-I) |
| Ph(3-CF₂CF₃,5-Cl) | Ph(3-CF₂CF₂H,5-CF₂H) | Ph(3-OMe,5-Me) |
| Ph(3-CF₂CF₃,5-F) | Ph(3-CF₂CF₂H,5-OMe) | Ph(3-OMe,5-Ei) |
| Ph(3-CF₂CF₃,5-Br) | Ph(3-CF₂CF₂H,5-OCF₃) | Ph(3-OMe,5-n-Pr) |
| Ph(3-CF₂CF₃,5-I) | Ph(3-CF₂CF₂H,5-OCHF₂) | Ph(3-OMe,5-t-Bu) |
| Ph(3-CF₂CF₃,5-Me) | Ph(3-CF₂CF₂H,5-OCF₂CF₂H) | Ph(3-OMe,5-i-Pr) |
| Ph(3-CF₂CF₃,5-Ei) | Ph(3-CF₂CF₂H,5-OCF₂CF₃) | Ph(3-OMe,5-c-Pr) |
| Ph(3-CF₂CF₃,5-n-Pr) | Ph(3-CF₂CF₂H,5-SO₂Me) | Ph(3-OMeCF₃,5-CF₃) |
| Ph(3-CF₂CF₃,5-t-Bu) | Ph(3-CF₂CF₂H,5-TMS) | Ph(3-OMe,5-CF₂CF₃) |
| Ph(3-CF₂CF₃,5-i-Pr) | Ph(3-CF₂CF₂H,5-CN) | Ph(3-OMe,5-CF₂CF₂H) |
| Ph(3-CF₂CF₃,5-c-Pr) | Ph(3-CF₂H,5-Cl) | Ph(3-OMe,5-CF₂H) |
| Ph(3-CF₂CF₃CF₃,5-CF₃) | Ph(3-CF₂H,5-F) | Ph(3,5-di-OMe) |
| Ph(3,5-di-CF₂CF₃) | Ph(3-CF₂H,5-Br) | Ph(3-OMe,5-OCF₃) |
| Ph(3-CF₂CF₃,5-CF₂CF₂H) | Ph(3-CF₂H,5-I) | Ph(3-OMe,5-OCHF₂) |
| Ph(3-CF₂CF₃,5-CF₂H) | Ph(3-CF₂H,5-Me) | Ph(3-OMe,5-OCF₂CF₂H) |
| Ph(3-CF₂CF₃,5-OMe) | Ph(3-CF₂H,5-Ei) | Ph(3-OMe,5-OCF₂CF₃) |
| Ph(3-CF₂CF₃,5-OCF₃) | Ph(3-CF₂H,5-n-Pr) | Ph(3-OMe,5-SO₂Me) |
| Ph(3-CF₂CF₃,5-OCHF₂) | Ph(3-CF₂H,5-t-Bu) | Ph(3-OMe,5-TMS) |
| Ph(3-CF₂CF₃,5-OCF₂CF₂H) | Ph(3-CF₂H,5-i-Pr) | Ph(3-OMe,5-CN) |
| Ph(3-CF₂CF₃,5-OCF₂CF₃) | Ph(3-CF₂H,5-c-Pr) | Ph(3-OCF₃,5-Cl) |

TABLE 1-continued

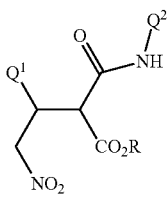

R is Me; Q² is Ph(2-F) and Q¹ is

| | | |
|---|---|---|
| Ph(3-CF$_2$CF$_3$,5-SO$_2$Me) | Ph(3-CF$_2$H,5-CF$_3$) | Ph(3-OCF$_3$,5-F) |
| Ph(3-CF$_2$CF$_3$,5-TMS) | Ph(3-CF$_2$H,5-CF$_2$CF$_3$) | Ph(3-OCF$_3$,5-Br) |
| Ph(3-CF$_2$CF$_3$,5-CN) | Ph(3-CF$_2$H,5-CF$_2$CF$_2$H) | Ph(3-OCF$_3$,5-I) |
| Ph(3-CF$_2$CF$_2$H,5-Cl) | Ph(3,5-di-CF$_2$H) | Ph(3-OCF$_3$,5-Me) |
| Ph(3-CF$_2$CF$_2$H,5-F) | Ph(3-CF$_2$H,5-OMe) | Ph(3-OCF$_3$,5-Ei) |
| Ph(3-CF$_2$CF$_2$H,5-Br) | Ph(3-CF$_2$H,5-OCF$_3$) | Ph(3-OCF$_3$,5-n-Pr) |
| Ph(3-CF$_2$CF$_2$H,5-I) | Ph(3-CF$_2$H,5-OCHF$_2$) | Ph(3-OCF$_3$,5-t-Bu) |
| Ph(3-CF$_2$CF$_2$H,5-Me) | Ph(3-CF$_2$H,5-OCF$_2$CF$_2$H) | Ph(3-OCF$_3$,5-i-Pr) |
| Ph(3-CF$_2$CF$_2$H,5-Ei) | Ph(3-CF$_2$H,5-OCF$_2$CF$_3$) | Ph(3-OCF$_3$,5-c-Pr) |
| Ph(3-CF$_2$CF$_2$H,5-n-Pr) | Ph(3-CF$_2$H,5-SO$_2$Me) | Ph(3-OCF$_3$,5-CF$_3$) |
| Ph(3-OCF$_3$,5-CF$_2$CF$_3$) | Ph(3-OCF$_2$CF$_2$H,5-Br) | Ph(3-OCF$_2$CF$_3$,5-OCF$_3$) |
| Ph(3-OCF$_3$,5-CF$_2$CF$_2$H) | Ph(3-OCF$_2$CF$_2$H,5-I) | Ph(3-OCF$_2$CF$_3$,5-OCHF$_2$) |
| Ph(3-OCF$_3$,5-CF$_2$H) | Ph(3-OCF$_2$CF$_2$H,5-Me) | Ph(3-OCF$_2$CF$_3$,5-OCF$_2$CF$_2$H) |
| Ph(3-OCF$_3$,5-OMe) | Ph(3-OCF$_2$CF$_2$H,5-Ei) | Ph(3,5-di-OCF$_2$CF$_3$) |
| Ph(3,5-di-OCF$_3$) | Ph(3-OCF$_2$CF$_2$H,5-n-Pr) | Ph(3-OCF$_2$CF$_3$,5-SO$_2$Me) |
| Ph(3-OCF$_3$,5-OCHF$_2$) | Ph(3-OCF$_2$CF$_2$H,5-t-Bu) | Ph(3-CF$_2$CF$_3$,5-TMS) |
| Ph(3-OCF$_3$,5-OCF$_2$CF$_2$H) | Ph(3-OCF$_2$CF$_2$H,5-i-Pr) | Ph(3-OCF$_2$CF$_3$,5-CN) |
| Ph(3-OCF$_3$,5-OCF$_2$CF$_3$) | Ph(3-OCF$_2$CF$_2$H,5-c-Pr) | Ph(3-SO$_2$Me,5-Cl) |
| Ph(3-OCF$_3$,5-SO$_2$Me) | Ph(3-OCF$_2$CF$_2$HCF$_3$,5-CF$_3$) | Ph(3-SO$_2$Me,5-F) |
| Ph(3-OCF$_3$,5-TMS) | Ph(3-OCF$_2$CF$_2$H,5-CF$_2$CF$_3$) | Ph(3-SO$_2$Me,5-Br) |
| Ph(3-OCF$_3$,5-CN) | Ph(3-OCF$_2$C$_2$H,5-CF$_2$CF$_2$H) | Ph(3-SO$_2$Me,5-I) |
| Ph(3-OCHF$_2$,5-Cl) | Ph(3-OCF$_2$CF$_2$H,5-CF$_2$H) | Ph(3-SO$_2$Me,5-Me) |
| Ph(3-OCHF$_2$,5-F) | Ph(3-OCF$_2$CF$_2$H,5-OMe) | Ph(3-SO$_2$Me,5-Ei) |
| Ph(3-OCHF$_2$,5-Br) | Ph(3-OCF$_2$CF$_2$H,5-OCF$_3$) | Ph(3-SO$_2$Me,5-n-Pr) |
| Ph(3-OCHF$_2$,5-I) | Ph(3-OCF$_2$CF$_2$H,5-OCHF$_2$) | Ph(3-SO$_2$Me,5-t-Bu) |
| Ph(3-OCHF$_2$,5-Me) | Ph(3,5-di-OCF$_2$CF$_2$H) | Ph(3-SO$_2$Me,5-i-Pr) |
| Ph(3-OCHF$_2$,5-Ei) | Ph(3-OCF$_2$CF$_2$H,5-OCF$_2$CF$_3$) | Ph(3-SO$_2$Me,5-c-Pr) |
| Ph(3-OCHF$_2$,5-n-Pr) | Ph(3-OCF$_2$CF$_2$H,5-SO$_2$Me) | Ph(3-SO$_2$MeCF$_3$,5-CF$_3$) |
| Ph(3-OCHF$_2$,5-t-Bu) | Ph(3-OCF$_2$CF$_2$H,5-TMS) | Ph(3-SO$_2$Me,5-CF$_2$CF$_3$) |
| Ph(3-OCHF$_2$,5-i-Pr) | Ph(3-OCF$_2$CF$_2$H,5-CN) | Ph(3-SO$_2$Me,5-CF$_2$CF$_2$H) |
| Ph(3-OCHF$_2$,5-c-Pr) | Ph(3-OCF$_2$CF$_3$,5-Cl) | Ph(3-SO$_2$Me,5-CF$_2$H) |
| Ph(3-OCHF$_2$CF$_3$,5-CF$_3$) | Ph(3-OCF$_2$CF$_3$,5-F) | Ph(3-SO$_2$Me,5-OMe) |
| Ph(3-OCF$_2$CF$_3$,5-CF$_2$CF$_3$) | Ph(3-OCF$_2$CF$_3$,5-Br) | Ph(3-SO$_2$Me,5-OCF$_3$) |
| Ph(3-OCHF$_2$,5-CF$_2$CF$_2$H) | Ph(3-OCF$_2$CF$_3$,5-I) | Ph(3-SO$_2$Me,5-OCHF$_2$) |
| Ph(3-OCHF$_2$,5-CF$_2$H) | Ph(3-OCF$_2$CF$_3$,5-Me) | Ph(3-SO$_2$Me,5-OCF$_2$CF$_2$H) |
| Ph(3-OCHF$_2$,5-OMe) | Ph(3-OCF$_2$CF$_3$,5-Ei) | Ph(3-SO$_2$Me,5-OCF$_2$CF$_3$) |
| Ph(3-OCHF$_2$,5-OCF$_2$) | Ph(3-OCF$_2$CF$_3$,5-n-Pr) | Ph(3,5-di-SO$_2$Me) |
| Ph(3,5-di-OCHF$_2$) | Ph(3-OCF$_2$CF$_3$,5-t-Bu) | Ph(3-SO$_2$Me,5-TMS) |
| Ph(3-OCHF$_2$,5-OCF$_2$CF$_2$H) | Ph(3-OCF$_2$CF$_3$,5-i-Pr) | Ph(3-SO$_2$Me,5-CN) |
| Ph(3-OCHF$_2$,5-OCF$_2$CF$_3$) | Ph(3-OCF$_2$CF$_3$,5-c-Pr) | Ph(3-TMS,5-Cl) |
| Ph(3-OCHF$_2$,5-SO$_2$Me) | Ph(3-OCF$_2$CF$_3$CF$_3$,5-CF$_3$) | Ph(3-TMS,5-F) |
| Ph(3-OCHF$_2$,5-TMS) | Ph(3-OCF$_2$CF$_3$,5-CF$_2$CF$_3$) | Ph(3-TMS,5-Br) |
| Ph(3-OCHF$_2$,5-CN) | Ph(3-OCF$_2$CF$_3$,5-CF$_2$CF$_2$H) | Ph(3-TMS,5-I) |
| Ph(3-OCF$_2$CF$_2$H,5-Cl) | Ph(3-OCF$_2$CF$_3$,5-CF$_2$H) | Ph(3-TMS,5-Me) |
| Ph(3-OCF$_2$CF$_2$H,5-F) | Ph(3-OCF$_2$CF$_3$,5-OMe) | Ph(3-TMS,5-Ei) |
| Ph(3-TMS,5-n-Pr) | Ph(3-CN,5-SO$_2$Me) | Ph(2-Cl,3-F,4-CF$_3$) |
| Ph(3-TMS,5-t-Bu) | Ph(3-CN,5-TMS) | Ph(2-Cl,3-F,4-CF$_2$CF$_3$) |
| Ph(3-TMS,5-i-Pr) | Ph(3,5-di-CN) | Ph(2-Cl,3-F,4-CF$_2$CF$_2$H) |
| Ph(3-TMS,5-c-Pr) | Ph(2,3,4-tri-Cl) | Ph(2-Cl,3-F,4-CF$_2$H) |
| Ph(3-TMS,5-CF$_3$) | Ph(2-Cl,3-Cl,4-F) | Ph(2-Cl,3-F,4-OMe) |
| Ph(3-TMS,5-CF$_2$CF$_3$) | Ph(2-Cl,3-Cl,4-Br) | Ph(2-Cl,3-F,4-OCF$_3$) |
| Ph(3-TMS,5-CF$_2$CF$_2$H) | Ph(2-Cl,3-Cl,4-I) | Ph(2-Cl,3-F,4-OCHF$_2$) |
| Ph(3-TMS,5-CF$_2$H) | Ph(2-Cl,3-Cl,4-Me) | Ph(2-Cl,3-F,4-OCF$_2$CF$_2$H) |
| Ph(3-TMS,5-OMe) | Ph(2-Cl,3-Cl,4-Et) | Ph(2-Cl,3-F,4-OCF$_2$CF$_3$) |
| Ph(3-TMS,5-OCF$_3$) | Ph(2-Cl,3-Cl,4-n-Pr) | Ph(2-Cl,3-F,4-SO$_2$Me) |
| Ph(3-TMS,5-OCHF$_2$) | Ph(2-Cl,3-Cl,4-t-Bu) | Ph(2-Cl,3-F,4-TMS) |
| Ph(3-TMS,5-OCF$_2$CF$_2$H) | Ph(2-Cl,3-Cl,4-i-Pr) | Ph(2-Cl,3-F,4-CN) |
| Ph(3-TMS,5-OCF$_2$CF$_3$) | Ph(2-Cl,3-Cl,4-c-Pr) | Ph(2-Cl,3-Br,4-Cl) |
| Ph(3-TMS,5-SO$_2$Me) | Ph(2-Cl,3-Cl,4-CF$_3$) | Ph(2-Cl,3-Br,4-F) |
| Ph(3,5-di-TMS) | Ph(2-Cl,3-Cl,4-CF$_2$CF$_3$) | Ph(2-Cl,3,4-di-Br) |
| Ph(3-TMS,5-CN) | Ph(2-Cl,3-Cl,4-CF$_2$CF$_2$H) | Ph(2-Cl,3-Br,4-I) |
| Ph(3-CN,5-Cl) | Ph(2-Cl,3-Cl,4-CF$_2$H) | Ph(2-Cl,3-Br,4-Me) |
| Ph(3-CN,5-F) | Ph(2-Cl,3-Cl,4-OMe) | Ph(2-Cl,3-Br,4-Et) |
| Ph(3-CN,5-Br) | Ph(2-Cl,3-Cl,4-OCF$_3$) | Ph(2-Cl,3-Br,4-n-Pr) |
| Ph(3-CN,5-I) | Ph(2-Cl,3-Cl,4-OCHF$_2$) | Ph(2-Cl,3-Br,4-t-Bu) |
| Ph(3-CN,5-Me) | Ph(2-Cl,3-Cl,4-OCF$_2$CF$_2$H) | Ph(2-Cl,3-Br,4-i-Pr) |
| Ph(3-CN,5-Ei) | Ph(2-Cl,3-Cl,4-OCF$_2$CF$_3$) | Ph(2-Cl,3-Br,4-c-Pr) |
| Ph(3-CN,5-n-Pr) | Ph(2-Cl,3-Cl,4-SO$_2$Me) | Ph(2-Cl,3-Br,4-CF$_3$) |
| Ph(3-CN,5-t-Bu) | Ph(2-Cl,3-Cl,4-TMS) | Ph(2-Cl,3-Br,4-CF$_2$CF$_3$) |

TABLE 1-continued

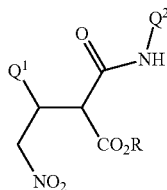

R is Me; Q² is Ph(2-F) and Q¹ is

| | | |
|---|---|---|
| Ph(3-CN,5-i-Pr) | Ph(2-Cl,3-Cl,4-CN) | Ph(2-Cl,3-Br,4-CF₂CF₂H) |
| Ph(3-CN,5-c-Pr) | Ph(2-Cl,3-F,4-Cl) | Ph(2-Cl,3-Br,4-CF₂H) |
| Ph(3-CN,5-CF₃) | Ph(2-Cl,3,4-di-F) | Ph(2-Cl,3-Br,4-OMe) |
| Ph(3-CN,5-CF₂CF₃) | Ph(2-Cl,3-F,4-Br) | Ph(2-Cl,3-Br,4-OCF₃) |
| Ph(3-CN,5-CF₂CF₂H) | Ph(2-Cl,3-F,4-I) | Ph(2-Cl,3-Br,4-OCHF₂) |
| Ph(3-CN,5-CF₂H) | Ph(2-Cl,3-F,4-Me) | Ph(2-Cl,3-Br,4-OCF₂CF₂H) |
| Ph(3-CN,5-OMe) | Ph(2-Cl,3-F,4-Et) | Ph(2-Cl,3-Br,4-OCF₂CF₃) |
| Ph(3-CN,5-OCF₃) | Ph(2-Cl,3-F,4-n-Pr) | Ph(2-Cl,3-Br,4-SO₂Me) |
| Ph(3-CN,5-OCHF₂) | Ph(2-Cl,3-F,4-t-Bu) | Ph(2-Cl,3-Br,4-TMS) |
| Ph(3-CN,5-OCF₂CF₂H) | Ph(2-Cl,3-F,4-i-Pr) | Ph(2-Cl,3-Br,4-CN) |
| Ph(3-CN,5-OCF₂CF₃) | Ph(2-Cl,3-F,4-c-Pr) | Ph(2-Cl,3-I,4-Cl) |
| Ph(2-Cl,3-I,4-F) | Ph(2-Cl,3-Me,4-OMe) | Ph(2-Cl,3-n-Pr,4-Et) |
| Ph(2-Cl,3-I,4-Br) | Ph(2-Cl,3-Me,4-OCFH₃) | Ph(2-Cl,3,4-di-n-Pr) |
| Ph(2-Cl,3,4-di-I) | Ph(2-Cl,3-Me,4-OCHF₂) | Ph(2-Cl,3-n-Pr,4-t-Bu) |
| Ph(2-Cl,3-I,4-Me) | Ph(2-Cl,3-Me,4-OCF₂CF₂H) | Ph(2-Cl,3-n-Pr,4-i-Pr) |
| Ph(2-Cl,3-I,4-Et) | Ph(2-Cl,3-Me,4-OCF₂CF₃) | Ph(2-Cl,3-n-Pr,4-c-Pr) |
| Ph(2-Cl,3-I,4-n-Pr) | Ph(2-Cl,3-Me,4-SO₂Me) | Ph(2-Cl,3-n-Pr,4-CF₃) |
| Ph(2-Cl,3-I,4-t-Bu) | Ph(2-Cl,3-Me,4-TMS) | Ph(2-Cl,3-n-Pr,4-CF₂CF₃) |
| Ph(2-Cl,3-I,4-i-Pr) | Ph(2-Cl,3-Me,4-CN) | Ph(2-Cl,3-n-Pr,4-CF₂CF₂H) |
| Ph(2-Cl,3-I,4-c-Pr) | Ph(2-Cl,3-Et,4-Cl) | Ph(2-Cl,3-n-Pr,4-CF₂H) |
| Ph(2-Cl,3-I,4-CF₃) | Ph(2-Cl,3-Et,4-F) | Ph(2-Cl,3-n-Pr,4-OMe) |
| Ph(2-Cl,3-I,4-CF₂CF₃) | Ph(2-Cl,3-Et,4-Br) | Ph(2-Cl,3-n-Pr,4-OCF₃) |
| Ph(2-Cl,3-I,4-CF₂CF₂H) | Ph(2-Cl,3-Et,4-I) | Ph(2-Cl,3-n-Pr,4-OCHF₂) |
| Ph(2-Cl,3-I,4-CF₂H) | Ph(2-Cl,3-Et,4-Me) | Ph(2-Cl,3-n-Pr,4-OCF₂CF₂H) |
| Ph(2-Cl,3-I,4-OMe) | Ph(2-Cl,3,4-di-Et) | Ph(2-Cl,3-n-Pr,4-OCF₂CF₃) |
| Ph(2-Cl,3-I,4-OCF₃) | Ph(2-Cl,3-Et,4-n-Pr) | Ph(2-Cl,3-n-Pr,4-SO₂Me) |
| Ph(2-Cl,3-I,4-OCHF₂) | Ph(2-Cl,3-Et,4-t-Bu) | Ph(2-Cl,3-n-Pr,4-TMS) |
| Ph(2-Cl,3-I,4-OCF₂CF₂H) | Ph(2-Cl,3-Et,4-i-Pr) | Ph(2-Cl,3-n-Pr,4-CN) |
| Ph(2-Cl,3-I,4-OCF₂CF₃) | Ph(2-Cl,3-Et,4-c-Pr) | Ph(2-Cl,3-t-Bu,4-Cl) |
| Ph(2-Cl,3-I,4-SO₂Me) | Ph(2-Cl,3-Et,4-CF₃) | Ph(2-Cl,3-t-Bu,4-F) |
| Ph(2-Cl,3-I,4-TMS) | Ph(2-Cl,3-Et,4-CF₂CF₃) | Ph(2-Cl,3-t-Bu,4-Br) |
| Ph(2-Cl,3-I,4-CN) | Ph(2-Cl,3-Et,4-CF₂Cg₂H) | Ph(2-Cl,3-t-Bu,4-I) |
| Ph(2-Cl,3-Me,4-Cl) | Ph(2-Cl,3-Et,4-CF₂H) | Ph(2-Cl,3-t-Bu,4-Me) |
| Ph(2-Cl,3-Me,4-F) | Ph(2-Cl,3-Et,4-OMe) | Ph(2-Cl,3-t-Bu,4-Et) |
| Ph(2-Cl,3-Me,4-Br) | Ph(2-Cl,3-Et,4-OCF₃) | Ph(2-Cl,3-t-Bu,4-n-Pr) |
| Ph(2-Cl,3-Me,4-I) | Ph(2-Cl,3-Et,4-OCHF₂) | Ph(2-Cl,3,4-di-t-Bu) |
| Ph(2-Cl,3,4-di-Me) | Ph(2-Cl,3-Et,4-OCF₂CF₂H) | Ph(2-Cl,3-t-Bu,4-i-Pr) |
| Ph(2-Cl,3-Me,4-Et) | Ph(2-Cl,3-Et,4-OCF₂CF₃) | Ph(2-Cl,3-t-Bu,4-c-Pr) |
| Ph(2-Cl,3-Me,4-n-Pr) | Ph(2-Cl,3-Et,4-SO₂Me) | Ph(2-Cl,3-t-Bu,4-CF₃) |
| Ph(2-Cl,3-Me,4-t-Bu) | Ph(2-Cl,3-Et,4-TMS) | Ph(2-Cl,3-t-Bu,4-CF₂CF₃) |
| Ph(2-Cl,3-Me,4-i-Pr) | Ph(2-Cl,3-Et,4-CN) | Ph(2-Cl,3-t-Bu,4-CF₂CF₂H) |
| Ph(2-Cl,3-Me,4-c-Pr) | Ph(2-Cl,3-n-Pr,4-Cl) | Ph(2-Cl,3-t-Bu,4-CF₂H) |
| Ph(2-Cl,3-Me,4-CF₃) | Ph(2-Cl,3-n-Pr,4-F) | Ph(2-Cl,3-t-Bu,4-OMe) |
| Ph(2-Cl,3-Me,4-CF₂CF₃) | Ph(2-Cl,3-n-Pr,4-Br) | Ph(2-Cl,3-t-Bu,4-OCF) |
| Ph(2-Cl,3-Me,4-CF₂CF₂H) | Ph(2-Cl,3-n-Pr,4-I) | Ph(2-Cl,3-t-Bu,4-OCHF₂) |
| Ph(2-Cl,3-Me,4-CF₂H) | Ph(2-Cl,3-n-Pr,4-Me) | Ph(2-Cl,3-t-Bu,4-OCF₂CF₂H) |
| Ph(2-Cl,3-t-Bu,4-OCF₂CF₃) | Ph(2-Cl,3,4-di-c-Pr) | Ph(2-Cl,3-CF₂CF₃,4-Cl) |
| Ph(2-Cl,3-t-Bu,4-SO₂Me) | Ph(2-Cl,3-c-Pr,4-CF₃) | Ph(2-Cl,3-CF₂CF₃,4-F) |
| Ph(2-Cl,3-t-Bu,4-TMS) | Ph(2-Cl,3-c-Pr,4-CF₂CF₃) | Ph(2-Cl,3-CF₂CF₃,4-Br) |
| Ph(2-Cl,3-t-Bu,4-CN) | Ph(2-Cl,3-c-Pr,4-CF₂CF₂H) | Ph(2-Cl,3-CF₂CF₃,4-I) |
| Ph(2-Cl,3-i-Pr,4-Cl) | Ph(2-Cl,3-c-Pr,4-CF₂H) | Ph(2-Cl,3-CF₂CF₃,4-Me) |
| Ph(2-Cl,3-i-Pr,4-F) | Ph(2-Cl,3-c-Pr,4-OMe) | Ph(2-Cl,3-CF₂CF₃,4-Ei) |
| Ph(2-Cl,3-i-Pr,4-Br) | Ph(2-Cl,3-c-Pr,4-OCF₃) | Ph(2-Cl,3-CF₂CF₃,4-n-Pr) |
| Ph(2-Cl,3-i-Pr,4-I) | Ph(2-Cl,3-c-Pr,4-OCHF₂) | Ph(2-Cl,3-CF₂CF₃,4-t-Bu) |
| Ph(2-Cl,3-i-Pr,4-Me) | Ph(2-Cl,3-c-Pr,4-OCF₂CF₂H) | Ph(2-Cl,3-CF₂CF₃,4-i-Pr) |
| Ph(2-Cl,3-i-Pr,4-Ei) | Ph(2-Cl,3-c-Pr,4-OCF₂CF₃) | Ph(2-Cl,3-CF₂CF₃,4-c-Pr) |
| Ph(2-Cl,3-i-Pr,4-n-Pr) | Ph(2-Cl,3-c-Pr,4-SO₂Me) | Ph(2-Cl,3-CF₂CF₃,4-CF₃) |
| Ph(2-Cl,3-i-Pr,4-t-Bu) | Ph(2-Cl,3-c-Pr,4-TMS) | Ph(2-Cl,3,4-di-CF₂CF₃) |
| Ph(2-Cl,3,4-di-i-Pr) | Ph(2-Cl,3-c-Pr,4-CN) | Ph(2-Cl,3-CF₂CF₃,4-CF₂CF₂H) |
| Ph(2-Cl,3-i-Pr,4-c-Pr) | Ph(2-Cl,3-CF₃,4-Cl) | Ph(2-Cl,3-CF₂CF₃,4-CF₂H) |
| Ph(2-Cl,3-i-Pr,4-CF₃) | Ph(2-Cl,3-CF₃,4-F) | Ph(2-Cl,3-CF₂CF₃,4-OMe) |
| Ph(2-Cl,3-i-Pr,4-CF₂CF₃) | Ph(2-Cl,3-CF₃,4-Br) | Ph(2-Cl,3-CF₂CF₃, 4-OCF₃) |
| Ph(2-Cl,3-i-Pr,4-CF₂CF₂H) | Ph(2-Cl,3-CF₃,4-I) | Ph(2-Cl,3-CF₂CF₃,4-OCHF₂) |
| Ph(2-Cl,3-i-Pr,4-CF₂H) | Ph(2-Cl,3-CF₃,4-Me) | Ph(2-Cl,3-CF₂CF₃,4-OCF₂CF₂H) |
| Ph(2-Cl,3-i-Pr,4-OMe) | Ph(2-Cl,3-CF₃,4-Ei) | Ph(2-Cl,3-CF₂CF₃,4-OCF₂CF₃) |
| Ph(2-Cl,3-i-Pr,4-OCF₃) | Ph(2-Cl,3-CF₃,4-n-Pr) | Ph(2-Cl,3-CF₂CF₃,4-SO₂Me) |
| Ph(2-Cl,3-i-Pr,4-OCHF₂) | Ph(2-Cl,3-CF₃,4-t-Bu) | Ph(2-Cl,3-CF₂CF₃,4-TMS) |
| Ph(2-Cl,3-i-Pr,4-OCF₂CF₃) | Ph(2-Cl,3-CF₃,4-i-Pr) | Ph(2-Cl,3-CF₂CF₃,4-CN) |
| Ph(2-Cl,3-i-Pr,4-OCF₂CF₃H) | Ph(2-Cl,3-CF₃,4-c-Pr) | Ph(2-Cl,3-CF₂CF₂H, 4-Cl) |

TABLE 1-continued

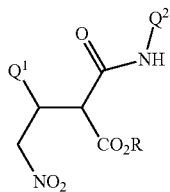

R is Me; Q² is Ph(2-F) and Q¹ is

| | | |
|---|---|---|
| Ph(2-Cl,3-i-Pr,4-SO₂Me) | Ph(2-Cl,3,4-di-CF₃) | Ph(2-Cl,3-CF₂CF₂H, 4-F) |
| Ph(2-Cl,3-i-Pr,4-TMS) | Ph(2-Cl,3-CF₃,4-CF₂CF₃) | Ph(2-Cl,3-CF₂CF₂H, 4-Br) |
| Ph(2-Cl,3-i-Pr,4-CN) | Ph(2-Cl,3-CF₃,4-CF₂CF₂H) | Ph(2-Cl,3-CF₂CF₂H, 4-I) |
| Ph(2-Cl,3-c-Pr,4-Cl) | Ph(2-Cl,3-CF₃,4-CF₂H) | Ph(2-Cl,3-CF₂CF₂H, 4-Me) |
| Ph(2-Cl,3-c-Pr,4-F) | Ph(2-Cl,3-CF₃,4-OMe) | Ph(2-Cl,3-CF₂CF₂H, 4-Ei) |
| Ph(2-Cl,3-c-Pr,4-Br) | Ph(2-Cl,3-CF₃,4-OCF₃) | Ph(2-Cl,3-CF₂CF₂H, 4-n-Pr) |
| Ph(2-Cl,3-c-Pr,4-I) | Ph(2-Cl,3-CF₃,4-OCHF₂) | Ph(2-Cl,3-CF₂CF₂H, 4-t-Bu) |
| Ph(2-Cl,3-c-Pr,4-Me) | Ph(2-Cl,3-CF₃,4-OCF₂CF₂H) | Ph(2-Cl,3-CF₂CF₂H, 4-i-Pr) |
| Ph(2-Cl,3-c-Pr,4-Ei) | Ph(2-Cl,3-CF₃,4-OCF₂CF₃) | Ph(2-Cl,3-CF₂CF₂H, 4-c-Pr) |
| Ph(2-Cl,3-c-Pr,4-n-Pr) | Ph(2-Cl,3-CF₃,4-SO₂Me) | Ph(2-Cl,3-CF₂CF₂HCF₃, 4-CF₃) |
| Ph(2-Cl,3-c-Pr,4-t-Bu) | Ph(2-Cl,3-CF₃,4-TMS) | Ph(2-C,3-CF₂CF₂H,4-CF₂CF₃) |
| Ph(2-Cl,3-c-Pr,4-i-Pr) | Ph(2-Cl,3-CF₃,4-CN) | Ph(2-Cl,3,4-di-CF₂CF₂H) |
| Ph(2-Cl,3-CF₂CF₂H,4-CF₂H) | Ph(2-Cl,3-OMe,4-Me) | Ph(2-Cl,3-OCF₃,4-OCF₂CF₂H) |
| Ph(2-Cl,3-CF₂CF₂H,4-OMe) | Ph(2-Cl,3-OMe,4-Ei) | Ph(2-Cl,3-OCF₃,4-OCF₂CF₃) |
| Ph(2-Cl,3-CF₂CF₂H,4-OCF₃) | Ph(2-Cl,3-OMe,4-n-Pr) | Ph(2-Cl,3-OCF₃,4-SO₂Me) |
| Ph(2-Cl,3-CF₂CF₂H,4-OCHF₂) | Ph(2-Cl,3-OMe,4-t-Bu) | Ph(2-Cl,3-OCF₃,4-TMS) |
| Ph(2-Cl,3-CF₂CF₂H,4-OCHF₂H) | Ph(2-Cl,3-OMe,4-i-Pr) | Ph(2-Cl,3-OCF₃,4-CN) |
| Ph(2-Cl,3-CF₂CF₂H,4-OCF₂CF₃) | Ph(2-Cl,3-OMe,4-c-Pr) | Ph(2-Cl,3-OCHF₂,4-Cl) |
| Ph(2-Cl,3-CF₂CF₂H, 4-SO₂Me) | Ph(2-Cl,3-OMeCF₃,4-CF₃) | Ph(2-Cl,3-OCHF₂,4-F) |
| Ph(2-Cl,3-CF₂CF₂H,4-TMS) | Ph(2-Cl,3-OMe,4-CF₂CF₃) | Ph(2-Cl,3-OCHF₂,4-Br) |
| Ph(2-Cl,3-CF₂CF₂H,4-CN) | Ph(2-Cl,3-OMe,4-CF₂CF₂H) | Ph(2-Cl,3-OCHF₂,4-I) |
| Ph(2-Cl,3-CF₂H,4-Cl) | Ph(2-Cl,3-OMe,4-CF₂H) | Ph(2-Cl,3-OCHF₂,4-Me) |
| Ph(2-Cl,3-CF₂H,4-F) | Ph(2-Cl,3,4-di-OMe) | Ph(2-Cl,3-OCHF₂,4-Ei) |
| Ph(2-Cl,3-CF₂H,4-Br) | Ph(2-Cl,3-OMe,4-OCF₃) | Ph(2-Cl,3-OCHF₂,4-n-Pr) |
| Ph(2-Cl,3-CF₂H,4-I) | Ph(2-Cl,3-OMe,4-OCHF₂) | Ph(2-Cl,3-OCHF₂,4-t-Bu) |
| Ph(2-Cl,3-CF₂H,4-Me) | Ph(2-Cl,3-OMe,4-OCF₂CF₂H) | Ph(2-Cl,3-OCHF₂,4-i-Pr) |
| Ph(2-Cl,3-CF₂H,4-Ei) | Ph(2-Cl,3-OMe,4-OCF₂CF₃) | Ph(2-Cl,3-OCHF₂,4-c-Pr) |
| Ph(2-Cl,3-CF₂H,4-n-Pr) | Ph(2-Cl,3-OMe,4-SO₂Me) | Ph(2-Cl,3-OCHF₂CF₃,4-CF₃) |
| Ph(2-Cl,3-CF₂H,4-t-Bu) | Ph(2-Cl,3-OMe,4-TMS) | Ph(2-Cl,3-OCF₂CF₃,4-CF₂CF₃) |
| Ph(2-Cl,3-CF₂H,4-i-Pr) | Ph(2-Cl,3-OMe,4-CN) | Ph(2-Cl,3-OCHF₂CF₃,4-CF₃) |
| Ph(2-Cl,3-CF₂H,4-c-Pr) | Ph(2-Cl,3-OCF₃,4-Cl) | Ph(2-Cl,3-OCHF₂,4-CF₂H) |
| Ph(2-Cl,3-CF₂H,4-CF₃) | Ph(2-Cl,3-OCF₃,4-F) | Ph(2-Cl,3-OCHF₂,4-OMe) |
| Ph(2-Cl,3-CF₂H,4-CF₂CF₃) | Ph(2-Cl,3-OCF₃,4-Br) | Ph(2-Cl,3-OCHF₂,4-OCF₃) |
| Ph(2-Cl,3-CF₂H,4-CF₂CF₂H) | Ph(2-Cl,3-OCF₃,4-I) | Ph(2-Cl,3,4-di-OCHF₂) |
| Ph(2-Cl,3,4-di-CF₂H) | Ph(2-Cl,3-OCF₃,4-Me) | Ph(2-Cl,3-OCHF₂,4-OCF₂CF₂H) |
| Ph(2-Cl,3-CF₂H,4-OMe) | Ph(2-Cl,3-OCF₃,4-Ei) | Ph(2-Cl,3-OCHF₂,4-OCF₂CF₃) |
| Ph(2-Cl,3-CF₂H,4-OCF₃) | Ph(2-Cl,3-OCF₃,4-n-Pr) | Ph(2-Cl,3-OCHF₂,4-SO₂Me) |
| Ph(2-Cl,3-CF₂H,4-OCHF₂) | Ph(2-Cl,3-OCF₃,4-t-Bu) | Ph(2-Cl,3-OCHF₂,4-TMS) |
| Ph(2-Cl,3-CF₂H,4-OCF₂CF₂H) | Ph(2-Cl,3-OCF₃,4-i-Pr) | Ph(2-Cl,3-OCHF₂,4-CN) |
| Ph(2-Cl,3-CF₂H,4-OCF₂CF₃) | Ph(2-Cl,3-OCF₃,4-c-Pr) | Ph(2-Cl,3-OCF₂CF₂H,4-Cl) |
| Ph(2-Cl,3-CF₂H,4-SO₂Me) | Ph(2-Cl,3-OCF₃,4-CF₃) | Ph(2-Cl,3-OCF₂CF₂H,4-F) |
| Ph(2-Cl,3-CF₂H,4-TMS) | Ph(2-Cl,3-OCF₃,4-CF₂CF₃) | Ph(2-Cl,3-OCF₂CF₂H,4-Br) |
| Ph(2-Cl,3-CF₂H,4-CN) | Ph(2-Cl,3-OCF₃,4-CF₂CF₂H) | Ph(2-Cl,3-OCF₂CF₂H,4-I) |
| Ph(2-Cl,3-OMe,4-Cl) | Ph(2-Cl,3-OCF₃,4-CF₂H) | Ph(2-Cl,3-OCF₂CF₂H,4-Me) |
| Ph(2-Cl,3-OMe,4-F) | Ph(2-Cl,3-OCF₃,4-OMe) | Ph(2-Cl,3-OCF₂CF₂H,4-Ei) |
| Ph(2-Cl,3-OMe,4-Br) | Ph(2-Cl,3,4-di-OCF₃) | Ph(2-Cl,3-OCF₂CF₂H,4-n-Pr) |
| Ph(2-Cl,3-OMe,4-I) | Ph(2-Cl,3-OCF₃,4-OCHF₂) | Ph(2-Cl,3OCF₂CF₂H,4-t-Bu) |
| Ph(2-Cl,3-OCF₂CF₂H,4-i-Pr) | Ph(2-Cl,3-OCF₂CF₃,4-CN) | Ph(2-Cl,3-TMS,4-CF₂CF₂H) |
| Ph(2-Cl,3-OCF₂CF₂H,4-c-Pr) | Ph(2-Cl,3-SO₂Me,4-Cl) | Ph(2-Cl,3-TMS,4-CF₂H) |
| Ph(2-Cl,3-OCF₂CF₂HCF₃,4-CF₃) | Ph(2-Cl,3-SO₂Me,4-F) | Ph(2-Cl,3-TMS,4-OMe) |
| Ph(2-Cl,3-OCF₂CF₂H,4-CF₂CF₃) | Ph(2-Cl,3-SO₂Me,4-Br) | Ph(2-Cl,3-TMS,4-OCF₃) |
| Ph(2-Cl,3-OCF₂CF₂H,4-CF₂CF₂H) | Ph(2-Cl,3-SO₂Me,4-I) | Ph(2-Cl,3-TMS,4-OCHF₂) |
| Ph(2-Cl,3-OCF₂CF₂H,4-CF₂H) | Ph(2-Cl,3-SO₂Me,4-Me) | Ph(2-Cl,3-TMS,4-OCF₂CF₂H) |
| Ph(2-C1,3-OCF₂CF₂H,4-OMe) | Ph(2-Cl,3-SO₂Me,4-Ei) | Ph(2-Cl,3-TMS,4-OCF₂CF₃) |
| Ph(2-Cl,3-OCF₂CF₂H,4-OCF₃) | Ph(2-Cl,3-SO₂Me,4-n-Pr) | Ph(2-Cl,3-TMS,4-SO₂Me) |
| Ph(2-Cl,3-OCF₂CF₂H,4-OCHF₂) | Ph(2-Cl,3-SO₂Me,4-t-Bu) | Ph(2-Cl,3,4-di-TMS) |
| Ph(2-Cl,3,4-di-OCF₂CF₂H) | Ph(2-Cl,3-SO₂Me,4-i-Pr) | Ph(2-Cl,3-TMS,4-CN) |
| Ph(2-Cl,3-OCF₂CF₂H,4-OCF₂CF₃) | Ph(2-Cl,3-SO₂Me,4-c-Pr) | Ph(2-Cl,3-CN,4-Cl) |
| Ph(2-Cl,3-OCF₂CF₂H,4-SO₂Me) | Ph(2-Cl,3-SO₂MeCF₃,4-CF₃) | Ph(2-Cl,3-CN,4-F) |
| Ph(2-Cl,3-OCF₂CF₂H,4-TMS) | Ph(2-Cl,3-SO₂Me,4-CF₂CF₃) | Ph(2-Cl,3-CN,4-Br) |
| Ph(2-Cl,3-OCF₂CF₂H,4-CN) | Ph(2-Cl,3-SO₂Me,4-CF₂CF₂H) | Ph(2-Cl,3-CN,4-I) |
| Ph(2-Cl,3-OCF₂CF₃,4-Cl) | Ph(2-Cl,3-SO₂Me,4-CF₂H) | Ph(2-Cl,3-CN,4-Me) |
| Ph(2-Cl,3-OCF₂CF₃,4-F) | Ph(2-Cl,3-SO₂Me,4-OMe) | Ph(2-Cl,3-CN,4-Ei) |
| Ph(2-Cl,3-OCF₂CF₃,4-Br) | Ph(2-Cl,3-SO₂Me,4-OCF₃) | Ph(2-Cl,3-CN,4-n-Pr) |
| Ph(2-Cl,3-OCF₂CF₃,4-I) | Ph(2-Cl,3-SO₂Me,4-OCHF₂) | Ph(2-Cl,3-CN,4-t-Bu) |
| Ph(2-Cl,3-OCF₂CF₃,4-Me) | Ph(2-Cl,3-SO₂Me,4-OCF₂CF₂H) | Ph(2-Cl,3-CN,4-i-Pr) |
| Ph(2-Cl,3-OCF₂CF₃,4-Ei) | Ph(2-Cl,3-SO₂Me,4-OCF₂CF₃) | Ph(2-Cl,3-CN,4-c-Pr) |
| Ph(2-Cl,3-OCF₂CF₃,4-n-Pr) | Ph(2-Cl,3,4-di-SO₂Me) | Ph(2-Cl,3-CN,4-CF₃) |
| Ph(2-Cl,3-OCF₂CF₃,4-t-Bu) | Ph(2-Cl,3-SO₂Me,4-TMS) | Ph(2-Cl,3-CN,4-CF₂CF₃) |

TABLE 1-continued

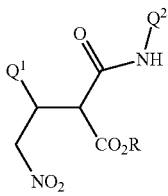

R is Me; $Q^2$ is Ph(2-F) and $Q^1$ is

| | | |
|---|---|---|
| Ph(2-Cl,3-OCF$_2$CF$_3$,4-i-Pr) | Ph(2-Cl,3-SO$_2$Me,4-Cl) | Ph(2-Cl,3-CN,4-CF$_2$CF$_2$H) |
| Ph(2-Cl,3-OCF$_2$CF$_3$,4-c-Pr) | Ph(2-Cl,3-TMS,4-Cl) | Ph(2-Cl,3-CN,4-CF$_2$H) |
| Ph(2-Cl,3-OCF$_2$CF$_3$,4-CF$_3$) | Ph(2-Cl,3-TMS,4-F) | Ph(2-Cl,3-CN,4-OMe) |
| Ph(2-Cl,3-OCF$_2$CF$_3$,4-CF$_2$CF$_3$) | Ph(2-Cl,3-TMS,4-Br) | Ph(2-Cl,3-CN,4-OCF$_3$) |
| Ph(2-Cl,3-OCF$_2$CF$_3$,4-CF$_2$CF$_2$H) | Ph(2-Cl,3-TMS,4-I) | Ph(2-Cl,3-CN,4-OCHF$_2$) |
| Ph(2-Cl,3-OCF$_2$CF$_3$,4-CF$_2$H) | Ph(2-Cl,3-TMS,4-Me) | Ph(2-Cl,3-CN,4-OCF$_2$CF$_2$H) |
| Ph(2-Cl,3-OCF$_2$CF$_3$,4-OMe) | Ph(2-Cl,3-TMS,4-Ei) | Ph(2-Cl,3-CN,4-OCF$_2$CF$_3$) |
| Ph(2-Cl,3-OCF$_2$CF$_3$,4-OCF$_3$) | Ph(2-Cl,3-TMS,4-n-Pr) | Ph(2-Cl,3-CN,4-SO$_2$Me) |
| Ph(2-Cl,3-OCF$_2$CF$_3$,4-OCHF$_2$) | Ph(2-Cl,3-TMS,4-t-Bu) | Ph(2-Cl,3-CN,4-TMS) |
| Ph(2-Cl,3-OCF$_2$CF$_3$,4-OCF$_2$CF$_2$H) | Ph(2-Cl,3-TMS,4-i-Pr) | Ph(2-Cl,3,4-di-CN) |
| Ph(2-Cl,3,4-di-OCF$_2$CF$_3$) | Ph(2-Cl,3-TMS,4-c-Pr) | Ph(2,3,5-tri-Cl) |
| Ph(2-Cl,3-OCF$_2$CF$_3$,4-SO$_2$Me) | Ph(2-Cl,3-TMS,4-CF$_3$) | Ph(2-Cl,3-Cl,5-F) |
| Ph(2-Cl,3-OCF$_2$CF$_3$,4-TMS) | Ph(2-Cl,3-TMS,4-CF$_2$CF$_3$) | Ph(2-Cl,3-Cl,5-Br) |
| Ph(2-Cl,3-Cl,5-I) | Ph(2-Cl,3-F,5-OCHF$_2$) | Ph(2-Cl,3-I,5-t-Bu) |
| Ph(2-Cl,3-Cl,5-Me) | Ph(2-Cl,3-F,5-OCF$_2$CF$_2$H) | Ph(2-Cl,3-I,-i-Pr) |
| Ph(2-Cl,3-Cl,5-Et) | Ph(2-Cl,3-F,5-OCF$_2$CF$_3$) | Ph(2-Cl,3-I,5-c-Pr) |
| Ph(2-Cl,3-Cl,5-n-Pr) | Ph(2-Cl,3-F,5-SO$_2$Me) | Ph(2-Cl,3-I,5-CF$_3$) |
| Ph(2-Cl,3-Cl,5-t-Bu) | Ph(2-Cl,3-F,5-TMS) | Ph(2-Cl,3-I,5-CF$_2$CF$_3$) |
| Ph(2-Cl,3-Cl,5-i-Pr) | Ph(2-Cl,3-F,5-CN) | Ph(2-Cl,3-I,5-CF$_2$CF$_2$H) |
| Ph(2-Cl,3-Cl,5-c-Pr) | Ph(2-Cl,3-Br,5-Cl) | Ph(2-Cl,3-I,5-CF$_2$H) |
| Ph(2-Cl,3-Cl,5-CF$_3$) | Ph(2-Cl,3-Br,5-F) | Ph(2-Cl,3-I,5-OMe) |
| Ph(2-Cl,3-Cl,5-CF$_2$CF$_3$) | Ph(2-Cl,3,5-di-Br) | Ph(2-Cl,3-I,5-OCF$_3$) |
| Ph(2-Cl,3-Cl,5-CF$_2$CF$_2$H) | Ph(2-Cl,3-Br,5-I) | Ph(2-Cl,3-I,5-OCHF$_2$) |
| Ph(2-Cl,3-Cl,5-CF$_2$H) | Ph(2-Cl,3-Br,5-Me) | Ph(2-Cl,3-I,5-OCF$_2$CF$_2$H) |
| Ph(2-Cl,3-Cl,5-OMe) | Ph(2-Cl,3-Br,5-Et) | Ph(2-Cl,3-I,5-OCF$_2$CF$_3$) |
| Ph(2-Cl,3-Cl,5-OCF$_3$) | Ph(2-Cl,3-Br,5-n-Pr) | Ph(2-Cl,3-I,5-SO$_2$Me) |
| Ph(2-Cl,3-Cl,5-OCHF$_2$) | Ph(2-Cl,3-Br,5-t-Bu) | Ph(2-Cl,3-I,5-TMS) |
| Ph(2-Cl,3-Cl,5-OCF$_2$CF$_2$H) | Ph(2-Cl,3-Br,5-i-Pr) | Ph(2-Cl,3-I,5-CN) |
| Ph(2-Cl,3-Cl,5-OCF$_2$CF$_3$) | Ph(2-Cl,3-Br,5-c-Pr) | Ph(2-Cl,3-Me,5-Cl) |
| Ph(2-Cl,3-Cl,5-SO$_2$Me) | Ph(2-Cl,3-Br,5-CF$_3$) | Ph(2-Cl,3-Me,5-F) |
| Ph(2-Cl,3-Cl,5-TMS) | Ph(2-Cl,3-Br,5-CF$_2$CF$_3$) | Ph(2-Cl,3-Me,5-Br) |
| Ph(2-Cl,3-Cl,5-CN) | Ph(2-Cl,3-Br,5-CF$_2$CF$_2$H) | Ph(2-Cl,3-Me,5-I) |
| Ph(2-Cl,3-F,5-Cl) | Ph(2-Cl,3-Br,5-CF$_2$H) | Ph(2-Cl,3,5-di-Me) |
| Ph(2-Cl,3,5-di-F) | Ph(2-Cl,3-Br,5-OMe) | Ph(2-Cl,3-Me,5-Et) |
| Ph(2-Cl,3-F,5-Br) | Ph(2-Cl,3-Br,5-OCF$_3$) | Ph(2-Cl,3-Me,5-n-Pr) |
| Ph(2-Cl,3-F,5-I) | Ph(2-Cl,3-Br,5-OCHF$_2$) | Ph(2-Cl,3-Me,5-t-Bu) |
| Ph(2-Cl,3-F,5-Me) | Ph(2-Cl,3-Br,5-OCF$_2$CF$_2$H) | Ph(2-Cl,3-Me,5-i-Pr) |
| Ph(2-Cl,3-F,5-Et) | Ph(2-Cl,3-Br,5-OCF$_2$CF$_3$) | Ph(2-Cl,3-Me,5-c-Pr) |
| Ph(2-Cl,3-F,5-n-Pr) | Ph(2-Cl,3-Br,5-SO$_2$Me) | Ph(2-Cl,3-Me,5-CF$_3$) |
| Ph(2-Cl,3-F,5-t-Bu) | Ph(2-Cl,3-Br,5-TMS) | Ph(2-Cl,3-Me,5-CF$_2$CF$_3$) |
| Ph(2-Cl,3-F,5-i-Pr) | Ph(2-Cl,3-Br,5-CN) | Ph(2-Cl,3-Me,5-CF$_2$CF$_2$H) |
| Ph(2-Cl,3-F,5-c-Pr) | Ph(2-Cl,34,5-Cl) | Ph(2-Cl,3-Me,5-CF$_2$H) |
| Ph(2-Cl,3-F,5-CF$_3$) | Ph(2-Cl,34,5-F) | Ph(2-Cl,3-Me,5-OMe) |
| Ph(2-Cl,3-F,5-CF$_2$CF$_3$) | Ph(2-Cl,34,5-Br) | Ph(2-Cl,3-Me,5-OCF$_3$) |
| Ph(2-Cl,3-F,5-CF$_2$CF$_2$H) | Ph(2-Cl,3,5-di-I) | Ph(2-Cl,3-Me,5-OCHF$_2$) |
| Ph(2-Cl,3-F,5-CF$_2$H) | Ph(2-Cl,34,5-Me) | Ph(2-Cl,3-Me,5-OCF$_2$CF$_2$H) |
| Ph(2-Cl,3-F,5-OMe) | Ph(2-Cl,34,5-Et) | Ph(2-Cl,3-Me,5-OCF$_2$CF$_3$) |
| Ph(2-Cl,3-F,5-OCF$_3$) | Ph(2-Cl,3-I,5-n-Pr) | Ph(2-Cl,3-Me,5-SO$_2$Me) |
| Ph(2-Cl,3-Me,5-TMS) | Ph(2-Cl,3-n-Pr,5-CF$_2$CF$_3$) | Ph(2-Cl,3-i-Pr,5-Br) |
| Ph(2-Cl,3-Me,5-CN) | Ph(2-Cl,3-n-Pr,5-CF$_2$CF$_2$H) | Ph(2-Cl,3-i-Pr,5-I) |
| Ph(2-Cl,3-Et,5-Cl) | Ph(2-Cl,3-n-Pr,5-CF$_2$H) | Ph(2-Cl,3-i-Pr,5-Me) |
| Ph(2-Cl,3-Et,5-F) | Ph(2-Cl,3-n-Pr,5-OMe) | Ph(2-Cl,3-i-Pr,5-Ei) |
| Ph(2-Cl,3-Et,5-Br) | Ph(2-Cl,3-n-Pr,5-OCF$_3$) | Ph(2-Cl,3-i-Pr,5-n-Pr) |
| Ph(2-Cl,3-Et,5-I) | Ph(2-Cl,3-n-Pr,5-OCHF$_2$) | Ph(2-Cl,3-i-Pr,5-t-Bu) |
| Ph(2-Cl,3-Et,5-Me) | Ph(2-Cl,3-n-Pr,5-OCF$_2$CF$_2$H) | Ph(2-Cl,3,5-di-i-Pr) |
| Ph(2-Cl,3,5-di-Et) | Ph(2-Cl,3-n-Pr,5-OCF$_2$CF$_3$) | Ph(2-Cl,3-i-Pr,5-c-Pr) |
| Ph(2-Cl,3-Et,5-n-Pr) | Ph(2-Cl,3-n-Pr,5-SO$_2$Me) | Ph(2-Cl,3-i-Pr,5-CF$_3$) |
| Ph(2-Cl,3-Et,5-t-Bu) | Ph(2-Cl,3-n-Pr,5-TMS) | Ph(2-Cl,3-i-Pr,5-CF$_2$CF$_3$) |
| Ph(2-Cl,3-Et,5-i-Pr) | Ph(2-Cl,3-n-Pr,5-CN) | Ph(2-Cl,3-i-Pr,5-CF$_2$CF$_2$H) |
| Ph(2-Cl,3-Et,5-c-Pr) | Ph(2-Cl,3-t-Bu,5-Cl) | Ph(2-Cl,3-i-Pr,5-CF$_2$H) |
| Ph(2-Cl,3-Et,5-CF$_3$) | Ph(2-Cl,3-t-Bu,5-F) | Ph(2-Cl,3-i-Pr,5-OMe) |
| Ph(2-Cl,3-Et,5-CF$_2$CF$_3$) | Ph(2-Cl,3-t-Bu,5-Br) | Ph(2-Cl,3-i-Pr,5-OCF$_3$) |
| Ph(2-Cl,3-Et,5-CF$_2$CF$_2$H) | Ph(2-Cl,3-t-Bu,5-I) | Ph(2-Cl,3-i-Pr,5-OCHF$_2$) |
| Ph(2-Cl,3-Et,5-CF$_2$H) | Ph(2-Cl,3-t-Bu,5-Me) | Ph(2-Cl,3-i-Pr,5-OCF$_2$CF$_2$H) |
| Ph(2-Cl,3-Et,5-OMe) | Ph(2-Cl,3-t-Bu,5-Et) | Ph(2-Cl,3-i-Pr,5-OCF$_2$CF$_3$) |
| Ph(2-Cl,3-Et,5-OCF$_3$) | Ph(2-Cl,3-t-Bu,5-n-Pr) | Ph(2-Cl,3-i-Pr,5-SO$_2$Me) |
| Ph(2-Cl,3-Et,5-OCHF$_2$) | Ph(2-Cl,3,5-di-t-Bu) | Ph(2-Cl,3-i-Pr,5-TMS) |
| Ph(2-Cl,3-Et,5-OCF$_2$CF$_2$H) | Ph(2-Cl,3-t-Bu,5-i-Pr) | Ph(2-Cl,3-i-Pr,5-CN) |
| Ph(2-Cl,3-Et,5-OCF$_2$CF$_3$) | Ph(2-Cl,3-t-Bu,5-c-Pr) | Ph(2-Cl,3-c-Pr,5-Cl) |

TABLE 1-continued

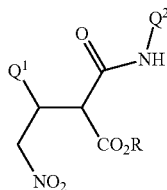

R is Me; Q² is Ph(2-F) and Q¹ is

| | | |
|---|---|---|
| Ph(2-Cl,3-Et,5-SO₂Me) | Ph(2-Cl,3-t-Bu,5-CF₃) | Ph(2-Cl,3-c-Pr,5-F) |
| Ph(2-Cl,3-Et,5-TMS) | Ph(2-Cl,3-t-Bu,5-CF₂CF₃) | Ph(2-Cl,3-c-Pr,5-Br) |
| Ph(2-Cl,3-Et,5-CN) | Ph(2-Cl,3-t-Bu,5-CF₂CF₂H) | Ph(2-Cl,3-c-Pr,5-I) |
| Ph(2-Cl,3-n-Pr,5-Cl) | Ph(2-Cl,3-t-Bu,5-CF₂H) | Ph(2-Cl,3-c-Pr,5-Me) |
| Ph(2-Cl,3-n-Pr,5-F) | Ph(2-Cl,3-t-Bu,5-OMe) | Ph(2-Cl,3-c-Pr,5-Ei) |
| Ph(2-Cl,3-n-Pr,5-Br) | Ph(2-Cl,3-t-Bu,5-OCF₃) | Ph(2-Cl,3-c-Pr,5-n-Pr) |
| Ph(2-Cl,3-n-Pr,5-I) | Ph(2-Cl,3-t-Bu,5-OCHF₂) | Ph(2-Cl,3-c-Pr,5-t-Bu) |
| Ph(2-Cl,3-n-Pr,5-Me) | Ph(2-Cl,3-t-Bu,5-OCF₂CF₂H) | Ph(2-Cl,3-c-Pr,5-i-Pr) |
| Ph(2-Cl,3-n-Pr,5-Et) | Ph(2-Cl,3-t-Bu,5-OCF₂CF₃) | Ph(2-Cl,3,5-di-c-Pr) |
| Ph(2-Cl,3,5-di-n-Pr) | Ph(2-Cl,3-t-Bu,5-SO₂Me) | Ph(2-Cl,3-c-Pr,5-CF₃) |
| Ph(2-Cl,3-n-Pr,5-t-Bu) | Ph(2-Cl,3-t-Bu,5-TMS) | Ph(2-Cl,3-c-Pr,5-CF₂CF₃) |
| Ph(2-Cl,3-n-Pr,5-i-Pr) | Ph(2-Cl,3-t-Bu,5-CN) | Ph(2-Cl,3-c-Pr,5-CF₂CF₂H) |
| Ph(2-Cl,3-n-Pr,5-c-Pr) | Ph(2-Cl,3-i-Pr,5-Cl) | Ph(2-Cl,3-c-Pr,5-CF₂H) |
| Ph(2-Cl,3-n-Pr,5-CF₃) | Ph(2-Cl,3-i-Pr,5-F) | Ph(2-Cl,3-c-Pr,5-OMe) |
| Ph(2-Cl,3-c-Pr,5-OCF) | Ph(2-Cl,3-CF₂CF₃,5-n-Pr) | Ph(2-Cl,3-CF₂CF₂H,5-SO₂Me) |
| Ph(2-Cl,3-c-Pr,5-OCHF₂) | Ph(2-Cl,3-CF₂CF₃,5-t-Bu) | Ph(2-Cl,3-CF₂CF₂H,5-TMS) |
| Ph(2-Cl,3-c-Pr,5-OCF₂CF₂H) | Ph(2-Cl,3-CF₂CF₃,5-i-Pr) | Ph(2-Cl,3-CF₂CF₂H,5-CN) |
| Ph(2-Cl,3-c-Pr,5-OCF₂CF₃) | Ph(2-Cl,3-CF₂CF₃,5-c-Pr) | Ph(2-Cl,3-CF₂H,5-Cl) |
| Ph(2-Cl,3-c-Pr,5-SO₂Me) | Ph(2-Cl,3-CF₂CF₃CF₃,5-CF₃) | Ph(2-Cl,3-CF₂H,5-F) |
| Ph(2-Cl,3-c-Pr,5-TMS) | Ph(2-Cl,3,5-di-CF₂CF₃) | Ph(2-Cl,3-CF₂H,5-Br) |
| Ph(2-Cl,3-c-Pr,5-CN) | Ph(2-Cl,3-CF₂CF₃,5-CF₂CF₂H) | Ph(2-Cl,3-CF₂H,5-I) |
| Ph(2-Cl,3-CF₃,5-Cl) | Ph(2-Cl,3-CF₂CF₃,5-CF₂H) | Ph(2-Cl,3-CF₂H,5-Me) |
| Ph(2-Cl,3-CF₃,5-F) | Ph(2-Cl,3-CF₂CF₃,5-OMe) | Ph(2-Cl,3-CF₂H,5-Et) |
| Ph(2-Cl,3-CF₃,5-Br) | Ph(2-Cl,3-CF₂CF₃,5-OCF₃) | Ph(2-Cl,3-CF₂H,5-n-Pr) |
| Ph(2-Cl,3-CF₃,5-I) | Ph(2-Cl,3-CF₂CF₃,5-OCHF₂) | Ph(2-Cl,3-CF₂H,5-t-Bu) |
| Ph(2-Cl,3-CF₃,5-Me) | Ph(2-Cl,3-CF₂CF₃,5-OCF₂CF₂H) | Ph(2-Cl,3-CF₂H,5-i-Pr) |
| Ph(2-Cl,3-CF₃,5-Ei) | Ph(2-Cl,3-CF₂CF₃,5-OCF₂CF₃) | Ph(2-Cl,3-CF₂H,5-c-Pr) |
| Ph(2-Cl,3-CF₃,5-n-Pr) | Ph(2-Cl,3-CF₂CF₃,5-SO₂Me) | Ph(2-Cl,3-CF₂H,5-CF₃) |
| Ph(2-Cl,3-CF₃,5-t-Bu) | Ph(2-Cl,3-CF₂CF₃,5-TMS) | Ph(2-Cl,3-CF₂H,5-CF₂CF₃) |
| Ph(2-Cl,3-CF₃,5-i-Pr) | Ph(2-Cl,3-CF₂CF₃,5-CN) | Ph(2-Cl,3-CF₂H,5-CF₂CF₂H) |
| Ph(2-Cl,3-CF₃,5-c-Pr) | Ph(2-Cl,3-CF₂CF₂H,5-Cl) | Ph(2-Cl,3,5-di-CF₂H) |
| Ph(2-Cl,3,5-di-CF₃) | Ph(2-Cl,3-CF₂CF₂H,5-F) | Ph(2-Cl,3-CF₂H,5-OMe) |
| Ph(2-Cl,3-CF₃,5-CF₂CF₃) | Ph(2-Cl,3-CF₂CF₂H,5-Br) | Ph(2-Cl,3-CF₂H,5-OCF₃) |
| Ph(2-Cl,3-CF₃,5-CF₂CF₂H) | Ph(2-Cl,3-CF₂CF₂H,5-I) | Ph(2-Cl,3-CF₂H,5-OCHF₂) |
| Ph(2-Cl,3-CF₃,5-CF₂H) | Ph(2-Cl,3-CF₂CF₂H,5-Me) | Ph(2-Cl,3-CF₂H,5-OCF₂CF₂H) |
| Ph(2-Cl,3-CF₃,5-OMe) | Ph(2-Cl,3-CF₂CF₂H,5-Ei) | Ph(2-Cl,3-CF₂H,5-OCF₂CF₃) |
| Ph(2-Cl,3-CF₃,5-OCF₃) | Ph(2-Cl,3-CF₂CF₂H,5-n-Pr) | Ph(2-Cl,3-CF₂H,5-SO₂Me) |
| Ph(2-Cl,3-CF₃,5-OCHF₂) | Ph(2-Cl,3-CF₂CF₂H,5-t-Bu) | Ph(2-Cl,3-CF₂H,5-TMS) |
| Ph(2-Cl,3-CF₃,5-OCF₂CF₂H) | Ph(2-Cl,3-CF₂CF₂H,5-i-Pr) | Ph(2-Cl,3-CF₂H,5-CN) |
| Ph(2-Cl,3-CF₃,5-OCF₂CF₃) | Ph(2-Cl,3-CF₂CF₂H,5-c-Pr) | Ph(2-Cl,3-OMe,5-Cl) |
| Ph(2-Cl,3-CF₃,5-SO₂Me) | Ph(2-Cl,3-CF₂CF₂HCF₃,5-CF₃) | Ph(2-Cl,3-OMe,5-F) |
| Ph(2-Cl,3-CF₃,5-IMS) | Ph(2-Cl,3-CF₂CF₂H,5-CF₂CF₃) | Ph(2-Cl,3-OMe,5-Br) |
| Ph(2-Cl,3-CF₃,5-CN) | Ph(2-Cl,3,5-di-CF₂CF₂H) | Ph(2-Cl,3-OMe,5-I) |
| Ph(2-Cl,3-CF₂CF₃,5-Cl) | Ph(2-Cl,3-CF₂CF₂H,5-CF₂H) | Ph(2-Cl,3-OMe,5-Me) |
| Ph(2-Cl,3-CF₂CF₃,5-F) | Ph(2-Cl,3-CF₂CF₂H,5-OMe) | Ph(2-Cl,3-OMe,5-Ei) |
| Ph(2-Cl,3-CF₂CF₃,5-Br) | Ph(2-Cl,3-CF₂CF₂H,5-OCF₃) | Ph(2-Cl,3-OMe,5-n-Pr) |
| Ph(2-Cl,3-CF₂CF₃,5-I) | Ph(2-Cl,3-CF₂CF₂H,5-OCHF₂) | Ph(2-Cl,3-OMe,5-t-Bu) |
| Ph(2-Cl,3-CF₂CF₃,5-Me) | Ph(2-Cl,3-CF₂CF₂H,5-OCF₂CF₂H) | Ph(2-Cl,3-OMe,5-i-Pr) |
| Ph(2-Cl,3-CF₂CF₃,5-Ei) | Ph(2-Cl,3-CF₂CF₂H,5-OCF₂CF₃) | Ph(2-Cl,3-OMe,5-c-Pr) |
| Ph(2-Cl,3-OMeCF₃,5-CF₃) | Ph(2-Cl,3-OCHF₂,5-F) | Ph(2-Cl,3-OCF₂CF₂H,5-OMe) |
| Ph(2-Cl,3-OMe,5-CF₂CF₃) | Ph(2-Cl,3-OCHF₂,5-Br) | Ph(2-Cl,3-OCF₂CF₂H,5-OCF₃) |
| Ph(2-Cl,3-OMe,5-CF₂CF₂H) | Ph(2-Cl,3-OCHF₂,5-I) | Ph(2-Cl,3-OCF₂CF₂H,5-OCHF₂) |
| Ph(2-Cl,3-OMe,5-CF₂H) | Ph(2-Cl,3-OCHF₂,5-Me) | Ph(2-Cl,3,5-di-OCF₂CF₂H) |
| Ph(2-Cl,3,5-di-OMe) | Ph(2-Cl,3-OCHF₂,5-Ei) | Ph(2-Cl,3-OCF₂CF₂H,5-OCF₂CF₃) |
| Ph(2-Cl,3-OMe,5-OCF₃) | Ph(2-Cl,3-OCHF₂,5-n-Pr) | Ph(2-Cl,3-OCF₂CF₂H,5-SO₂Me) |
| Ph(2-Cl,3-OMe,5-OCHF₂) | Ph(2-Cl,3-OCHF₂,5-t-Bu) | Ph(2-Cl,3-OCF₂CF₂H,5-TMS) |
| Ph(2-Cl,3-OMe,5-OCF₂CF₂H) | Ph(2-Cl,3-OCHF₂,5-i-Pr) | Ph(2-Cl,3-OCF₂CF₂H,5-CN) |
| Ph(2-Cl,3-OMe,5-OCF₂CF₃) | Ph(2-Cl,3-OCHF₂,5-c-Pr) | Ph(2-Cl,3-OCF₂CF₃,5-Cl) |
| Ph(2-Cl,3-OMe,5-SO₂Me) | Ph(2-Cl,3-OCHF₂CF₃,5-CF₃) | Ph(2-Cl,3-OCF₂CF₃,5-F) |
| Ph(2-Cl,3-OMe,5-TMS) | Ph(2-Cl,3-OCF₂CF₃,5-CF₂CF₃) | Ph(2-Cl,3-OCF₂CF₃,5-Br) |
| Ph(2-Cl,3-OMe,5-CN) | Ph(2-Cl,3-OCHF₂,5-CF₂CF₂H) | Ph(2-Cl,3-OCF₂CF₃,5-I) |
| Ph(2-Cl,3-OCF₃,5-Cl) | Ph(2-Cl,3-OCHF₂,5-CF₂H) | Ph(2-Cl,3-OCF₂CF₃,5-Me) |
| Ph(2-Cl,3-OCF₃,5-F) | Ph(2-Cl,3-OCHF₂,5-OMe) | Ph(2-Cl,3-OCF₂CF₃,5-Ei) |
| Ph(2-Cl,3-OCF₃,5-Br) | Ph(2-Cl,3-OCHF₂,5-OCF₃) | Ph(2-Cl,3-OCF₂CF₃,5-n-Pr) |
| Ph(2-Cl,3-OCF₃,5-I) | Ph(2-Cl,3,5-di-OCHF₂) | Ph(2-Cl,3-OCF₂CF₃,5-t-Bu) |
| Ph(2-Cl,3-OCF₃,5-Me) | Ph(2-Cl,3-OCHF₂,5-OCF₂CF₂H) | Ph(2-Cl,3-OCF₂CF₃,5-i-Pr) |
| Ph(2-Cl,3-OCF₃,5-Ei) | Ph(2-Cl,3-OCHF₂,5-OCF₂CF₃) | Ph(2-Cl,3-OCF₂CF₃,5-c-Pr) |
| Ph(2-Cl,3-OCF₃,5-n-Pr) | Ph(2-Cl,3-OCHF₂,5-SO₂Me) | Ph(2-Cl,3-OCF₂CF₃CF₃,5-CF₃) |
| Ph(2-Cl,3-OCF₃,5-t-Bu) | Ph(2-Cl,3-OCHF₂,5-TMS) | Ph(2-Cl,3-OCF₂CF₃,5-CF₂CF₃) |

TABLE 1-continued

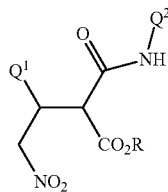

R is Me; $Q^2$ is Ph(2-F) and $Q^1$ is

| | | |
|---|---|---|
| Ph(2-Cl,3-OCF$_3$,5-i-Pr) | Ph(2-Cl,3-OCHF$_2$,5-CN) | Ph(2-Cl,3-OCF$_2$CF$_3$,5-CF$_2$CF$_2$H) |
| Ph(2-Cl,3-OCF$_3$,5-c-Pr) | Ph(2-Cl,3-OCF$_2$CF$_2$H,5-Cl) | Ph(2-Cl,3-OCF$_2$CF$_3$,5-CF$_2$H) |
| Ph(2-Cl,3-OCF$_3$,5-CF$_3$) | Ph(2-Cl,3-OCF$_2$CF$_2$H,5-F) | Ph(2-Cl,3-OCF$_2$CF$_3$,5-OMe) |
| Ph(2-Cl,3-OCF$_3$,5-CF$_2$CF$_3$) | Ph(2-Cl,3-OCF$_2$CF$_2$H,5-Br) | Ph(2-Cl,3-OCF$_2$CF$_3$,5-OCF$_3$) |
| Ph(2-Cl,3-OCF$_3$,5-CF$_2$CF$_2$H) | Ph(2-Cl,3-OCF$_2$CF$_2$H,5-I) | Ph(2-Cl,3-OCF$_2$CF$_3$,5-OCHF$_2$) |
| Ph(2-Cl,3-OCF$_3$,5-CF$_2$H) | Ph(2-Cl,3-OCF$_2$CF$_2$H,5-Me) | Ph(2-Cl,3-OCF$_2$CF$_3$,5-OCF$_2$CF$_2$H) |
| Ph(2-Cl,3-OCF$_3$,5-OMe) | Ph(2-Cl,3-OCF$_2$CF$_2$H,5-Ei) | Ph(2-Cl,3,5-di-OCF$_2$CF$_3$) |
| Ph(2-Cl,3,5-di-OCF$_3$) | Ph(2-Cl,3-OCF$_{2l\ CF2}$H,5-n-Pr) | Ph(2-Cl,3-OCF$_2$CF$_3$,5-SO$_2$Me) |
| Ph(2-Cl,3-OCHF$_2$) | Ph(2-Cl,3-OCF$_2$CF$_2$H,5-t-Bu) | Ph(2-Cl,3-OCF$_2$CF$_3$,5-TMS) |
| Ph(2-Cl,3-OCF$_3$,5-OCF$_2$CF$_2$H) | Ph(2-Cl,3-OCF$_2$CF$_2$H,5-i-Pr) | Ph(2-Cl,3-OCF$_2$CF$_3$,5-CN) |
| Ph(2-Cl,3-OCF$_3$,5-OCF$_2$CF$_3$) | Ph(2-Cl,3-OCF$_2$CF$_2$H,5-c-Pr) | Ph(2-Cl,3-SO$_2$Me,5-Cl) |
| Ph(2-Cl,3-OCF$_3$,5-SO$_2$Me) | Ph(2-Cl,3-OCF$_2$CF$_2$HCF$_3$,5-CF$_3$) | Ph(2-Cl,3-SO$_2$Me,5-F) |
| Ph(2-Cl,3-OCF$_3$,5-TMS) | Ph(2-Cl,3-OCF$_2$CF$_2$H,5-CF$_2$CF$_3$) | Ph(2-Cl,3-SO$_2$Me,5-Br) |
| Ph(2-Cl,3-OCF$_3$,5-CN) | Ph(2-Cl,3-OCF$_2$CF$_2$H,5-CF$_2$CF$_2$H) | Ph(2-Cl,3-SO$_2$Me,5-I) |
| Ph(2-Cl,3-OCHF$_2$,5-Cl) | Ph(2-Cl,3-OCF$_2$CF$_2$H,5-CF$_2$H) | Ph(2-Cl,3-SO$_2$Me,5-Me) |
| Ph(2-Cl,3-SO$_2$Me,5-Ei) | Ph(2-Cl,3-TMS,5-OCF$_2$CF$_3$) | Ph(2-Cl,4-Cl,5-c-Pr) |
| Ph(2-Cl,3-SO$_2$Me,5-n-Pr) | Ph(2-Cl,3-TMS,5-SO$_2$Me) | Ph(2-Cl,4-Cl,5-CF$_3$) |
| Ph(2-Cl,3-SO$_2$Me,5-t-Bu) | Ph(2-Cl,3,5-di-TMS) | Ph(2-Cl,4-Cl,5-CF$_2$CF$_3$) |
| Ph(2-Cl,3-SO$_2$Me,5-i-Pr) | Ph(2-Cl,3-TMS,5-CN) | Ph(2-Cl,4-Cl,5-CFCF$_2$H) |
| Ph(2-Cl,3-SO$_2$Me,5-c-Pr) | Ph(2-Cl,3-CN,5-Cl) | Ph(2-Cl,4-Cl,5-CF$_2$H) |
| Ph(2-Cl,3-SO$_2$MeCF$_3$,5-CF$_3$) | Ph(2-Cl,3-CN,5-F) | Ph(2-Cl,4-Cl,5-OMe) |
| Ph(2-Cl,3-SO$_2$Me,5-CF$_2$CF$_3$) | Ph(2-Cl,3-CN,5-Br) | Ph(2-Cl,4-Cl,5-OCF$_3$) |
| PPh(2-Cl,3-SO$_2$Me,5-CF$_2$CF$_2$H) | Ph(2-Cl,3-CN,5-I) | Ph(2-Cl,4-Cl,5-OCHF$_2$) |
| Ph(2-Cl,3-SO$_2$Me,5-CF$_2$H) | Ph(2-Cl,3-CN,5-Me) | Ph(2-Cl,4-Cl,5-OCF$_2$CF$_2$H) |
| Ph(2-Cl,3-SO$_2$Me,5-OMe) | Ph(2-Cl,3-CN,5-Ei) | Ph(2-Cl,4-Cl,5-OCF$_2$CF$_3$) |
| Ph(2-Cl,3-SO$_2$Me,5-OCF$_3$) | Ph(2-Cl,3-CN,5-n-Pr) | Ph(2-Cl,4-Cl,5-SO$_2$Me) |
| Ph(2-Cl,3-SO$_2$Me,5-OCHF$_2$) | Ph(2-Cl,3-CN,5-t-Bu) | Ph(2-Cl,4-Cl,5-TMS) |
| Ph(2-Cl,3-SO$_2$Me,5-OCF$_2$CF$_2$H) | Ph(2-Cl,3-CN,5-i-Pr) | Ph(2-Cl,4-Cl,5-CN) |
| Ph(2-Cl,3-SO$_2$Me,5-OCF$_2$CF$_3$) | Ph(2-Cl,3-CN,5-c-Pr) | Ph(2-Cl,4-F,5-Cl) |
| Ph(2-Cl,3,5-di-SO$_2$Me) | Ph(2-Cl,3-CN,5-CF$_3$) | Ph(2-Cl,4,5-di-F) |
| Ph(2-Cl,3-SO$_2$Me,5-TMS) | Ph(2-Cl,3-CN,5-CF$_2$CF$_3$) | Ph(2-Cl,4-F,5-Br) |
| Ph(2-Cl,3-SO$_2$Me,5-CN) | Ph(2-Cl,3-CN,5-CF$_2$CF$_2$H) | Ph(2-Cl,4-F,5-I) |
| Ph(2-Cl,3-TMS,5-Cl) | Ph(2-Cl,3-CN,5-CF$_2$H) | Ph(2-Cl,4-F,5-Me) |
| Ph(2-Cl,3-TMS,5-F) | Ph(2-Cl,3-CN,5-OMe) | Ph(2-Cl,4-F,5-Et) |
| Ph(2-Cl,3-TMS,5-Br) | Ph(2-Cl,3-CN,5-OCF) | Ph(2-Cl,4-F,5-n-Pr) |
| Ph(2-Cl,3-TMS,5-I) | Ph(2-Cl,3-CN,5-OCHF$_2$) | Ph(2-Cl,4-F,5-t-Bu) |
| Ph(2-Cl,3-TMS,5-Me) | Ph(2-Cl,3-CN,5-OCF$_2$CF$_2$H) | Ph(2-Cl,4-F,5-i-Pr) |
| Ph(2-Cl,3-TMS,5-Ei) | Ph(2-Cl,3-CN,5-OCF$_2$CF) | Ph(2-Cl,4-F,5-c-Pr) |
| Ph(2-Cl,3-TMS,5-n-Pr) | Ph(2-Cl,3-CN,5-SO$_2$Me) | Ph(2-Cl,4-F,5-CF$_3$) |
| Ph(2-Cl,3-TMS,5-t-Bu) | Ph(2-Cl,3-CN,5-TMS) | Ph(2-Cl,4-F,5-CF$_2$CF$_3$) |
| Ph(2-Cl,3-TMS,5-i-Pr) | Ph(2-Cl,3,5-di-CN) | Ph(2-Cl,4-F,5-CF$_2$CF$_2$H) |
| Ph(2-Cl,3-TMS,5-c-Pr) | Ph(2,4,5-tri-Cl) | Ph(2-Cl,4-F,5-CF$_2$H) |
| Ph(2-Cl,3-TMS,5-CF$_3$) | Ph(2-Cl,4-Cl,5-F) | Ph(2-Cl,4-F,5-OMe) |
| Ph(2-Cl,3-TMS,5-CF$_2$CF$_3$) | Ph(2-Cl,4-Cl,5-Br) | Ph(2-Cl,4-F,5-OCF) |
| Ph(2-Cl,3-TMS,5-CF$_2$CF$_2$H) | Ph(2-Cl,4-Cl,5-I) | Ph(2-Cl,4-F,5-OCHF$_2$) |
| Ph(2-Cl,3-TMS,5-CF$_2$H) | Ph(2-Cl,4-Cl,5-Me) | Ph(2-Cl,4-F,5-OCF$_2$CF$_2$H) |
| Ph(2-Cl,3-TMS,5-OMe) | Ph(2-Cl,4-Cl,5-Et) | Ph(2-Cl,4-F,5-OCF$_2$CF$_3$) |
| Ph(2-Cl,3-TMS,5-OCF$_3$) | Ph(2-Cl,4-Cl,5-n-Pr) | Ph(2-Cl,4-F,5-SO$_2$Me) |
| Ph(2-Cl,3-TMS,5-OCHF$_2$) | Ph(2-Cl,4-Cl,5-t-Bu) | Ph(2-Cl,4-F,5-TMS) |
| Ph(2-Cl,3-TMS,5-OCF$_2$CF$_2$H) | Ph(2-Cl,4-Cl,5-i-Pr) | Ph(2-Cl,4-F,5-CN) |
| Ph(2-Cl,4-Br,5-Cl) | Ph(2-Cl,4-I,5-CF$_2$H) | Ph(2-Cl,4-Et,5-Me) |
| Ph(2-Cl,4-Br,5-F) | Ph(2-Cl,4-I,5-OMe) | Ph(2-Cl,4,5-di-Et) |
| Ph(2-Cl,4,5-di-Br) | Ph(2-Cl,4-I,5-OCF$_3$) | Ph(2-Cl,4-Et,5-n-Pr) |
| Ph(2-Cl,4-Br,5-I) | Ph(2-Cl,4-I,5-OCHF$_2$) | Ph(2-Cl,4-Et,5-t-Bu) |
| Ph(2-Cl,4-Br,5-Me) | Ph(2-Cl,4-I,5-OCF$_2$CF$_2$H) | Ph(2-Cl,4-Et,5-i-Pr) |
| Ph(2-Cl,4-Br,5-Et) | Ph(2-Cl,4-I,5-OCF$_2$CF$_3$) | Ph(2-Cl,4-Et,5-c-Pr) |
| Ph(2-Cl,4-Br,5-n-Pr) | Ph(2-Cl,4-I,5-SO$_2$Me) | Ph(2-Cl,4-Et,5-CF$_3$) |
| Ph(2-Cl,4-Br,5-t-Bu) | Ph(2-Cl,4-I,5-TMS) | Ph(2-Cl,4-Et,5-CF$_2$CF$_3$) |
| Ph(2-Cl,4-Br,5-i-Pr) | Ph(2-Cl,4-I,5-CN) | Ph(2-Cl,4-Et,5-CF$_2$CF$_2$H) |
| Ph(2-Cl,4-Br,5-c-Pr) | Ph(2-Cl,4-Me,5-Cl) | Ph(2-Cl,4-Et,5-CF$_2$H) |
| Ph(2-Cl,4-Br,5-CF$_3$) | Ph(2-Cl,4-Me,5-F) | Ph(2-Cl,4-Et,5-OMe) |
| Ph(2-Cl,4-Br,5-CF$_2$CF$_3$) | Ph(2-Cl,4-Me,5-Br) | Ph(2-Cl,4-Et,5-OCF$_3$) |
| Ph(2-Cl,4-Br,5-CF$_2$CF$_2$H) | Ph(2-Cl,4-Me,5-I) | Ph(2-Cl,4-Et,5-OCHF$_2$) |
| Ph(2-Cl,4-Br,5-CF$_2$H) | Ph(2-Cl,4,5-di-Me) | Ph(2-Cl,4-Et,5-OCF$_2$CF$_2$H) |
| Ph(2-Cl,4-Br,5-OMe) | Ph(2-Cl,4-Me,5-Et) | Ph(2-Cl,4-Et,5-OCF$_2$CF$_3$) |
| Ph(2-Cl,4-Br,5-OCF$_3$) | Ph(2-Cl,4-Me,5-n-Pr) | Ph(2-Cl,4-Et,5-SO$_2$Me) |
| Ph(2-Cl,4-Br,5-OCHF$_2$) | Ph(2-Cl,4-Me,5-t-Bu) | Ph(2-Cl,4-Et,5-TMS) |
| Ph(2-Cl,4-Br,5-CF$_2$CF$_2$H) | Ph(2-Cl,4-Me,5-i-Pr) | Ph(2-Cl,4-Et,5-CN) |
| Ph(2-Cl,4-Br,5-OCF$_2$CF$_3$) | Ph(2-Cl,4-Me,5-c-Pr) | Ph(2-Cl,4-n-Pr,5-Cl) |

TABLE 1-continued

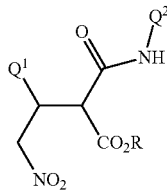

R is Me; $Q^2$ is Ph(2-F) and $Q^1$ is

| | | |
|---|---|---|
| Ph(2-Cl,4-Br,5-SO$_2$Me) | Ph(2-Cl,4-Me,5-CF$_3$) | Ph(2-Cl,4-n-Pr,5-F) |
| Ph(2-Cl,4-Br,5-TMS) | Ph(2-Cl,4-Me,5-CF$_2$CF$_3$) | Ph(2-Cl,4-n-Pr,5-Br) |
| Ph(2-Cl,4-Br,5-CN) | Ph(2-Cl,4-Me,5-CF$_2$CF$_2$H) | Ph(2-Cl,4-n-Pr,5-I) |
| Ph(2-Cl,4-I,5-Cl) | Ph(2-Cl,4-Me,5-CFH) | Ph(2-Cl,4-n-Pr,5-Me) |
| Ph(2-Cl,4-I,5-F) | Ph(2-Cl,4-Me,5-OMe) | Ph(2-Cl,4-n-Pr,5-Et) |
| Ph(2-Cl,4-I,5-Br) | Ph(2-Cl,4-Me,5-OCF$_3$) | Ph(2-Cl,4,5-di-n-Pr) |
| Ph(2-Cl,4,5-di-I) | Ph(2-Cl,4-Me,5-OCHF$_2$) | Ph(2-Cl,4-n-Pr,5-t-Bu) |
| Ph(2-Cl,4-I,5-Me) | Ph(2-Cl,4-Me,5-OCF$_2$CF$_2$H) | Ph(2-Cl,4-n-Pr,5-i-Pr) |
| Ph(2-Cl,4-I,5-Et) | Ph(2-Cl,4-Me,5-OCFCF$_3$) | Ph(2-Cl,4-n-Pr,5-c-Pr) |
| Ph(2-Cl,4-I,5-n-Pr) | Ph(2-Cl,4-Me,5-SO$_2$Me) | Ph(2-Cl,4-n-Pr,5-CF$_3$) |
| Ph(2-Cl,4-I,5-t-Bu) | Ph(2-Cl,4-Me,5-TMS) | Ph(2-Cl,4-n-Pr,5-CF$_2$CF$_3$) |
| Ph(2-Cl,4-I,5-i-Pr) | Ph(2-Cl,4-Me,5-CN) | Ph(2-Cl,4-n-Pr,5-CF$_2$CF$_2$H) |
| Ph(2-Cl,4-I,5-c-Pr) | Ph(2-Cl,4-Et,5-Cl) | Ph(2-Cl,4-n-Pr,5-CF$_2$H) |
| Ph(2-Cl,4-I,5-CF$_3$) | Ph(2-Cl,4-Et,5-F) | Ph(2-Cl,4-n-Pr,5-OMe) |
| Ph(2-Cl,4-I,5-CF$_2$CF$_3$) | Ph(2-Cl,4-Et,5-Br) | Ph(2-Cl,4-n-Pr,5-OCF$_3$) |
| Ph(2-Cl,4-I,5-CF$_2$CF$_2$H) | Ph(2-Cl,4-Et,5-I) | Ph(2-Cl,4-n-Pr,5-OCHF$_2$) |
| Ph(2-Cl,4-n-Pr,5-OCF$_2$CF$_2$H) | Ph(2-Cl,4,5-di-i-Pr) | Ph(2-Cl,4-c-Pr,5-CN) |
| Ph(2-Cl,4-n-Pr,5-OCF$_2$CF$_3$) | Ph(2-Cl,4-i-Pr,5-c-Pr) | Ph(2-Cl,4-CF$_3$,5-Cl) |
| Ph(2-Cl,4-n-Pr,5-SO$_2$Me) | Ph(2-Cl,4-i-Pr,5-CF$_3$H) | Ph(2-Cl,4-CF$_3$,5-F) |
| Ph(2-Cl,4-n-Pr,5-TMS) | Ph(2-Cl,4-i-Pr,5-CF$_2$CF$_3$) | Ph(2-Cl,4-CF$_3$,5-Br) |
| Ph(2-Cl,4-n-Pr,5-CN) | Ph(2-Cl,4-i-Pr,5-CF$_2$CF$_2$H) | Ph(2-Cl,4-CF$_3$,5-I) |
| Ph(2-Cl,4-t-Bu,5-Cl) | Ph(2-Cl,4-i-Pr,5-CF$_2$H) | Ph(2-Cl,4-CF$_3$,5-Me) |
| Ph(2-Cl,4-t-Bu,5-F) | Ph(2-Cl,4-i-Pr,5-OMe) | Ph(2-Cl,4-CF$_3$,5-Ei) |
| Ph(2-Cl,4-t-Bu,5-Br) | Ph(2-Cl,4-i-Pr,5-OCF$_3$) | Ph(2-Cl,4-CF$_3$,5-n-Pr) |
| Ph(2-Cl,4-t-Bu,5-I) | Ph(2-Cl,4-i-Pr,5-OCHF$_2$) | Ph(2-Cl,4-CF$_3$,5-t-Bu) |
| Ph(2-Cl,4-t-Bu,5-Me) | Ph(2-Cl,4-i-Pr,5-OCF$_2$CF$_2$H) | Ph(2-Cl,4-CF$_3$,5-i-Pr) |
| Ph(2-Cl,4-t-Bu,5-Et) | Ph(2-Cl,4-i-Pr,5-OCF$_2$CF$_3$) | Ph(2-Cl,4-CF$_3$,5-c-Pr) |
| Ph(2-Cl,4-t-Bu,5-n-Pr) | Ph(2-Cl,4-i-Pr,5-SO$_2$Me) | Ph(2-Cl,4,5-di-CF$_3$) |
| Ph(2-Cl,4,5-di-t-Bu) | Ph(2-Cl,4-i-Pr,5-TMS) | Ph(2-Cl,4-CF$_3$,5-CF$_2$CF$_3$) |
| Ph(2-Cl,4-t-Bu,5-i-Pr) | Ph(2-Cl,4-i-Pr,5-CN) | Ph(2-Cl,4-CF$_3$,5-CF$_2$CF$_2$H) |
| Ph(2-Cl,4-t-Bu,5-c-Pr) | Ph(2-Cl,4-c-Pr,5-Cl) | Ph(2-Cl,4-CF$_3$,5-CF$_2$H) |
| Ph(2-Cl,4-t-Bu,5-CF$_3$) | Ph(2-Cl,4-c-Pr,5-F) | Ph(2-Cl,4-CF$_3$,5-OMe) |
| Ph(2-Cl,4-t-Bu,5-CF$_2$CF$_3$) | Ph(2-Cl,4-c-Pr,5-Br) | Ph(2-Cl,4-CF$_3$,5-OCF$_3$) |
| Ph(2-Cl,4-t-Bu,5-CF$_2$CF$_2$H) | Ph(2-Cl,4-c-Pr,5-I) | Ph(2-Cl,4-CF$_3$,5-OCHF$_2$) |
| Ph(2-Cl,4-t-Bu,5-CF$_2$H) | Ph(2-Cl,4-c-Pr,5-Me) | Ph(2-Cl,4-CF$_3$,5-OCF$_2$CF$_2$H) |
| Ph(2-Cl,4-t-Bu,5-OMe) | Ph(2-Cl,4-c-Pr,5-Ei) | Ph(2-Cl,4-CF$_3$,5-OCF$_2$CF$_3$) |
| Ph(2-Cl,4-t-Bu,5-OCF$_3$) | Ph(2-Cl,4-c-Pr,5-n-Pr) | Ph(2-Cl,4-CF$_3$,5-SO$_2$Me) |
| Ph(2-Cl,4-t-Bu,5-OCHF$_2$) | Ph(2-Cl,4-c-Pr,5-t-Bu) | Ph(2-Cl,4-CF$_3$,5-IMS) |
| Ph(2-Cl,4-t-Bu,5-OCF$_2$CF$_2$H) | Ph(2-Cl,4-c-Pr,5-i-Pr) | Ph(2-Cl,4-CF$_3$,5-CN) |
| Ph(2-Cl,4-t-Bu,5-OCF$_2$CF$_3$) | Ph(2-Cl,4,5-di-c-Pr) | Ph(2-Cl,4-CF$_2$CF$_3$,5-Cl) |
| Ph(2-Cl,4-t-Bu,5-SO$_2$Me) | Ph(2-Cl,4-c-Pr,5-CF$_3$H) | Ph(2-Cl,4-CF$_2$CF$_3$,5-F) |
| Ph(2-Cl,4-t-Bu,5-TMS) | Ph(2-Cl,4-c-Pr,5-CF$_2$CF$_3$) | Ph(2-Cl,4-CF$_2$CF$_3$,5-Br) |
| Ph(2-Cl,4-t-Bu,5-CN) | Ph(2-Cl,4-c-Pr,5-CF$_2$CF$_2$H) | Ph(2-Cl,4-CF$_2$CF$_3$,5-I) |
| Ph(2-Cl,4-i-Pr,5-Cl) | Ph(2-Cl,4-c-Pr,5-CF$_2$H) | Ph(2-Cl,4-CF$_2$CF$_3$,5-Me) |
| Ph(2-Cl,4-i-Pr,5-F) | Ph(2-Cl,4-c-Pr,5-OMe) | Ph(2-Cl,4-CF$_2$CF$_3$,5-Ei) |
| Ph(2-Cl,4-i-Pr,5-Br) | Ph(2-Cl,4-c-Pr,5-OCF$_3$) | Ph(2-Cl,4-CF$_2$CF$_3$,5-n-Pr) |
| Ph(2-Cl,4-i-Pr,5-I) | Ph(2-Cl,4-c-Pr,5-OCHF$_2$) | Ph(2-Cl,4-CF$_2$CF$_3$,5-t-Bu) |
| Ph(2-Cl,4-i-Pr,5-Me) | Ph(2-Cl,4-c-Pr,5-OCF$_2$CF$_2$H) | Ph(2-Cl,4-CF$_2$CF$_3$,5-i-Pr) |
| Ph(2-Cl,4-i-Pr,5-Ei) | Ph(2-Cl,4-c-Pr,5-OCF$_2$CF$_3$) | Ph(2-Cl,4-CF$_2$CF$_3$,5-c-Pr) |
| Ph(2-Cl,4-i-Pr,5-n-Pr) | Ph(2-Cl,4-c-Pr,5-SO$_2$Me) | Ph(2-Cl,4-CF$_2$CF$_3$CF$_3$,5-CF$_3$) |
| Ph(2-Cl,4-i-Pr,5-t-Bu) | Ph(2-Cl,4-c-Pr,5-TMS) | Ph(2-Cl,4,5-di-CF$_2$CF$_3$) |
| Ph(2-Cl,4-CF$_2$CF$_3$,5-CF$_2$CF$_2$H) | Ph(2-Cl,4-CF$_2$H,5-Cl) | Ph(2-Cl,4-OMe,5-OCHF$_2$) |
| Ph(2-Cl,4-CF$_2$CF$_3$,5-CF$_2$H) | Ph(2-Cl,4-CF$_2$H,5-Me) | Ph(2-Cl,4-OMe,5-OCF$_2$CF$_2$H) |
| Ph(2-Cl,4-CF$_2$CF$_3$,5-OMe) | Ph(2-Cl,4-CF$_2$H,5-Ei) | Ph(2-Cl,4-OMe,5-OCF$_2$CF$_3$) |
| Ph(2-Cl,4-CF$_2$CF$_3$,5-OCF$_3$) | Ph(2-Cl,4-CF$_2$H,5-n-Pr) | Ph(2-Cl,4-OMe,5-SO$_2$Me) |
| Ph(2-Cl,4-CF$_2$CF$_3$,5-OCHF$_2$) | Ph(2-Cl,4-CF$_2$H,5-t-Bu) | Ph(2-Cl,4-OMe,5-TMS) |
| Ph(2-Cl,4-CF$_2$CF$_3$,5-OCF$_2$CF$_2$H) | Ph(2-Cl,4-CF$_2$H,5-i-Pr) | Ph(2-Cl,4-OMe,5-CN) |
| PPh(2-Cl,4-CF$_2$CF$_3$,5-OCF$_2$CF$_3$) | Ph(2-Cl,4-CF$_2$H,5-c-Pr) | Ph(2-Cl,4-OCF$_3$,5-Cl) |
| Ph(2-Cl,4-CF$_2$CF$_3$,5-SO$_2$Me) | Ph(2-Cl,4-CF$_2$H,5-CF$_3$) | Ph(2-Cl,4-OCF$_3$,5-F) |
| Ph(2-Cl,4-CF$_2$CF$_3$,5-TMS) | Ph(2-Cl,4-CF$_2$H,5-CF$_2$CF$_3$) | Ph(2-Cl,4-OCF$_3$,5-Br) |
| Ph(2-Cl,4-CF$_2$CF$_3$,5-CN) | Ph(2-Cl,4-CF$_2$H,5-CF$_2$CF$_2$H) | Ph(2-Cl,4-OCF$_3$,5-I) |
| Ph(2-Cl,4-CF$_2$CF$_2$H,5-Cl) | Ph(2-Cl,4,5-di-CF$_2$H) | Ph(2-Cl,4-OCF$_3$,5-Me) |
| Ph(2-Cl,4-CF$_2$CF$_2$H,5-F) | Ph(2-Cl,4-CF$_2$H,5-OMe) | Ph(2-Cl,4-OCF$_3$,5-Ei) |
| Ph(2-Cl,4-CF$_2$CF$_2$H,5-Br) | Ph(2-Cl,4-CF$_2$H,5-OCF$_3$) | Ph(2-Cl,4-OCF$_3$,5-n-Pr) |
| Ph(2-Cl,4-CF$_2$CF$_2$H,5-I) | Ph(2-Cl,4-CF$_2$H,5-OCHF$_2$) | Ph(2-Cl,4-OCF$_3$,5-t-Bu) |
| Ph(2-Cl,4-CF$_2$CF$_2$H,5-Me) | Ph(2-Cl,4-CF$_2$H,5-OCF$_2$CF$_2$H) | Ph(2-Cl,4-OCF$_3$,5-i-Pr) |
| Ph(2-Cl,4-CF$_2$CF$_2$H,5-Ei) | Ph(2-Cl,4-CF$_2$H,5-OCF$_2$CF$_3$) | Ph(2-Cl,4-OCF$_3$,5-c-Pr) |
| Ph(2-Cl,4-CF$_2$CF$_2$H,5-n-Pr) | Ph(2-Cl,4-CF$_2$H,5-SO$_2$Me) | Ph(2-Cl,4-OCF$_3$,5-CF$_3$) |
| Ph(2-Cl,4-CF$_2$CF$_2$H,5-t-Bu) | Ph(2-Cl,4-CF$_2$H,5-TMS) | Ph(2-Cl,4-OCF$_3$,5-CF$_2$CF$_3$) |

TABLE 1-continued

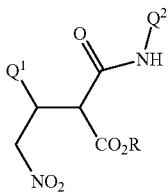

R is Me; Q² is Ph(2-F) and Q¹ is

| | | |
|---|---|---|
| Ph(2-Cl,4-CF₂CF₂H,5-i-Pr) | Ph(2-Cl,4-CF₂H,5-CN) | Ph(2-Cl,4-OCF₃,5-CF₂CF₂H) |
| Ph(2-Cl,4-CF₂CF₂H,5-c-Pr) | Ph(2-Cl,4-OMe,5-Cl) | Ph(2-Cl,4-OCF₃,5-CF₂H) |
| Ph(2-Cl,4-CF₂CF₂HCF₃,5-CF₃) | Ph(2-Cl,4-OMe,5-F) | Ph(2-Cl,4-OCF₃,5-OMe) |
| Ph(2-Cl,4-CF₂CF₂H,5-CF₂CF₃) | Ph(2-Cl,4-OMe,5-Br) | Ph(2-Cl,4,5-di-OCF₃) |
| Ph(2-Cl,4,5-di-CF₂CF₂H) | Ph(2-Cl,4-OMe,5-I) | Ph(2-Cl,4-OCF₃,5-OCHF₂) |
| Ph(2-Cl,4-CF₂CF₂H,5-CF₂H) | Ph(2-Cl,4-OMe,5-Me) | Ph(2-Cl,4-OCF₃,5-OCF₂CF₂H) |
| Ph(2-Cl,4-CF₂CF₂H,5-OMe) | Ph(2-Cl,4-OMe,5-Ei) | Ph(2-Cl,4-OCF₃,5-OCF₂CF₃) |
| Ph(2-Cl,4-CF₂CF₂H,5-OCF₃) | Ph(2-Cl,4-OMe,5-n-Pr) | Ph(2-Cl,4-OCF₃,5-SO₂Me) |
| Ph(2-Cl,4-CF₂CF₂H,5-OCHF₂) | Ph(2-Cl,4-OMe,5-t-Bu) | Ph(2-Cl,4-OCF₃,5-TMS) |
| Ph(2-Cl,4-CF₂CF₂H,5-OCF₂CF₂H) | Ph(2-Cl,4-OMe,5-i-Pr) | Ph(2-Cl,4-OCF₃,5-CN) |
| Ph(2-Cl,4-CF₂CF₂H,5-OCF₂CF₃) | Ph(2-Cl,4-OMe,5-c-Pr) | Ph(2-Cl,4-OCHF₂,5-Cl) |
| Ph(2-Cl,4-CF₂CF₂H,5-SO₂Me) | Ph(2-Cl,4-OMeCF₃,5-CF₃) | Ph(2-Cl,4-OCHF₂,5-F) |
| Ph(2-Cl,4-CF₂CF₂H,5-TMS) | Ph(2-Cl,4-OMe,5-CF₂CF₃) | Ph(2-Cl,4-OCHF₂,5-Br) |
| Ph(2-Cl,4-CF₂CF₂H,5-CN) | Ph(2-Cl,4-OMe,5-CF₂CF₂H) | Ph(2-Cl,4-OCHF₂,5-I) |
| Ph(2-Cl,4-CF₂H,5-Cl) | Ph(2-Cl,4-OMe,5-CF₂H) | Ph(2-Cl,4-OCHF₂,5-Me) |
| Ph(2-Cl,4-CF₂H,5-F) | Ph(2-Cl,4,5-di-OMe) | Ph(2-Cl,4-OCHF₂,5-Ei) |
| Ph(2-Cl,4-CF₂H,5-Br) | Ph(2-Cl,4-OMe,5-OCF₃) | Ph(2-Cl,4-OCHF₂,5-n-Pr) |
| Ph(2-Cl,4-OCHF₂,5-t-Bu) | Ph(2-Cl,4-oCF₂CF₂H,5-TMS) | Ph(2-Cl,4-SO₂Me,5-CF₂CF₃) |
| Ph(2-Cl,4-OCHF₂,5-i-Pr) | Ph(2-Cl,4-OCF₂CF₂H,5-CN) | Ph(2-Cl,4-SO₂Me,5-CF₂CF₂H) |
| Ph(2-Cl,4-OCHF₂,5-c-Pr) | Ph(2-Cl,4-OCF₂CF₃,5-Cl) | Ph(2-Cl,4-SO₂Me,5-CF₂H) |
| Ph(2-Cl,4-OCHF₂CF₃,5-CF₃) | Ph(2-Cl,4-OCF₂CF₃,5-F) | Ph(2-Cl,4-SO₂Me,5-OMe) |
| Ph(2-Cl,4-OCF₂CF₃,5-CF₂CF₃) | Ph(2-Cl,4-OCF₂CF₃,5-Br) | Ph(2-Cl,4-SO₂Me,5-OCF₃) |
| Ph(2-Cl,4-OCHF₂,5-CF₂CF₂H) | Ph(2-Cl,4-OCF₂CF₃,5-I) | Ph(2-Cl,4-SO₂Me,5-OCHF₂) |
| Ph(2-Cl,4-OCHF₂,5-CF₂H) | Ph(2-Cl,4-OCF₂CF₃,5-Me) | Ph(2-Cl,4-SO₂Me,5-OCF₂CF₂H) |
| Ph(2-Cl,4-OCHF₂,5-OMe) | Ph(2-Cl,4-OCF₂CF₃,5-Ei) | Ph(2-Cl,4-SO₂Me,5-OCF₂CF₃) |
| Ph(2-Cl,4-OCHF₂,5-OCF₃) | Ph(2-Cl,4-OCF₂CF₃,5-n-Pr) | Ph(2-Cl,4,5-di-SO₂Me) |
| Ph(2-Cl,4,5-di-OCHF₂) | Ph(2-Cl,4-OCF₂CF₃,5-t-Bu) | Ph(2-Cl,4-SO₂Me,5-TMS) |
| Ph(2-Cl,4-OCHF₂,5-OCF₂CF₂H) | Ph(2-Cl,4-OCF₂CF₃,5-i-Pr) | Ph(2-Cl,4-SO₂Me,5-CN) |
| Ph(2-Cl,4-OCHF₂,5-OCF₂CF₃) | Ph(2-Cl,4-OCF₂CF₃,5-c-Pr) | Ph(2-Cl,4-TMS,5-Cl) |
| Ph(2-Cl,4-OCHF₂,5-SO₂Me) | Ph(2-Cl,4-OCF₂CF₃CF₃,5-CF₃) | Ph(2-Cl,4-TMS,5-F) |
| Ph(2-Cl,4-OCHF₂,5-TMS) | Ph(2-Cl,4-OCF₂CF₃,5-CF₂CF₃) | Ph(2-Cl,4-TMS,5-Br) |
| Ph(2-Cl,4-OCHF₂,5-CN) | Ph(2-Cl,4-OCF₂CF₃,5-CF₂CF₂H) | Ph(2-Cl,4-TMS,5-I) |
| Ph(2-Cl,4-OCF₂CF₂H,5-Cl) | Ph(2-Cl,4-OCF₂CF₃,5-CF₂H) | Ph(2-Cl,4-TMS,5-Me) |
| Ph(2-Cl,4-OCF₂CF₂H,5-F) | Ph(2-Cl,4-OCF₂CF₃,5-OMe) | Ph(2-Cl,4-TMS,5-Ei) |
| Ph(2-Cl,4-OCF₂CF₂H,5-Br) | Ph(2-Cl,4-OCF₂CF₃,5-OCF₃) | Ph(2-Cl,4-TMS,5-n-Pr) |
| Ph(2-Cl,4-OCF₂CF₂H,5-I) | Ph(2-Cl,4-OCF₂CF₃,5-OCHF₂) | Ph(2-Cl,4-TMS,5-t-Bu) |
| Ph(2-Cl,4-OCF₂CF₂H,5-Me) | Ph(2-Cl,4-OCF₂CF₃,5-OCF₂CF₂H) | Ph(2-Cl,4-TMS,5-i-Pr) |
| Ph(2-Cl,4-OCF₂CF₂H,5-Ei) | Ph(2-Cl,4,5-di-OCF₂CF₃) | Ph(2-Cl,4-TMS,5-c-Pr) |
| Ph(2-Cl,4-OCF₂CF₂H,5-n-Pr) | Ph(2-Cl,4-OCF₂CF₃,5-SO₂Me) | Ph(2-Cl,4-TMS,5-CF₃) |
| Ph(2-Cl,4-OCF₂CF₂H,5-t-Bu) | Ph(2-Cl,4-OCF₂CF₃,5-TMS) | Ph(2-Cl,4-TMS,5-CF₂CF₃) |
| Ph(2-Cl,4-OCF₂CF₂H,5-i-Pr) | Ph(2-Cl,4-OCF₂CF₃,5-CN) | Ph(2-Cl,4-TMS,5-CF₂CF₂H) |
| Ph(2-Cl,4-OCF₂CF₂H,5-c-Pr) | Ph(2-Cl,4-SO₂Me,5-Cl) | Ph(2-Cl,4-TMS,5-CF₂H) |
| Ph(2-Cl,4-OCF₂CF₂HCF₃,5-CF₃) | Ph(2-Cl,4-SO₂Me,5-F) | Ph(2-Cl,4-TMS,5-OMe) |
| Ph(2-Cl,4-OCF₂CF₂H,5-CF₂CF₃) | Ph(2-Cl,4-SO₂Me,5-Br) | Ph(2-Cl,4-TMS,5-OCF₃) |
| Ph(2-Cl,4-OCF₂CF₂H,5-CF₂CF₂H) | Ph(2-Cl,4-SO₂Me,5-I) | Ph(2-Cl,4-TMS,5-OCHF₂) |
| Ph(2-Cl,4-OCF₂CF₂H,5-CF₂H) | Ph(2-Cl,4-SO₂Me,5-Me) | Ph(2-Cl,4-TMS,5-OCF₂CF₂H) |
| Ph(2-Cl,4-OCF₂CF₂H,5-OMe) | Ph(2-Cl,4-SO₂Me,5-Ei) | Ph(2-Cl,4-TMS,5-OCF₂CF₃) |
| Ph(2-Cl,4-OCF₂CF₂H,5-OCF₃) | Ph(2-Cl,4-SO₂Me,5-n-Pr) | Ph(2-Cl,4-TMS,5-SO₂Me) |
| Ph(2-Cl,4-OCF₂CF₂H,5-OCHF₂) | Ph(2-Cl,4-SO₂Me,5-t-Bu) | Ph(2-Cl,4,5-di-TMS) |
| Ph(2-Cl,4,5-di-OCF₂CF₂H) | Ph(2-Cl,4-SO₂Me,5-i-Pr) | Ph(2-Cl,4-TMS,5-CN) |
| Ph(2-Cl,4-OCF₂CF₂H,5-OCF₂CF₃) | Ph(2-Cl,4-SO₂Me,5-c-Pr) | Ph(2-Cl,4-CN,5-Cl) |
| Ph(2-Cl,4-OCF₂CF₂H,5-SO₂Me) | Ph(2-Cl,4-SO₂MeCF₃,5-CF₃) | Ph(2-Cl,4-CN,5-F) |
| Ph(2-Cl,4-CN,5-Br) | Ph(2-F,3-Cl,4-OCF₃) | Ph(2-F,3-Br,4-n-Pr) |
| Ph(2-Cl,4-CN,5-I) | Ph(2-F,3-Cl,4-OCHF₂) | Ph(2-F,3-Br,4-t-Bu) |
| Ph(2-Cl,4-CN,5-Me) | Ph(2-F,3-Cl,4-OCF₂CF₂H) | Ph(2-F,3-Br,4-i-Pr) |
| Ph(2-Cl,4-CN,5-Ei) | Ph(2-F,3-Cl,4-OCF₂CF₃) | Ph(2-F,3-Br,4-c-Pr) |
| Ph(2-Cl,4-CN,5-n-Pr) | Ph(2-F,3-Cl,4-SO₂Me) | Ph(2-F,3-Br,4-CF₃) |
| Ph(2-Cl,4-CN,5-t-Bu) | Ph(2-F,3-Cl,4-TMS) | Ph(2-F,3-Br,4-CF₂CF₃) |
| Ph(2-Cl,4-CN,5-i-Pr) | Ph(2-F,3-Cl,4-CN) | Ph(2-F,3-Br,4-CF₂CF₂H) |
| Ph(2-Cl,4-CN,5-c-Pr) | Ph(2-F,3-F,4-Cl) | Ph(2-F,3-Br,4-CF₂H) |
| Ph(2-Cl,4-CN,5-CF₃) | Ph(2,3,4-tri-F) | Ph(2-F,3-Br,4-OMe) |
| Ph(2-Cl,4-CN,5-CF₂CF₃) | Ph(2-F,3-F,4-Br) | Ph(2-F,3-Br,4-OCF₃) |
| Ph(2-Cl,4-CN,5-CF₂CF₂H) | Ph(2-F,3-F,4-I) | Ph(2-F,3-Br,4-OCHF₂) |
| Ph(2-Cl,4-CN,5-CF₂H) | Ph(2-F,3-F,4-Me) | Ph(2-F,3-Br,4-OCF₂CF₂H) |
| Ph(2-Cl,4-CN,5-OMe) | Ph(2-F,3-F,4-Et) | Ph(2-F,3-Br,4-OCF₂CF₃) |
| Ph(2-Cl,4-CN,5-OCF₃) | Ph(2-F,3-F,4-n-Pr) | Ph(2-F,3-Br,4-SO₂Me) |
| Ph(2-Cl,4-CN,5-OCHF₂) | Ph(2-F,3-F,4-t-Bu) | Ph(2-F,3-Br,4-TMS) |
| Ph(2-Cl,4-CN,5-OCF₂CF₂H) | Ph(2-F,3-F,4-i-Pr) | Ph(2-F,3-Br,4-CN) |
| Ph(2-Cl,4-CN,5-OCF₂CF₃) | Ph(2-F,3-F,4-c-Pr) | Ph(2-F,3-I,4-Cl) |

TABLE 1-continued

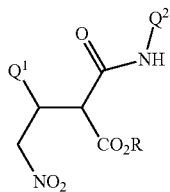

R is Me; Q² is Ph(2-F) and Q¹ is

| | | |
|---|---|---|
| Ph(2-Cl,4-CN,5-SO₂Me) | Ph(2-F,3-F,4-CF₃) | Ph(2-F,3-I,4-F) |
| Ph(2-Cl,4-CN,5-TMS) | Ph(2-F,3-F,4-CF₂CF₃) | Ph(2-F,3-I,4-Br) |
| Ph(2-Cl,4,5-di-CN) | Ph(2-F,3-F,4-CF₂CF₂H) | Ph(2-F,3,4-di-I) |
| Ph(2-F,3,4-di-Cl) | Ph(2-F,3-F,4-CF₂H) | Ph(2-F,3-I,4-Me) |
| Ph(2-F,3-Cl,4-F) | Ph(2-F,3-F,4-OMe) | Ph(2-F,3-I,4-Et) |
| Ph(2-F,3-Cl,4-Br) | Ph(2-F,3-F,4-OCF₃) | Ph(2-F,3-I,4-n-Pr) |
| Ph(2-F,3-Cl,4-I) | Ph(2-F,3-F,4-OCHF₂) | Ph(2-F,3-I,4-t-Bu) |
| Ph(2-F,3-Cl,4-Me) | Ph(2-F,3-F,4-OCF₂CF₂H) | Ph(2-F,3-I,4-i-Pr) |
| Ph(2-F,3-Cl,4-Et) | Ph(2-F,3-F,4-OCF₂CF₃) | Ph(2-F,3-I,4-c-Pr) |
| Ph(2-F,3-Cl,4-n-Pr) | Ph(2-F,3-F,4-SO₂Me) | Ph(2-F,3-I,4-CF₃) |
| Ph(2-F,3-Cl,4-t-Bu) | Ph(2-F,3-F,4-TMS) | Ph(2-F,3-I,4-CF₂CF₃) |
| Ph(2-F,3-Cl,4-i-Pr) | Ph(2-F,3-F,4-CN) | Ph(2-F,3-I,4-CF₂CF₂H) |
| Ph(2-F,3-Cl,4-c-Pr) | Ph(2-F,3-Br,4-Cl) | Ph(2-F,3-I,4-CF₂H) |
| Ph(2-F,3-Cl,4-CF₃) | Ph(2-F,3-Br,4-F) | Ph(2-F,3-I,4-OMe) |
| Ph(2-F,3-Cl,4-CF₂CF₃) | Ph(2-F,3,4-di-Br) | Ph(2-F,3-I,4-OCF₃) |
| Ph(2-F,3-Cl,4-CF₂CF₂H) | Ph(2-F,3-Br,4-I) | Ph(2-F,3-I,4-OCHF₂) |
| Ph(2-F,3-Cl,4-CF₂H) | Ph(2-F,3-Br,4-Me) | Ph(2-F,3-I,4-OCF₂CF₂H) |
| Ph(2-F,3-Cl,4-OMe) | Ph(2-F,3-Br,4-Et) | Ph(2-F,3-I,4-OCF₂CF₃) |
| Ph(2-F,3-I,4-SO₂Me) | Ph(2-F,3-Et,4-CF₃) | Ph(2-F,3-t-Bu,4-F) |
| Ph(2-F,3-I,4-TMS) | Ph(2-F,3-Et,4-CF₂CF₃) | Ph(2-F,3-t-Bu,4-Br) |
| Ph(2-F,3-I,4-CN) | Ph(2-F,3-Et,4-CF₂CF₂H) | Ph(2-F,3-t-Bu,4-I) |
| Ph(2-F,3-Me,4-Cl) | Ph(2-F,3-Et,4-CF₂H) | Ph(2-F,3-t-Bu,4-Me) |
| Ph(2-F,3-Me,4-F) | Ph(2-F,3-Et,4-OMe) | Ph(2-F,3-t-Bu,4-Et) |
| Ph(2-F,3-Me,4-Br) | Ph(2-F,3-Et,4-OCF₃) | Ph(2-F,3-t-Bu,4-n-Pr) |
| Ph(2-F,3-Me,4-I) | Ph(2-F,3-Et,4-OCHF₂) | Ph(2-F,3,4-di-t-Bu) |
| Ph(2-F,3,4-di-Me) | Ph(2-F,3-Et,4-OCF₂CF₂H) | Ph(2-F,3-t-Bu,4-i-Pr) |
| Ph(2-F,3-Me,4-Et) | Ph(2-F,3-Et,4-OCF₂CF₃) | Ph(2-F,3-t-Bu,4-c-Pr) |
| Ph(2-F,3-Me,4-n-Pr) | Ph(2-F,3-Et,4-SO₂Me) | Ph(2-F,3-t-Bu,4-CF₃) |
| Ph(2-F,3-Me,4-t-Bu) | Ph(2-F,3-Et,4-TMS) | Ph(2-F,3-t-Bu,4-CF₂CF₃) |
| Ph(2-F,3-Me,4-i-Pr) | Ph(2-F,3-Et,4-CN) | Ph(2-F,3-t-Bu,4-CF₂CF₂H) |
| Ph(2-F,3-Me,4-c-Pr) | Ph(2-F,3-n-Pr,4-Cl) | Ph(2-F,3-t-Bu,4-CF₂H) |
| Ph(2-F,3-Me,4-CF₃) | Ph(2-F,3-n-Pr,4-F) | Ph(2-F,3-t-Bu,4-OMe) |
| Ph(2-F,3-Me,4-CF₂CF₃) | Ph(2-F,3-n-Pr,4-Br) | Ph(2-F,3-t-Bu,4-OCF₃) |
| Ph(2-F,3-Me,4-CF₂CF₂H) | Ph(2-F,3-n-Pr,4-I) | Ph(2-F,3-t-Bu,4-OCHF₂) |
| Ph(2-F,3-Me,4-CF₂H) | Ph(2-F,3-n-Pr,4-Me) | Ph(2-F,3-t-Bu,4-OCF₂CF₂H) |
| Ph(2-F,3-Me,4-OMe) | Ph(2-F,3-n-Pr,4-Et) | Ph(2-F,3-t-Bu,4-OCF₂CF₃) |
| Ph(2-F,3-Me,4-OCF₃) | Ph(2-F,3,4-di-n-Pr) | Ph(2-F,3-t-Bu,4-SO₂Me) |
| Ph(2-F,3-Me,4-OCHF₂) | Ph(2-F,3-n-Pr,4-t-Bu) | Ph(2-F,3-t-Bu,4-TMS) |
| Ph(2-F,3-Me,4-OCF₂CF₂H) | Ph(2-F,3-n-Pr,4-i-Pr) | Ph(2-F,3-t-Bu,4-CN) |
| Ph(2-F,3-Me,4-OCF₂CF₃) | Ph(2-F,3-n-Pr,4-c-Pr) | Ph(2-F,3-i-Pr,4-Cl) |
| Ph(2-F,3-Me,4-SO₂Me) | Ph(2-F,3-n-Pr,4-CF₃) | Ph(2-F,3-i-Pr,4-F) |
| Ph(2-F,3-Me,4-TMS) | Ph(2-F,3-n-Pr,4-CF₂CF₃) | Ph(2-F,3-i-Pr,4-Br) |
| Ph(2-F,3-Me,4-CN) | Ph(2-F,3-n-Pr,4-CF₂CF₂H) | Ph(2-F,3-i-Pr,4-I) |
| Ph(2-F,3-Et,4-Cl) | Ph(2-F,3-n-Pr,4-CF₂H) | Ph(2-F,3-i-Pr,4-Me) |
| Ph(2-F,3-Et,4-F) | Ph(2-F,3-n-Pr,4-OMe) | Ph(2-F,3-i-Pr,4-Ei) |
| Ph(2-F,3-Et,4-Br) | Ph(2-F,3-n-Pr,4-OCF₃) | Ph(2-F,3-i-Pr,4-n-Pr) |
| Ph(2-F,3-Et,4-I) | Ph(2-F,3-n-Pr,4-OCHF₂) | Ph(2-F,3-i-Pr,4-t-Bu) |
| Ph(2-F,3-Et,4-Me) | Ph(2-F,3-n-Pr,4-OCF₂CF₂H) | Ph(2-F,3,4-di-i-Pr) |
| Ph(2-F,3,4-di-Et) | Ph(2-F,3-n-Pr,4-OCF₂CF₃) | Ph(2-F,3-i-Pr,4-c-Pr) |
| Ph(2-F,3-Et,4-n-Pr) | Ph(2-F,3-n-Pr,4-SO₂Me) | Ph(2-F,3-i-Pr,4-CF₃) |
| Ph(2-F,3-Et,4-t-Bu) | Ph(2-F,3-n-Pr,4-TMS) | Ph(2-F,3-i-Pr,4-CF₂CF₃) |
| Ph(2-F,3-Et,4-i-Pr) | Ph(2-F,3-n-Pr,4-CN) | Ph(2-F,3-i-Pr,4-CF₂CF₂H) |
| Ph(2-F,3-Et,4-c-Pr) | Ph(2-F,3-t-Bu,4-Cl) | Ph(2-F,3-i-Pr,4-CF₂H) |
| Ph(2-F,3-i-Pr,4-OMe) | Ph(2-F,3-CF3,4-Ei) | Ph(2-F,3-CF2CF3,4-OCF2CF3) |
| Ph(2-F,3-i-Pr,4-OCF₃) | Ph(2-F,3-CF3,4-n-Pr) | Ph(2-F,3-CF2CF3,4-SO2Me) |
| Ph(2-F,3-i-Pr,4-OCHF₂) | Ph(2-F,3-CF3,4-t-Bu) | Ph(2-F,3-CF2CF3,4-TMS) |
| Ph(2-F,3-i-Pr,4-OCF₂CF₂H) | Ph(2-F,3-CF3,4-i-Pr) | Ph(2-F,3-CF2CF3,4-CN) |
| Ph(2-F,3-i-Pr,4-OCF₂CF₃) | Ph(2-F,3-CF3,4-c-Pr) | Ph(2-F,3-CF2CF2H,4-Cl) |
| Ph(2-F,3-i-Pr,4-SO₂Me) | Ph(2-F,3,4-di-CF₃) | Ph(2-F,3-CF₂CF₂H,4-F) |
| Ph(2-F,3-i-Pr,4-TMS) | Ph(2-F,3-CF₃,4-CF₂CF₃) | Ph(2-F,3-CF₂CF₂H,4-Br) |
| Ph(2-F,3-i-Pr,4-CN) | Ph(2-F,3-CF₃,4-CF₂CF₂H) | Ph(2-F,3-CF₂CF₂H,4-I) |
| Ph(2-F,3-c-Pr,4-Cl) | Ph(2-F,3-CF₃,4-CF₂H) | Ph(2-F,3-CF₂CF₂H,4-Me) |
| Ph(2-F,3-c-Pr,4-F) | Ph(2-F,3-CF₃,4-OMe) | Ph(2-F,3-CF₂CF₂H,4-Ei) |
| Ph(2-F,3-c-Pr,4-Br) | Ph(2-F,3-CF₃,4-OCF₃) | Ph(2-F,3-CF₂CF₂H,4-n-Pr) |
| Ph(2-F,3-c-Pr,4-I) | Ph(2-F,3-CF₃,4-OCHF₂) | Ph(2-F,3-CF₂CF₂,4-t-Bu) |
| Ph(2-F,3-c-Pr,4-Me) | Ph(2-F,3-CF₃,4-OCF₂CF₂H) | Ph(2-F,3-CF₂CF₂H,4-i-Pr) |
| Ph(2-F,3-c-Pr,4-Ei) | Ph(2-F,3-CF₃,4-OCF₂CF₃) | Ph(2-F,3-CF₂CF₂H,4-c-Pr) |
| Ph(2-F,3-c-Pr,4-n-Pr) | Ph(2-F,3-CF₃,4-SO₂Me) | Ph(2-F,3-CF₂CF₂HCF₃,4-CF₃) |
| Ph(2-F,3-c-Pr,4-t-Bu) | Ph(2-F,3-CF₃,4-IMS) | Ph(2-F,3-CF₂CF₂H,4-CF₂CF₃) |

TABLE 1-continued

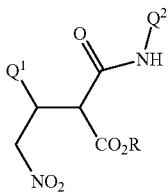

R is Me; Q² is Ph(2-F) and Q¹ is

| | | |
|---|---|---|
| Ph(2-F,3-c-Pr,4-i-Pr) | Ph(2-F,3-CF₃,4-CN) | Ph(2-F,3,4-di-CF₂CF₂H) |
| Ph(2-F,3,4-di-c-Pr) | Ph(2-F,3-CF₂CF₃,4-Cl) | Ph(2-F,3-CF₂CF₂H,4-CF₂H) |
| Ph(2-F,3-c-Pr,4-CF₃) | Ph(2-F,3-CF₂CF₃,4-F) | Ph(2-F,3-CF₂CF₂H,4-OMe) |
| Ph(2-F,3-c-Pr,4-CF₂CF₃) | Ph(2-F,3-CF₂CF₃,4-Br) | Ph(2-F,3-CF₂CF₂H,4-OCF₃) |
| Ph(2-F,3-c-Pr,4-CF₂CF₂H) | Ph(2-F,3-CF₂CF₃,4-I) | Ph(2-F,3-CF₂CF₂H,4-OCHF₂) |
| Ph(2-F,3-c-Pr,4-CF₂H) | Ph(2-F,3-CF₂CF₃,4-Me) | Ph(2-F,3-CF₂CF₂H,4-OCF₂CF₂H |
| Ph(2-F,3-c-Pr,4-OMe) | Ph(2-F,3-CF₂CF₃,4-Et) | Ph(2-F,3-CF₂CF₂H,4-OCF₂CF₃) |
| Ph(2-F,3-c-Pr,4-OCF₃) | Ph(2-F,3-CF₂CF₃,4-n-Pr) | Ph(2-F,3-CF₂CF₂H,4-SO₂Me) |
| Ph(2-F,3-c-Pr,4-OCHF₂) | Ph(2-F,3-CF₂CF₃,4-t-Bu) | Ph(2-F,3-CF₂CF₂H,4-TMS) |
| Ph(2-F,3-c-Pr,4-OCF₂CF₂H) | Ph(2-F,3-CF₂CF₃,4-i-Pr) | Ph(2-F,3-CF₂CF₂H,4-CN) |
| Ph(2-F,3-c-Pr,4-OCF₂CF₃) | Ph(2-F,3-CF₂CF₃,4-c-Pr) | Ph(2-F,3-CF₂H,4-Cl) |
| Ph(2-F,3-c-Pr,4-SO₂Me) | Ph(2-F,3-CF₂CF₃CF₃,4-CF₃) | Ph(2-F,3-CF₂H,4-F) |
| Ph(2-F,3-c-Pr,4-TMS) | Ph(2-F,3,4-di-CF₂CF₃) | Ph(2-F,3-CF₂H,4-Br) |
| Ph(2-F,3-c-Pr,4-CN) | Ph(2-F,3-CF₂CF₃,4-CF₂CF₂H) | Ph(2-F,3-CF₂H,4-I) |
| Ph(2-F,3-CF3,4-Cl) | Ph(2-F,3-CF₂CF₃,4-CF₂H) | Ph(2-F,3-CF₂H,4-Me) |
| Ph(2-F,3-CF3,4-F) | Ph(2-F,3-CF₂CF₃,4-OMe) | Ph(2-F,3-CF₂H,4-Ei) |
| Ph(2-F,3-CF3,4-Br) | Ph(2-F,3-CF₂CF₃,4-OCF₃) | Ph(2-F,3-CF₂H,4-n-Pr) |
| Ph(2-F,3-CF3,4-I) | Ph(2-F,3-CF₂CF₃,4-OOCHF₂) | Ph(2-F,3-CF₂H,4-t-Bu) |
| Ph(2-F,3-CF3,4-Me) | Ph(2-F,3-CF₂CF₃,4-OCF₂CF₂H) | Ph(2-F,3-CF₂H,4-i-Pr) |
| Ph(2-F,3-CF₂H,4-c-Pr) | Ph(2-F,3-OCF₃,4-Cl) | Ph(2-F,3-OCHF₂,4-CF₂H) |
| Ph(2-F,3-CF₂H,4-CF₃) | Ph(2-F,3-OCF₃,4-F) | Ph(2-F,3-OCHF₂,4-OMe) |
| Ph(2-F,3-CF₂H,4-CF₂CF₃) | Ph(2-F,3-OCF₃,4-Br) | Ph(2-F,3-OCHF₂,4-OCF₃) |
| Ph(2-F,3-CF₂H,4-CF₂CF₂H) | Ph(2-F,3-OCF₃,4-I) | Ph(2-F,3,4-di-OCHF₂) |
| Ph(2-F,3,4-di-CF₂H) | Ph(2-F,3-OCF₃,4-Me) | Ph(2-F,3-OCHF₂,4-OCF₂CF₂H) |
| Ph(2-F,3-CF₂H,4-OMe) | Ph(2-F,3-OCF₃,4-Ei) | Ph(2-F,3-OCHF₂,4-OCF₂CF₃) |
| Ph(2-F,3-CF₂H,4-OCF₃) | Ph(2-F,3-OCF₃,4-n-Pr) | Ph(2-F,3-OCHF₂,4-SO₂Me) |
| Ph(2-F,3-CF₂H,4-OCHF₂) | Ph(2-F,3-OCF₃,4-t-Bu) | Ph(2-F,3-OCHF₂,4-TMS) |
| Ph(2-F,3-CF₂H,4-OCF₂CF₂H) | Ph(2-F,3-OCF₃,4-i-Pr) | Ph(2-F,3-OCHF₂,4-CN) |
| Ph(2-F,3-CF₂H,4-OCF₂CF₃) | Ph(2-F,3-OCF₃,4-c-Pr) | Ph(2-F,3-OCF₂CF₂H,4-Cl) |
| Ph(2-F,3-CF₂H,4-SO₂Me) | Ph(2-F,3-OCF₃,4-CF₃) | Ph(2-F,3-OCF₂CF₂H,4-F) |
| Ph(2-F,3-CF₂H,4-TMS) | Ph(2-F,3-OCF₃,4-CF₂CF₃) | Ph(2-F,3-OCF₂CF₂H,4-Br) |
| Ph(2-F,3-CF₂H,4-CN) | Ph(2-F,3-OCF₃,4-CF₂CF₂H) | Ph(2-F,3-OCF₂CF₂H,4-I) |
| Ph(2-F,3-OMe,4-Cl) | Ph(2-F,3-OCF₃,4-CF₂H) | Ph(2-F,3-OCF₂CF₂H,4-Me) |
| Ph(2-F,3-OMe,4-F) | Ph(2-F,3-OCF₃,4-OMe) | Ph(2-F,3-OCF₂CF₂H,4-Ei) |
| Ph(2-F,3-OMe,4-Br) | Ph(2-F,3,4-di-OCF₃) | Ph(2-F,3-OCF₂CF₂H,4-n-Pr) |
| Ph(2-F,3-OMe,4-I) | Ph(2-F,3-OCF₃,4-OCHF₂) | Ph(2-F,3-OCF₂CF₂H,4-t-Bu) |
| Ph(2-F,3-OMe,4-Me) | Ph(2-F,3-OCF₃,4-OCF₂CF₂H) | Ph(2-F,3-OCF₂CF₂H,4-i-Pr) |
| Ph(2-F,3-OMe,4-Ei) | Ph(2-F,3-OCF₃,4-OCF₂CF₃) | Ph(2-F,3-OCF₂CF₂H,4-c-Pr) |
| Ph(2-F,3-OMe,4-n-Pr) | Ph(2-F,3-OCF₃,4-SO₂Me) | Ph(2-F,3-OCF₂CF₂HCF₃,4-CF₃) |
| Ph(2-F,3-OMe,4-t-Bu) | Ph(2-F,3-OCF₃,4-TMS) | Ph(2-F,3-OCF₂CF₂H,4-CF₂CF₃) |
| Ph(2-F,3-OMe,4-i-Pr) | Ph(2-F,3-OCF₃,4-CN) | Ph(2-F,3-OCF₂CF₂H,4-CF₂CF₂H) |
| Ph(2-F,3-OMe,4-c-Pr) | Ph(2-F,3-OCHF₂,4-Cl) | Ph(2-F,3-OCF₂CF₂H,4-CF₂H) |
| Ph(2-F,3-OMeCF₃,4-CF₃) | Ph(2-F,3-OCHF₂,4-F) | Ph(2-F,3-OCF₂CF₂H,4-OMe) |
| Ph(2-F,3-OMe,4-CF₂CF₃) | Ph(2-F,3-OCHF₂,4-Br) | Ph(2-F,3-OCF₂CF₂H,4-OCF₃) |
| Ph(2-F,3-OMe,4-CF₂CF₂H) | Ph(2-F,3-OCHF₂,4-I) | Ph(2-F,3-OCF₂CF₂H,4-OCHF₂) |
| Ph(2-F,3-OMe,4-CF₂H) | Ph(2-F,3-OCHF₂,4-Me) | Ph(2-F,3,4-di-OCF₂CF₂H) |
| Ph(2-F,3,4-di-OMe) | Ph(2-F,3-OCHF₂,4-Ei) | Ph(2-F,3-OCF₂CF₂H,4-OCF₂CF₃) |
| Ph(2-F,3-OMe,4-OCF₃) | Ph(2-F,3-OCHF₂,4-n-Pr) | Ph(2-F,3-OCF₂CF₃H,4-SO₂Me) |
| Ph(2-F,3-OMe,4-OCHF₂) | Ph(2-F,3-OCHF₂,4-t-Bu) | Ph(2-F,3-OCF₂CF₂H,4-TMS) |
| Ph(2-F,3-OMe,4-OCF₂CF₂H) | Ph(2-F,3-OCHF₂,4-i-Pr) | Ph(2-F,3-OCF₂CF₂H,4-CN) |
| Ph(2-F,3-OMe,4-OCF₂CF₃) | Ph(2-F,3-OCHF₂,4-c-Pr) | Ph(2-F,3-OCF₂CF₃,4-Cl) |
| Ph(2-F,3-OMe,4-SO₂Me) | Ph(2-F,3-OCHF₂CF₃,4-CF₃) | Ph(2-F,3-OCF₂CF₃,4-F) |
| Ph(2-F,3-OMe,4-TMS) | Ph(2-F,3-OCHF₂CF₃,4-CF₂CF₃) | Ph(2-F,3-OCF₂CF₃,4-Br) |
| Ph(2-F,3-OMe,4-CN) | Ph(2-F,3-OCHF₂,4-CF₂CF₂H) | Ph(2-F,3-OCF₂CF₃,4-I) |
| Ph(2-F,3-OCF₂CF₃,4-Me) | Ph(2-F,3-SO₂Me,4-OCF₂CF₂H) | Ph(2-F,3-CN,4-i-Pr) |
| Ph(2-F,3-OCF₂CF₃,4-Ei) | Ph(2-F,3-SO₂Me,4-OCF₂CF₃) | Ph(2-F,3-CN,4-c-Pr) |
| Ph(2-F,3-OCF₂CF₃,4-n-Pr) | Ph(2-F,3,4-di-SO₂Me) | Ph(2-F,3-CN,4-CF₃) |
| Ph(2-F,3-OCF₂CF₃,4-t-Bu) | Ph(2-F,3-SO₂Me,4-TMS) | Ph(2-F,3-CN,4-CF₂CF₃) |
| Ph(2-F,3-OCF₂CF₃,4-i-Pr) | Ph(2-F,3-SO₂Me,4-CN) | Ph(2-F,3-CN,4-CF₂CF₂H) |
| Ph(2-F,3-OCF₂CF₃,4-c-Pr) | Ph(2-F,3-TMS,4-Cl) | Ph(2-F,3-CN,4-CF₂H) |
| Ph(2-F,3-OCF₂CF₃,CF₂,4-CF₃) | Ph(2-F,3-TMS,4-F) | Ph(2-F,3-CN,4-OMe) |
| Ph(2-F,3-OCF₂CF₃,4-CF₂CF₃) | Ph(2-F,3-TMS,4-Br) | Ph(2-F,3-CN,4-OCF₃) |
| Ph(2-F,3-OCF₂CF₃,4-CF₂CF₂H) | Ph(2-F,3-TMS,4-I) | Ph(2-F,3-CN,4-OCHF₂) |
| Ph(2-F,3-OCF₂CF₃,4-CF₂H) | Ph(2-F,3-TMS,4-Me) | Ph(2-F,3-CN,4-OCF₂CF₂H) |
| Ph(2-F,3-OCF₂CF₃,4-OMe) | Ph(2-F,3-TMS,4-Ei) | Ph(2-F,3-CN,4-OCF₂CF₂H) |
| Ph(2-F,3-OCF₂CF₃,4-OCF₃) | Ph(2-F,3-TMS,4-n-Pr) | Ph(2-F,3-CN,4-SO₂Me) |
| Ph(2-F,3-OCF₂CF₃,4-OCHF₂) | Ph(2-F,3-TMS,4-t-Bu) | Ph(2-F,3-CN,4-TMS) |
| Ph(2-F,3-OCF₂CF₃,4-OCF₂CF₂H) | Ph(2-F,3-TMS,4-i-Pr) | Ph(2-F,3,4-di-CN) |
| Ph(2-F,3,4-di-OCF₂CF₃) | Ph(2-F,3-TMS,4-c-Pr) | Ph(2-F,3,5-di-Cl) |

TABLE 1-continued

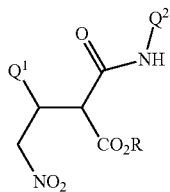

R is Me; Q² is Ph(2-F) and Q¹ is

| | | |
|---|---|---|
| Ph(2-F,3-OCF₂CF₃,4-SO₂Me) | Ph(2-F,3-TMS,4-CF₃) | Ph(2-F,3-Cl,5-F) |
| Ph(2-F,3-OCF₂CF₃,4-TMS) | Ph(2-F,3-TMS,4-CF₂CF₃) | Ph(2-F,3-Cl,5-Br) |
| Ph(2-F,3-OCF₂CF₃,4-CN) | Ph(2-F,3-TMS,4-CF₂CF₂H) | Ph(2-F,3-Cl,5-I) |
| Ph(2-F,3-SO₂Me,4-Cl) | Ph(2-F,3-TMS,4-CF₂H) | Ph(2-F,3-Cl,5-Me) |
| Ph(2-F,3-SO₂Me,4-F) | Ph(2-F,3-TMS,4-OMe) | Ph(2-F,3-Cl,5-Et) |
| Ph(2-F,3-SO₂Me,4-Br) | Ph(2-F,3-TMS,4-OCF₃) | Ph(2-F,3-Cl,5-n-Pr) |
| Ph(2-F,3-SO₂Me,4-I) | Ph(2-F,3-TMS,4-OCHF₂) | Ph(2-F,3-Cl,5-t-Bu) |
| Ph(2-F,3-SO₂Me,4-Me) | Ph(2-F,3-TMS,4-OCF₂CF₂H) | Ph(2-F,3-Cl,5-i-Pr) |
| Ph(2-F,3-SO₂Me,4-Ei) | Ph(2-F,3-TMS,4-OCF₂CF₃) | Ph(2-F,3-Cl,5-c-Pr) |
| Ph(2-F,3-SO₂Me,4-n-Pr) | Ph(2-F,3-TMS,4-SO₂Me) | Ph(2-F,3-Cl,5-CF₃) |
| Ph(2-F,3-SO₂Me,4-t-Bu) | Ph(2-F,3,4-di-TMS) | Ph(2-F,3-Cl,5-CF₂CF₃) |
| Ph(2-F,3-SO₂Me,4-i-Pr) | Ph(2-F,3-TMS,4-CN) | Ph(2-F,3-Cl,5-CF₂CF₂H) |
| Ph(2-F,3-SO₂Me,4-c-Pr) | Ph(2-F,3-CN,4-Cl) | Ph(2-F,3-Cl,5-CF₂H) |
| Ph(2-F,3-SO₂MeCF₃,4-CF₃) | Ph(2-F,3-CN,4-F) | Ph(2-F,3-Cl,5-OMe) |
| Ph(2-F,3-SO₂Me,4-CF₂CF₃) | Ph(2-F,3-CN,4-Br) | Ph(2-F,3-Cl,5-OCF₃) |
| Ph(2-F,3-SO₂Me,4-CF₂CF₂H) | Ph(2-F,3-CN,4-I) | Ph(2-F,3-Cl,5-OCHF₂) |
| Ph(2-F,3-SO₂Me,4-CF₂H) | Ph(2-F,3-CN,4-Me) | Ph(2-F,3-Cl,5-OCF₂CF₂H) |
| Ph(2-F,3-SO₂Me,4-OMe) | Ph(2-F,3-CN,4-Ei) | Ph(2-F,3-Cl,5-OCF₂CF₃) |
| Ph(2-F,3-SO₂Me,4-OCF₃) | Ph(2-F,3-CN,4-n-Pr) | Ph(2-F,3-Cl,5-SO₂Me) |
| Ph(2-F,3-SO₂Me,4-OCHF₂) | Ph(2-F,3-CN,4-t-Bu) | Ph(2-F,3-Cl,5-TMS) |
| Ph(2-F,3-Cl,5-CN) | Ph(2-F,3-Br,5-CF₂CF₂H) | Ph(2-F,3-Me,5-I) |
| Ph(2-F,3-F,5-Cl) | Ph(2-F,3-Br,5-CF₂H) | Ph(2-F,3,5-di-Me) |
| Ph(2,3,5-tri-F) | Ph(2-F,3-Br,5-OMe) | Ph(2-F,3-Me,5-Et) |
| Ph(2-F,3-F,5-Br) | Ph(2-F,3-Br,5-OCF₃) | Ph(2-F,3-Me,5-n-Pr) |
| Ph(2-F,3-F,5-I) | Ph(2-F,3-Br,5-OCHF₂) | Ph(2-F,3-Me,5-t-Bu) |
| Ph(2-F,3-F,5-Me) | Ph(2-F,3-Br,5-OCF₂CF₂H) | Ph(2-F,3-Me,5-i-Pr) |
| Ph(2-F,3-F,5-Et) | Ph(2-F,3-Br,5-OCF₂CF₃) | Ph(2-F,3-Me,5-c-Pr) |
| Ph(2-F,3-F,5-n-Pr) | Ph(2-F,3-Br,5-SO₂Me) | Ph(2-F,3-Me,5-CF₃) |
| Ph(2-F,3-F,5-t-Bu) | Ph(2-F,3-Br,5-TMS) | Ph(2-F,3-Me,5-CF₂CF₃) |
| Ph(2-F,3-F,5-i-Pr) | Ph(2-F,3-Br,5-CN) | Ph(2-F,3-Me,5-CF₂CF₂H) |
| Ph(2-F,3-F,5-c-Pr) | Ph(2-F,3-I,5-Cl) | Ph(2-F,3-Me,5-CF₂H) |
| Ph(2-F,3-F,5-CF₃) | Ph(2-F,3-I,5-F) | Ph(2-F,3-Me,5-OMe) |
| Ph(2-F,3-F,5-CF₂CF₃) | Ph(2-F,3-I,5-Br) | Ph(2-F,3-Me,5-OCF₃) |
| Ph(2-F,3-F,5-CF₂CF₂H) | Ph(2-F,3,5-di-I) | Ph(2-F,3-Me,5-OCHF₂) |
| Ph(2-F,3-F,5-CF₂H) | Ph(2-F,3-I,5-Me) | Ph(2-F,3-Me,5-OCF₂CF₂H) |
| Ph(2-F,3-F,5-OMe) | Ph(2-F,3-I,5-Et) | Ph(2-F,3-Me,5-OCF₂CF₃) |
| Ph(2-F,3-F,5-OCF₃) | Ph(2-F,3-I,5-n-Pr) | Ph(2-F,3-Me,5-SO₂Me) |
| Ph(2-F,3-F,5-OCHF₂) | Ph(2-F,3-I,5-t-Bu) | Ph(2-F,3-Me,5-TMS) |
| Ph(2-F,3-F,5-OCF₂CF₂H) | Ph(2-F,3-I,5-i-Pr) | Ph(2-F,3-Me,5-CN) |
| Ph(2-F,3-F,5-OCF₂CF₃) | Ph(2-F,3-I,5-c-Pr) | Ph(2-F,3-Et,5-Cl) |
| Ph(2-F,3-F,5-SO₂Me) | Ph(2-F,3-I,5-CF₃) | Ph(2-F,3-Et,5-F) |
| Ph(2-F,3-F,5-TMS) | Ph(2-F,3-I,5-CF₂CF₃) | Ph(2-F,3-Et,5-Br) |
| Ph(2-F,3-F,5-CN) | Ph(2-F,3-I,5-CF₂CF₂H) | Ph(2-F,3-Et,5-I) |
| Ph(2-F,3-Br,5-Cl) | Ph(2-F,3-I,5-CF₂H) | Ph(2-F,3-Et,5-Me) |
| Ph(2-F,3-Br,5-F) | Ph(2-F,3-I,5-OMe) | Ph(2-F,3,5-di-Et) |
| Ph(2-F,3,5-di-Br) | Ph(2-F,34,5-OCF₃) | Ph(2-F,3-Et,5-n-Pr) |
| Ph(2-F,3-Br,5-I) | Ph(2-F,34,5-OCHF₂) | Ph(2-F,3-Et,5-t-Bu) |
| Ph(2-F,3-Br,5-Me) | Ph(2-F,34,5-OCF₂CF₂H) | Ph(2-F,3-Et,5-i-Pr) |
| Ph(2-F,3-Br,5-Et) | Ph(2-F,34,5-OCF₂CF₃) | Ph(2-F,3-Et,5-c-Pr) |
| Ph(2-F,3-Br,5-n-Pr) | Ph(2-F,3-I,5-SO₂Me) | Ph(2-F,3-Et,5-CF₃) |
| Ph(2-F,3-Br,5-t-Bu) | Ph(2-F,3-I,5-TMS) | Ph(2-F,3-Et,5-CF₂CF₃) |
| Ph(2-F,3-Br,5-i-Pr) | Ph(2-F,3-I,5-CN) | Ph(2-F,3-Et,5-CF₂CF₂H) |
| Ph(2-F,3-Br,5-c-Pr) | Ph(2-F,3-Me,5-Cl) | Ph(2-F,3-Et,5-CF₂H) |
| Ph(2-F,3-Br,5-CF₃) | Ph(2-F,3-Me,5-F) | Ph(2-F,3-Et,5-OMe) |
| Ph(2-F,3-Br,5-CF₂CF₃) | Ph(2-F,3-Me,5-Br) | Ph(2-F,3-Et,5-OCF₃) |
| Ph(2-F,3-Et,5-OCHF₂) | Ph(2-F,3,5-di-t-Bu) | Ph(2-F,3-i-Pr,5-TMS) |
| Ph(2-F,3-Et,5-OCF₂CF₂H) | Ph(2-F,3-t-Bu,5-i-Pr) | Ph(2-F,3-i-Pr,5-CN) |
| Ph(2-F,3-Et,5-OCF₂CF₃) | Ph(2-F,3-t-Bu,5-c-Pr) | Ph(2-F,3-c-Pr,5-Cl) |
| Ph(2-F,3-Et,5-SO₂Me) | Ph(2-F,3-t-Bu,5-CF₃) | Ph(2-F,3-c-Pr,5-F) |
| Ph(2-F,3-Et,5-TMS) | Ph(2-F,3-t-Bu,5-CF₂CF₃) | Ph(2-F,3-c-Pr,5-Br) |
| Ph(2-F,3-Et,5-CN) | Ph(2-F,3-t-Bu,5-CF₂CF₂H) | Ph(2-F,3-c-Pr,5-I) |
| Ph(2-F,3-n-Pr,5-Cl) | Ph(2-F,3-t-Bu,5-CF₂H) | Ph(2-F,3-c-Pr,5-Me) |
| Ph(2-F,3-n-Pr,5-F) | Ph(2-F,3-t-Bu,5-OMe) | Ph(2-F,3-c-Pr,5-Ei) |
| Ph(2-F,3-n-Pr,5-Br) | Ph(2-F,3-t-Bu,5-OCF₃) | Ph(2-F,3-c-Pr,5-n-Pr) |
| Ph(2-F,3-n-Pr,5-I) | Ph(2-F,3-t-Bu,5-OCHF₂) | Ph(2-F,3-c-Pr,5-t-Bu) |
| Ph(2-F,3-n-Pr,5-Me) | Ph(2-F,3-t-Bu,5-OCF₂CF₂H) | Ph(2-F,3-c-Pr,5-i-Pr) |
| Ph(2-F,3-n-Pr,5-Et) | Ph(2-F,3-t-Bu,5-OCF₂CF₃) | Ph(2-F,3,5-di-c-Pr) |
| Ph(2-F,3,5-di-n-Pr) | Ph(2-F,3-t-Bu,5-SO₂Me) | Ph(2-F,3-c-Pr,5-CF₃) |
| Ph(2-F,3-n-Pr,5-t-Bu) | Ph(2-F,3-t-Bu,5-TMS) | Ph(2-F,3-c-Pr,5-CF₂CF₃) |

TABLE 1-continued

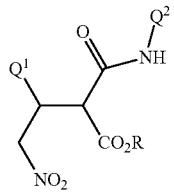

R is Me; $Q^2$ is Ph(2-F) and $Q^1$ is

| | | |
|---|---|---|
| Ph(2-F,3-n-Pr,5-i-Pr) | Ph(2-F,3-t-Bu,5-CN) | Ph(2-F,3-c-Pr,5-CF$_2$CF$_2$H) |
| Ph(2-F,3-n-Pr,5-c-Pr) | Ph(2-F,3-i-Pr,5-Cl) | Ph(2-F,3-c-Pr,5-CF$_2$H) |
| Ph(2-F,3-n-Pr,5-CF$_3$) | Ph(2-F,3-i-Pr,5-F) | Ph(2-F,3-c-Pr,5-OMe) |
| Ph(2-F,3-n-Pr,5-CF$_2$CF$_3$) | Ph(2-F,3-i-Pr,5-Br) | Ph(2-F,3-c-Pr,5-OCF$_3$) |
| Ph(2-F,3-n-Pr,5-CF$_2$CF$_2$H) | Ph(2-F,3-i-Pr,5-I) | Ph(2-F,3-c-Pr,5-OCHF$_2$) |
| Ph(2-F,3-n-Pr,5-CF$_2$H) | Ph(2-F,3-i-Pr,5-Me) | Ph(2-F,3-c-Pr,5-OCF$_2$CF$_2$H) |
| Ph(2-F,3-n-Pr,5-OMe) | Ph(2-F,3-i-Pr,5-Ei) | Ph(2-F,3-c-Pr,5-OCF$_2$CF$_3$) |
| Ph(2-F,3-n-Pr,5-OCF$_3$) | Ph(2-F,3-i-Pr,5-n-Pr) | Ph(2-F,3-c-Pr,5-SO$_2$Me) |
| Ph(2-F,3-n-Pr,5-OCHF$_2$) | Ph(2-F,3-i-Pr,5-t-Bu) | Ph(2-F,3-c-Pr,5-TMS) |
| Ph(2-F,3-n-Pr,5-OCF$_2$CF$_2$H) | Ph(2-F,3,5-di-i-Pr) | Ph(2-F,3-c-Pr,5-CN) |
| Ph(2-F,3-n-Pr,5-OCF$_2$CF$_3$) | Ph(2-F,3-i-Pr,5-c-Pr) | Ph(2-F,3-CF$_3$,5-Cl) |
| Ph(2-F,3-n-Pr,5-SO$_2$Me) | Ph(2-F,3-i-Pr,5-CF$_3$) | Ph(2-F,3-CF$_3$,5-F) |
| Ph(2-F,3-n-Pr,5-TMS) | Ph(2-F,3-i-Pr,5-CF$_2$CF$_3$) | Ph(2-F,3-CF$_3$,5-Br) |
| Ph(2-F,3-n-Pr,5-CN) | Ph(2-F,3-i-Pr,5-CF$_2$CF$_2$H) | Ph(2-F,3-CF$_3$,5-I) |
| Ph(2-F,3-t-Bu,5-Cl) | Ph(2-F,3-i-Pr,5-CF$_2$H) | Ph(2-F,3-CF$_3$,5-Me) |
| Ph(2-F,3-t-Bu,5-F) | Ph(2-F,3-i-Pr,5-OMe) | Ph(2-F,3-CF$_3$,5-Ei) |
| Ph(2-F,3-t-Bu,5-Br) | Ph(2-F,3-i-Pr,5-OCF$_3$) | Ph(2-F,3-CF$_3$,5-n-Pr) |
| Ph(2-F,3-t-Bu,5-I) | Ph(2-F,3-i-Pr,5-OCHF$_2$) | Ph(2-F,3-CF$_3$,5-t-Bu) |
| Ph(2-F,3-t-Bu,5-Me) | Ph(2-F,3-i-Pr,5-OCF$_2$CF$_2$H) | Ph(2-F,3-CF$_3$,5-i-Pr) |
| Ph(2-F,3-t-Bu,5-Et) | Ph(2-F,3-i-Pr,5-OCF$_2$CF$_3$) | Ph(2-F,3-CF$_3$,5-c-Pr) |
| Ph(2-F,3-t-Bu,5-n-Pr) | Ph(2-F,3-i-Pr,5-SO$_2$Me) | Ph(2-F,3,5-di-CF$_3$) |
| Ph(2-F,3-CF$_3$,5-CF$_2$CF$_3$) | Ph(2-F,3-CF$_2$CF$_2$H,5-Br) | Ph(2-F,3-CF$_2$H,5-OCF$_3$) |
| Ph(2-F,3-CF$_3$,5-CF$_2$CF$_2$H) | Ph(2-F,3-CF$_2$CF$_2$H,5-I) | Ph(2-F,3-CF$_2$H,5-OCHF$_2$) |
| Ph(2-F,3-CF$_3$,5-CF$_2$H) | Ph(2-F,3-CF$_2$CF$_2$H,5-Me) | Ph(2-F,3-CF$_2$H,5-OCF$_2$CF$_2$H) |
| Ph(2-F,3-CF$_3$,5-OMe) | Ph(2-F,3-CF$_2$CF$_2$H,5-Ei) | Ph(2-F,3-CF$_2$H,5-OCF$_2$CF$_3$) |
| Ph(2-F,3-CF$_3$,5-OCF$_3$) | Ph(2-F,3-CF$_2$CF$_2$H,5-n-Pr) | Ph(2-F,3-CF$_2$H,5-SO$_2$Me) |
| Ph(2-F,3-CF$_3$,5-OCHF$_2$) | Ph(2-F,3-CF$_2$CF$_2$H,5-t-Bu) | Ph(2-F,3-CF$_2$H,5-TMS) |
| Ph(2-F,3-CF$_3$,5-OCF$_2$CF$_2$H) | Ph(2-F,3-CF$_2$CF$_2$H,5-i-Pr) | Ph(2-F,3-CF$_2$H,5-CN) |
| Ph(2-F,3-CF$_3$,5-OCF$_2$CF$_3$) | Ph(2-F,3-CF$_2$CF$_2$H,5-c-Pr) | Ph(2-F,3-OMe,5-Cl) |
| Ph(2-F,3-CF$_3$,5-SO$_2$Me) | Ph(2-F,3-CF$_2$CF$_2$HCF$_3$,5-CF$_3$) | Ph(2-F,3-OMe,5-F) |
| Ph(2-F,3-CF$_3$,5-IMS) | Ph(2-F,3-CF$_2$CF$_2$H,5-CF$_2$CF$_3$) | Ph(2-F,3-OMe,5-Br) |
| Ph(2-F,3-CF$_3$,5-CN) | Ph(2-F,3,5-di-CF$_2$CF$_2$H) | Ph(2-F,3-OMe,5-I) |
| Ph(2-F,3-CF$_2$CF$_3$,5-Cl) | Ph(2-F,3-CF$_2$CF$_2$H,5-CF$_2$H) | Ph(2-F,3-OMe,5-Me) |
| Ph(2-F,3-CF$_2$CF$_3$,5-F) | Ph(2-F,3-CF$_2$CF$_2$H,5-OMe) | Ph(2-F,3-OMe,5-Ei) |
| Ph(2-F,3-CF$_2$CF$_3$,5-Br) | Ph(2-F,3-CF$_2$CF$_2$H,5-OCF$_3$) | Ph(2-F,3-OMe,5-n-Pr) |
| Ph(2-F,3-CF$_2$CF$_3$,5-I) | Ph(2-F,3-CF$_2$CF$_2$H,5-OCHF$_2$) | Ph(2-F,3-OMe,5-t-Bu) |
| Ph(2-F,3-CF$_2$CF$_3$,5-Me) | Ph(2-F,3-CF$_2$CF$_2$H,5-OCF$_2$CF$_2$H) | Ph(2-F,3-OMe,5-i-Pr) |
| Ph(2-F,3-CF$_2$CF$_3$,5-Ei) | Ph(2-F,3-CF$_2$CF$_2$H,5-OCF$_2$CF$_3$) | Ph(2-F,3-OMe,5-c-Pr) |
| Ph(2-F,3-CF$_2$CF$_3$,5-n-Pr) | Ph(2-F,3-CF$_2$CF$_2$H,5-SO$_2$Me) | Ph(2-F,3-OMeCF$_3$,5-CF$_3$) |
| Ph(2-F,3-CF$_2$CF$_3$,5-t-Bu) | Ph(2-F,3-CF$_2$CF$_2$H,5-TMS) | Ph(2-F,3-OMe,5-CF$_2$CF$_3$) |
| Ph(2-F,3-CF$_2$CF$_3$,5-i-Pr) | Ph(2-F,3-CF$_2$CF$_2$H,5-CN) | Ph(2-F,3-OMe,5-CF$_2$CF$_2$H) |
| Ph(2-F,3-CF$_2$CF$_3$,5-c-Pr) | Ph(2-F,3-CF$_2$H,5-Cl) | Ph(2-F,3-OMe,5-CF$_2$H) |
| Ph(2-F,3-CF$_2$CF$_3$CF$_3$,5-CF$_3$) | Ph(2-F,3-CF$_2$H,5-F) | Ph(2-F,3,5-di-OMe) |
| Ph(2-F,3,5-di-CF$_2$CF$_3$) | Ph(2-F,3-CF$_2$H,5-Br) | Ph(2-F,3-OMe,5-OCF$_3$) |
| Ph(2-F,3-CF$_2$CF$_3$,5-CF$_2$CF$_2$H) | Ph(2-F,3-CF$_2$H,5-I) | Ph(2-F,3-OMe,5-OCHF$_2$) |
| Ph(2-F,3-CF$_2$CF$_3$,5-CF$_2$H) | Ph(2-F,3-CF$_2$H,5-Me) | Ph(2-F,3-OMe,5-OCF$_2$CF$_2$H) |
| Ph(2-F,3-CF$_2$CF$_3$,5-OMe) | Ph(2-F,3-CF$_2$H,5-Ei) | Ph(2-F,3-OMe,5-OCF$_2$CF$_3$) |
| Ph(2-F,3-CF$_2$CF$_3$, 5-OCF$_3$) | Ph(2-F,3-CF$_2$H,5-n-Pr) | Ph(2-F,3-OMe,5-SO$_2$Me) |
| Ph(2-F,3-CF$_2$CF$_3$, 5-OCHF$_2$) | Ph(2-F,3-CF$_2$H,5-t-Bu) | Ph(2-F,3-OMe,5-TMS) |
| Ph(2-F,3-CF$_2$CF$_3$,5-OCF$_2$CF$_2$H) | Ph(2-F,3-CF$_2$H,5-i-Pr) | Ph(2-F,3-OMe,5-CN) |
| Ph(2-F,3-CF$_2$CF$_3$,5-OCF$_2$CF$_3$) | Ph(2-F,3-CF$_2$H,5-c-Pr) | Ph(2-F,3-OCF$_3$,5-Cl) |
| Ph(2-F,3-CF$_2$CF$_3$,5-SO$_2$Me) | Ph(2-F,3-CF$_2$H,5-CF$_3$) | Ph(2-F,3-OCF$_3$,5-F) |
| Ph(2-F,3-CF$_2$CF$_3$,5-TMS) | Ph(2-F,3-CF$_2$H,5-CF$_2$CF$_3$) | Ph(2-F,3-OCF$_3$,5-Br) |
| Ph(2-F,3-CF$_2$CF$_3$,5-CN) | Ph(2-F,3-CF$_2$H,5-CF$_2$CF$_2$H) | Ph(2-F,3-OCF$_3$,5-I) |
| Ph(2-F,3-CF$_2$CF$_2$H,5-Cl) | Ph(2-F,3,5-di-CF$_2$H) | Ph(2-F,3-OCF$_3$,5-Me) |
| Ph(2-F,3-CF$_2$CF$_2$H,5-F) | Ph(2-F,3-CF$_2$H,5-OMe) | Ph(2-F,3-OCF$_3$,5-Ei) |
| Ph(2-F,3-OCF$_3$,5-n-Pr) | Ph(2-F,3-OCHF$_2$,5-SO$_2$Me) | Ph(2-F,3-OCF$_2$CF$_3$CF$_3$,5-CF$_3$) |
| Ph(2-F,3-OCF$_3$,5-t-Bu) | Ph(2-F,3-OCHF$_2$,5-TMS) | Ph(2-F,3-OCF$_2$CF$_3$,5-CF$_2$CF$_3$) |
| Ph(2-F,3-OCF$_3$,5-i-Pr) | Ph(2-F,3-OCHF$_2$,5-CN) | Ph(2-F,3-OCF$_2$CF$_3$,5-CF$_2$CF$_2$H) |
| Ph(2-F,3-OCF$_3$,5-c-Pr) | Ph(2-F,3-OCF$_2$CF$_2$H,5-Cl) | Ph(2-F,3-OCF$_2$CF$_3$,5-CF$_2$H) |
| Ph(2-F,3-OCF$_3$,5-CF$_3$) | Ph(2-F,3-OCF$_2$CF$_2$H,5-F) | Ph(2-F,3-OCF$_2$CF$_3$,5-OMe) |
| Ph(2-F,3-OCF$_3$,5-CF$_2$CF$_3$) | Ph(2-F,3-OCF$_2$CF$_2$H,5-Br) | Ph(2-F,3-OCF$_2$CF$_3$,5-OCF$_3$) |
| Ph(2-F,3-OCF$_3$,5-CF$_2$CF$_2$H) | Ph(2-F,3-OCF$_2$CF$_2$H,5-I) | Ph(2-F,3-OCF$_2$CF$_3$,5-OCHF$_2$) |
| Ph(2-F,3-OCF$_3$,5-CF$_2$H) | Ph(2-F,3-OCF$_2$CF$_2$H,5-Me) | Ph(2-F,3-OCF$_2$CF$_3$,5-OCF$_2$CF$_2$H) |
| Ph(2-F,3-OCF$_3$,5-OMe) | Ph(2-F,3-OCF$_2$CF$_2$H,5-Ei) | Ph(2-F,3,5-di-OCF$_2$CF$_3$) |
| Ph(2-F,3,5-di-OCF$_3$) | Ph(2-F,3-OCF$_2$CF$_2$H,5-n-Pr) | Ph(2-F,3-OCF$_2$CF$_3$,5-SO$_2$Me) |
| Ph(2-F,3-OCF$_3$,5-OCHF$_2$) | Ph(2-F,3-OCF$_2$CF$_2$H,5-t-Bu) | Ph(2-F,3-OCF$_2$CF$_3$,5-TMS) |
| Ph(2-F,3-OCF$_3$,5-OCF$_2$CF$_2$H) | Ph(2-F,3-OCF$_2$CF$_2$H,5-i-Pr) | Ph(2-F,3-OCF$_2$CF$_3$,5-CN) |
| Ph(2-F,3-OCF$_3$,5-OCF$_2$CF$_3$) | Ph(2-F,3-OCF$_2$CF$_2$H,5-c-Pr) | Ph(2-F,3-SO$_2$Me,5-Cl) |

TABLE 1-continued

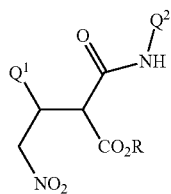

R is Me; $Q^2$ is Ph(2-F) and $Q^1$ is

| | | |
|---|---|---|
| Ph(2-F,3-OCF$_3$,5-SO$_2$Me) | Ph(2-F,3-OCF$_2$CF$_2$HCF$_3$,5-CF$_3$) | Ph(2-F,3-SO$_2$Me,5-F) |
| Ph(2-F,3-OCF$_3$,5-TMS) | Ph(2-F,3-OCF$_2$CF$_2$H,5-CF$_2$CF$_3$) | Ph(2-F,3-SO$_2$Me,5-Br) |
| Ph(2-F,3-OCF$_3$,5-CN) | Ph(2-F,3-OCF$_2$CF$_2$H,5-CF$_2$CF$_2$H) | Ph(2-F,3-SO$_2$Me,5-I) |
| Ph(2-F,3-OCHF$_2$,5-Cl) | Ph(2-F,3-OCF$_2$CF$_2$H,5-CF$_2$H) | Ph(2-F,3-SO$_2$Me,5-Me) |
| Ph(2-F,3-OCHF$_2$,5-F) | Ph(2-F,3-OCF$_2$CF$_2$H,5-OMe) | Ph(2-F,3-SO$_2$Me,5-Ei) |
| Ph(2-F,3-OCHF$_2$,5-Br) | Ph(2-F,3-OCF$_2$CF$_2$H,5-OCF$_3$) | Ph(2-F,3-SO$_2$Me,5-n-Pr) |
| Ph(2-F,3-OCHF$_2$,5-I) | Ph(2-F,3-OCF$_2$CF$_2$H,5-OCHF$_2$) | Ph(2-F,3-SO$_2$Me,5-t-Bu) |
| Ph(2-F,3-OCHF$_2$,5-Me) | Ph(2-F,3,5-di-OCF$_2$CF$_2$H) | Ph(2-F,3-SO$_2$Me,5-i-Pr) |
| Ph(2-F,3-OCHF$_2$,5-Ei) | Ph(2-F,3-OCF$_2$CF$_2$H,5-OCF$_2$CF$_3$) | Ph(2-F,3-SO$_2$Me,5-c-Pr) |
| Ph(2-F,3-OCHF$_2$,5-n-Pr) | Ph(2-F,3-OCF$_2$CF$_2$H,5-SO$_2$Me) | Ph(2-F,3-SO$_2$MeCF$_3$,5-CF$_3$) |
| Ph(2-F,3-OCHF$_2$,5-t-Bu) | Ph(2-F,3-OCF$_2$CF$_2$H,5-TMS) | Ph(2-F,3-SO$_2$Me,5-CF$_2$CF$_3$) |
| Ph(2-F,3-OCHF$_2$,5-i-Pr) | Ph(2-F,3-OCF$_2$CF$_2$H,5-CN) | Ph(2-F,3-SO$_2$Me,5-CF$_2$CF$_2$H) |
| Ph(2-F,3-OCHF$_2$,5-c-Pr) | Ph(2-F,3-OCF$_2$CF$_3$,5-Cl) | Ph(2-F,3-SO$_2$Me,5-CF$_2$H) |
| Ph(2-F,3-OCHF$_2$CF$_3$,5-CF$_3$) | Ph(2-F,3-OCF$_2$CF$_3$,5-F) | Ph(2-F,3-SO$_2$Me,5-OMe) |
| Ph(2-F,3-OCF$_2$CF$_3$,5-CF$_2$CF$_3$) | Ph(2-F,3-OCF$_2$CF$_3$,5-Br) | Ph(2-F,3-SO$_2$Me,5-OCF$_3$) |
| Ph(2-F,3-OCHF$_2$,5-CF$_2$CF$_2$H) | Ph(2-F,3-OCF$_2$CF$_3$,5-I) | Ph(2-F,3-SO$_2$Me,5-OCHF$_2$) |
| Ph(2-F,3-OCHF$_2$,5-CF$_2$H) | Ph(2-F,3-OCF$_2$CF$_3$,5-Me) | Ph(2-F,3-SO$_2$Me,5-OCF$_2$CF$_2$H) |
| Ph(2-F,3-OCHF$_2$,5-OMe) | Ph(2-F,3-OCF$_2$CF$_3$,5-Ei) | Ph(2-F,3-SO$_2$Me,5-OCF$_2$CF$_3$) |
| Ph(2-F,3-OCHF$_2$,5-OCF$_3$) | Ph(2-F,3-OCF$_2$CF$_3$,5-n-Pr) | Ph(2-F,3,5-di-SO$_2$Me) |
| Ph(2-F,3,5-di-OCHF$_2$) | Ph(2-F,3-OCF$_2$CF$_3$,5-t-Bu) | Ph(2-F,3-SO$_2$Me,5-TMS) |
| Ph(2-F,3-OCHF$_2$,5-OCF$_2$CF$_2$H) | Ph(2-F,3-OCF$_2$CF$_3$,5-i-Pr) | Ph(2-F,3-SO$_2$Me,5-CN) |
| Ph(2-F,3-OCHF$_2$,5-OCF$_2$CF$_3$) | Ph(2-F,3-OCF$_2$CF$_3$,5-c-Pr) | Ph(2-F,3-TMS,5-Cl) |
| Ph(2-F,3-TMS,5-F) | Ph(2-F,3-CN,5-OMe) | Ph(2-F,4-F,5-Et) |
| Ph(2-F,3-TMS,5-Br) | Ph(2-F,3-CN,5-OCF$_3$) | Ph(2-F,4-F,5-n-Pr) |
| Ph(2-F,3-TMS,5-I) | Ph(2-F,3-CN,5-OCHF$_2$) | Ph(2-F,4-F,5-t-Bu) |
| Ph(2-F,3-TMS,5-Me) | Ph(2-F,3-CN,5-OCF$_2$CF$_2$H) | Ph(2-F,4-F,5-i-Pr) |
| Ph(2-F,3-TMS,5-Ei) | Ph(2-F,3-CN,5-OCF$_2$CF$_3$) | Ph(2-F,4-F,5-c-Pr) |
| Ph(2-F,3-TMS,5-n-Pr) | Ph(2-F,3-CN,5-SO$_2$Me) | Ph(2-F,4-F,5-CF$_3$) |
| Ph(2-F,3-TMS,5-t-Bu) | Ph(2-F,3-CN,5-TMS) | Ph(2-F,4-F,5-CF$_2$CF$_3$) |
| Ph(2-F,3-TMS,5-i-Pr) | Ph(2-F,3,5-di-CN) | Ph(2-F,4-F,5-CF$_2$CF$_2$H) |
| Ph(2-F,3-TMS,5-c-Pr) | Ph(2-F,4,5-di-Cl) | Ph(2-F,4-F,5-CF$_2$H) |
| Ph(2-F,3-TMS,5-CF$_3$) | Ph(2-F,4-Cl,5-F) | Ph(2-F,4-F,5-OMe) |
| Ph(2-F,3-TMS,5-CF$_2$CF$_3$) | Ph(2-F,4-Cl,5-Br) | Ph(2-F,4-F,5-OCF$_3$) |
| Ph(2-F,3-TMS,5-CF$_2$CF$_2$H) | Ph(2-F,4-Cl,5-I) | Ph(2-F,4-F,5-OCHF$_2$) |
| Ph(2-F,3-TMS,5-CF$_2$H) | Ph(2-F,4-Cl,5-Me) | Ph(2-F,4-F,5-OCF$_2$CF$_2$H) |
| Ph(2-F,3-TMS,5-OMe) | Ph(2-F,4-Cl,5-Et) | Ph(2-F,4-F,5-OCF$_2$CF$_3$) |
| Ph(2-F,3-TMS,5-OCF$_3$) | Ph(2-F,4-Cl,5-n-Pr) | Ph(2-F,4-F,5-SO$_2$Me) |
| Ph(2-F,3-TMS,5-OCHF$_2$) | Ph(2-F,4-Cl,5-t-Bu) | Ph(2-F,4-F,5-TMS) |
| Ph(2-F,3-TMS,5-OCF$_2$CF$_2$H) | Ph(2-F,4-Cl,5-i-Pr) | Ph(2-F,4-F,5-CN) |
| Ph(2-F,3-TMS,5-OCF$_2$CF$_3$) | Ph(2-F,4-Cl,5-c-Pr) | Ph(2-F,4-Br,5-Cl) |
| Ph(2-F,3-TMS,5-SO$_2$Me) | Ph(2-F,4-Cl,5-CF$_3$) | Ph(2-F,4-Br,5-F) |
| Ph(2-F,3,5-di-TMS) | Ph(2-F,4-Cl,5-CF$_2$CF$_3$) | Ph(2-F,4,5-di-Br) |
| Ph(2-F,3-TMS,5-CN) | Ph(2-F,4-Cl,5-CF$_2$CF$_2$H) | Ph(2-F,4-Br,5-I) |
| Ph(2-F,3-CN,5-Cl) | Ph(2-F,4-Cl,5-CF$_2$H) | Ph(2-F,4-Br,5-Me) |
| Ph(2-F,3-CN,5-F) | Ph(2-F,4-Cl,5-OMe) | Ph(2-F,4-Br,5-Et) |
| Ph(2-F,3-CN,5-Br) | Ph(2-F,4-Cl,5-OCF$_3$) | Ph(2-F,4-Br,5-n-Pr) |
| Ph(2-F,3-CN,5-I) | Ph(2-F,4-Cl,5-OCHF$_2$) | Ph(2-F,4-Br,5-t-Bu) |
| Ph(2-F,3-CN,5-Me) | Ph(2-F,4-Cl,5-OCF$_2$CF$_2$H) | Ph(2-F,4-Br,5-i-Pr) |
| Ph(2-F,3-CN,5-Ei) | Ph(2-F,4-Cl,5-OCF$_2$CF$_3$) | Ph(2-F,4-Br,5-c-Pr) |
| Ph(2-F,3-CN,5-n-Pr) | Ph(2-F,4-Cl,5-SO$_2$Me) | Ph(2-F,4-Br,5-CF$_3$) |
| Ph(2-F,3-CN,5-t-Bu) | Ph(2-F,4-Cl,5-TMS) | Ph(2-F,4-Br,5-CF$_2$CF$_3$) |
| Ph(2-F,3-CN,5-i-Pr) | Ph(2-F,4-Cl,5-CN) | Ph(2-F,4-Br,5-CF$_2$CF$_2$H) |
| Ph(2-F,3-CN,5-c-Pr) | Ph(2-F,4-F,5-Cl) | Ph(2-F,4-Br,5-CF$_2$H) |
| Ph(2-F,3-CN,5-CF$_3$) | Ph(2,4,5-tri-F) | Ph(2-F,4-Br,5-OMe) |
| Ph(2-F,3-CN,5-CF$_2$CF$_3$) | Ph(2-F,4-F,5-Br) | Ph(2-F,4-Br,5-OCF$_3$) |
| Ph(2-F,3-CN,5-CF$_2$CF$_2$H) | Ph(2-F,4-F,5-I) | Ph(2-F,4-Br,5-OCHF$_2$) |
| Ph(2-F,3-CN,5-CF$_2$H) | Ph(2-F,4-F,5-Me) | Ph(2-F,4-Br,5-OCF$_2$CF$_2$H) |
| Ph(2-F,4-Br,5-OCF$_2$CF$_3$) | Ph(2-F,4-Me,5-c-Pr) | Ph(2-F,4-n-Pr,5-Cl) |
| Ph(2-F,4-Br,5-SO$_2$Me) | Ph(2-F,4-Me,5-CF$_3$) | Ph(2-F,4-n-Pr,5-F) |
| Ph(2-F,4-Br,5-TMS) | Ph(2-F,4-Me,5-CF$_2$CF$_3$) | Ph(2-F,4-n-Pr,5-Br) |
| Ph(2-F,4-Br,5-CN) | Ph(2-F,4-Me,5-CF$_2$CF$_2$H) | Ph(2-F,4-n-Pr,5-I) |
| Ph(2-F,4-I,5-Cl) | Ph(2-F,4-Me,5-CF$_2$H) | Ph(2-F,4-n-Pr,5-Me) |
| Ph(2-F,4-I,5-F) | Ph(2-F,4-Me,5-OMe) | Ph(2-F,4-n-Pr,5-Et) |
| Ph(2-F,4-I,5-Br) | Ph(2-F,4-Me,5-OCF$_3$) | Ph(2-F,4,5-di-n-Pr) |
| Ph(2-F,4,5-di-I) | Ph(2-F,4-Me,5-OCHF$_2$) | Ph(2-F,4-n-Pr,5-t-Bu) |
| Ph(2-F,4-I,5-Me) | Ph(2-F,4-Me,5-OCF$_2$CF$_2$H) | Ph(2-F,4-n-Pr,5-i-Pr) |
| Ph(2-F,4-I,5-Et) | Ph(2-F,4-Me,5-OCF$_2$CF$_3$) | Ph(2-F,4-n-Pr,5-c-Pr) |
| Ph(2-F,4-I,5-n-Pr) | Ph(2-F,4-Me,5-SO$_2$Me) | Ph(2-F,4-n-Pr,5-CF$_3$) |
| Ph(2-F,4-I,5-t-Bu) | Ph(2-F,4-Me,5-TMS) | Ph(2-F,4-n-Pr,5-CF$_2$CF$_3$) |

TABLE 1-continued

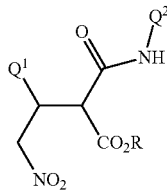

R is Me; Q² is Ph(2-F) and Q¹ is

| | | |
|---|---|---|
| Ph(2-F,4-I,5-i-Pr) | Ph(2-F,4-Me,5-CN) | Ph(2-F,4-n-Pr,5-CF₂CF₂H) |
| Ph(2-F,4-I,5-c-Pr) | Ph(2-F,4-Et,5-Cl) | Ph(2-F,4-n-Pr,5-CF₂H) |
| Ph(2-F,4-I,5-CF₃) | Ph(2-F,4-Et,5-F) | Ph(2-F,4-n-Pr,5-OMe) |
| Ph(2-F,4-I,5-CF₂CF₃) | Ph(2-F,4-Et,5-Br) | Ph(2-F,4-n-Pr,5-OCF₃) |
| Ph(2-F,4-I,5-CF₂CF₂H) | Ph(2-F,4-Et,5-I) | Ph(2-F,4-n-Pr,5-OCHF₂) |
| Ph(2-F,4-I,5-CF₂H) | Ph(2-F,4-Et,5-Me) | Ph(2-F,4-n-Pr,5-OCF₂CF₂H) |
| Ph(2-F,4-I,5-OMe) | Ph(2-F,4,5-di-Et) | Ph(2-F,4-n-Pr,5-OCF₂CF₃) |
| Ph(2-F,4-I,5-OCF₃) | Ph(2-F,4-Et,5-n-Pr) | Ph(2-F,4-n-Pr,5-SO₂Me) |
| Ph(2-F,4-I,5-OCHF₂) | Ph(2-F,4-Et,5-t-Bu) | Ph(2-F,4-n-Pr,5-TMS) |
| Ph(2-F,4-I,5-OCF₂CF₂H) | Ph(2-F,4-Et,5-i-Pr) | Ph(2-F,4-n-Pr,5-CN) |
| Ph(2-F,4-I,5-OCF₂CF₃) | Ph(2-F,4-Et,5-c-Pr) | Ph(2-F,4-t-Bu,5-Cl) |
| Ph(2-F,4-I,5-SO₂Me) | Ph(2-F,4-Et,5-CF₃) | Ph(2-F,4-t-Bu,5-F) |
| Ph(2-F,4-I,5-TMS) | Ph(2-F,4-Et,5-CF₂CF₃) | Ph(2-F,4-t-Bu,5-Br) |
| Ph(2-F,4-I,5-CN) | Ph(2-F,4-Et,5-CF₂CF₂H) | Ph(2-F,4-t-Bu,5-I) |
| Ph(2-F,4-Me,5-Cl) | Ph(2-F,4-Et,5-CF₂H) | Ph(2-F,4-t-Bu,5-Me) |
| Ph(2-F,4-Me,5-F) | Ph(2-F,4-Et,5-OMe) | Ph(2-F,4-t-Bu,5-Et) |
| Ph(2-F,4-Me,5-Br) | Ph(2-F,4-Et,5-OCF₃) | Ph(2-F,4-t-Bu,5-n-Pr) |
| Ph(2-F,4-Me,5-I) | Ph(2-F,4-Et,5-OCHF₂) | Ph(2-F,4,5-di-t-Bu) |
| Ph(2-F,4,5-di-Me) | Ph(2-F,4-Et,5-OCF₂CF₂H) | Ph(2-F,4-t-Bu,5-i-Pr) |
| Ph(2-F,4-Me,5-Et) | Ph(2-F,4-Et,5-OCF₂CF₃) | Ph(2-F,4-t-Bu,5-c-Pr) |
| Ph(2-F,4-Me,5-n-Pr) | Ph(2-F,4-Et,5-SO₂Me) | Ph(2-F,4-t-Bu,5-CF₃) |
| Ph(2-F,4-Me,5-t-Bu) | Ph(2-F,4-Et,5-TMS) | Ph(2-F,4-t-Bu,5-CF₂CF₃) |
| Ph(2-F,4-Me,5-i-Pr) | Ph(2-F,4-Et,5-CN) | Ph(2-F,4-t-Bu,5-CF₂CF₂H) |
| Ph(2-F,4-t-Bu,5-CF₂H) | Ph(2-F,4-c-Pr,5-Me) | Ph(2-F,4-CF₃,5-OCF₂CF₂H) |
| Ph(2-F,4-t-Bu,5-OMe) | Ph(2-F,4-c-Pr,5-Ei) | Ph(2-F,4-CF₃,5-OCF₂CF₃) |
| Ph(2-F,4-t-Bu,5-OCF₃) | Ph(2-F,4-c-Pr,5-n-Pr) | Ph(2-F,4-CF₃,5-SO₂Me) |
| Ph(2-F,4-t-Bu,5-OCHF₂) | Ph(2-F,4-c-Pr,5-t-Bu) | Ph(2-F,4-CF₃,5-IMS) |
| Ph(2-F,4-t-Bu,5-OCF₂CF₂H) | Ph(2-F,4-c-Pr,5-i-Pr) | Ph(2-F,4-CF₃,5-CN) |
| Ph(2-F,4-t-Bu,5-OCF₂CF₃) | Ph(2-F,4,5-di-c-Pr) | Ph(2-F,4-CF₂CF₃,5-Cl) |
| Ph(2-F,4-t-Bu,5-SO₂Me) | Ph(2-F,4-c-Pr,5-CF₃) | Ph(2-F,4-CF₂CF₃,5-F) |
| Ph(2-F,4-t-Bu,5-TMS) | Ph(2-F,4-c-Pr,5-CF₂CF₃) | Ph(2-F,4-CF₂CF₃,5-Br) |
| Ph(2-F,4-t-Bu,5-CN) | Ph(2-F,4-c-Pr,5-CF₂CF₂H) | Ph(2-F,4-CF₂CF₃,5-I) |
| Ph(2-F,4-i-Pr,5-Cl) | Ph(2-F,4-c-Pr,5-CF₂H) | Ph(2-F,4-CF₂ₗ CF₃,5-Me) |
| Ph(2-F,4-i-Pr,5-F) | Ph(2-F,4-c-Pr,5-OMe) | Ph(2-F,4-CF₂CF₃,5-Ei) |
| Ph(2-F,4-i-Pr,5-Br) | Ph(2-F,4-c-Pr,5-OCF₃) | Ph(2-F,4-CF₂CF₃,5-n-Pr) |
| Ph(2-F,4-i-Pr,5-I) | Ph(2-F,4-c-Pr,5-OCHF₂) | Ph(2-F,4-CF₂CF₃,5-t-Bu) |
| Ph(2-F,4-i-Pr,5-Me) | Ph(2-F,4-c-Pr,5-OCF₂CF₂H) | Ph(2-F,4-CF₂CF₃,5-i-Pr) |
| Ph(2-F,4-i-Pr,5-Ei) | Ph(2-F,4-c-Pr,5-OCF₂CF₃) | Ph(2-F,4-CF₂CF₃,5-c-Pr) |
| Ph(2-F,4-i-Pr,5-n-Pr) | Ph(2-F,4-c-Pr,5-SO₂Me) | Ph(2-F,4-CF₂CF₃CF₃,5-CF₃) |
| Ph(2-F,4-i-Pr,5-t-Bu) | Ph(2-F,4-c-Pr,5-TMS) | Ph(2-F,4,5-di-CF₂CF₃) |
| Ph(2-F,4,5-di-i-Pr) | Ph(2-F,4-c-Pr,5-CN) | Ph(2-F,4-CF₂CF₃,5-CF₂CF₂H) |
| Ph(2-F,4-i-Pr,5-c-Pr) | Ph(2-F,4-CF₃,5-Cl) | Ph(2-F,4-CF₂CF₃,5-CF₂H) |
| Ph(2-F,4-i-Pr,5-CF₃) | Ph(2-F,4-CF₃,5-F) | Ph(2-F,4-CF₂CF₃,5-OMe) |
| Ph(2-F,4-i-Pr,5-CF₂CF₃) | Ph(2-F,4-CF₃,5-Br) | Ph(2-F,4-CF₂CF₃,5-OCF₃) |
| Ph(2-F,4-i-Pr,5-CF₂CF₂H) | Ph(2-F,4-CF₃,5-I) | Ph(2-F,4-CF₂CF₃,5-OCHF₂) |
| Ph(2-F,4-i-Pr,5-CF₂H) | Ph(2-F,4-CF₃,5-Me) | Ph(2-F,4-CF₂CF₃,5-OCF₂CF₂H) |
| Ph(2-F,4-i-Pr,5-OMe) | Ph(2-F,4-CF₃,5-Ei) | Ph(2-F,4-CF₂CF₃,5-OCF₂CF₃) |
| Ph(2-F,4-i-Pr,5-OCF₃) | Ph(2-F,4-CF₃,5-n-Pr) | Ph(2-F,4-CF₂CF₃,5-SO₂Me) |
| Ph(2-F,4-i-Pr,5-OCHF₂) | Ph(2-F,4-CF₃,5-t-Bu) | Ph(2-F,4-CF₂CF₃,5-TMS) |
| Ph(2-F,4-i-Pr,5-OCF₂CF₂H) | Ph(2-F,4-CF₃,5-i-Pr) | Ph(2-F,4-CF₂CF₃,5-CN) |
| Ph(2-F,4-i-Pr,5-OCF₂CF₃) | Ph(2-F,4-CF₃,5-c-Pr) | Ph(2-F,4-CF₂CF₂H,5-Cl) |
| Ph(2-F,4-i-Pr,5-SO₂Me) | Ph(2-F,4,5-di-CF₃) | Ph(2-F,4-CF₂CF₂H,5-F) |
| Ph(2-F,4-i-Pr,5-TMS) | Ph(2-F,4-CF₃,5-CF₂CF₃) | Ph(2-F,4-CF₂CF₂H,5-Br) |
| Ph(2-F,4-i-Pr,5-CN) | Ph(2-F,4-CF₃,5-CF₂CF₂H) | Ph(2-F,4-CF₂CF₂H,5-I) |
| Ph(2-F,4-c-Pr,5-Cl) | Ph(2-F,4-CF₃,5-CF₂H) | Ph(2-F,4-CF₂CF₂H,5-Me) |
| Ph(2-F,4-c-Pr,5-F) | Ph(2-F,4-CF₃,5-OMe) | Ph(2-F,4-CF₂CF₂H,5-Ei) |
| Ph(2-F,4-c-Pr,5-Br) | Ph(2-F,4-CF₃,5-OCF₃) | Ph(2-F,4-CF₂CF₂H,5-n-Pr) |
| Ph(2-F,4-c-Pr,5-I) | Ph(2-F,4-CF₃,5-OCHF₂) | Ph(2-F,4-CF₂CF₂H,5-t-Bu) |
| Ph(2-F,4-CF₂CF₂H,5-i-Pr) | Ph(2-F,4-CF₂H,5-CN) | Ph(2-F,4-OCF₃,5-CF₂CF₂H) |
| Ph(2-F,4-CF₂CF₂H,5-c-Pr) | Ph(2-F,4-OMe,5-Cl) | Ph(2-F,4-OCF₃,5-CF₂H) |
| Ph(2-F,4-CF₂CF₂HCF₃,5-CF₃) | Ph(2-F,4-OMe,5-F) | Ph(2-F,4-OCF₃,5-OMe) |
| Ph(2-F,4-CF₂CF₂H,5-CF₂CF₃) | Ph(2-F,4-OMe,5-Br) | Ph(2-F,4,5-di-OCF₃) |
| Ph(2-F,4,5-di-CF₂CF₂H) | Ph(2-F,4-OMe,5-I) | Ph(2-F,4-OCF₃,5-OCHF₂) |
| Ph(2-F,4-CF₂CF₂H,5-CF₂H) | Ph(2-F,4-OMe,5-Me) | Ph(2-F,4-OCF₃,5-OCF₂CF₂H) |
| Ph(2-F,4-CF₂CF₂H,5-OMe) | Ph(2-F,4-OMe,5-Ei) | Ph(2-F,4-OCF₃,5-OCF₂CF₃) |
| Ph(2-F,4-CF₂CF₂H,5-OCF₃) | Ph(2-F,4-OMe,5-n-Pr) | Ph(2-F,4-OCF₃,5-SO₂Me) |
| Ph(2-F,4-CF₂CF₂H,5-OCHF₂) | Ph(2-F,4-OMe,5-t-Bu) | Ph(2-F,4-OCF₃,5-TMS) |
| Ph(2-F,4-CF₂CF₂H,5-OCF₂CF₂H) | Ph(2-F,4-OMe,5-i-Pr) | Ph(2-F,4-OCF₃,5-CN) |
| Ph(2-F,4-CF₂CF₂H,5-OCF₂CF₃) | Ph(2-F,4-OMe,5-c-Pr) | Ph(2-F,4-OCHF₂,5-Cl) |

TABLE 1-continued

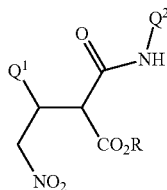

R is Me; $Q^2$ is Ph(2-F) and $Q^1$ is

| | | |
|---|---|---|
| Ph(2-F,4-CF$_2$CF$_2$H,5-SO$_2$Me) | Ph(2-F,4-OMeCF$_3$,5-CF$_3$) | Ph(2-F,4-OCHF$_2$,5-F) |
| Ph(2-F,4-CF$_2$CF$_2$H,5-TMS) | Ph(2-F,4-OMe,5-CF$_2$CF$_3$) | Ph(2-F,4-OCHF$_2$,5-Br) |
| Ph(2-F,4-CF$_2$CF$_2$H,5-CN) | Ph(2-F,4-OMe,5-CF$_2$CF$_2$H) | Ph(2-F,4-OCHF$_2$,5-I) |
| Ph(2-F,4-CF$_2$H,5-Cl) | Ph(2-F,4-OMe,5-CF$_2$H) | Ph(2-F,4-OCHF$_2$,5-Me) |
| Ph(2-F,4-CF$_2$H,5-F) | Ph(2-F,4,5-di-OMe) | Ph(2-F,4-OCHF$_2$,5-Ei) |
| Ph(2-F,4-CF$_2$H,5-Br) | Ph(2-F,4-OMe,5-OCF$_3$) | Ph(2-F,4-OCHF$_2$,5-n-Pr) |
| Ph(2-F,4-CF$_2$H,5-I) | Ph(2-F,4-OMe,5-OCHF$_2$) | Ph(2-F,4-OCHF$_2$,5-t-Bu) |
| Ph(2-F,4-CF$_2$H,5-Me) | Ph(2-F,4-OMe,5-OCF$_2$CF$_2$H) | Ph(2-F,4-OCHF$_2$,5-i-Pr) |
| Ph(2-F,4-CF$_2$H,5-Ei) | Ph(2-F,4-OMe,5-OCF$_2$CF$_3$) | Ph(2-F,4-OCHF$_2$,5-c-Pr) |
| Ph(2-F,4-CF$_2$H,5-n-Pr) | Ph(2-F,4-OMe,5-SO$_2$Me) | Ph(2-F,4-OCHF$_2$CF$_3$,5-CF$_3$) |
| Ph(2-F,4-CF$_2$H,5-t-Bu) | Ph(2-F,4-OMe,5-TMS) | Ph(2-F,4-OCF$_2$CF$_3$,5-CF$_2$CF$_3$) |
| Ph(2-F,4-CF$_2$H,5-i-Pr) | Ph(2-F,4-OMe,5-CN) | Ph(2-F,4-OCHF$_2$,5-CF$_2$CF$_2$H) |
| Ph(2-F,4-CF$_2$H,5-c-Pr) | Ph(2-F,4-OCF$_3$,5-Cl) | Ph(2-F,4-OCHF$_2$,5-CF$_2$H) |
| Ph(2-F,4-CF$_2$H,5-CF$_3$) | Ph(2-F,4-OCF$_3$,5-F) | Ph(2-F,4-OCHF$_2$,5-OMe) |
| Ph(2-F,4-CF$_2$H,5-CF$_2$CF$_3$) | Ph(2-F,4-OCF$_3$,5-Br) | Ph(2-F,4-OCHF$_2$,5-OCF$_3$) |
| Ph(2-F,4-CF$_2$H,5-CF$_2$CF$_2$H) | Ph(2-F,4-OCF$_3$,5-I) | Ph(2-F,4,5-di-OCHF$_2$) |
| Ph(2-F,4,5-di-CF$_2$H) | Ph(2-F,4-OCF$_3$,5-Me) | Ph(2-F,4-OCHF$_2$,5-OCF$_2$CF$_2$H) |
| Ph(2-F,4-CF$_2$H,5-OMe) | Ph(2-F,4-OCF$_3$,5-Ei) | Ph(2-F,4-OCHF$_2$,5-OCF$_2$CF$_3$) |
| Ph(2-F,4-CF$_2$H,5-OCF$_3$) | Ph(2-F,4-OCF$_3$,5-n-Pr) | Ph(2-F,4-OCHF$_2$,5-SO$_2$Me) |
| Ph(2-F,4-CF$_2$H,5-OCHF$_2$) | Ph(2-F,4-OCF$_3$,5-t-Bu) | Ph(2-F,4-OCHF$_2$,5-TMS) |
| Ph(2-F,4-CF$_2$H,5-OCF$_2$CF$_2$H) | Ph(2-F,4-OCF$_3$,5-i-Pr) | Ph(2-F,4-OCHF$_2$,5-CN) |
| Ph(2-F,4-CF$_2$H,5-OCF$_2$CF$_3$) | Ph(2-F,4-OCF$_3$,5-c-Pr) | Ph(2-F,4-OCF$_2$CF$_2$H,5-Cl) |
| Ph(2-F,4-CF$_2$H,5-SO$_2$Me) | Ph(2-F,4-OCF$_3$,5-CF$_3$) | Ph(2-F,4-OCF$_2$CF$_2$H,5-F) |
| Ph(2-F,4-CF$_2$H,5-TMS) | Ph(2-F,4-OCF$_3$,5-CF$_2$CF$_3$) | Ph(2-F,4-OCF$_2$CF$_2$H,5-Br) |
| Ph(2-F,4-OCF$_2$CF$_2$H,5-I) | Ph(2-F,4-OCF$_2$CF$_3$,5-OCHF$_2$) | Ph(2-F,4-TMS,5-t-Bu) |
| Ph(2-F,4-OCF$_2$CF$_2$H,5-Me) | Ph(2-F,4-OCF$_2$CF$_3$,5-OCF$_2$CFH) | Ph(2-F,4-TMS,5-i-Pr) |
| Ph(2-F,4-OCF$_2$CF$_2$H,5-Ei) | Ph(2-F,4,5-di-OCF$_2$CF$_3$) | Ph(2-F,4-TMS,5-c-Pr) |
| Ph(2-F,4-OCF$_2$CF$_2$H,5-n-Pr) | Ph(2-F,4-OCF$_2$CF$_3$,5-SO$_2$Me) | Ph(2-F,4-TMS,5-CF$_3$) |
| Ph(2-F,4-OCF$_2$CF$_2$H,5-t-Bu) | Ph(2-F,4-OCF$_2$CF$_3$,5-TMS) | Ph(2-F,4- TMS,5-CF$_2$CF$_3$) |
| Ph(2-F,4-OCF$_2$CF$_2$H,5-i-Pr) | Ph(2-F,4-OCF$_2$CF$_3$,5-CN) | Ph(2-F,4-TMS,5-CF$_2$CF$_2$H) |
| Ph(2-F,4-OCF$_2$CF$_2$H,5-c-Pr) | Ph(2-F,4-SO$_2$Me,5-Cl) | Ph(2-F,4-TMS,5-CF$_2$H) |
| Ph(2-F,4-OCF$_2$CF$_2$HCF$_3$,5-CF$_3$) | Ph(2-F,4-SO$_2$Me,5-F) | Ph(2-F,4-TMS,5-OMe) |
| Ph(2-F,4-OCF$_2$CF$_2$H,5-CFCF$_3$) | Ph(2-F,4-SO$_2$Me,5-Br) | Ph(2-F,4-TMS,5-OCF$_3$) |
| Ph(2-F,4-OCF$_2$CF$_2$H,5-CF$_2$CF$_2$H | Ph(2-F,4-SO$_2$Me,5-I) | Ph(2-F,4-TMS,5-OCHF$_2$) |
| Ph(2-F,4-OCF$_2$CF$_2$H,5-CF$_2$H) | Ph(2-F,4-SO$_2$Me,5-Me) | Ph(2-F,4-TMS,5-OCF$_2$CF$_2$H) |
| Ph(2-F,4-OCF$_2$CF$_2$H,5-OMe) | Ph(2-F,4-SO$_2$Me,5-Ei) | Ph(2-F,4-TMS,5-OCF$_2$CF$_3$) |
| Ph(2-F,4-OCF$_2$CF$_2$H,5-OCF$_3$) | Ph(2-F,4-SO$_2$Me,5-n-Pr) | Ph(2-F,4-TMS,5-SO$_2$Me) |
| Ph(2-F,4-OCF$_2$CF$_2$H,5-OCHF$_2$) | Ph(2-F,4-SO$_2$Me,5-t-Bu) | Ph(2-F,4,5-di-TMS) |
| Ph(2-F,4,5-di-OCFCF$_2$H) | Ph(2-F,4-SO$_2$Me,5-i-Pr) | Ph(2-F,4-TMS,5-CN) |
| Ph(2-F,4-OCF$_2$CF$_2$H,5-OCF$_2$CF$_3$) | Ph(2-F,4-SO$_2$Me,5-c-Pr) | Ph(2-F,4-CN,5-Cl) |
| Ph(2-F,4-OCF$_2$CF$_2$H,5-SO$_2$Me) | Ph(2-F,4SO$_2$MeCF$_3$,5-CF$_3$) | Ph(2-F,4-CN,5-F) |
| Ph(2-F,4-OCF$_2$CF$_2$H,5-TMS) | Ph(2-F,4-SO$_2$Me,5-CF$_2$CF$_3$) | Ph(2-F,4-CN,5-Br) |
| Ph(2-F,4-OCF$_2$CF$_2$,5-CN) | Ph(2-F,4-SO$_2$Me,5-CF$_2$CF$_2$H) | Ph(2-F,4-CN,5-I) |
| Ph(2-F,4-OCF$_2$CF$_3$,5-Cl) | Ph(2-F,4-SO$_2$Me,5-CF$_2$H) | Ph(2-F,4-CN,5-Me) |
| Ph(2-F,4-OCF$_2$CF$_3$,5-F) | Ph(2-F,4-SO$_2$Me,5-OMe) | Ph(2-F,4-CN,5-Ei) |
| Ph(2-F,4-OCF$_2$CF$_3$,5-Br) | Ph(2-F,4-SO$_2$Me,5-OCF$_3$) | Ph(2-F,4-CN,5-n-Pr) |
| Ph(2-F,4-OCF$_2$CF$_3$,5-I) | Ph(2-F,4-SO$_2$Me,5-OCHF$_2$) | Ph(2-F,4-CN,5-t-Bu) |
| Ph(2-F,4-OCF$_2$CF$_3$,5-Me) | Ph(2-F,4-SO$_2$Me,5-OCF$_2$CF$_2$H) | Ph(2-F,4-CN,5-i-Pr) |
| Ph(2-F,4-OCF$_2$CF$_3$,5-Ei) | Ph(2-F,4-SO$_2$Me,5-OCF$_2$CF$_3$) | Ph(2-F,4-CN,5-c-Pr) |
| Ph(2-F,4-OCF$_2$CF$_3$,5-n-Pr) | Ph(2-F,4,5-di-SO$_2$Me) | Ph(2-F,4-CN,5-CF$_3$) |
| Ph(2-F,4-OCF$_2$CF$_3$,5-t-Bu) | Ph(2-F,4-SO$_2$Me,5-TMS) | Ph(2-F,4-CN,5-CF$_2$CF$_3$) |
| Ph(2-F,4-OCF$_2$CF$_3$,5-i-Pr) | Ph(2-F,4-SO$_2$Me,5-CN) | Ph(2-F,4-CN,5-CF$_2$CF$_2$H) |
| Ph(2-F,4-OCF$_2$CF$_3$,5-c-Pr) | Ph(2-F,4-TMS,5-Cl) | Ph(2-F,4-CN,5-CF$_2$H) |
| Ph(2-F,4-OCF$_2$CF$_3$CF$_3$,5-CF$_3$) | Ph(2-F,4-TMS,5-F) | Ph(2-F,4-CN,5-OMe) |
| Ph(2-F,4-OCF$_2$CF$_3$,5-CF$_2$CF$_3$) | Ph(2-F,4-TMS,5-Br) | Ph(2-F,4-CN,5-OCF$_3$) |
| Ph(2-F,4-OCF$_2$CF$_3$,5-CF$_2$CF$_2$H) | Ph(2-F,4-TMS,5-I) | Ph(2-F,4-CN,5-OCHF$_2$) |
| Ph(2-F,4-OCF$_2$CF$_3$,5-CF$_2$H) | Ph(2-F,4-TMS,5-Me) | Ph(2-F,4-CN,5-OCF$_2$CF$_2$H) |
| Ph(2-F,4-OCF$_2$CF$_3$,5-OMe) | Ph(2-F,4-TMS,5-Ei) | Ph(2-F,4-CN,5-OCF$_2$CF$_3$) |
| Ph(2-F,4-OCF$_2$CF$_3$,5-OCF$_3$) | Ph(2-F,4-TMS,5-n-Pr) | Ph(2-F,4-CN,5-SO$_2$Me) |
| Ph(2-F,4-CN,5-TMS) | Ph(3-Me,4-CF$_2$CF$_3$,5-F) | Ph(3-Me,4-Br,5-Me) |
| Ph(2-F,4,5-di-CN) | Ph(3-F,4-CF$_2$CF$_2$H,5-F) | Ph(3-Me,4-I,5-Me) |
| Ph(3,4,5-tri-Cl) | Ph(3-F,4-CF$_2$H,5-F) | Ph(3,4-tri-Me) |
| Ph(3-Cl,4-F,5-Cl) | Ph(3-F,4-OMe,5-F) | Ph(3-Me,4-Et,5-Me) |
| Ph(3-Cl,4-Br,5-Cl) | Ph(3-F,4-OCF$_3$,5-F) | Ph(3-Me,4-n-Pr,5-Me) |
| Ph(3-Cl,4-I,5-Cl) | Ph(3-F,4-OCHF$_2$,5-F) | Ph(3-Me,4-t-Bu,5-Me) |
| Ph(3-Cl,4-Me,5-Cl) | Ph(3-F,4-OCF$_2$CF$_2$H,5-F) | Ph(3-Me,4-i-Pr,5-Me) |
| Ph(3-Cl,4-Et,5-Cl) | Ph(3-F,4-OCF$_2$CF$_3$,5-F) | Ph(3-Me,4-c-Pr,5-Me) |
| Ph(3-Cl,4-n-Pr,5-Cl) | Ph(3-F,4-SO$_2$Me,5-F) | Ph(3-Me,4-CF$_3$,5-Me) |
| Ph(3-Cl,4-t-Bu,5-Cl) | Ph(3-F,4-TMS,5-F) | Ph(3-Me,4-CF$_2$CF$_3$,5-Me) |

TABLE 1-continued

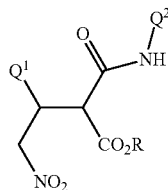

R is Me; Q² is Ph(2-F) and Q¹ is

| | | |
|---|---|---|
| Ph(3-Cl,4-i-Pr,5-Cl) | Ph(3-F,4-CN,5-F) | Ph(3-Me,4-CF$_2$CF$_2$H,5-Me) |
| Ph(3-Cl,4-c-Pr,5-Cl) | Ph(3-Br,4-Cl,5-Br) | Ph(3-Me,4-CF$_2$H,5-Me) |
| Ph(3-Cl,4-CF$_3$,5-Cl) | Ph(3-Br,4-F,5-Br) | Ph(3-Me,4-OMe,5-Me) |
| Ph(3-Cl,4-CF$_2$CF$_3$,5-Cl) | Ph(3,4,5-tri-Br) | Ph(3-Me,4-OCF$_3$,5-Me) |
| Ph(3-Cl,4-CF$_2$CF$_2$H,5-Cl) | Ph(3-Br,4-I,5-Br) | Ph(3-Me,4-OCHF$_2$,5-Me) |
| Ph(3-Cl,4-CF$_2$H,5-Cl) | Ph(3-Br,4-Me,5-Br) | Ph(3-Me,4-OCF$_2$CF$_2$H,5-Me) |
| Ph(3-Cl,4-OMe,5-Cl) | Ph(3-Br,4-Et,5-Br) | Ph(3-Me,4-OCF$_2$CF$_3$,5-Me) |
| Ph(3-Cl,4-OCF$_3$,5-Cl) | Ph(3-Br,4-n-Pr,5-Br) | Ph(3-Me,4-SO$_2$Me,5-Me) |
| Ph(3-Cl,4-OCHF$_2$,5-Cl) | Ph(3-Br,4-t-Bu,5-Br) | Ph(3-Me,4-TMS,5-Me) |
| Ph(3-Cl,4-OCF$_2$CF$_2$H,5-Cl) | Ph(3-Br,4-i-Pr,5-Br) | Ph(3-Me,4-CN,5-Me) |
| Ph(3-Cl,4-OCF$_2$CF$_3$,5-Cl) | Ph(3-Br,4-c-Pr,5-Br) | Ph(3-CF$_3$,4-Cl,5-CF$_3$) |
| Ph(3-Cl,4-SO$_2$Me,5-Cl) | Ph(3-Br,4-CF$_3$,5-Br) | Ph(3-CF$_3$,4-F,5-CF$_3$) |
| Ph(3-Cl,4-TMS,5-Cl) | Ph(3-Br,4-CF$_2$CF$_3$,5-Br) | Ph(3-CF$_3$,4-Br,5-CF$_3$) |
| Ph(3-Cl,4-CN,5-Cl) | Ph(3-Br,4-CF$_2$CF$_2$H,5-Br) | Ph(3-CF$_3$,4-I,5-CF$_3$) |
| Ph(3-F,4-Cl,5-F) | Ph(3-Br,4-CF$_2$H,5-Br) | Ph(3-CF$_3$,4-Me,5-CF$_3$) |
| Ph(3,4,5-tri-F) | Ph(3-Br,4-OMe,5-Br) | Ph(3-CF$_3$,4-Et,5-CF$_3$) |
| Ph(3-F,4-Br,5-F) | Ph(3-Br,4-OCF$_3$,5-Br) | Ph(3-CF$_3$,4-n-Pr,5-CF$_3$) |
| Ph(3-F,4-I,5-F) | Ph(3-Br,4-OCHF$_2$,5-Br) | Ph(3-CF$_3$,4-t-Bu,5-CF$_3$) |
| Ph(3-F,4-Me,5-F) | Ph(3-Br,4-OCF$_2$CF$_2$H,5-Br) | Ph(3-CF$_3$,4-i-Pr,5-CF$_3$) |
| Ph(3-F,4-Et,5-F) | Ph(3-Br,4-OCF$_2$CF$_3$,5-Br) | Ph(3-CF$_3$,4-c-Pr,5-CF$_3$) |
| Ph(3-F,4-n-Pr,5-F) | Ph(3-Br,4-SO$_2$Me,5-Br) | Ph(3,4,5-tri-CF$_3$) |
| Ph(3-F,4-t-Bu,5-F) | Ph(3-Br,4-TMS,5-Br) | Ph(3-CF$_3$,4-CF$_2$CF$_3$,5-CF$_3$) |
| Ph(3-F,4-i-Pr,5-F) | Ph(3-Br,4-CN,5-Br) | Ph(3-CF$_3$,4-CF$_2$CF$_2$H,5-CF$_3$) |
| Ph(3-F,4-c-Pr,5-F) | Ph(3-Me,4-Cl,5-Me) | Ph(3-CF$_3$,4-CF$_2$H,5-CF$_3$) |
| Ph(3-F,4-CF$_3$,5-F) | Ph(3-Me,4-F,5-Me) | Ph(3-CF$_3$,4-OMe,5-CF$_3$) |
| Ph(3-CF$_3$,4-OCF$_3$,5-CF$_3$) | Ph(2-Cl,3-Cl,4-n-Pr,5-Cl) | Ph(2-Cl,3-F,4-SO$_2$Me,5-F) |
| Ph(3-CF$_3$,4-OCHF$_2$,5-CF$_3$) | Ph(2-Cl,3-Cl,4-t-Bu,5-Cl) | Ph(2-Cl,3-F,4-TMS,5-F) |
| Ph(3-CF$_3$,4-OCF$_2$CF$_2$H,5-CF$_3$) | Ph(2-Cl,3-Cl,4-i-Pr,5-Cl) | Ph(2-Cl,3-F,4-CN,5-F) |
| Ph(3-CF$_3$,4-OCF$_2$CF$_3$,5-CF$_3$) | Ph(2-Cl,3-Cl,4-c-Pr,5-Cl) | Ph(2-Cl,3-Br,4-Cl,5-Br) |
| Ph(3-CF$_3$,4-SO$_2$Me,5-CF$_3$) | Ph(2-Cl,3-Cl,4-CF$_3$,5-Cl) | Ph(2-Cl,3-Br,4-F,5-Br) |
| Ph(3-CF$_3$,4-IMS,5-CF$_3$) | Ph(2-Cl,3-Cl,4-CF$_2$CF$_3$,5-Cl) | Ph(2-Cl,3,4,5-tri-Br) |
| Ph(3-CF$_3$,4-CN,5-CF$_3$) | Ph(2-Cl,3-Cl,4-CF$_2$CF$_2$H,5-Cl) | Ph(2-Cl,3-Br,4-I,5-Br) |
| Ph(3-OCHF$_2$,4-Cl,5-OCHF$_2$) | Ph(2-Cl,3-Cl,4-CF$_2$H,5-Cl) | Ph(2-Cl,3-Br,4-Me,5-Br) |
| Ph(3-OCHF$_2$,4-F,5-OCHF$_2$) | Ph(2-Cl,3-Cl,4-OMe,5-Cl) | Ph(2-Cl,3-Br,4-Et,5-Br) |
| Ph(3-OCHF$_2$,4-Br,5-OCHF$_2$) | Ph(2-Cl,3-Cl,4-OCF$_3$,5-Cl) | Ph(2-Cl,3-Br,4-n-Pr,5-Br) |
| Ph(3-OCHF$_2$,4-I,5-OCHF$_2$) | Ph(2-Cl,3-Cl,4-OCHF$_2$,5-Cl) | Ph(2-Cl,3-Br,4-t-Bu,5-Br) |
| Ph(3-OCHF$_2$,4-Me,5-OCHF$_2$) | Ph(2-Cl,3-Cl,4-OCF$_2$CF$_2$H,5-Cl) | Ph(2-Cl,3-Br,4-i-Pr,5-Br) |
| Ph(3-OCHF$_2$,4-Ei,5-OCHF$_2$) | Ph(2-Cl,3-Cl,4-OCF$_2$CF$_3$,5-Cl) | Ph(2-Cl,3-Br,4-c-Pr,5-Br) |
| Ph(3-OCHF$_2$,4-n-Pr,5-OCHF$_2$) | Ph(2-Cl,3-Cl,4-SO$_2$Me,5-Cl) | Ph(2-Cl,3-Br,4-CF$_3$,5-Br) |
| Ph(3-OCHF$_2$,4-t-Bu,5-OCHF$_2$) | Ph(2-Cl,3-Cl,4-TMS,5-Cl) | Ph(2-Cl,3-Br,4-CF$_2$CF$_3$,5-Br) |
| Ph(3-OCHF$_2$,4-i-Pr,5-OCHF$_2$) | Ph(2-Cl,3-Cl,4-CN,5-Cl) | Ph(2-Cl,3-Br,4-CF$_2$CF$_2$H,5-Br) |
| Ph(3-OCHF$_2$,4-c-Pr,5-OCHF$_2$) | Ph(2-Cl,3-F,4-Cl,5-F) | Ph(2-Cl,3-Br,4-CF$_2$H,5-Br) |
| Ph(3-OCHF$_2$CF$_3$,4-CF$_3$,5-OCHF$_2$) | Ph(2-Cl,3,4,5-tri-F) | Ph(2-Cl,3-Br,4-OMe,5-Br) |
| Ph(3-OCF$_2$CF$_3$,4-CF$_2$CF$_3$,5-OCHF$_2$) | Ph(2-Cl,3-F,4-Br,5-F) | Ph(2-Cl,3-Br,4-OCF$_3$,5-Br) |
| Ph(3-OCHF$_2$,4-CF$_2$CF$_2$H,5-OCHF$_2$) | Ph(2-Cl,3-F,4-I,5-F) | Ph(2-Cl,3-Br,4-OCHF$_2$,5-Br) |
| Ph(3-OCHF$_2$,4-CF$_2$H,5-OCHF$_2$) | Ph(2-Cl,3-F,4-Me,5-F) | Ph(2-Cl,3-Br,4-OCF$_2$CF$_2$H,5-Br) |
| Ph(3-OCHF$_2$,4-OMe,5-OCHF$_2$) | Ph(2-Cl,3-F,4-Et,5-F) | Ph(2-Cl,3-Br,4-OCF$_2$CF$_3$,5-Br) |
| Ph(3-OCHF$_2$,4-OCF$_2$,5-OCHF$_2$) | Ph(2-Cl,3-F,4-n-Pr,5-F) | Ph(2-C1,3-Br,4-SO$_2$SO$_2$Me,5-Br) |
| Ph(3,4,5-tri-OCHF$_2$) | Ph(2-Cl,3-F,4-t-Bu,5-F) | Ph(2-Cl,3-Br,4-TMS,5-Br) |
| Ph(3-OCHF$_2$,4-OCF$_2$CF$_2$H,5-OCHF$_2$) | Ph(2-Cl,3-F,4-i-Pr,5-F) | Ph(2-Cl,3-Br,4-CN,5-Br) |
| Ph(3-OCHF$_2$,4-OCF$_2$CF$_3$,5-OCHF$_2$) | Ph(2-Cl,3-F,4-c-Pr,5-F) | Ph(2-Cl,3-Me,4-Cl,5-Me) |
| Ph(3-OCHF$_2$,4-SO$_2$Me,5-OCHF$_2$) | Ph(2-Cl,3-F,4-CF$_3$,5-F) | Ph(2-Cl,3-Me,4-F,5-Me) |
| Ph(3-OCHF$_2$,4-TMS,5-OCHF$_2$) | Ph(2-Cl,3-F,4-CF$_2$CF$_3$,5-F) | Ph(2-Cl,3-Me,4-Br,5-Me) |
| Ph(3-OCHF$_2$,4-CN,5-OCHF$_2$) | Ph(2-Cl,3-F,4-CF$_2$CF$_2$H,5-F) | Ph(2-Cl,3-Me,4-I,5-Me) |
| Ph(2,3,4,5-tetra-Cl) | Ph(2-Cl,3-F,4-CF$_2$H,5-F) | Ph(2-Cl,3,4-tri-Me) |
| Ph(2-Cl,3-Cl,4-F,5-Cl) | Ph(2-Cl,3-F,4-OMe,5-F) | Ph(2-Cl,3-Me,4-Et,5-Me) |
| Ph(2-Cl,3-Cl,4-Br,5-Cl) | Ph(2-Cl,3-F,4-OCF$_3$,5-F) | Ph(2-Cl,3-Me,4-n-Pr,5-Me) |
| Ph(2-Cl,3-Cl,4-I,5-Cl) | Ph(2-Cl,3-F,4-OCHF$_2$,5-F) | Ph(2-Cl,3-Me,4-t-Bu,5-Me) |
| Ph(2-Cl,3-Cl,4-Me,5-Cl) | Ph(2-Cl,3-F,4-OCF$_2$CF$_2$H,5-F) | Ph(2-Cl,3-Me,4-i-Pr,5-Me) |
| Ph(2-Cl,3-Cl,4-Et,5-Cl) | Ph(2-Cl,3-F,4-OCF$_2$CF$_3$,5-F) | Ph(2-Cl,3-Me,4-c-Pr,5-Me) |
| Ph(2-Cl,3-Me,4-CF$_2$,5-Me) | Ph(2-Cl,3-Me,4-CF$_2$H,5-Me) | Ph(2-Cl,3-Me,4-OCHF$_2$,5-Me) |
| Ph(2-Cl,3-Me,4-CF$_2$CF$_2$,5-Me) | Ph(2-Cl,3-Me,4-OMe,5-Me) | Ph(2-Cl,3-Me,4-OCF$_2$CF$_2$H,5-Me) |
| Ph(2-Cl,3-Me,4-CF$_2$CF$_2$H,5-Me) | Ph(2-Cl,3-Me,4-OCF$_2$,5-Me) | |

| Q¹ | Q¹ |
|---|---|
| Ph(2-Cl,3-Me,4-OCF$_2$CF$_3$,5-Me) | Ph(2-Cl,3-OCHF$_2$CF$_3$,4-CF$_3$,5-OCHF$_2$) |
| Ph(2-Cl,3-Me,4-SO$_2$Me,5-Me) | Ph(2-Cl,3-OCF$_2$CF$_3$,4-CF$_2$CF$_3$,5-OCHF$_2$) |
| Ph(2-Cl,3-Me,4-TMS,5-Me) | Ph(2-Cl,3-OCHF$_2$,4-CF$_2$CF$_2$,5-OCHF$_2$) |

TABLE 1-continued

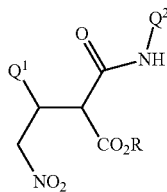

R is Me; $Q^2$ is Ph(2-F) and $Q^1$ is

Ph(2-Cl,3-Me,4-CN,5-Me)
Ph(2-Cl,3-CF$_3$,4-Cl,5-CF$_3$)
Ph(2-Cl,3-CF$_3$,4-F,5-CF$_3$)
Ph(2-Cl,3-CF$_3$,4-Br,5-CF$_3$)
Ph(2-Cl,3-CF$_3$,4-I,5-CF$_3$)
Ph(2-Cl,3-CF$_3$,4-Me,5-CF$_3$)
Ph(2-Cl,3-CF$_3$,4-Ei,5-CF$_3$)
Ph(2-Cl,3-CF$_3$,4-n-Pr,5-CF$_3$)
Ph(2-Cl,3-CF$_3$,4-t-Bu,5-CF$_3$)
Ph(2-Cl,3-CF$_3$,4-i-Pr,5-CF$_3$)
Ph(2-Cl,3-CF$_3$,4-c-Pr,5-CF$_3$)
Ph(2-Cl,3,4,5-tri-CF$_3$)
Ph(2-Cl,3-CF$_3$,4-CF$_2$CF$_3$,5-CF$_3$)
Ph(2-Cl,3-CF$_3$,4-CF$_2$CF$_2$H,5-CF$_3$)
Ph(2-Cl,3-CF$_3$,4-CF$_2$H,5-CF$_3$)
Ph(2-Cl,3-CF$_3$,4-OMe,5-CF$_3$)
Ph(2-Cl,3-CF$_3$,4-OCF$_3$,5-CF$_3$)
Ph(2-Cl,3-CF$_3$,4-OCHF$_2$,5-CF$_3$)
Ph(2-Cl,3-CF$_3$,4-OCF$_2$CF$_2$H,5-CF$_3$)
Ph(2-Cl,3-CF$_3$,4-OCF$_2$CF$_3$,5-CF$_3$)
Ph(2-Cl,3-CF$_3$,4-SO$_2$Me,5-CF$_3$)
Ph(2-Cl,3-CF$_3$,4-IMS,5-CF$_3$)
Ph(2-Cl,3-CF$_3$,4-CN,5-CF$_3$)
Ph(2-Cl,3-OCHF$_2$,4-Cl,5-OCHF$_2$)
Ph(2-Cl,3-OCHF$_2$,4-F,5-OCHF$_2$)
Ph(2-Cl,3-OCHF$_2$,4-Br,5-OCHF$_2$)
Ph(2-Cl,3-OCHF$_2$,4-I,5-OCHF$_2$)
Ph(2-Cl,3-OCHF$_2$,4-Me,5-OCHF$_2$)
Ph(2-Cl,3-OCHF$_2$,4-Ei,5-OCHF$_2$)
Ph(2-Cl,3-OCHF$_2$,4-n-Pr,5-OCHF$_2$)
Ph(2-Cl,3-OCHF$_2$,4-t-Bu,5-OCHF$_2$)
Ph(2-Cl,3-OCHF$_2$,4-i-Pr,5-OCHF$_2$)
Ph(2-Cl,3-OCHF$_2$,4-c-Pr,5-OCHF$_2$)
Ph(2-F,3-F,4-Br,5-F)
Ph(2-F,3-F,4-I,5-F)
Ph(2-F,3-F,4-Me,5-F)
Ph(2-F,3-F,4-Et,5-F)
Ph(2-F,3-F,4-n-Pr,5-F)
Ph(2-F,3-F,4-t-Bu,5-F)
Ph(2-F,3-F,4-i-Pr,5-F)
Ph(2-F,3-F,4-c-Pr,5-F)
Ph(2-F,3-F,4-CF$_3$,5-F)
Ph(2-F,3-F,4-CF$_2$CF$_3$,5-F)
Ph(2-F,3-F,4-CF$_2$CF$_2$H,5-F)
Ph(2-F,3-F,4-CF$_2$H,5-F)
Ph(2-F,3-F,4-OMe,5-F)
Ph(2-F,3-F,4-OCF$_2$,5-F)
Ph(2-F,3-F,4-OCHF$_2$,5-F)
Ph(2-F,3-F,4-OCF$_2$CF$_2$H,5-F)
Ph(2-F,3-F,4-OCF$_2$CF$_3$,5-F)
Ph(2-F,3-F,4-SO$_2$Me,5-F)
Ph(2-F,3-F,4-TMS,5-F)
Ph(2-F,3-F,4-CN,5-F)
Ph(2-F,3-Br,4-Cl,5-Br)
Ph(2-F,3-Br,4-F,5-Br)
Ph(2-F,3,4,5-tri-Br)
Ph(2-F,3-Br,4-I,5-Br)
Ph(2-F,3-Br,4-Me,5-Br)
Ph(2-F,3-Br,4-Et,5-Br)
Ph(2-F,3-Br,4-n-Pr,5-Br)
Ph(2-F,3-Br,4-t-Bu,5-Br)
Ph(2-F,3-Br,4-i-Pr,5-Br)
Ph(2-F,3-Br,4-c-Pr,5-Br)
Ph(2-F,3-Br,4-CF$_3$,5-Br)
Ph(2-F,3-Br,4-CF$_2$CF$_3$,5-Br)
Ph(2-F,3-Br,4-CF$_2$CF$_2$H,5-Br)
Ph(2-F,3-Br,4-CF$_2$H,5-Br)
Ph(2-F,3-Br,4-OMe,5-Br)
Ph(2-F,3-Br,4-OCF$_3$,5-Br)

Ph(2-Cl,3-OCHF$_2$,4-CF$_2$H,5-OCHF$_2$)
Ph(2-Cl,3-OCHF$_2$,4-OMe,5-OCHF$_2$)
Ph(2-Cl,3-OCHF$_2$,4-OCF$_3$,5-OCHF$_2$)
Ph(2-Cl,3,4,5-tri-OCHF$_2$)
Ph(2-Cl,3-OCHF$_2$,4-OCF$_2$CF$_2$H,5-OCH$_2$)
Ph(2-Cl,3-OCHF$_2$,4-OCF$_2$CF$_3$,5-OCHF$_2$)
Ph(2-Cl,3-OCHF$_2$,4-SO$_2$Me,5-OCHF$_2$)
Ph(2-Cl,3-OCHF$_2$,4-TMS,5-OCHF$_2$)
Ph(2-Cl,3-OCHF$_2$,4-CN,5-OCHF$_2$)
Ph(2-F,3,4,5-tri-Cl)
Ph(2-F,3-Cl,4-F,5-Cl)
Ph(2-F,3-Cl,4-Br,5-Cl)
Ph(2-F,3-Cl,4-I,5-Cl)
Ph(2-F,3-Cl,4-Me,5-Cl)
Ph(2-F,3-Cl,4-Et,5-Cl)
Ph(2-F,3-Cl,4-n-Pr,5-Cl)
Ph(2-F,3-Cl,4-t-Bu,5-Cl)
Ph(2-F,3-Cl,4-i-Pr,5-Cl)
Ph(2-F,3-Cl,4-c-Pr,5-Cl)
Ph(2-F,3-Cl,4-CF$_3$,5-Cl)
Ph(2-F,3-Cl,4-CF$_2$CF$_3$,5-Cl)
Ph(2-F,3-Cl,4-CF$_2$CF$_2$H,5-Cl)
Ph(2-F,3-Cl,4-CF$_2$H,5-Cl)
Ph(2-F,3-Cl,4-OMe,5-Cl)
Ph(2-F,3-Cl,4-OCF$_3$,5-Cl)
Ph(2-F,3-Cl,4-OCHF$_2$,5-Cl)
Ph(2-F,3-Cl,4-OCF$_2$CF$_2$H,5-Cl)
Ph(2-F,3-Cl,4-OCF$_2$CF$_3$,5-Cl)
Ph(2-F,3-Cl,4-SO$_2$Me,5-Cl)
Ph(2-F,3-Cl,4-TMS,5-Cl)
Ph(2-F,3-Cl,4-CN,5-Cl)
Ph(2-F,3-F,4-Cl,5-F)
Ph(2,3,4,5-tetra-F)
Ph(2-F,3-Br,4-TMS,5-Br)
Ph(2-F,3-Br,4-CN,5-Br)
Ph(2-F,3-Me,4-Cl,5-Me)
Ph(2-F,3-Me,4-F,5-Me)
Ph(2-F,3-Me,4-Br,5-Me)
Ph(2-F,3-Me,4-I,5-Me)
Ph(2-F,3,4-tri-Me)
Ph(2-F,3-Me,4-Et,5-Me)
Ph(2-F,3-Me,4-n-Pr,5-Me)
Ph(2-F,3-Me,4-t-Bu,5-Me)
Ph(2-F,3-Me,4-i-Pr,5-Me)
Ph(2-F,3-Me,4-c-Pr,5-Me)
Ph(2-F,3-Me,4-CF$_3$,5-Me)
Ph(2-F,3-Me,4-CF$_2$CF$_3$,5-Me)
Ph(2-F,3-Me,4-CF$_2$CF$_2$H,5-Me)
Ph(2-F,3-Me,4-CF$_2$H,5-Me)
Ph(2-F,3-Me,4-OMe,5-Me)
Ph(2-F,3-Me,4-OCF$_3$,5-Me)
Ph(2-F,3-Me,4-OCHF$_2$,5-Me)
Ph(2-F,3-Me,4-OCF$_2$CF$_2$H,5-Me)
Ph(2-F,3-Me,4-OCF$_2$CF$_3$,5-Me)
Ph(2-F,3-Me,4-SO$_2$Me,5-Me)
Ph(2-F,3-Me,4-TMS,5-Me)
Ph(2-F,3-Me,4-CN,5-Me)
Ph(2-F,3-CF$_3$,4-Cl,5-CF$_3$)
Ph(2-F,3-CF$_3$,4-F,5-CF$_3$)
Ph(2-F,3-CF$_3$,4-Br,5-CF$_3$)
Ph(2-F,3-CF$_3$,4-I,5-CF$_3$)
Ph(2-F,3-CF$_3$,4-Me,5-CF$_3$)
Ph(2-F,3-CF$_3$,4-Ei,5-CF$_3$)
Ph(2-F,3-CF$_3$,4-n-Pr,5-CF$_3$)
Ph(2-F,3-CF$_3$,4-t-Bu,5-CF$_3$)
Ph(2-F,3-CF$_3$,4-i-Pr,5-CF$_3$)
Ph(2-F,3-CF$_3$,4-c-Pr,5-CF$_3$)
Ph(2-F,3,4,5-tri-CF$_3$)
Ph(2-F,3-CF$_3$,4-CF$_2$CF$_3$,5-CF$_3$)

TABLE 1-continued

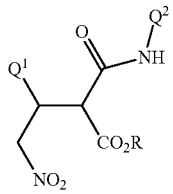

R is Me; Q² is Ph(2-F) and Q¹ is

Ph(2-F,3-Br,4-OCHF$_2$,5-Br)
Ph(2-F,3-Br,4-OCF$_2$CF$_2$H,5-Br)
Ph(2-F,3-Br,4-OCF$_2$CF$_3$,5-Br)
Ph(2-F,3-Br,4-SO$_2$Me,5-Br)
Ph(2-F,3-CF$_3$,4-OCHF$_2$,5-CF$_3$)
Ph(2-F,3-CF$_3$,4-OCF$_2$CF$_2$H,5-CF$_3$)
Ph(2-F,3-CF$_3$,4-OCF$_2$CF$_3$,5-CF$_3$)
Ph(2-F,3-CF$_3$,4-SO$_2$Me,5-CF$_3$)
Ph(2-F,3-CF$_3$,4-IMS,5-CF$_3$)
Ph(2-F,3-CF$_3$,4-CN,5-CF$_3$)
Ph(2-F,3-OCHF$_2$,4-Cl,5-OCHF$_2$)
Ph(2-F,3-OCHF$_2$,4-F,5-OCHF$_2$)
Ph(2-F,3-OCHF$_2$,4-Br,5-OCHF$_2$)
Ph(2-F,3-OCHF$_2$,4-I,5-OCHF$_2$)
Ph(2-F,3-OCHF$_2$,4-Me,5-OCHF$_2$)
Ph(2-F,3-OCHF$_2$,4-Ei,5-OCHF$_2$)
Ph(2-F,3-OCHF$_2$,4-n-Pr,5-OCHF$_2$)
Ph(2-F,3-OCHF$_2$,4-t-Bu,5-OCHF$_2$)
Ph(2-F,3-OCHF$_2$,4-i-Pr,5-OCHF$_2$)
Ph(2-F,3-OCHF$_2$,4-c-Pr,5-OCHF$_2$)
Ph(2-F,3-OCH$_2$,4-CF$_3$,5-OCHF$_2$)
Ph(2-F,3-OCHF$_2$CF$_3$,4-CF$_2$CF$_3$,5-OCHF$_2$)
Ph(2-F,3-OCHF$_2$,4-CF$_2$CF$_2$CF$_2$H,5-OCHF$_2$)
Ph(2-F,3-OCHF$_2$,4-CF$_2$H,5-OCHF$_2$)
Ph(2-F,3-OCHF$_2$,4-OMe,5-OCHF$_2$)
Ph(2-F,3-OCHF$_2$,4-OCF$_3$,5-OCHF$_2$)
Ph(2-F,3,4,5-tri-OCHF$_2$)
Ph(2-F,3-OCHF$_2$,4-OCF$_2$CF$_2$H,5-OCHF$_2$)

Ph(2-F,3-CF$_3$,4-CF$_2$CF$_2$H,5-CF$_3$)
Ph(2-F,3-CF$_3$,4-CF$_2$H,5-CF$_3$)
Ph(2-F,3-CF$_3$,4-OMe,5-CF$_3$)
Ph(2-F,3-CF$_3$,4-OCF$_3$,5-CF$_3$)
Ph(2-F,3-OCHF$_2$,4-OCF$_2$CF$_3$,5-OCHF$_2$)
Ph(2-F,3-OCHF$_2$,4-SO$_2$Me,5-OCHF$_2$)
Ph(2-F,3-OCHF$_2$,4-TMS,5-OCHF$_2$)
Ph(2-F,3-OCHF$_2$,4-CN,5-OCHF$_2$)
1H-Imidazol-2-yl(1-CF$_2$CF$_2$H,5-Cl)
1H-Imidazol-2-yl(1-CF$_2$CF$_2$H,5-F)
1H-Imidazol-2-yl(1-CH$_2$CF$_3$,5-Cl)
1H-Imidazol-2-yl(1-CH$_2$CF$_3$,5-F)
1H-Imidazol-2-yl(1-Me,5-CF$_2$H)
1H-Imidazol-2-yl(1-CF$_2$CF$_2$H,5-CF$_2$H)
1H-Imidazol-2-yl(1-CH$_2$CF$_3$,5-CF$_2$H)
1H-Imidazol-2-yl(1-Me,5-CF$_3$)
1H-Imidazol-2-yl(1-CF$_2$CF$_2$H,5-CF$_3$)
1H-Imidazol-2-yl(1-CF$_2$CF$_3$,5-CF$_3$)
1,3-Benzodioxol-4-yl
1,3-Benzodioxol-4-yl(2,2-di-Me)
1,3-Benzodioxol-4-yl(2,2-di-F)
1,4-Benzodioxol-4-yl(2,3-dihydro)
1,4-Benzodioxol-4-yl(2,2,3,3-tetrafluoro)
1H-Pyrazol-3-yl(1-CH$_2$CF$_3$,4-F)
1H-Pyrazol-3-yl(1-CH$_2$CF$_3$,4-Cl)
1H-Pyrazol-3-yl(1-CF$_2$CF$_2$H,4-F)
1H-Pyrazol-3-yl(1-CF$_2$CF$_2$H,4-Cl)

Table 2 is constructed in the same manner except that the Row Heading "R is Me; Q² is Ph(2-F) and Q¹ is" is replaced with the Row Heading listed for Table 2 below (i.e. "R is Me; Q² is Ph(2,3-diF) and Q¹ is"). Therefore the first entry in Table 2 is a compound of Formula I wherein R is Me; Q² is Ph(2,3-diF) and Q¹ is Ph(2-Cl) (i.e. 2-chlorophenyl). Tables 3 through 688 are constructed similarly.

| Table | Row Heading |
|---|---|
| 2 | R is Me; Q² is Ph(2,3-diF); and Q¹ is |
| 3 | R is Me; Q² is Ph(2,4-diF); and Q¹ is |
| 4 | R is Me; Q² is Ph(2,5-di-F); and v is |
| 5 | R is Me; Q² is Ph(2,3,4-tri-F); and Q¹ is |
| 6 | R is Me; Q² is Ph(2,3,5-tri-F); and Q¹ is |
| 7 | R is Me; Q² is Ph(2,3,4,5-tetra-F); and Q¹ is |
| 8 | R is Me; Q² is Ph(2-F,3-Cl,4-Br); and Q¹ is |
| 9 | R is Me; Q² is Ph(2-F,3-Cl,4-F); and Q¹ is |
| 10 | R is Me; Q² is Ph(2-F,3-Br,4-F); and Q¹ is |
| 11 | R is Me; Q² is Ph(2-F,3-Me); and Q¹ is |
| 12 | R is Me; Q² is Ph(2-F,3-Me,4-F); and Q¹ is |
| 13 | R is Me; Q² is Ph(2-F,3-Me,4-Cl); and Q¹ is |
| 14 | R is Me; Q² is Ph(2-F,3-Cl); and Q¹ is |
| 15 | R is Me; Q² is Ph(2-F,4-Cl); and Q¹ is |
| 16 | R is Me; Q² is Ph(2-F,3,4-di-Cl); and Q¹ is |
| 17 | R is Me; Q² is Ph(2-F,4-Br); and Q¹ is |
| 18 | R is Me; Q² is Ph(2-F,3-OMe); and Q¹ is |
| 19 | R is Me; Q² is Ph(2-F,3-OMe,4-F); and Q¹ is |
| 20 | R is Me; Q² is Ph(2-F,3-OMe,4-Cl); and Q¹ is |
| 21 | R is Me; Q² is Ph(2-F,3-CF$_2$H); and Q¹ is |
| 22 | R is Me; Q² is Ph(2-F,3-CF$_3$); and Q¹ is |
| 23 | R is Me; Q² is Ph(2-F,3-CF$_3$,4-F); and Q¹ is |
| 24 | R is Me; Q² is Ph(2-F,3-NO$_2$); and Q¹ is |
| 25 | R is Me; Q² is Ph(2-F,3-NO$_2$,4-F); and Q¹ is |
| 26 | R is Me; Q² is Ph(2-F,3-SO$_2$Me); and Q¹ is |

| Table | Row Heading |
|---|---|
| 27 | R is Me; Q² is Ph(2-F,3-SO$_2$Me,4-F); and Q¹ is |
| 28 | R is Me; Q² is Ph(2-CF$_3$); and Q¹ is |
| 29 | R is Me; Q² is Ph(2-CF$_3$,3-F); and Q¹ is |
| 30 | R is Me; Q² is Ph(2-CF$_3$,3-Me); and Q¹ is |
| 31 | R is Me; Q² is Ph(2-CF$_3$,4-F); and Q¹ is |
| 32 | R is Me; Q² is Ph(2-CF$_3$,3-Cl); and Q¹ is |
| 33 | R is Me; Q² is Ph(2-CF$_3$,4-F); and Q¹ is |
| 34 | R is Me; Q² is Ph(2-CF$_3$,4-Cl); and Q¹ is |
| 35 | R is Me; Q² is Ph(2-CF$_3$,3,4-di-F); and Q¹ is |
| 36 | R is Me; Q² is Ph(2-CF$_2$H); and Q¹ is |
| 37 | R is Me; Q² is Ph(2-CF$_2$H,3-F); and Q¹ is |
| 38 | R is Me; Q² is Ph(2-CF$_2$H,3-Me); and Q¹ is |
| 39 | R is Me; Q² is Ph(2-CF$_2$H,4-F); and Q¹ is |
| 40 | R is Me; Q² is Ph(2-CF$_2$H,3-Cl); and Q¹ is |
| 41 | R is Me; Q² is Ph(2-CF$_2$H,4-F); and Q¹ is |
| 42 | R is Me; Q² is Ph(2-CF$_2$H,4-Cl); and Q¹ is |
| 43 | R is Me; Q² is Ph(2-CF$_2$H,3,4-di-F); and Q¹ is |
| 44 | R is Me; Q² is Ph(2-Me); and Q¹ is |
| 45 | R is Me; Q² is Ph(2,3-di-Me); and Q¹ is |
| 46 | R is Me; Q² is Ph(2-Me,3-F); and Q¹ is |
| 47 | R is Me; Q² is Ph(2-Me,3-Cl); and Q¹ is |
| 48 | R is Me; Q² is Ph(2-Me,3-CF$_3$); and Q¹ is |
| 49 | R is Me; Q² is Ph(2-Me,3,4-di-Cl); and Q¹ is |
| 50 | R is Me; Q² is Ph(2-Me,3-Cl,4-F); and Q¹ is |
| 51 | R is Me; Q² is Ph(2-Me,4-Cl); and Q¹ is |
| 52 | R is Me; Q² is Ph(2-Me,4-F); and Q¹ is |
| 53 | R is Me; Q² is Ph(2-Me,5-F); and Q¹ is |
| 54 | R is Me; Q² is Ph(2-Me,3,4-di-F); and Q¹ is |
| 55 | R is Me; Q² is Ph(2-Me,3,5-di-F); and Q¹ is |
| 56 | R is Me; Q² is Ph(2-Et); and Q¹ is |
| 57 | R is Me; Q² is Ph(2-Et,3-F); and Q¹ is |
| 58 | R is Me; Q² is Ph(2-Et,3-Cl); and Q¹ is |
| 59 | R is Me; Q² is Ph(2-Et,4-F); and Q¹ is |

| Table Row | Heading |
|---|---|
| 60 | R is Me; $Q^2$ is Ph(2-Et,3,4-di-F); and $Q^1$ is |
| 61 | R is Me; $Q^2$ is Ph(2-i-Pr); and $Q^1$ is |
| 62 | R is Me; $Q^2$ is Ph(2-i-Pr,3-F); and $Q^1$ is |
| 63 | R is Me; $Q^2$ is Ph(2-i-Pr,3-Cl); and $Q^1$ is |
| 64 | R is Me; $Q^2$ is Ph(2-i-Pr,4-F); and $Q^1$ is |
| 65 | R is Me; $Q^2$ is Ph(2-i-Pr,3,4-di-F); and $Q^1$ is |
| 66 | R is Me; $Q^2$ is Ph(2-c-Pr); and $Q^1$ is |
| 67 | R is Me; $Q^2$ is Ph(2-c-Pr,3-F); and $Q^1$ is |
| 68 | R is Me; $Q^2$ is Ph(2-c-Pr,3-Cl); and $Q^1$ is |
| 69 | R is Me; $Q^2$ is Ph(2-c-Pr,4-F); and $Q^1$ is |
| 70 | R is Me; $Q^2$ is Ph(2-c-Pr,3,4-di-F); and $Q^1$ is |
| 71 | R is Me; $Q^2$ is Ph(2-$NO_2$); and $Q^1$ is |
| 72 | R is Me; $Q^2$ is Ph(2-$NO_2$,3-F); and $Q^1$ is |
| 73 | R is Me; $Q^2$ is Ph(2-$NO_2$,3-Cl); and $Q^1$ is |
| 74 | R is Me; $Q^2$ is Ph(2-$NO_2$,4-F); and $Q^1$ is |
| 75 | R is Me; $Q^2$ is Ph(2-$NO_2$,3,4-di-F); and $Q^1$ is |
| 76 | R is Me; $Q^2$ is Ph(2-$OCF_3$); and $Q^1$ is |
| 77 | R is Me; $Q^2$ is Ph(2-$OCF_3$,3-F); and $Q^1$ is |
| 78 | R is Me; $Q^2$ is Ph(2-$OCF_3$,4-F); and $Q^1$ is |
| 79 | R is Me; $Q^2$ is Ph(2-Cl); and $Q^1$ is |
| 80 | R is Me; $Q^2$ is Ph(2-Cl,3-Me); and $Q^1$ is |
| 81 | R is Me; $Q^2$ is Ph(2-Cl,3-Me,4-F); and $Q^1$ is |
| 82 | R is Me; $Q^2$ is Ph(2,3-di-Cl); and $Q^1$ is |
| 83 | R is Me; $Q^2$ is Ph(2,4-di-Cl); and $Q^1$ is |
| 84 | R is Me; $Q^2$ is Ph(2-Cl,3-F); and $Q^1$ is |
| 85 | R is Me; $Q^2$ is Ph(2-Cl,4-F); and $Q^1$ is |
| 86 | R is Me; $Q^2$ is Ph(2-Cl,5-F); and $Q^1$ is |
| 87 | R is Me; $Q^2$ is Ph(2-Cl,3,4-di-F); and $Q^1$ is |
| 88 | R is Me; $Q^2$ is Ph(2-Cl,3,5-di-F); and $Q^1$ is |
| 89 | R is Me; $Q^2$ is Ph(2-$OCF_2$H); and $Q^1$ is |
| 90 | R is Me; $Q^2$ is Ph(2-$OCF_2$H,3-Me); and $Q^1$ is |
| 91 | R is Me; $Q^2$ is Ph(2-$OCF_2$H,3-Cl); and $Q^1$ is |
| 92 | R is Me; $Q^2$ is Ph(2-$OCF_2$H,3-F); and $Q^1$ is |
| 93 | R is Me; $Q^2$ is Ph(2-$OCF_2$H,4-F); and $Q^1$ is |
| 94 | R is Me; $Q^2$ is Ph(2-$OCF_2CF_2$H); and $Q^1$ is |
| 95 | R is Me; $Q^2$ is Ph(2-$OCF_2CF_2$H,3-F); and $Q^1$ is |
| 96 | R is Me; $Q^2$ is Ph(2-$OCF_2CF_2$H,4-F); and $Q^1$ is |
| 97 | R is Me; $Q^2$ is Ph(2-Br); and $Q^1$ is |
| 98 | R is Me; $Q^2$ is Ph(2-Br,3-F); and $Q^1$ is |
| 99 | R is Me; $Q^2$ is Ph(2-Br,4-F); and $Q^1$ is |
| 100 | R is Me; $Q^2$ is Ph(2-Br,3,4-di-F); and $Q^1$ is |
| 101 | R is Me; $Q^2$ is Ph(2-I); and $Q^1$ is |
| 102 | R is Me; $Q^2$ is Ph(2-I,3-F); and $Q^1$ is |
| 103 | R is Me; $Q^2$ is Ph(2-I,4-F); and $Q^1$ is |
| 104 | R is Me; $Q^2$ is Ph(2-I,3,4-di-F); and $Q^1$ is |
| 105 | R is Me; $Q^2$ is Ph(2-CN); and $Q^1$ is |
| 106 | R is Me; $Q^2$ is Ph(2-CN,3-Me); and $Q^1$ is |
| 107 | R is Me; $Q^2$ is Ph(2-CN,3-F); and $Q^1$ is |
| 108 | R is Me; $Q^2$ is Ph(2-CN,4-F); and $Q^1$ is |
| 109 | R is Me; $Q^2$ is Ph(2-CN,3-Cl); and $Q^1$ is |
| 110 | R is Me; $Q^2$ is Ph(2-CN,4-Cl); and $Q^1$ is |
| 111 | R is Me; $Q^2$ is Ph(2-CN,3,4-di-F); and $Q^1$ is |
| 112 | R is Me; $Q^2$ is 2-Pyridinyl; and $Q^1$ is |
| 113 | R is Me; $Q^2$ is 2-Pyridinyl,3-F; and $Q^1$ is |
| 114 | R is Me; $Q^2$ is 2-Pyridinyl,4-F; and $Q^1$ is |
| 115 | R is Me; $Q^2$ is 2-Pyridinyl,3,4-di-F; and $Q^1$ is |
| 116 | R is Me; $Q^2$ is 2-Pyridinyl,3-Cl; and $Q^1$ is |
| 117 | R is Me; $Q^2$ is 2-Pyridinyl,4-Cl; and $Q^1$ is |
| 118 | R is Me; $Q^2$ is 2-Pyridinyl,3-Cl,4-F; and $Q^1$ is |
| 119 | R is Me; $Q^2$ is Ph(2-$SO_2$Me); and $Q^1$ is |
| 120 | R is Me; $Q^2$ is Ph(2-$SO_2$Me,3-F); and $Q^1$ is |
| 121 | R is Me; $Q^2$ is Ph(2-$SO_2$Me,3-Me); and $Q^1$ is |
| 122 | R is Me; $Q^2$ is Ph(2-$SO_2$Me,4-F); and $Q^1$ is |
| 123 | R is Me; $Q^2$ is Ph(2-$SO_2$Me,5-F); and $Q^1$ is |
| 124 | R is Me; $Q^2$ is Ph(2-$SO_2$Me,3,4-di-F); and $Q^1$ is |
| 125 | R is Me; $Q^2$ is Ph(2-$SO_2$Me,3-Cl); and $Q^1$ is |
| 126 | R is Me; $Q^2$ is Ph(2-$SO_2$Me,4-Cl); and $Q^1$ is |
| 127 | R is Me; $Q^2$ is Ph(2-$SO_2$Me,3-Cl,4-F); and $Q^1$ is |
| 128 | R is Me; $Q^2$ is Ph(2-$SO_2NH_2$); and $Q^1$ is |
| 129 | R is Me; $Q^2$ is Ph(2-$SO_2NH_2$,3-F); and $Q^1$ is |
| 130 | R is Me; $Q^2$ is Ph(2-$SO_2NH_2$,3-Cl); and $Q^1$ is |
| 131 | R is Me; $Q^2$ is Ph(2-$SO_2NH_2$,4-F); and $Q^1$ is |
| 132 | R is Me; $Q^2$ is Ph(2-$SO_2NH_2$,5-F); and $Q^1$ is |
| 133 | R is Me; $Q^2$ is Ph(2-$SO_2NH_2$,3,4-di-F); and $Q^1$ is |
| 134 | R is Me; $Q^2$ is Ph(3-F); and $Q^1$ is |
| 135 | R is Me; $Q^2$ is Ph(3,4-di-F); and $Q^1$ is |
| 136 | R is Me; $Q^2$ is Ph(3,5-di-F); and $Q^1$ is |
| 137 | R is Me; $Q^2$ is Ph(3,4,5-tri-F); and $Q^1$ is |
| 138 | R is Me; $Q^2$ is Ph(3-F,4-Cl); and $Q^1$ is |
| 139 | R is Me; $Q^2$ is Ph(3-$CF_3$); and $Q^1$ is |
| 140 | R is Me; $Q^2$ is Ph(3-$CF_3$,4-F); and $Q^1$ is |
| 141 | R is Me; $Q^2$ is Ph(3-$CF_3$,4-Cl); and $Q^1$ is |
| 142 | R is Me; $Q^2$ is Ph(3-$CF_3$,5-F); and $Q^1$ is |
| 143 | R is Me; $Q^2$ is Ph(3-$CF_3$,4,5-di-F); and $Q^1$ is |
| 144 | R is Me; $Q^2$ is Ph(3-$SO_2$Me); and $Q^1$ is |
| 145 | R is Me; $Q^2$ is Ph(3-$SO_2$Me,4-Cl); and $Q^1$ is |
| 146 | R is Me; $Q^2$ is Ph(3-$SO_2$Me,4-F); and $Q^1$ is |
| 147 | R is Me; $Q^2$ is Ph(3-$SO_2$Me,4,5-di-F); and $Q^1$ is |
| 148 | R is Me; $Q^2$ is Ph(3-$SO_2$Me,5-F); and $Q^1$ is |
| 149 | R is Me; $Q^2$ is Ph(3-$SO_2NH_2$); and $Q^1$ is |
| 150 | R is Me; $Q^2$ is Ph(3-$SO_2NH_2$,4-F); and $Q^1$ is |
| 151 | R is Me; $Q^2$ is Ph(3-$SO_2NH_2$,4,5-di-F); and $Q^1$ is |
| 152 | R is Me; $Q^2$ is Ph(3-$SO_2NH_2$,4-Cl); and $Q^1$ is |
| 153 | R is Me; $Q^2$ is Ph(3-$SO_2NH_2$,5-F); and $Q^1$ is |
| 154 | R is Me; $Q^2$ is Ph(3-Me); and $Q^1$ is |
| 155 | R is Me; $Q^2$ is Ph(3-Me,4-F); and $Q^1$ is |
| 156 | R is Me; $Q^2$ is Ph(3-Me,4-Cl); and $Q^1$ is |
| 157 | R is Me; $Q^2$ is Ph(3-Me,5-F); and $Q^1$ is |
| 158 | R is Me; $Q^2$ is Ph(3-Me,4,5-di-F); and $Q^1$ is |
| 159 | R is Me; $Q^2$ is Ph(3-Cl); and $Q^1$ is |
| 160 | R is Me; $Q^2$ is Ph(3-Cl,4-F); and $Q^1$ is |
| 161 | R is Me; $Q^2$ is Ph(3,4-di-Cl); and $Q^1$ is |
| 162 | R is Me; $Q^2$ is Ph(3-Cl,5-F); and $Q^1$ is |
| 163 | R is Me; $Q^2$ is Ph(3-Cl,4,5-di-F); and $Q^1$ is |
| 164 | R is Me; $Q^2$ is Ph(3,5-di-Cl); and $Q^1$ is |
| 165 | R is Me; $Q^2$ is Ph(4-F); and $Q^1$ is |
| 166 | R is Me; $Q^2$ is Ph(4-Cl); and $Q^1$ is |
| 167 | R is Me; $Q^2$ is 2,2-difluoro-1,3-benzodioxol-4-yl; and $Q^1$ is |
| 168 | R is Me; $Q^2$ is 2,2-difluoro-1,3-benzodioxol-5-yl; and $Q^1$ is |
| 169 | R is Me; $Q^2$ is 2,2-dimethyl-1,3-benzodioxol-4-yl; and $Q^1$ is |
| 170 | R is Me; $Q^2$ is 2,2-dimethyl-1,3-benzodioxol-5-yl; and $Q^1$ is |
| 171 | R is Me; $Q^2$ is 1,3-benzodioxol-4-yl; and $Q^1$ is |
| 172 | R is Me; $Q^2$ is 1,3-benzodioxol-5-yl; and $Q^1$ is |
| 173 | R is Et; $Q^2$ is Ph(2-F); and $Q^1$ is |
| 174 | R is Et; $Q^2$ is Ph(2,3-diF); and $Q^1$ is |
| 175 | R is Et; $Q^2$ is Ph(2,4-diF); and $Q^1$ is |
| 176 | R is Et; $Q^2$ is Ph(2,5-di-F); and $Q^1$ is |
| 177 | R is Et; $Q^2$ is Ph(2,3,4-tri-F); and $Q^1$ is |
| 178 | R is Et; $Q^2$ is Ph(2,3,5-tri-F); and $Q^1$ is |
| 179 | R is Et; $Q^2$ is Ph(2,3,4,5-tetra-F); and $Q^1$ is |
| 180 | R is Et; $Q^2$ is Ph(2-F,3-Cl,4-Br); and $Q^1$ is |
| 181 | R is Et; $Q^2$ is Ph(2-F,3-Cl,4-F); and $Q^1$ is |
| 182 | R is Et; $Q^2$ is Ph(2-F,3-Br,4-F); and $Q^1$ is |
| 183 | R is Et; $Q^2$ is Ph(2-F,3-Me); and $Q^1$ is |
| 184 | R is Et; $Q^2$ is Ph(2-F,3-Me,4-F); and $Q^1$ is |
| 185 | R is Et; $Q^2$ is Ph(2-F,3-Me,4-Cl); and $Q^1$ is |
| 186 | R is Et; $Q^2$ is Ph(2-F,3-Cl); and $Q^1$ is |
| 187 | R is Et; $Q^2$ is Ph(2-F,4-Cl); and $Q^1$ is |
| 188 | R is Et; $Q^2$ is Ph(2-F,3,4-di-Cl); and $Q^1$ is |
| 189 | R is Et; $Q^2$ is Ph(2-F,4-Br); and $Q^1$ is |
| 190 | R is Et; $Q^2$ is Ph(2-F,3-OMe); and $Q^1$ is |
| 191 | R is Et; $Q^2$ is Ph(2-F,3-OMe,4-F); and $Q^1$ is |
| 192 | R is Et; $Q^2$ is Ph(2-F,3-OMe,4-Cl); and $Q^1$ is |
| 193 | R is Et; $Q^2$ is Ph(2-F,3-$CF_2$H); and $Q^1$ is |
| 194 | R is Et; $Q^2$ is Ph(2-F,3-$CF_3$); and $Q^1$ is |
| 195 | R is Et; $Q^2$ is Ph(2-F,3-$CF_3$,4-F); and $Q^1$ is |
| 196 | R is Et; $Q^2$ is Ph(2-F,3-$NO_2$); and $Q^1$ is |
| 197 | R is Et; $Q^2$ is Ph(2-F,3-$NO_2$,4-F); and $Q^1$ is |
| 198 | R is Et; $Q^2$ is Ph(2-F,3-$SO_2$Me); and $Q^1$ is |
| 199 | R is Et; $Q^2$ is Ph(2-F,3-$SO_2$Me,4-F); and $Q^1$ is |
| 200 | R is Et; $Q^2$ is Ph(2-$CF_3$); and $Q^1$ is |
| 201 | R is Et; $Q^2$ is Ph(2-$CF_3$,3-F); and $Q^1$ is |
| 202 | R is Et; $Q^2$ is Ph(2-$CF_3$,3-Me); and $Q^1$ is |
| 203 | R is Et; $Q^2$ is Ph(2-$CF_3$,4-F); and $Q^1$ is |
| 204 | R is Et; $Q^2$ is Ph(2-$CF_3$,3-Cl); and $Q^1$ is |
| 205 | R is Et; $Q^2$ is Ph(2-$CF_3$,4-F); and $Q^1$ is |
| 206 | R is Et; $Q^2$ is Ph(2-$CF_3$,4-Cl); and $Q^1$ is |
| 207 | R is Et; $Q^2$ is Ph(2-$CF_3$,3,4-di-F); and $Q^1$ is |
| 208 | R is Et; $Q^2$ is Ph(2-$CF_2$H); and $Q^1$ is |
| 209 | R is Et; $Q^2$ is Ph(2-$CF_2$H,3-F); and $Q^1$ is |
| 210 | R is Et; $Q^2$ is Ph(2-$CF_2$H,3-Me); and $Q^1$ is |
| 211 | R is Et; $Q^2$ is Ph(2-$CF_2$H,4-F); and $Q^1$ is |
| 212 | R is Et; $Q^2$ is Ph(2-$CF_2$H,3-Cl); and $Q^1$ is |
| 213 | R is Et; $Q^2$ is Ph(2-$CF_2$H,4-F); and $Q^1$ is |

| Table | Row Heading |
|---|---|
| 214 | R is Et; $Q^2$ is Ph(2-CF$_2$H,4-Cl); and $Q^1$ is |
| 215 | R is Et; $Q^2$ is Ph(2-CF$_2$H,3,4-di-F); and $Q^1$ is |
| 216 | R is Et; $Q^2$ is Ph(2-Me); and $Q^1$ is |
| 217 | R is Et; $Q^2$ is Ph(2,3-di-Me); and $Q^1$ is |
| 218 | R is Et; $Q^2$ is Ph(2-Me,3-F); and $Q^1$ is |
| 219 | R is Et; $Q^2$ is Ph(2-Me,3-Cl); and $Q^1$ is |
| 220 | R is Et; $Q^2$ is Ph(2-Me,3-CF$_3$); and $Q^1$ is |
| 221 | R is Et; $Q^2$ is Ph(2-Me,3,4-di-Cl); and $Q^1$ is |
| 222 | R is Et; $Q^2$ is Ph(2-Me,3-Cl,4-F); and $Q^1$ is |
| 223 | R is Et; $Q^2$ is Ph(2-Me,4-Cl); and $Q^1$ is |
| 224 | R is Et; $Q^2$ is Ph(2-Me,4-F); and $Q^1$ is |
| 225 | R is Et; $Q^2$ is Ph(2-Me,5-F); and $Q^1$ is |
| 226 | R is Et; $Q^2$ is Ph(2-Me,3,4-di-F); and $Q^1$ is |
| 227 | R is Et; $Q^2$ is Ph(2-Me,3,5-di-F); and $Q^1$ is |
| 228 | R is Et; $Q^2$ is Ph(2-Et); and $Q^1$ is |
| 229 | R is Et; $Q^2$ is Ph(2-Et,3-F); and $Q^1$ is |
| 230 | R is Et; $Q^2$ is Ph(2-Et,3-Cl); and $Q^1$ is |
| 231 | R is Et; $Q^2$ is Ph(2-Et,4-F); and $Q^1$ is |
| 232 | R is Et; $Q^2$ is Ph(2-Et,3,4-di-F); and $Q^1$ is |
| 233 | R is Et; $Q^2$ is Ph(2-i-Pr); and $Q^1$ is |
| 234 | R is Et; $Q^2$ is Ph(2-i-Pr,3-F); and $Q^1$ is |
| 235 | R is Et; $Q^2$ is Ph(2-i-Pr,3-Cl); and $Q^1$ is |
| 236 | R is Et; $Q^2$ is Ph(2-i-Pr,4-F); and $Q^1$ is |
| 237 | R is Et; $Q^2$ is Ph(2-i-Pr,3,4-di-F); and $Q^1$ is |
| 238 | R is Et; $Q^2$ is Ph(2-c-Pr); and $Q^1$ is |
| 239 | R is Et; $Q^2$ is Ph(2-c-Pr,3-F); and $Q^1$ is |
| 240 | R is Et; $Q^2$ is Ph(2-c-Pr,3-Cl); and $Q^1$ is |
| 241 | R is Et; $Q^2$ is Ph(2-c-Pr,4-F); and $Q^1$ is |
| 242 | R is Et; $Q^2$ is Ph(2-c-Pr,3,4-di-F); and $Q^1$ is |
| 243 | R is Et; $Q^2$ is Ph(2-NO$_2$); and $Q^1$ is |
| 244 | R is Et; $Q^2$ is Ph(2-NO$_2$,3-F); and $Q^1$ is |
| 245 | R is Et; $Q^2$ is Ph(2-NO$_2$,3-Cl); and $Q^1$ is |
| 246 | R is Et; $Q^2$ is Ph(2-NO$_2$,4-F); and $Q^1$ is |
| 247 | R is Et; $Q^2$ is Ph(2-NO$_2$,3,4-di-F); and $Q^1$ is |
| 248 | R is Et; $Q^2$ is Ph(2-OCF$_3$); and $Q^1$ is |
| 249 | R is Et; $Q^2$ is Ph(2-OCF$_3$,3-F); and $Q^1$ is |
| 250 | R is Et; $Q^2$ is Ph(2-OCF$_3$,4-F); and $Q^1$ is |
| 251 | R is Et; $Q^2$ is Ph(2-Cl); and $Q^1$ is |
| 252 | R is Et; $Q^2$ is Ph(2-Cl,3-Me); and $Q^1$ is |
| 253 | R is Et; $Q^2$ is Ph(2-Cl,3-Me,4-F); and $Q^1$ is |
| 254 | R is Et; $Q^2$ is Ph(2,3-di-Cl); and $Q^1$ is |
| 255 | R is Et; $Q^2$ is Ph(2,4-di-Cl); and $Q^1$ is |
| 256 | R is Et; $Q^2$ is Ph(2-Cl,3-F); and $Q^1$ is |
| 257 | R is Et; $Q^2$ is Ph(2-Cl,4-F); and $Q^1$ is |
| 258 | R is Et; $Q^2$ is Ph(2-Cl,5-F); and $Q^1$ is |
| 259 | R is Et; $Q^2$ is Ph(2-Cl,3,4-di-F); and $Q^1$ is |
| 260 | R is Et; $Q^2$ is Ph(2-Cl,3,5-di-F); and $Q^1$ is |
| 261 | R is Et; $Q^2$ is Ph(2-OCF$_2$H); and $Q^1$ is |
| 262 | R is Et; $Q^2$ is Ph(2-OCF$_2$H,3-Me); and $Q^1$ is |
| 263 | R is Et; $Q^2$ is Ph(2-OCF$_2$H,3-Cl); and $Q^1$ is |
| 264 | R is Et; $Q^2$ is Ph(2-OCF$_2$H,3-F); and $Q^1$ is |
| 265 | R is Et; $Q^2$ is Ph(2-OCF$_2$H,4-F); and $Q^1$ is |
| 266 | R is Et; $Q^2$ is Ph(2-OCF$_2$CF$_2$H); and $Q^1$ is |
| 267 | R is Et; $Q^2$ is Ph(2-OCF$_2$CF$_2$H,3-F); and $Q^1$ is |
| 268 | R is Et; $Q^2$ is Ph(2-OCF$_2$CF$_2$H,4-F); and $Q^1$ is |
| 269 | R is Et; $Q^2$ is Ph(2-Br); and $Q^1$ is |
| 270 | R is Et; $Q^2$ is Ph(2-Br,3-F); and $Q^1$ is |
| 271 | R is Et; $Q^2$ is Ph(2-Br,4-F); and $Q^1$ is |
| 272 | R is Et; $Q^2$ is Ph(2-Br,3,4-di-F); and $Q^1$ is |
| 273 | R is Et; $Q^2$ is Ph(2-I); and $Q^1$ is |
| 274 | R is Et; $Q^2$ is Ph(2-I,3-F); and $Q^1$ is |
| 275 | R is Et; $Q^2$ is Ph(2-I,4-F); and $Q^1$ is |
| 276 | R is Et; $Q^2$ is Ph(2-I,3,4-di-F); and $Q^1$ is |
| 277 | R is Et; $Q^2$ is Ph(2-CN); and $Q^1$ is |
| 278 | R is Et; $Q^2$ is Ph(2-CN,3-Me); and $Q^1$ is |
| 279 | R is Et; $Q^2$ is Ph(2-CN,3-F); and $Q^1$ is |
| 280 | R is Et; $Q^2$ is Ph(2-CN,4-F); and $Q^1$ is |
| 281 | R is Et; $Q^2$ is Ph(2-CN,3-Cl); and $Q^1$ is |
| 282 | R is Et; $Q^2$ is Ph(2-CN,4-Cl); and $Q^1$ is |
| 283 | R is Et; $Q^2$ is Ph(2-CN,3,4-di-F); and $Q^1$ is |
| 284 | R is Et; $Q^2$ is 2-Pyridyl; and $Q^1$ is |
| 285 | R is Et; $Q^2$ is 2-Pyridyl,3-F; and $Q^1$ is |
| 286 | R is Et; $Q^2$ is 2-Pyridyl,4-F; and $Q^1$ is |
| 287 | R is Et; $Q^2$ is 2-Pyridyl,3,4-di-F; and $Q^1$ is |
| 288 | R is Et; $Q^2$ is 2-Pyridyl,3-Cl; and $Q^1$ is |
| 289 | R is Et; $Q^2$ is 2-Pyridyl,4-Cl; and $Q^1$ is |
| 290 | R is Et; $Q^2$ is 2-Pyridyl,3-Cl,4-F; and $Q^1$ is |
| 291 | R is Et; $Q^2$ is Ph(2-SO$_2$Me); and $Q^1$ is |
| 292 | R is Et; $Q^2$ is Ph(2-SO$_2$Me,3-F); and $Q^1$ is |
| 293 | R is Et; $Q^2$ is Ph(2-SO$_2$Me,3-Me); and $Q^1$ is |
| 294 | R is Et; $Q^2$ is Ph(2-SO$_2$Me,4-F); and $Q^1$ is |
| 295 | R is Et; $Q^2$ is Ph(2-SO$_2$Me,5-F); and $Q^1$ is |
| 296 | R is Et; $Q^2$ is Ph(2-SO$_2$Me,3,4-di-F); and $Q^1$ is |
| 297 | R is Et; $Q^2$ is Ph(2-SO$_2$Me,3-Cl); and $Q^1$ is |
| 298 | R is Et; $Q^2$ is Ph(2-SO$_2$Me,4-Cl); and $Q^1$ is |
| 299 | R is Et; $Q^2$ is Ph(2-SO$_2$Me,3-Cl,4-F); and $Q^1$ is |
| 300 | R is Et; $Q^2$ is Ph(2-SO$_2$NH$_2$); and $Q^1$ is |
| 301 | R is Et; $Q^2$ is Ph(2-SO$_2$NH$_2$,3-F); and $Q^1$ is |
| 302 | R is Et; $Q^2$ is Ph(2-SO$_2$NH$_2$,3-Cl); and $Q^1$ is |
| 303 | R is Et; $Q^2$ is Ph(2-SO$_2$NH$_2$,4-F); and $Q^1$ is |
| 304 | R is Et; $Q^2$ is Ph(2-SO$_2$NH$_2$,5-F); and $Q^1$ is |
| 305 | R is Et; $Q^2$ is Ph(2-SO$_2$NH$_2$,3,4-di-F); and $Q^1$ is |
| 306 | R is Et; $Q^2$ is Ph(3-F); and $Q^1$ is |
| 307 | R is Et; $Q^2$ is Ph(3,4-di-F); and $Q^1$ is |
| 308 | R is Et; $Q^2$ is Ph(3,5-di-F); and $Q^1$ is |
| 309 | R is Et; $Q^2$ is Ph(3,4,5-tri-F); and $Q^1$ is |
| 310 | R is Et; $Q^2$ is Ph(3-F,4-Cl); and $Q^1$ is |
| 311 | R is Et; $Q^2$ is Ph(3-CF$_3$); and $Q^1$ is |
| 312 | R is Et; $Q^2$ is Ph(3-CF$_3$,4-F); and $Q^1$ is |
| 313 | R is Et; $Q^2$ is Ph(3-CF$_3$,4-Cl); and $Q^1$ is |
| 314 | R is Et; $Q^2$ is Ph(3-CF$_3$,5-F); and $Q^1$ is |
| 315 | R is Et; $Q^2$ is Ph(3-CF$_3$,4,5-di-F); and $Q^1$ is |
| 316 | R is Et; $Q^2$ is Ph(3-SO$_2$Me); and $Q^1$ is |
| 317 | R is Et; $Q^2$ is Ph(3-SO$_2$Me,4-Cl); and $Q^1$ is |
| 318 | R is Et; $Q^2$ is Ph(3-SO$_2$Me,4-F); and $Q^1$ is |
| 319 | R is Et; $Q^2$ is Ph(3-SO$_2$Me,4,5-di-F); and $Q^1$ is |
| 320 | R is Et; $Q^2$ is Ph(3-SO$_2$Me,5-F); and $Q^1$ is |
| 321 | R is Et; $Q^2$ is Ph(3-SO$_2$NH$_2$); and $Q^1$ is |
| 322 | R is Et; $Q^2$ is Ph(3-SO$_2$NH$_2$,4-F); and $Q^1$ is |
| 323 | R is Et; $Q^2$ is Ph(3-SO$_2$NH$_2$,4,5-di-F); and $Q^1$ is |
| 324 | R is Et; $Q^2$ is Ph(3-SO$_2$NH$_2$,4-Cl); and $Q^1$ is |
| 325 | R is Et; $Q^2$ is Ph(3-SO$_2$NH$_2$,5-F); and $Q^1$ is |
| 326 | R is Et; $Q^2$ is Ph(3-Me); and $Q^1$ is |
| 327 | R is Et; $Q^2$ is Ph(3-Me,4-F); and $Q^1$ is |
| 328 | R is Et; $Q^2$ is Ph(3-Me,4-Cl); and $Q^1$ is |
| 329 | R is Et; $Q^2$ is Ph(3-Me,5-F); and $Q^1$ is |
| 330 | R is Et; $Q^2$ is Ph(3-Me,4,5-di-F); and $Q^1$ is |
| 331 | R is Et; $Q^2$ is Ph(3-Cl); and $Q^1$ is |
| 332 | R is Et; $Q^2$ is Ph(3-Cl,4-F); and $Q^1$ is |
| 333 | R is Et; $Q^2$ is Ph(3,4-di-Cl); and $Q^1$ is |
| 334 | R is Et; $Q^2$ is Ph(3-Cl,5-F); and $Q^1$ is |
| 335 | R is Et; $Q^2$ is Ph(3-Cl,4,5-di-F); and $Q^1$ is |
| 336 | R is Et; $Q^2$ is Ph(3,5-di-Cl); and $Q^1$ is |
| 337 | R is Et; $Q^2$ is Ph(4-F); and $Q^1$ is |
| 338 | R is Et; $Q^2$ is Ph(4-Cl); and $Q^1$ is |
| 339 | R is Et; $Q^2$ is 2,2-difluoro-1,3-benzodioxol-4-yl; and $Q^1$ is |
| 340 | R is Et; $Q^2$ is 2,2-difluoro-1,3-benzodioxol-5-yl; and $Q^1$ is |
| 341 | R is Et; $Q^2$ is 2,2-dimethyl-1,3-benzodioxol-4-yl; and $Q^1$ is |
| 342 | R is Et; $Q^2$ is 2,2-dimethyl-1,3-benzodioxol-5-yl; and $Q^1$ is |
| 343 | R is Et; $Q^2$ is 1,3-benzodioxol-4-yl; and $Q^1$ is |
| 344 | R is Et; $Q^2$ is 1,3-benzodioxol-5-yl; and $Q^1$ is |
| 345 | R is Ph; $Q^2$ is Ph(2-F); and $Q^1$ is |
| 346 | R is Ph; $Q^2$ is Ph(2,3-diF); and $Q^1$ is |
| 347 | R is Ph; $Q^2$ is Ph(2,4-diF); and $Q^1$ is |
| 348 | R is Ph; $Q^2$ is Ph(2,5-di-F); and $Q^1$ is |
| 349 | R is Ph; $Q^2$ is Ph(2,3,4-tri-F); and $Q^1$ is |
| 350 | R is Ph; $Q^2$ is Ph(2,3,5-tri-F); and $Q^1$ is |
| 351 | R is Ph; $Q^2$ is Ph(2,3,4,5-tetra-F); and $Q^1$ is |
| 352 | R is Ph; $Q^2$ is Ph(2-F,3-Cl,4-Br); and $Q^1$ is |
| 353 | R is Ph; $Q^2$ is Ph(2-F,3-Cl,4-F); and $Q^1$ is |
| 354 | R is Ph; $Q^2$ is Ph(2-F,3-Br,4-F); and $Q^1$ is |
| 355 | R is Ph; $Q^2$ is Ph(2-F,3-Me); and $Q^1$ is |
| 356 | R is Ph; $Q^2$ is Ph(2-F,3-Me,4-F); and $Q^1$ is |
| 357 | R is Ph; $Q^2$ is Ph(2-F,3-Me,4-Cl); and $Q^1$ is |
| 358 | R is Ph; $Q^2$ is Ph(2-F,3-Cl); and $Q^1$ is |
| 359 | R is Ph; $Q^2$ is Ph(2-F,4-Cl); and $Q^1$ is |
| 360 | R is Ph; $Q^2$ is Ph(2-F,3,4-di-Cl); and $Q^1$ is |
| 361 | R is Ph; $Q^2$ is Ph(2-F,4-Br); and $Q^1$ is |
| 362 | R is Ph; $Q^2$ is Ph(2-F,3-OMe); and $Q^1$ is |
| 363 | R is Ph; $Q^2$ is Ph(2-F,3-OMe,4-F); and $Q^1$ is |
| 364 | R is Ph; $Q^2$ is Ph(2-F,3-OMe,4-Cl); and $Q^1$ is |
| 365 | R is Ph; $Q^2$ is Ph(2-F,3-CF$_2$H); and $Q^1$ is |
| 366 | R is Ph; $Q^2$ is Ph(2-F,3-CF$_3$); and $Q^1$ is |
| 367 | R is Ph; $Q^2$ is Ph(2-F,3-CF$_3$,4-F); and $Q^1$ is |

| Table | Row Heading |
|---|---|
| 368 | R is Ph; Q² is Ph(2-F,3-NO₂); and Q¹ is |
| 369 | R is Ph; Q² is Ph(2-F,3-NO₂,4-F); and Q¹ is |
| 370 | R is Ph; Q² is Ph(2-F,3-SO₂Me); and Q¹ is |
| 371 | R is Ph; Q² is Ph(2-F,3-SO₂Me,4-F); and Q¹ is |
| 372 | R is Ph; Q² is Ph(2-CF₃); and Q¹ is |
| 373 | R is Ph; Q² is Ph(2-CF₃,3-F); and Q¹ is |
| 374 | R is Ph; Q² is Ph(2-CF₃,3-Me); and Q¹ is |
| 375 | R is Ph; Q² is Ph(2-CF₃,4-F); and Q¹ is |
| 376 | R is Ph; Q² is Ph(2-CF₃,3-Cl); and Q¹ is |
| 377 | R is Ph; Q² is Ph(2-CF₃,4-F); and Q¹ is |
| 378 | R is Ph; Q² is Ph(2-CF₃,4-Cl); and Q¹ is |
| 379 | R is Ph; Q² is Ph(2-CF₃,3,4-di-F); and Q¹ is |
| 380 | R is Ph; Q² is Ph(2-CF₂H); and Q¹ is |
| 381 | R is Ph; Q² is Ph(2-CF₂H,3-F); and Q¹ is |
| 382 | R is Ph; Q² is Ph(2-CF₂H,3-Me); and Q¹ is |
| 383 | R is Ph; Q² is Ph(2-CF₂H,4-F); and Q¹ is |
| 384 | R is Ph; Q² is Ph(2-CF₂H,3-Cl); and Q¹ is |
| 385 | R is Ph; Q² is Ph(2-CF₂H,4-F); and Q¹ is |
| 386 | R is Ph; Q² is Ph(2-CF₂H,4-Cl); and Q¹ is |
| 387 | R is Ph; Q² is Ph(2-CF₂H,3,4-di-F); and Q¹ is |
| 388 | R is Ph; Q² is Ph(2-Me); and Q¹ is |
| 389 | R is Ph; Q² is Ph(2,3-di-Me); and Q¹ is |
| 390 | R is Ph; Q² is Ph(2-Me,3-F); and Q¹ is |
| 391 | R is Ph; Q² is Ph(2-Me,3-Cl); and Q¹ is |
| 392 | R is Ph; Q² is Ph(2-Me,3-CF₃); and Q¹ is |
| 393 | R is Ph; Q² is Ph(2-Me,3,4-di-Cl); and Q¹ is |
| 394 | R is Ph; Q² is Ph(2-Me,3-Cl,4-F); and Q¹ is |
| 395 | R is Ph; Q² is Ph(2-Me,4-Cl); and Q¹ is |
| 396 | R is Ph; Q² is Ph(2-Me,4-F); and Q¹ is |
| 397 | R is Ph; Q² is Ph(2-Me,5-F); and Q¹ is |
| 398 | R is Ph; Q² is Ph(2-Me,3,4-di-F); and Q¹ is |
| 399 | R is Ph; Q² is Ph(2-Me,3,5-di-F); and Q¹ is |
| 400 | R is Ph; Q² is Ph(2-Et); and Q¹ is |
| 401 | R is Ph; Q² is Ph(2-Et,3-F); and Q¹ is |
| 402 | R is Ph; Q² is Ph(2-Et,3-Cl); and Q¹ is |
| 403 | R is Ph; Q² is Ph(2-Et,4-F); and Q¹ is |
| 404 | R is Ph; Q² is Ph(2-Et,3,4-di-F); and Q¹ is |
| 405 | R is Ph; Q² is Ph(2-i-Pr); and Q¹ is |
| 406 | R is Ph; Q² is Ph(2-i-Pr,3-F); and Q¹ is |
| 407 | R is Ph; Q² is Ph(2-i-Pr,3-Cl); and Q¹ is |
| 408 | R is Ph; Q² is Ph(2-i-Pr,4-F); and Q¹ is |
| 409 | R is Ph; Q² is Ph(2-i-Pr,3,4-di-F); and Q¹ is |
| 410 | R is Ph; Q² is Ph(2-c-Pr); and Q¹ is |
| 411 | R is Ph; Q² is Ph(2-c-Pr,3-F); and Q¹ is |
| 412 | R is Ph; Q² is Ph(2-c-Pr,3-Cl); and Q¹ is |
| 413 | R is Ph; Q² is Ph(2-c-Pr,4-F); and Q¹ is |
| 414 | R is Ph; Q² is Ph(2-c-Pr,3,4-di-F); and Q¹ is |
| 415 | R is Ph; Q² is Ph(2-NO₂); and Q¹ is |
| 416 | R is Ph; Q² is Ph(2-NO₂,3-F); and Q¹ is |
| 417 | R is Ph; Q² is Ph(2-NO₂,3-Cl); and Q¹ is |
| 418 | R is Ph; Q² is Ph(2-NO₂,4-F); and Q¹ is |
| 419 | R is Ph; Q² is Ph(2-NO₂,3,4-di-F); and Q¹ is |
| 420 | R is Ph; Q² is Ph(2-OCF₃); and Q¹ is |
| 421 | R is Ph; Q² is Ph(2-OCF₃,3-F); and Q¹ is |
| 422 | R is Ph; Q² is Ph(2-OCF₃,4-F); and Q¹ is |
| 423 | R is Ph; Q² is Ph(2-Cl); and Q¹ is |
| 424 | R is Ph; Q² is Ph(2-Cl,3-Me); and Q¹ is |
| 425 | R is Ph; Q² is Ph(2-Cl,3-Me,4-F); and Q¹ is |
| 426 | R is Ph; Q² is Ph(2,3-di-Cl); and Q¹ is |
| 427 | R is Ph; Q² is Ph(2,4-di-Cl); and Q¹ is |
| 428 | R is Ph; Q² is Ph(2-Cl,3-F); and Q¹ is |
| 429 | R is Ph; Q² is Ph(2-Cl,4-F); and Q¹ is |
| 430 | R is Ph; Q² is Ph(2-Cl,5-F); and Q¹ is |
| 431 | R is Ph; Q² is Ph(2-Cl,3,4-di-F); and Q¹ is |
| 432 | R is Ph; Q² is Ph(2-Cl,3,5-di-F); and Q¹ is |
| 433 | R is Ph; Q² is Ph(2-OCF₂H); and Q¹ is |
| 434 | R is Ph; Q² is Ph(2-OCF₂H,3-Me); and Q¹ is |
| 435 | R is Ph; Q² is Ph(2-OCF₂H,3-Cl); and Q¹ is |
| 436 | R is Ph; Q² is Ph(2-OCF₂H,3-F); and Q¹ is |
| 437 | R is Ph; Q² is Ph(2-OCF₂H,4-F); and Q¹ is |
| 438 | R is Ph; Q² is Ph(2-OCF₂CF₂H); and Q¹ is |
| 439 | R is Ph; Q² is Ph(2-OCF₂CF₂H,3-F); and Q¹ is |
| 440 | R is Ph; Q² is Ph(2-OCF₂CF₂H,4-F); and Q¹ is |
| 441 | R is Ph; Q² is Ph(2-Br); and Q¹ is |
| 442 | R is Ph; Q² is Ph(2-Br,3-F); and Q¹ is |
| 443 | R is Ph; Q² is Ph(2-Br,4-F); and Q¹ is |
| 444 | R is Ph; Q² is Ph(2-Br,3,4-di-F); and Q¹ is |
| 445 | R is Ph; Q² is Ph(2-I); and Q¹ is |
| 446 | R is Ph; Q² is Ph(2-I,3-F); and Q¹ is |
| 447 | R is Ph; Q² is Ph(2-I,4-F); and Q¹ is |
| 448 | R is Ph; Q² is Ph(2-I,3,4-di-F); and Q¹ is |
| 449 | R is Ph; Q² is Ph(2-CN); and Q¹ is |
| 450 | R is Ph; Q² is Ph(2-CN,3-Me); and Q¹ is |
| 451 | R is Ph; Q² is Ph(2-CN,3-F); and Q¹ is |
| 452 | R is Ph; Q² is Ph(2-CN,4-F); and Q¹ is |
| 453 | R is Ph; Q² is Ph(2-CN,3-Cl); and Q¹ is |
| 454 | R is Ph; Q² is Ph(2-CN,4-Cl); and Q¹ is |
| 455 | R is Ph; Q² is Ph(2-CN,3,4-di-F); and Q¹ is |
| 456 | R is Ph; Q² is 2-Pyridinyl; and Q¹ is |
| 457 | R is Ph; Q² is 2-Pyridinyl,3-F; and Q¹ is |
| 458 | R is Ph; Q² is 2-Pyridinyl,4-F; and Q¹ is |
| 459 | R is Ph; Q² is 2-Pyridinyl,3,4-di-F; and Q¹ is |
| 460 | R is Ph; Q² is 2-Pyridinyl,3-Cl; and Q¹ is |
| 461 | R is Ph; Q² is 2-Pyridinyl,4-Cl; and Q¹ is |
| 462 | R is Ph; Q² is 2-Pyridinyl,3-Cl,4-F; and Q¹ is |
| 463 | R is Ph; Q² is Ph(2-SO₂Me); and Q¹ is |
| 464 | R is Ph; Q² is Ph(2-SO₂Me,3-F); and Q¹ is |
| 465 | R is Ph; Q² is Ph(2-SO₂Me,3-Me); and Q¹ is |
| 466 | R is Ph; Q² is Ph(2-SO₂Me,4-F); and Q¹ is |
| 467 | R is Ph; Q² is Ph(2-SO₂Me,5-F); and Q¹ is |
| 468 | R is Ph; Q² is Ph(2-SO₂Me,3,4-di-F); and Q¹ is |
| 469 | R is Ph; Q² is Ph(2-SO₂Me,3-Cl); and Q¹ is |
| 470 | R is Ph; Q² is Ph(2-SO₂Me,4-Cl); and Q¹ is |
| 471 | R is Ph; Q² is Ph(2-SO₂Me,3-Cl,4-F); and Q¹ is |
| 472 | R is Ph; Q² is Ph(2-SO₂NH₂); and Q¹ is |
| 473 | R is Ph; Q² is Ph(2-SO₂NH₂,3-F); and Q¹ is |
| 474 | R is Ph; Q² is Ph(2-SO₂NH₂,3-Cl); and Q¹ is |
| 475 | R is Ph; Q² is Ph(2-SO₂NH₂,4-F); and Q¹ is |
| 476 | R is Ph; Q² is Ph(2-SO₂NH₂,5-F); and Q¹ is |
| 477 | R is Ph; Q² is Ph(2-SO₂NH₂,3,4-di-F); and Q¹ is |
| 478 | R is Ph; Q² is Ph(3-F); and Q¹ is |
| 479 | R is Ph; Q² is Ph(3,4-di-F); and Q¹ is |
| 480 | R is Ph; Q² is Ph(3,5-di-F); and Q¹ is |
| 481 | R is Ph; Q² is Ph(3,4,5-tri-F); and Q¹ is |
| 482 | R is Ph; Q² is Ph(3-F,4-Cl); and Q¹ is |
| 483 | R is Ph; Q² is Ph(3-CF₃); and Q¹ is |
| 484 | R is Ph; Q² is Ph(3-CF₃,4-F); and Q¹ is |
| 485 | R is Ph; Q² is Ph(3-CF₃,4-Cl); and Q¹ is |
| 486 | R is Ph; Q² is Ph(3-CF₃,5-F); and Q¹ is |
| 487 | R is Ph; Q² is Ph(3-CF₃,4,5-di-F); and Q¹ is |
| 488 | R is Ph; Q² is Ph(3-SO₂Me); and Q¹ is |
| 489 | R is Ph; Q² is Ph(3-SO₂Me,4-Cl); and Q¹ is |
| 490 | R is Ph; Q² is Ph(3-SO₂Me,4-F); and Q¹ is |
| 491 | R is Ph; Q² is Ph(3-SO₂Me,4,5-di-F); and Q¹ is |
| 492 | R is Ph; Q² is Ph(3-SO₂Me,5-F); and Q¹ is |
| 493 | R is Ph; Q² is Ph(3-SO₂NH₂); and Q¹ is |
| 494 | R is Ph; Q² is Ph(3-SO₂NH₂,4-F); and Q¹ is |
| 495 | R is Ph; Q² is Ph(3-SO₂NH₂,4,5-di-F); and Q¹ is |
| 496 | R is Ph; Q² is Ph(3-SO₂NH₂,4-Cl); and Q¹ is |
| 497 | R is Ph; Q² is Ph(3-SO₂NH₂,5-F); and Q¹ is |
| 498 | R is Ph; Q² is Ph(3-Me); and Q¹ is |
| 499 | R is Ph; Q² is Ph(3-Me,4-F); and Q¹ is |
| 500 | R is Ph; Q² is Ph(3-Me,4-Cl); and Q¹ is |
| 501 | R is Ph; Q² is Ph(3-Me,5-F); and Q¹ is |
| 502 | R is Ph; Q² is Ph(3-Me,4,5-di-F); and Q¹ is |
| 503 | R is Ph; Q² is Ph(3-Cl); and Q¹ is |
| 504 | R is Ph; Q² is Ph(3-Cl,4-F); and Q¹ is |
| 505 | R is Ph; Q² is Ph(3,4-di-Cl); and Q¹ is |
| 506 | R is Ph; Q² is Ph(3-Cl,5-F); and Q¹ is |
| 507 | R is Ph; Q² is Ph(3-Cl,4,5-di-F); and Q¹ is |
| 508 | R is Ph; Q² is Ph(3,5-di-Cl); and Q¹ is |
| 509 | R is Ph; Q² is Ph(4-F); and Q¹ is |
| 510 | R is Ph; Q² is Ph(4-Cl); and Q¹ is |
| 511 | R is Ph; Q² is 2,2-difluoro-1,3-benzodioxol-4-yl; and Q¹ is |
| 512 | R is Ph; Q² is 2,2-difluoro-1,3-benzodioxol-5-yl; and Q¹ is |
| 513 | R is Ph; Q² is 2,2-dimethyl-1,3-benzodioxol-4-yl; and Q¹ is |
| 514 | R is Ph; Q² is 2,2-dimethyl-1,3-benzodioxol-5-yl; and Q¹ is |
| 515 | R is Ph; Q² is 1,3-benzodioxol-4-yl; and Q¹ is |
| 516 | R is Ph; Q² is 1,3-benzodioxol-5-yl; and Q¹ is |
| 517 | R is t-Bu; Q² is Ph(2-F); and Q¹ is |
| 518 | R is t-Bu; Q² is Ph(2,3-diF); and Q¹ is |
| 519 | R is t-Bu; Q² is Ph(2,4-diF); and Q¹ is |
| 520 | R is t-Bu; Q² is Ph(2,5-di-F); and Q¹ is |
| 521 | R is t-Bu; Q² is Ph(2,3,4-tri-F); and Q¹ is |

-continued

| Table | Row Heading |
|---|---|
| 522 | R is t-Bu; $Q^2$ is Ph(2,3,5-tri-F); and $Q^1$ is |
| 523 | R is t-Bu; $Q^2$ is Ph(2,3,4,5-tetra-F); and $Q^1$ is |
| 524 | R is t-Bu; $Q^2$ is Ph(2-F,3-Cl,4-Br); and $Q^1$ is |
| 525 | R is t-Bu; $Q^2$ is Ph(2-F,3-Cl,4-F); and $Q^1$ is |
| 526 | R is t-Bu; $Q^2$ is Ph(2-F,3-Br,4-F); and $Q^1$ is |
| 527 | R is t-Bu; $Q^2$ is Ph(2-F,3-Me); and $Q^1$ is |
| 528 | R is t-Bu; $Q^2$ is Ph(2-F,3-Me,4-F); and $Q^1$ is |
| 529 | R is t-Bu; $Q^2$ is Ph(2-F,3-Me,4-Cl); and $Q^1$ is |
| 530 | R is t-Bu; $Q^2$ is Ph(2-F,3-Cl); and $Q^1$ is |
| 531 | R is t-Bu; $Q^2$ is Ph(2-F,4-Cl); and $Q^1$ is |
| 532 | R is t-Bu; $Q^2$ is Ph(2-F,3,4-di-Cl); and $Q^1$ is |
| 533 | R is t-Bu; $Q^2$ is Ph(2-F,4-Br); and $Q^1$ is |
| 534 | R is t-Bu; $Q^2$ is Ph(2-F,3-OMe); and $Q^1$ is |
| 535 | R is t-Bu; $Q^2$ is Ph(2-F,3-OMe,4-F); and $Q^1$ is |
| 536 | R is t-Bu; $Q^2$ is Ph(2-F,3-OMe,4-Cl); and $Q^1$ is |
| 537 | R is t-Bu; $Q^2$ is Ph(2-F,3-CF$_2$H); and $Q^1$ is |
| 538 | R is t-Bu; $Q^2$ is Ph(2-F,3-CF$_3$); and $Q^1$ is |
| 539 | R is t-Bu; $Q^2$ is Ph(2-F,3-CF$_3$,4-F); and $Q^1$ is |
| 540 | R is t-Bu; $Q^2$ is Ph(2-F,3-NO$_2$); and $Q^1$ is |
| 541 | R is t-Bu; $Q^2$ is Ph(2-F,3-NO$_2$,4-F); and $Q^1$ is |
| 542 | R is t-Bu; $Q^2$ is Ph(2-F,3-SO$_2$Me); and $Q^1$ is |
| 543 | R is t-Bu; $Q^2$ is Ph(2-F,3-SO$_2$Me,4-F); and $Q^1$ is |
| 544 | R is t-Bu; $Q^2$ is Ph(2-CF$_3$); and $Q^1$ is |
| 545 | R is t-Bu; $Q^2$ is Ph(2-CF$_3$,3-F); and $Q^1$ is |
| 546 | R is t-Bu; $Q^2$ is Ph(2-CF$_3$,3-Me); and $Q^1$ is |
| 547 | R is t-Bu; $Q^2$ is Ph(2-CF$_3$,4-F); and $Q^1$ is |
| 548 | R is t-Bu; $Q^2$ is Ph(2-CF$_3$,3-Cl); and $Q^1$ is |
| 549 | R is t-Bu; $Q^2$ is Ph(2-CF$_3$,4-F); and $Q^1$ is |
| 550 | R is t-Bu; $Q^2$ is Ph(2-CF$_3$,4-Cl); and $Q^1$ is |
| 551 | R is t-Bu; $Q^2$ is Ph(2-CF$_3$,3,4-di-F); and $Q^1$ is |
| 552 | R is t-Bu; $Q^2$ is Ph(2-CF$_2$H); and $Q^1$ is |
| 553 | R is t-Bu; $Q^2$ is Ph(2-CF$_2$H,3-F); and $Q^1$ is |
| 554 | R is t-Bu; $Q^2$ is Ph(2-CF$_2$H,3-Me); and $Q^1$ is |
| 555 | R is t-Bu; $Q^2$ is Ph(2-CF$_2$H,4-F); and $Q^1$ is |
| 556 | R is t-Bu; $Q^2$ is Ph(2-CF$_2$H,3-Cl); and $Q^1$ is |
| 557 | R is t-Bu; $Q^2$ is Ph(2-CF$_2$H,4-F); and $Q^1$ is |
| 558 | R is t-Bu; $Q^2$ is Ph(2-CF$_2$H,4-Cl); and $Q^1$ is |
| 559 | R is t-Bu; $Q^2$ is Ph(2-CF$_2$H,3,4-di-F); and $Q^1$ is |
| 560 | R is t-Bu; $Q^2$ is Ph(2-Me); and $Q^1$ is |
| 561 | R is t-Bu; $Q^2$ is Ph(2,3-di-Me); and $Q^1$ is |
| 562 | R is t-Bu; $Q^2$ is Ph(2-Me,3-F); and $Q^1$ is |
| 563 | R is t-Bu; $Q^2$ is Ph(2-Me,3-Cl); and $Q^1$ is |
| 564 | R is t-Bu; $Q^2$ is Ph(2-Me,3-CF$_3$); and $Q^1$ is |
| 565 | R is t-Bu; $Q^2$ is Ph(2-Me,3,4-di-Cl); and $Q^1$ is |
| 566 | R is t-Bu; $Q^2$ is Ph(2-Me,3-Cl,4-F); and $Q^1$ is |
| 567 | R is t-Bu; $Q^2$ is Ph(2-Me,4-Cl); and $Q^1$ is |
| 568 | R is t-Bu; $Q^2$ is Ph(2-Me,4-F); and $Q^1$ is |
| 569 | R is t-Bu; $Q^2$ is Ph(2-Me,5-F); and $Q^1$ is |
| 570 | R is t-Bu; $Q^2$ is Ph(2-Me,3,4-di-F); and $Q^1$ is |
| 571 | R is t-Bu; $Q^2$ is Ph(2-Me,3,5-di-F); and $Q^1$ is |
| 572 | R is t-Bu; $Q^2$ is Ph(2-Et); and $Q^1$ is |
| 573 | R is t-Bu; $Q^2$ is Ph(2-Et,3-F); and $Q^1$ is |
| 574 | R is t-Bu; $Q^2$ is Ph(2-Et,3-Cl); and $Q^1$ is |
| 575 | R is t-Bu; $Q^2$ is Ph(2-Et,4-F); and $Q^1$ is |
| 576 | R is t-Bu; $Q^2$ is Ph(2-Et,3,4-di-F); and $Q^1$ is |
| 577 | R is t-Bu; $Q^2$ is Ph(2-i-Pr); and $Q^1$ is |
| 578 | R is t-Bu; $Q^2$ is Ph(2-i-Pr,3-F); and $Q^1$ is |
| 579 | R is t-Bu; $Q^2$ is Ph(2-i-Pr,3-Cl); and $Q^1$ is |
| 580 | R is t-Bu; $Q^2$ is Ph(2-i-Pr,4-F); and $Q^1$ is |
| 581 | R is t-Bu; $Q^2$ is Ph(2-i-Pr,3,4-di-F); and $Q^1$ is |
| 582 | R is t-Bu; $Q^2$ is Ph(2-c-Pr); and $Q^1$ is |
| 583 | R is t-Bu; $Q^2$ is Ph(2-c-Pr,3-F); and $Q^1$ is |
| 584 | R is t-Bu; $Q^2$ is Ph(2-c-Pr,3-Cl); and $Q^1$ is |
| 585 | R is t-Bu; $Q^2$ is Ph(2-c-Pr,4-F); and $Q^1$ is |
| 586 | R is t-Bu; $Q^2$ is Ph(2-c-Pr,3,4-di-F); and $Q^1$ is |
| 587 | R is t-Bu; $Q^2$ is Ph(2-NO$_2$); and $Q^1$ is |
| 588 | R is t-Bu; $Q^2$ is Ph(2-NO$_2$,3-F); and $Q^1$ is |
| 589 | R is t-Bu; $Q^2$ is Ph(2-NO$_2$,3-Cl); and $Q^1$ is |
| 590 | R is t-Bu; $Q^2$ is Ph(2-NO$_2$,4-F); and $Q^1$ is |
| 591 | R is t-Bu; $Q^2$ is Ph(2-NO$_2$,3,4-di-F); and $Q^1$ is |
| 592 | R is t-Bu; $Q^2$ is Ph(2-OCF$_3$); and $Q^1$ is |
| 593 | R is t-Bu; $Q^2$ is Ph(2-OCF$_3$,3-F); and $Q^1$ is |
| 594 | R is t-Bu; $Q^2$ is Ph(2-OCF$_3$,4-F); and $Q^1$ is |
| 595 | R is t-Bu; $Q^2$ is Ph(2-Cl); and $Q^1$ is |
| 596 | R is t-Bu; $Q^2$ is Ph(2-Cl,3-Me); and $Q^1$ is |
| 597 | R is t-Bu; $Q^2$ is Ph(2-Cl,3-Me,4-F); and $Q^1$ is |
| 598 | R is t-Bu; $Q^2$ is Ph(2,3-di-Cl); and $Q^1$ is |
| 599 | R is t-Bu; $Q^2$ is Ph(2,4-di-Cl); and $Q^1$ is |
| 600 | R is t-Bu; $Q^2$ is Ph(2-Cl,3-F); and $Q^1$ is |
| 601 | R is t-Bu; $Q^2$ is Ph(2-Cl,4-F); and $Q^1$ is |
| 602 | R is t-Bu; $Q^2$ is Ph(2-Cl,5-F); and $Q^1$ is |
| 603 | R is t-Bu; $Q^2$ is Ph(2-Cl,3,4-di-F); and $Q^1$ is |
| 604 | R is t-Bu; $Q^2$ is Ph(2-Cl,3,5-di-F); and $Q^1$ is |
| 605 | R is t-Bu; $Q^2$ is Ph(2-OCF$_2$H); and $Q^1$ is |
| 606 | R is t-Bu; $Q^2$ is Ph(2-OCF$_2$H,3-Me); and $Q^1$ is |
| 607 | R is t-Bu; $Q^2$ is Ph(2-OCF$_2$H,3-Cl); and $Q^1$ is |
| 608 | R is t-Bu; $Q^2$ is Ph(2-OCF$_2$H,3-F); and $Q^1$ is |
| 609 | R is t-Bu; $Q^2$ is Ph(2-OCF$_2$H,4-F); and $Q^1$ is |
| 610 | R is t-Bu; $Q^2$ is Ph(2-OCF$_2$CF$_2$H); and $Q^1$ is |
| 611 | R is t-Bu; $Q^2$ is Ph(2-OCF$_2$CF$_2$H,3-F); and $Q^1$ is |
| 612 | R is t-Bu; $Q^2$ is Ph(2-OCF$_2$CF$_2$H,4-F); and $Q^1$ is |
| 613 | R is t-Bu; $Q^2$ is Ph(2-Br); and $Q^1$ is |
| 614 | R is t-Bu; $Q^2$ is Ph(2-Br,3-F); and $Q^1$ is |
| 615 | R is t-Bu; $Q^2$ is Ph(2-Br,4-F); and $Q^1$ is |
| 616 | R is t-Bu; $Q^2$ is Ph(2-Br,3,4-di-F); and $Q^1$ is |
| 617 | R is t-Bu; $Q^2$ is Ph(2-I); and $Q^1$ is |
| 618 | R is t-Bu; $Q^2$ is Ph(2-I,3-F); and $Q^1$ is |
| 619 | R is t-Bu; $Q^2$ is Ph(2-I,4-F); and $Q^1$ is |
| 620 | R is t-Bu; $Q^2$ is Ph(2-I,3,4-di-F); and $Q^1$ is |
| 621 | R is t-Bu; $Q^2$ is Ph(2-CN); and $Q^1$ is |
| 622 | R is t-Bu; $Q^2$ is Ph(2-CN,3-Me); and $Q^1$ is |
| 623 | R is t-Bu; $Q^2$ is Ph(2-CN,3-F); and $Q^1$ is |
| 624 | R is t-Bu; $Q^2$ is Ph(2-CN,4-F); and $Q^1$ is |
| 625 | R is t-Bu; $Q^2$ is Ph(2-CN,3-Cl); and $Q^1$ is |
| 626 | R is t-Bu; $Q^2$ is Ph(2-CN,4-Cl); and $Q^1$ is |
| 627 | R is t-Bu; $Q^2$ is Ph(2-CN,3,4-di-F); and $Q^1$ is |
| 628 | R is t-Bu; $Q^2$ is 2-Pyridinyl; and $Q^1$ is |
| 629 | R is t-Bu; $Q^2$ is 2-Pyridinyl,3-F; and $Q^1$ is |
| 630 | R is t-Bu; $Q^2$ is 2-Pyridinyl,4-F; and $Q^1$ is |
| 631 | R is t-Bu; $Q^2$ is 2-Pyridinyl,3,4-di-F; and $Q^1$ is |
| 632 | R is t-Bu; $Q^2$ is 2-Pyridinyl,3-Cl; and $Q^1$ is |
| 633 | R is t-Bu; $Q^2$ is 2-Pyridinyl,4-Cl; and $Q^1$ is |
| 634 | R is t-Bu; $Q^2$ is 2-Pyridinyl,3-Cl,4-F; and $Q^1$ is |
| 635 | R is t-Bu; $Q^2$ is Ph(2-SO$_2$Me); and $Q^1$ is |
| 636 | R is t-Bu; $Q^2$ is Ph(2-SO$_2$Me,3-F); and $Q^1$ is |
| 637 | R is t-Bu; $Q^2$ is Ph(2-SO$_2$Me,3-Me); and $Q^1$ is |
| 638 | R is t-Bu; $Q^2$ is Ph(2-SO$_2$Me,4-F); and $Q^1$ is |
| 639 | R is t-Bu; $Q^2$ is Ph(2-SO$_2$Me,5-F); and $Q^1$ is |
| 640 | R is t-Bu; $Q^2$ is Ph(2-SO$_2$Me,3,4-di-F); and $Q^1$ is |
| 641 | R is t-Bu; $Q^2$ is Ph(2-SO$_2$Me,3-Cl); and $Q^1$ is |
| 642 | R is t-Bu; $Q^2$ is Ph(2-SO$_2$Me,4-Cl); and $Q^1$ is |
| 643 | R is t-Bu; $Q^2$ is Ph(2-SO$_2$Me,3-Cl,4-F); and $Q^1$ is |
| 644 | R is t-Bu; $Q^2$ is Ph(2-SO$_2$NH$_2$); and $Q^1$ is |
| 645 | R is t-Bu; $Q^2$ is Ph(2-SO$_2$NH$_2$,3-F); and $Q^1$ is |
| 646 | R is t-Bu; $Q^2$ is Ph(2-SO$_2$NH$_2$,3-Cl); and $Q^1$ is |
| 647 | R is t-Bu; $Q^2$ is Ph(2-SO$_2$NH$_2$,4-F); and $Q^1$ is |
| 648 | R is t-Bu; $Q^2$ is Ph(2-SO$_2$NH$_2$,5-F); and $Q^1$ is |
| 649 | R is t-Bu; $Q^2$ is Ph(2-SO$_2$NH$_2$,3,4-di-F); and $Q^1$ is |
| 650 | R is t-Bu; $Q^2$ is Ph(3-F); and $Q^1$ is |
| 651 | R is t-Bu; $Q^2$ is Ph(3,4-di-F); and $Q^1$ is |
| 652 | R is t-Bu; $Q^2$ is Ph(3,5-di-F); and $Q^1$ is |
| 653 | R is t-Bu; $Q^2$ is Ph(3,4,5-tri-F); and $Q^1$ is |
| 654 | R is t-Bu; $Q^2$ is Ph(3-F,4-Cl); and $Q^1$ is |
| 655 | R is t-Bu; $Q^2$ is Ph(3-CF$_3$); and $Q^1$ is |
| 656 | R is t-Bu; $Q^2$ is Ph(3-CF$_3$,4-F); and $Q^1$ is |
| 657 | R is t-Bu; $Q^2$ is Ph(3-CF$_3$,4-Cl); and $Q^1$ is |
| 658 | R is t-Bu; $Q^2$ is Ph(3-CF$_3$,5-F); and $Q^1$ is |
| 659 | R is t-Bu; $Q^2$ is Ph(3-CF$_3$,4,5-di-F); and $Q^1$ is |
| 660 | R is t-Bu; $Q^2$ is Ph(3-SO$_2$Me); and $Q^1$ is |
| 661 | R is t-Bu; $Q^2$ is Ph(3-SO$_2$Me,4-Cl); and $Q^1$ is |
| 662 | R is t-Bu; $Q^2$ is Ph(3-SO$_2$Me,4-F); and $Q^1$ is |
| 663 | R is t-Bu; $Q^2$ is Ph(3-SO$_2$Me,4,5-di-F); and $Q^1$ is |
| 664 | R is t-Bu; $Q^2$ is Ph(3-SO$_2$Me,5-F); and $Q^1$ is |
| 665 | R is t-Bu; $Q^2$ is Ph(3-SO$_2$NH$_2$); and $Q^1$ is |
| 666 | R is t-Bu; $Q^2$ is Ph(3-SO$_2$NH$_2$,4-F); and $Q^1$ is |
| 667 | R is t-Bu; $Q^2$ is Ph(3-SO$_2$NH$_2$,4,5-di-F); and $Q^1$ is |
| 668 | R is t-Bu; $Q^2$ is Ph(3-SO$_2$NH$_2$,4-Cl); and $Q^1$ is |
| 669 | R is t-Bu; $Q^2$ is Ph(3-SO$_2$NH$_2$,5-F); and $Q^1$ is |
| 670 | R is t-Bu; $Q^2$ is Ph(3-Me); and $Q^1$ is |
| 671 | R is t-Bu; $Q^2$ is Ph(3-Me,4-F); and $Q^1$ is |
| 672 | R is t-Bu; $Q^2$ is Ph(3-Me,4-Cl); and $Q^1$ is |
| 673 | R is t-Bu; $Q^2$ is Ph(3-Me,5-F); and $Q^1$ is |
| 674 | R is t-Bu; $Q^2$ is Ph(3-Me,4,5-di-F); and $Q^1$ is |
| 675 | R is t-Bu; $Q^2$ is Ph(3-Cl); and $Q^1$ is |

-continued

| Table | Row | Heading |
|---|---|---|
| | 676 | R is t-Bu; $Q^2$ is Ph(3-Cl,4-F); and $Q^1$ is |
| | 677 | R is t-Bu; $Q^2$ is Ph(3,4-di-Cl); and $Q^1$ is |
| | 678 | R is t-Bu; $Q^2$ is Ph(3-Cl,5-F); and $Q^1$ is |
| | 679 | R is t-Bu; $Q^2$ is Ph(3-Cl,4,5-di-F); and $Q^1$ is |
| | 680 | R is t-Bu; $Q^2$ is Ph(3,5-di-Cl); and $Q^1$ is |
| | 681 | R is t-Bu; $Q^2$ is Ph(4-F); and $Q^1$ is |
| | 682 | R is t-Bu; $Q^2$ is Ph(4-Cl); and $Q^1$ is |
| | 683 | R is t-Bu; $Q^2$ is 2,2-difluoro-1,3-benzodioxol-4-yl; and $Q^1$ is |
| | 684 | R is t-Bu; $Q^2$ is 2,2-difluoro-1,3-benzodioxol-5-yl; and $Q^1$ is |
| | 685 | R is t-Bu; $Q^2$ is 2,2-dimethyl-1,3-benzodioxol-4-yl; and $Q^1$ is |
| | 686 | R is t-Bu; $Q^2$ is 2,2-dimethyl-1,3-benzodioxol-5-yl; and $Q^1$ is |
| | 687 | R is t-Bu; $Q^2$ is 1,3-benzodioxol-4-yl; and $Q^1$ is |
| | 688 | R is t-Bu; $Q^2$ is 1,3-benzodioxol-5-yl; and $Q^1$ is |

What is claimed is:
1. A compound selected from Formula I and salts thereof,

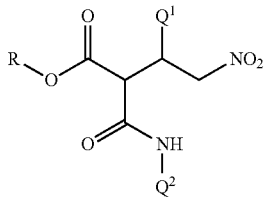

I wherein
$Q^1$ is a phenyl ring or a naphthalenyl ring system, each ring or ring system optionally substituted with up to 5 substituents independently selected from $R^1$; or a 5- to 6-membered fully unsaturated heterocyclic ring or an 8- to 10-membered heteroaromatic bicyclic ring system, each ring or ring system containing ring members selected from carbon atoms and 1 to 4 heteroatoms independently selected from up to 2 O, up to 2 S and up to 4 N atoms, wherein up to 3 carbon ring members are independently selected from C(=O) and C(=S), and the sulfur atom ring members are independently selected from $S(=O)_u(=NR^2)_v$, each ring or ring system optionally substituted with up to 5 substituents independently selected from $R^1$ on carbon atom ring members and selected from $R^3$ on nitrogen atom ring members;

$Q^2$ is a phenyl ring or a naphthalenyl ring system, each ring or ring system optionally substituted with up to 5 substituents independently selected from $R^4$; or a 5- to 6-membered fully unsaturated heterocyclic ring or an 8- to 10-membered heteroaromatic bicyclic ring system, each ring or ring system containing ring members selected from carbon atoms and 1 to 4 heteroatoms independently selected from up to 2 O, up to 2 S and up to 4 N atoms, wherein up to 3 carbon ring members are independently selected from C(=O) and C(=S), and the sulfur atom ring members are independently selected from $S(=O)_u(=NR^2)_v$, each ring or ring system optionally substituted with up to 5 substituents independently selected from $R^4$ on carbon atom ring members and selected from $R^5$ on nitrogen atom ring members;

R is $C_1$-$C_8$ alkyl or phenyl;
each $R^1$ and $R^4$ is independently halogen, cyano, nitro, $C_1$-$C_8$ alkyl, $C_1$-$C_8$ haloalkyl, $C_1$-$C_8$ nitroalkyl, $C_2$-$C_8$ alkenyl, $C_2$-$C_8$ haloalkenyl, $C_2$-$C_8$ haloalkoxyalkoxy, $C_2$-$C_8$ nitroalkenyl, $C_2$-$C_8$ alkynyl, $C_2$-$C_8$ haloalkynyl, $C_4$-$C_{10}$ cycloalkylalkyl, $C_4$-$C_{10}$ halocycloalkylalkyl, $C_5$-$C_{12}$ alkylcycloalkylalkyl, $C_5$-$C_{12}$ cycloalkylalkenyl, $C_5$-$C_{12}$ cycloalkylalkynyl, $C_3$-$C_8$ cycloalkyl, $C_3$-$C_8$ halocycloalkyl, $C_4$-$C_{10}$ alkylcycloalkyl, $C_6$-$C_{12}$ cycloalkylcycloalkyl, $C_3$-$C_8$ cycloalkenyl, $C_3$-$C_8$ halocycloalkenyl, $C_2$-$C_8$ alkoxyalkyl, $C_2$-$C_8$ haloalkoxyalkyl, $C_4$-$C_{10}$ cycloalkoxyalkyl, $C_3$-$C_{10}$ alkoxyalkoxyalkyl, $C_2$-$C_8$ alkylthioalkyl, $C_2$-$C_8$ alkylsulfinylalkyl, $C_2$-$C_8$ alkylsulfonylalkyl, $C_2$-$C_8$ alkylaminoalkyl, $C_2$-$C_8$ haloalkylaminoalkyl, $C_4$-$C_{10}$ cycloalkylaminoalkyl, $C_3$-$C_{10}$ dialkylaminoalkyl, —CHO, $C_2$-$C_8$ alkylcarbonyl, $C_2$-$C_8$ haloalkylcarbonyl, $C_4$-$C_{10}$ cycloalkylcarbonyl, —C(=O)OH, $C_2$-$C_8$ alkoxycarbonyl, $C_2$-$C_8$ haloalkoxycarbonyl, $C_4$-$C_{10}$ cycloalkoxycarbonyl, $C_5$-$C_{12}$ cycloalkylalkoxycarbonyl, —C(=O)NH$_2$, $C_2$-$C_8$ alkylaminocarbonyl, $C_4$-$C_{10}$ cycloalkylaminocarbonyl, $C_3$-$C_{10}$ dialkylaminocarbonyl, $C_1$-$C_8$ alkoxy, $C_1$-$C_8$ haloalkoxy, $C_2$-$C_8$ alkoxyalkoxy, $C_2$-$C_8$ alkenyloxy, $C_2$-$C_8$ haloalkenyloxy, $C_3$-$C_8$ alkynyloxy, $C_3$-$C_8$ haloalkynyloxy, $C_3$-$C_8$ cycloalkoxy, $C_3$-$C_8$ halocycloalkoxy, $C_4$-$C_{10}$ cycloalkylalkoxy, $C_3$-$C_{10}$ alkylcarbonylalkoxy, $C_2$-$C_8$ alkylcarbonyloxy, $C_2$-$C_8$ haloalkylcarbonyloxy, $C_4$-$C_{10}$ cycloalkylcarbonyloxy, $C_1$-$C_8$ alkylsulfonyloxy, $C_1$-$C_8$ haloalkylsulfonyloxy, $C_1$-$C_8$ alkylthio, $C_1$-$C_8$ haloalkylthio, $C_3$-$C_8$ cycloalkylthio, $C_1$-$C_8$ alkylsulfinyl, $C_1$-$C_8$ haloalkylsulfinyl, $C_1$-$C_8$ alkylsulfonyl, $C_1$-$C_8$ haloalkylsulfonyl, $C_3$-$C_8$ cycloalkylsulfonyl, formylamino, $C_2$-$C_8$ alkylcarbonylamino, $C_2$-$C_8$ haloalkylcarbonylamino, $C_2$-$C_8$ alkoxycarbonylamino, $C_1$-$C_6$ alkylsulfonylamino, $C_1$-$C_6$ haloalkylsulfonylamino, —SF$_5$, —SCN, $C_3$-$C_{12}$ trialkylsilyl, $C_4$-$C_{12}$ trialkylsilylalkyl or $C_4$-$C_{12}$ trialkylsilylalkoxy;

each $R^2$ is independently H, cyano, $C_2$-$C_3$ alkylcarbonyl or $C_2$-$C_3$ haloalkylcarbonyl;

each $R^3$ and $R^5$ is independently cyano, $C_1$-$C_3$ alkyl, $C_2$-$C_3$ alkenyl, $C_2$-$C_3$ alkynyl, $C_3$-$C_6$ cycloalkyl, $C_2$-$C_3$ alkoxyalkyl, $C_1$-$C_3$ alkoxy, $C_2$-$C_3$ alkylcarbonyl, $C_2$-$C_3$ alkoxycarbonyl, $C_2$-$C_3$ alkylaminoalkyl, $C_3$-$C_4$ dialkylaminoalkyl or $C_2$-$C_3$ haloalkyl; and each u and v are independently 0, 1 or 2 in each instance of $S(=O)_u(=NR^2)_v$, provided that the sum of u and v is 0, 1 or 2.

2. The compound of claim 1 wherein
$Q^1$ is a phenyl ring substituted with 1 to 3 substituents independently selected from $R^1$;
$Q^2$ is a phenyl ring substituted with 1 to 3 substituents independently selected from $R^4$;
R is $C_1$-$C_4$ alkyl;
$R^1$ is independently halogen, cyano, nitro, $C_1$-$C_8$ alkyl, $C_1$-$C_8$ haloalkyl or $C_2$-$C_8$ haloalkoxyalkoxy; and
$R^4$ is independently halogen, $C_1$-$C_3$ alkyl or $C_1$-$C_3$ haloalkyl.

3. The compound of claim 2 wherein
$Q^1$ is a phenyl ring having a substituent selected from $R^1$ at the meta (3-) position and optionally up to 2 additional $R^1$ substituents;
$Q^2$ is a phenyl ring having a substituent selected from $R^4$ at the ortho (2-) position and optionally up to 2 additional $R^4$ substituents;
R is methyl or ethyl;
$R^1$ is independently halogen, $C_1$-$C_3$ alkyl or $C_1$-$C_3$ haloalkyl; and
$R^4$ is independently halogen or $C_1$-$C_3$ haloalkyl.

4. The compound of claim 2 wherein
Q$^1$ is a phenyl ring having a substituent selected from R$^1$ at the para (4-) position and optionally up to 2 additional R$^1$ substituents;
Q$^2$ is a phenyl ring having a substituent selected from R$^4$ at the ortho (2-) position and optionally up to 2 additional R$^4$ substituents;
R is methyl or ethyl;
R$^1$ is independently halogen, C$_1$-C$_3$ alkyl or C$_1$-C$_3$ haloalkyl; and
R$^4$ is independently halogen or C$_1$-C$_3$ haloalkyl.

5. The compound of claim 1 wherein
Q$^1$ is a 5- to 6-membered fully unsaturated heterocyclic ring optionally substituted with up to 5 substituents independently selected from R$^1$ on carbon atom ring members and selected from R$^3$ on nitrogen atom ring members;
Q$^2$ is a phenyl ring substituted with 1 to 3 substituents independently selected from R$^4$;
R is C$_1$-C$_4$ alkyl;
R$^1$ is independently halogen, cyano, nitro, C$_1$-C$_8$ alkyl, C$_1$-C$_8$ haloalkyl or C$_2$-C$_8$ haloalkoxyalkoxy;
R$^3$ is independently C$_1$-C$_3$ alkyl, C$_2$-C$_3$ alkenyl, C$_2$-C$_3$ alkynyl, C$_3$-C$_6$ cycloalkyl or C$_1$-C$_3$ alkoxy; and
R$^4$ is independently halogen, C$_1$-C$_3$ alkyl or C$_1$-C$_3$ haloalkyl.

6. The compound of claim 5 wherein
Q$^1$ is a pyridyl ring optionally substituted with up to 2 R$^1$;
Q$^2$ is a phenyl ring substituted with 1 to 2 substituents independently selected from R$^4$;
R is methyl or ethyl;
R$^1$ is independently halogen or C$_1$-C$_3$ haloalkyl; and
R$^4$ is independently halogen or C$_1$-C$_3$ haloalkyl.

7. The compound of claim 5 wherein
Q$^1$ is a 3-pyridyl ring substituted with R$^1$ at the position para to the bond connecting Q$^1$ to the remainder of the compound of Formula I; or Q$^1$ is a thiophene or furan ring optionally substituted with up to 2 R$^1$;
Q$^2$ is a phenyl ring substituted with 1 to 2 substituents independently selected from R$^4$;
R is methyl or ethyl;
R$^1$ is independently halogen or C$_1$-C$_3$ haloalkyl; and
R$^4$ is independently halogen or C$_1$-C$_3$ haloalkyl.

8. The compound of claim 1 wherein
Q$^2$ is a 2-pyridyl or 3-pyridyl ring optionally substituted with up to 2 R$^4$;
R is methyl or ethyl;
R$^1$ is independently halogen or C$_1$-C$_3$ haloalkyl; and
R$^4$ is independently halogen or C$_1$-C$_3$ haloalkyl.

9. A method for preparing a compound of Formula I as defined in claim 1, comprising contacting a compound of Formula II

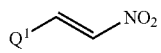

wherein Q$^1$ is as defined in claim 1,
with a compound of Formula III

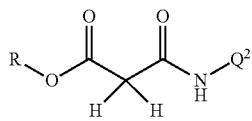

wherein R and Q$^2$ are as defined in claim 1,
optionally in the presence of a catalyst or a base to form a compound of Formula I.

10. The method of claim 9 wherein
Q$^1$ is a phenyl ring substituted with 1 to 3 substituents independently selected from R$^1$;
Q$^2$ is a phenyl ring substituted with 1 to 3 substituents independently selected from R$^4$;
R is C$_1$-C$_4$ alkyl;
R$^1$ is independently halogen, cyano, nitro, C$_1$-C$_8$ alkyl, C$_1$-C$_8$ haloalkyl or C$_2$-C$_8$ haloalkoxyalkoxy; and
R$^4$ is independently halogen, C$_1$-C$_3$ alkyl or C$_1$-C$_3$ haloalkyl.

11. The method of claim 10 wherein
Q$^1$ is a phenyl ring having a substituent selected from R$^1$ at the meta (3-) position and optionally up to 2 additional R$^1$ substituents;
Q$^2$ is a phenyl ring having a substituent selected from R$^4$ at the ortho (2-) position and optionally up to 2 additional R$^4$ substituents;
R is methyl or ethyl;
R$^1$ is independently halogen, C$_1$-C$_3$ alkyl or C$_1$-C$_3$ haloalkyl; and
R$^4$ is independently halogen or C$_1$-C$_3$ haloalkyl.

12. The method of claim 10 wherein
the catalyst is a nickel complex; and
the base is an organic base.

13. The method of claim 12 wherein
the nickel complex is Ni(II) with chiral vicinal diamine ligands.

14. The method of claim 13 wherein
the ligands are N substituted cyclohexane-1,2 diamines or 1,1'-Bi(tetrahydroisoquinoline)-diamines; and
the base is triethylamine, morpholine or piperidine.

15. The method of claim 10 wherein
the stereochemistry of the carbon center connecting Q$^1$ to the remainder of Formula I is S or R.

16. A method for preparing a compound of Formula IV

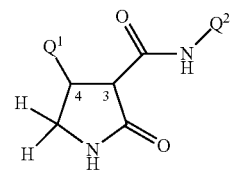

wherein
Q$^1$ is a phenyl ring or a naphthalenyl ring system, each ring or ring system optionally substituted with up to 5 substituents independently selected from R$^1$; or a 5- to 6-membered fully unsaturated heterocyclic ring or an 8- to 10-membered heteroaromatic bicyclic ring system, each ring or ring system containing ring members selected from carbon atoms and 1 to 4 heteroatoms independently selected from up to 2 O, up to 2 S and up to 4 N atoms, wherein up to 3 carbon ring members are independently selected from C(=O) and C(=S), and the sulfur atom ring members are independently selected from S(=O)$_u$(=NR$^2$)$_v$, each ring or ring system optionally substituted with up to 5 substituents independently selected from R$^1$ on carbon atom ring members and selected from R$^3$ on nitrogen atom ring members; and
Q$^2$ is a phenyl ring or a naphthalenyl ring system, each ring or ring system optionally substituted with up to 5 substituents independently selected from R$^4$; or a 5- to 6-membered fully unsaturated heterocyclic ring or an 8- to 10-membered heteroaromatic bicyclic ring system, each ring or ring system containing ring members selected from carbon atoms and 1 to 4 heteroatoms independently selected from up to 2 O, up to 2 S and up to 4 N atoms, wherein up to 3 carbon ring members are independently selected from C(=O) and C(=S), and the sulfur atom ring members are independently selected from $S(=O)_u(=NR^2)_v$, each ring or ring system optionally substituted with up to 5 substituents independently selected from $R^4$ on carbon atom ring members and selected from $R^5$ on nitrogen atom ring members
comprising reductively cyclizing a compound of Formula I

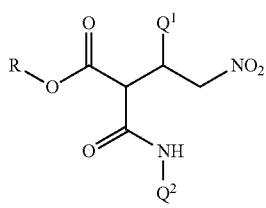

wherein
- $Q^1$ is a phenyl ring or a naphthalenyl ring system, each ring or ring system optionally substituted with up to 5 substituents independently selected from $R^1$; or a 5- to 6-membered fully unsaturated heterocyclic ring or an 8- to 10-membered heteroaromatic bicyclic ring system, each ring or ring system containing ring members selected from carbon atoms and 1 to 4 heteroatoms independently selected from up to 2 O, up to 2 S and up to 4 N atoms, wherein up to 3 carbon ring members are independently selected from C(=O) and C(=S), and the sulfur atom ring members are independently selected from $S(=O)_u(=NR^2)_v$, each ring or ring system optionally substituted with up to 5 substituents independently selected from $R^1$ on carbon atom ring members and selected from $R^3$ on nitrogen atom ring members;
- $Q^2$ is a phenyl ring or a naphthalenyl ring system, each ring or ring system optionally substituted with up to 5 substituents independently selected from $R^4$; or a 5- to 6-membered fully unsaturated heterocyclic ring or an 8- to 10-membered heteroaromatic bicyclic ring system, each ring or ring system containing ring members selected from carbon atoms and 1 to 4 heteroatoms independently selected from up to 2 O, up to 2 S and up to 4 N atoms, wherein up to 3 carbon ring members are independently selected from C(=O) and C(=S), and the sulfur atom ring members are independently selected from $S(=O)_u(=NR^2)_v$, each ring or ring system optionally substituted with up to 5 substituents independently selected from $R^4$ on carbon atom ring members and selected from $R^5$ on nitrogen atom ring members; and
- R is $C_1$-$C_8$ alkyl or phenyl;

in the presence of a reducing agent.

17. The method of claim 16 wherein
- $Q^1$ is a phenyl ring substituted with 1 to 3 substituents independently selected from $R^1$;
- $Q^2$ is a phenyl ring substituted with 1 to 3 substituents independently selected from $R^4$;
- R is $C_1$-$C_4$ alkyl;
- $R^1$ is independently halogen, cyano, nitro, $C_1$-$C_8$ alkyl, $C_1$-$C_8$ haloalkyl or $C_2$-$C_8$ haloalkoxyalkoxy; and
- $R^4$ is independently halogen, $C_1$-$C_3$ alkyl or $C_1$-$C_3$ haloalkyl.

18. The method of claim 17 wherein
- $Q^1$ is a phenyl ring having a substituent selected from $R^1$ at the meta (3-) position and optionally up to 2 additional $R^1$ substituents;
- $Q^2$ is a phenyl ring having a substituent selected from $R^4$ at the ortho (2-) position and optionally up to 2 additional $R^4$ substituents;
- $R^1$ is independently halogen, $C_1$-$C_3$ alkyl or $C_1$-$C_3$ haloalkyl;
- $R^4$ is independently halogen or $C_1$-$C_3$ haloalkyl.

19. The method of claim 16 wherein
- $Q^1$ is a pyridyl ring optionally substituted with up to 2 $R^1$;
- $Q^2$ is a phenyl ring substituted with 1 to 3 substituents independently selected from $R^4$;
- $R^1$ is independently halogen or $C_1$-$C_3$ haloalkyl; and
- $R^4$ is independently halogen or $C_1$-$C_3$ haloalkyl.

20. The method of claim 16 wherein
the stereochemistry of a compound of Formula IV is (3R,4S) or (3S,4R).

21. The compound of claim 1 that is ethyl a-[[2-fluorophenyl)amino]carbonyl]-(nitromethyl)-3-(trifluoromethyl)benzenepropanoate.

* * * * *